US007553489B2

(12) United States Patent
Young et al.

(10) Patent No.: US 7,553,489 B2
(45) Date of Patent: Jun. 30, 2009

(54) METHODS OF ADMINISTERING/DOSING ANTI-RSV ANTIBODIES FOR PROPHYLAXIS AND TREATMENT

(75) Inventors: James F. Young, Potomac, MD (US); Scott Koenig, Rockville, MD (US); Leslie S. Johnson, Germantown, MD (US); William D. Huse, Del Mar, CA (US); Jeffrey D. Watkins, Encinitas, CA (US); Herren Wu, Germantown, MD (US)

(73) Assignee: MedImmune, LLC, Gaithersburg, MD (US)

( * ) Notice: Subject to any disclaimer, the term of this patent is extended or adjusted under 35 U.S.C. 154(b) by 41 days.

(21) Appl. No.: 11/643,982

(22) Filed: Dec. 20, 2006

(65) Prior Publication Data

US 2007/0196916 A1 Aug. 23, 2007

Related U.S. Application Data

(63) Continuation of application No. 10/403,180, filed on Mar. 31, 2003, now Pat. No. 7,179,900, which is a continuation-in-part of application No. 09/996,288, filed on Nov. 28, 2001, now Pat. No. 6,818,216, and a continuation-in-part of application No. 09/996,265, filed on Nov. 28, 2001, now Pat. No. 6,855,493, said application No. 09/996,288 is a continuation-in-part of application No. 09/724,531, filed on Nov. 28, 2000, now Pat. No. 7,229,619, and a continuation-in-part of application No. 09/724,396, filed on Nov. 28, 2000, now abandoned, said application No. 09/996,265 is a continuation-in-part of application No. 09/724,531, and a continuation-in-part of application No. 09/724,396.

(60) Provisional application No. 60/368,729, filed on Mar. 29, 2002.

(51) Int. Cl.
*A61K 39/42* (2006.01)
*A61K 39/155* (2006.01)

(52) U.S. Cl. .................. 424/159.1; 424/211.1

(58) Field of Classification Search .............. None
See application file for complete search history.

(56) References Cited

U.S. PATENT DOCUMENTS

| 4,526,938 A | 7/1985 | Churchhill et al. |
| 4,800,078 A | 1/1989 | Prince et al. |
| 4,880,078 A | 11/1989 | Inoue et al. |
| 5,128,326 A | 7/1992 | Balazs et al. |
| 5,290,540 A | 3/1994 | Prince et al. |
| 5,585,089 A | 12/1996 | Queen et al. |
| 5,667,988 A | 9/1997 | Barbas et al. |
| 5,679,377 A | 10/1997 | Bernstein et al. |
| 5,693,762 A | 12/1997 | Queen et al. |
| 5,762,905 A | 6/1998 | Burton et al. |
| 5,811,524 A | 9/1998 | Brams et al. |
| 5,824,307 A | 10/1998 | Johnson |
| 5,840,298 A | 11/1998 | Brams et al. |
| 5,855,913 A | 1/1999 | Hanes et al. |
| 5,866,125 A | 2/1999 | Brams et al. |
| 5,874,064 A | 2/1999 | Edwards et al. |
| 5,912,015 A | 6/1999 | Bernstein et al. |
| 5,916,597 A | 6/1999 | Lee et al. |
| 5,929,212 A | 7/1999 | Adair et al. |
| 5,934,272 A | 8/1999 | Lloyd et al. |
| 5,939,068 A | 8/1999 | Brams et al. |
| 5,955,364 A | 9/1999 | Brams et al. |
| 5,958,765 A | 9/1999 | Brams et al. |
| 5,985,309 A | 11/1999 | Edwards et al. |
| 5,985,320 A | 11/1999 | Edwards et al. |
| 5,989,463 A | 11/1999 | Tracy et al. |
| 6,019,968 A | 2/2000 | Platz et al. |
| 6,096,551 A | 8/2000 | Barbas et al. |

(Continued)

FOREIGN PATENT DOCUMENTS

EP 0 699 756 A1 6/1996

(Continued)

OTHER PUBLICATIONS

U.S. Appl. No. 60/186,252, filed Mar. 1, 2000, Young et al.

(Continued)

*Primary Examiner*—Stacy B Chen
(74) *Attorney, Agent, or Firm*—Jones Day

(57) ABSTRACT

The present invention encompasses novel antibodies and fragments thereof which immunospecifically bind to one or more RSV antigens and compositions comprising said antibodies and antibody fragments. The present invention encompasses methods preventing respiratory syncytial virus (RSV) infection in a human, comprising administering to said human a prophylactically effective amount of one or more antibodies or fragments thereof that immunospecifically bind to one or more RSV antigens, wherein a certain serum titer of said antibodies or antibody fragments is achieved in said human subject. The present invention also encompasses methods for treating or ameliorating symptoms associated with a RSV infection in a human, comprising administering to said human a therapeutically effective amount of one or more antibodies or fragments thereof that immunospecifically bind to one or more RSV antigens, wherein a certain serum titer of said antibodies or antibody fragments is achieved in said human subject. The present invention further encompasses compositions comprising antibodies or fragments thereof that immunospecifically bind to a RSV antigen, and methods using said compositions for detection or diagnosis of a RSV infection.

18 Claims, 2 Drawing Sheets

U.S. PATENT DOCUMENTS

| | | | |
|---|---|---|---|
| 6,117,980 | A | 9/2000 | Gonzalez et al. |
| 6,413,771 | B1 | 7/2002 | Brams et al. |
| 6,537,809 | B2 | 3/2003 | Brams |
| 6,565,849 | B2 | 5/2003 | Koenig |
| 6,565,888 | B1 | 5/2003 | Tracy et al. |
| 6,656,467 | B2 | 12/2003 | Young et al. |
| 6,685,942 | B1 | 2/2004 | Burton et al. |
| 6,818,216 | B2 | 11/2004 | Young et al. |
| 6,855,493 | B2 | 2/2005 | Young et al. |
| 2001/0026798 | A1 | 10/2001 | Koenig |
| 2001/0034062 | A1 | 10/2001 | Koenig |
| 2001/0051787 | A1 | 12/2001 | Haller et al. |
| 2002/0001798 | A1 | 1/2002 | Brams et al. |
| 2002/0004046 | A1 | 1/2002 | Johnson |
| 2002/0018780 | A1 | 2/2002 | Koenig et al. |
| 2002/0098189 | A1 | 7/2002 | Young et al. |
| 2002/0102257 | A1 | 8/2002 | Johnson |
| 2002/0164326 | A1 | 11/2002 | Young et al. |
| 2004/0005323 | A1 | 1/2004 | Brams et al. |
| 2004/0005324 | A1 | 1/2004 | Pilkington et al. |
| 2004/0076631 | A1 | 4/2004 | Brams et al. |
| 2004/0131609 | A1 | 7/2004 | Young et al. |
| 2005/0002926 | A1 | 1/2005 | Young et al. |
| 2005/0147616 | A1 | 7/2005 | Young et al. |
| 2006/0099220 | A1 | 5/2006 | Tous et al. |

FOREIGN PATENT DOCUMENTS

| | | |
|---|---|---|
| WO | WO 91/05548 | 5/1991 |
| WO | WO 92/19244 | 11/1992 |
| WO | WO 94/06448 | 3/1994 |
| WO | WO 96/05229 | 2/1996 |
| WO | WO 96/20698 | 7/1996 |
| WO | WO 96/40252 | 12/1996 |
| WO | WO 97/32572 | 9/1997 |
| WO | WO 97/34631 | 9/1997 |
| WO | WO 97/44013 | 11/1997 |
| WO | WO 98/31346 | 7/1998 |
| WO | WO 98/33919 | 8/1998 |
| WO | WO 99/15154 | 4/1999 |
| WO | WO 99/20253 | 4/1999 |
| WO | WO 99/28471 | 6/1999 |
| WO | WO 99/66903 | 12/1999 |
| WO | WO 00/29584 | 5/2000 |
| WO | WO 00/56771 | 9/2000 |
| WO | WO 00/73346 | 12/2000 |
| WO | WO 01/55217 A | 8/2001 |
| WO | WO 01/64751 A | 9/2001 |
| WO | WO 2006/034292 | 3/2006 |

OTHER PUBLICATIONS

U.S. Appl. No. 60/168,426, filed Jan. 27, 2000, Young et al.
U.S. Appl. No. 09/724,396, filed Nov. 28, 2000, Young et al.
U.S. Appl. No. 09/724,531, filed Nov. 28, 2000, Young et al.
U.S. Appl. No. 11/230,593, filed Sep. 21, 2005, Tous et al.
Abman et al., 1988, "Role of Respiratory Syncytial Virus in Early Hospitalizations for Respiratory Distress of Young Infants With Cystic Fibrosis", J. Pediatr. 113(5):826-380.
American Academy of Pediatrics Committee on Infectious Diseases: Use of Ribavirin in the Treatment of Respiratory Syncytial Virus Infection. Pediatrics. Sep. 1993;92(3):501-504.
Beeler et al., 1989, "Neutralization Epitopes of the F Glycoprotein of Respiratory Syncytial Virus: Effect of Mutation Upon Fusion Function", J Virol. 63(7):2941-2950.
Bentley et al., 1980, "Human immunoglobulin variable region genes—DNA Sequences of Two V Kappa Genes and a Pseudogene", Nature 288: 5194-5198.
Cleek et al., 1997, "Biodegradable Polymeric Carriers for a bFGF Antibody for Cardiovascular Application" Pro. Int'l Symp. Control. Rel Bioact. Mater. 24:853-854.
Evans, A.S., 1989, *Viral Infections of Humans, Epidemiology and Control*, $3^{rd}$ ed., 525-544.
Falsey et al., 1991, "Noninfluenza Respiratory Virus Infection in Long-Term Care Facilities", Infect Control Hosp Epidemiol. 12(10):602-608.
Feigen et al., 1987, *Textbook of Pediatric Infectious Dieseases*, WB Saunders, Philadelphia, pp. 1653-1675.
Garvie et al., 1980, "Outbreak of Respiratory Syncytial Virus Infection in the Elderly", Br Med J. 281(6250):1253-1254.
Glezen et al., 1981, "Risk of Respiratory Syncytial Virus Infection for Infants From Low-Income Families in Relationship to Age, Sex, Ethnic Group, and Maternal Antibody Level", J. Pediatr. 98(5):708-715.
Groothuis et al., 1988, "Respiratory Syncytial Virus Infection in Children with Bronchopulmonary Dysplasia", Pediatrics. 82(2):199-203.
Groothuis et al., 1997, "Prophylactic Administration of Respiratory Syncytial Virus Immune Globulin to High-risk Infants and Young Children", The Respiratory Syncytial Virus Immune Globulin Study Group. N Engl J Med. 329(21):1524-1530.
Hall et al., 1979, "Neonatal Respiratory Syncytial Virus Infection", N Engl J Med. 300(8):393-396.
Hall, C.B., 1993, Respiratory Syncytial : What We Know Now, Comtemp. Pediatrics, 10:92-110.
Heard et al., 1999, "Two Neutralizing Human Anti RSV Antibodies: Cloning, Expression and Characterization", Molec. Med. 5:35-45.
Hemming et al., 1985, "Studies of Passive Immunotherapy for Infections of Respiratory Syncytial Virus in the Respiratory Tract of a Primate Model", J Infect Dis. 152(5):1083-1087.
Henderson et al., 1979, "Respiratory-Syncytial-Virus Infections, Reinfections and Immunity. A Prospective, Longitudinal Study in Young Children", N Engl J Med. 300(10):530-534.
Hertz et al., 1989, "Respiratory Syncytial Virus-Induced Acute Lung Injury in Adult Patients With Bone Marrow Transplants: a Clinical Approach and Review of the Literature", Medicine (Baltimore). 68(5):269-281.
Howard et al., 1989, "Intracerebral Drug Delivery in Rats with Lesion-Induced Deficits", J Neurosurg. 71(1):105-112.
Johnson et al., 1987, "Development of a Humanized Monoclonal Antibody (MEDI-493) With Potent In Vitro and In Vivo Activity Against Respiratory Syncytial Virus", J Infect Dis. 176(5):1215-1224.
Johnson et al., 1987, "The G Glycoprotein of Human Respiratory Syncytial Viruses of Subgroups A and B: Extensive Sequence Divergence Between Antigenically Related Proteins", Proc Natl Acad Sci U S A. 84(16):5625-5629.
Kapikian et al., 1969, "An Epidemiologic Study of Altered Clinical Reactivity to Respiratory Syncytial (RS) Virus Infection in Children Previously Vaccinated With an Inactivated RS Virsu Vaccine", Am J Epidemiol. 89(4):405-421.
Kim et al., 1969, "Respiratory Syncytial Virus Disease in Infants Despite Prior Administration of Antigenic Inactivated Vaccine", Am J Epidemiol. 89(4):422-434.
Lam et al., 1997, "Microencapsulation of Recombinant Humanized Monoclonal Antibody for Local Delivery", Proc. Int'l. Symp. Control Rel. Bioact. Mater. 24:759-760.
Lamprecht et al., 1976, "Role of Maternal Antibody in Pneumonia and Bronchiolitis Due to Respiratory Syncytial Virus", J Infect Dis. 134(3):211-217.
Levy et al., 1985, "Inhibition of Calcification of Bbioprosthetic Heart Valves by Local Controlled-release Diphosphonate", Science. 228(4696):190-192.
MacDonald et al., 1982, "Respiratory Syncytial Viral Infection in Infants With Congenital Heart Disease", N Engl J Med. 307(7):397-400.
MedImmune, Inc., 1999, "SYNAGIS™ package insert", last revised Dec. 2, 1999.
Morell et al., eds, 1986, "Clinical Use of Intravenous Immunoglobulins", Academic Press, London, pp. 285-294.
Murphy and Hall, 1994, "An Update on Approaches to the Development of Respiratory Syncytial Virus (RSV) and Parainfluenza Virus Type 3 (PIV3) Vaccines", Virus Res. 32(1):13-36.

Murphy et al., 1988, "Passive Transfer of Respiratory Syncytial Virus (RSV) Antiserum Suppresses The Immune Response to the RSV Fusion (F) and Large (G) Glycoproteins Expressed By Recombinant Vaccinia Viruses", J Virol. 62(10):3907-3910.

Murphy et al., 1991, "Effect of Passive Antibody on the Immune Response of Cotton Rats to Purified F and G HG Glycoproteins of Respiratory Syncytial Virus (RSV)", Vaccine. 9(3):185-189.

Navas et al., 1992, "Improved Outcome of Respiratory Syncytial Virus Infection in a High-Risk Hospitalized Population of Canadian children. Pediatric Investigators Collaborative Network on Infections in Canada", J Pediatr. 121(3):348-354.

Ning et al., 1996, "Intratumoral Radioimmunotherapy of a Human Colon Cancer Xenograft Using a Sustained Release Gel", Radiotherapy and Oncology 39: 179-189.

Ogra et al., 1988, "Respiratory Syncytial Virus Infection and the Immunocompromised Host", Pediatr Infect Dis J. Apr. 1988;7(4):246-249.

Palivizumab et al., 1998, "A Humanized Respiratory Syncytial Virus Monoclonal Antibody, Reduces Hospitalization From Respiratory Syncytial Virus Infection in High-Risk Infants", The IMpact-RSV Study Group. Pediatrics. 102(3 Pt 1):531-537.

Pohl et al., 1992, "Respiratory Syncytial Virus Infections in Pediatric Liver Transplant Recipients", J Infec Dis. 165(1):166-169.

Press et al., 1970, "The Amino Acid Sequences of the Fd Fragments of Two Human Gamma-1 Heavy chains", Biochem J. 117(4):641-660.

Prince et al., 1983, "Mechanisms of Immunity to Respiratory Syncytial Virus in Cotton Rats", Infect Immun. 42(1):81-87.

Prince et al., 1985, "Immunoprophylaxis and Immunotherapy of Respiratory Syncytial Virus Infection in the Cotton rat", Virus Res. 3(3):193-206.

Prince et al., 1985, "Quantitative Aspects of Passive Immunity to Respiratory Syncytial Virus Infection in Infant Cotton Rats" J Virol. 55(3):517-20.

Prince et al., 1990, "Mechanism of Antibody-mediated Viral Clearance in Immunotherapy of Respiratory Syncytial Virus Infection of Cotton Rats", J Virol. 64(6):3091-3092.

Ruuskanen et al., 1993, "Respiratory syncytial virus", Curr Probl Pediatr. 23(2):50-79.

Saez Llorens et al., 1998, "Safety and pharmacokinetics of an intramuscular humanized monoclonal antibody to respiratory synctial virus in premature infants and infants with bronchopulmonary dysplasia", Pediatr. Infect Dis J 17:787-791.

Saez-Llorens et al., 1997, "Phase I/II Open Label Multi Dose Escalation Trial of a Humanized Respiratory Synctial Virus (RSV) Monoclonal Antibody (MEDI-493) Administered Intramuscularly (IM) In High Risk Children", Abstracts in Non HIV Virology, ICAAC Toronto.

Saez-Llorens et al., 1998, "Safety and Pharmacokinetics of an Intramuscular Humanized Monoclonal Antibody to Respiratory Synctial Virus in Premature Infants and Infants with Bronchopulmonary Dysplasia", Pediatric Infect Dis J. 17:7870-7891.

Saudek et al., 1989, A Preliminary Trial of the Pprogrammable Implantable Medication System for Insulin Delivery. N Engl J Med. 321(9):574-579.

Sefton, 1987, "Implantable Pumps", CRC Crit. Ref. Biomed. Eng. 14:20.

Siva Subramanian et al., 1997, "Randomized Double Blind Placebo Controlled Dose Escalation Trial of a Humanized Respiratory Synctial Virus Monoclonal Antibody in High Risk Infants", Poster Session Infect. Dis. 130A:768.

Siva Subramanian et al., 1998, "Safety, tolerance and pharmacokinetics of a humanized monoclonal antibody to respiratory syncytial virus in premature infants and infants with bronchopulmonary dysplasia", Pediatr Infect Dis 17: 110-115.

Smith et al., 1991, "A Controlled Trial of Aerosolized Ribavirin in Infants Receiving Mechanical Ventilation for Severe Respiratory Syncytial Virus Infection", N Engl J Med. 325(1):24-29.

Song et al., 1995, "Antibody Mediated Lung Targeting of Long-Circulating Emulsions", PDA Journal of Pharmaceutical Science & Technology 50:372-397.

Sorbera et al., 1998, "Palivizumab", Drugs Data Report 20:702-703.

Sorbera et al., 1998, "Palivizumab", Drug of the Future 23:970-976.

Subramanian et al., 1998, "Safety, Tolerance and Pharmacokinetics of a Humanized Monoclonal Antibody to Respiratory Synctial Virus in Premature Infants and Infants with Bronchopulmonary Dysplasia", Pediatric Infect Dis J. 17:110-115.

Walsh et al., 1987, "Immunization with Glycoprotein Subunits of Respiratory Syncytial Virus to Protect Cotton Rats Against Viral Infection", J Infect Dis. 155(6):1198-1204.

Hacking et al., 2002, "Respiratory syncytial virus—viral biology and the host response", J Infect. 45(1):18-24.

Anderson et al., 1985, "Microneutralization test for respiratory syncytial virus based on an enzyme immunoassay," J. Clin. Microbiol. 22:1050-1052.

Boulianne et al., 1984, "Production of functional chimaeric mouse/human antibody," Nature 312(5995):643-646.

Carson et al., 1986, "Human lymphocyte hybridomas and monoclonal antibodies," Adv. Immunol. 38:275:311.

Conrad et al., 1987, "Aerosolized ribavirin treatment of respiratory syncytial virus infection in infants hospitalized during an epidemic," Pediatr. Infect. Dis. J. 6(2):152-158.

Cruse et al., 1995, Illustrated Dictionary of Immunology, Boca Raton: CRC Press, pp. 18-19.

Dorland's Illustrated Medical Dictionary, 1994, 28$^{th}$ ed., Philadelphia: WB Saunders p. 874.

Duenas et al., 1996, "In vitro immunization of naïve human B cells yields high affinity immunoglobulin G antibodies as illustrated by phage display," Blackwell Science Limited, pp. 1-7.

Duenas et al., 1996, "Selection of phage displayed antibodies based on kinetics constants," 33(3):279-285.

Everitt et al., 1996, "The pharmacokinetics, antigenicity, and fusion-inhibition activity of RSHZ19, a humanized monoclonal antibody to respiratory syncytial virus, in healthy volunteers," J. Infect. Dis.

Foote et al., 1995, "Kinetic and affinity limits on antibodies produced during immune response," Proc. Nat'l Acad. Science USA 92:1254-1256.

Foote et al., 1991, "Kinetic maturation of an immune response," Nature vol. 352.

Glaser et al., 1992, "Antibody engineering by codon-based mutagenesis in a filamentous phage vector system," J. Immunol. 149:3903-3913.

Greenspan et al., 1999, Nature Biotechnology 7:936-937.

Groves et al., 1987, "Production of an ovine monoclonal antibody to testosterone by an interspecies fusion," Hybridoma 6(1):71-76.

Hall et al., 1985, "Ribavirin treatment of respiratory syncytial viral infection in infants with underlying cardiopulmonary disease," JAMA 254(21):3047-3051.

Hall et al., 1983, "Aerosolized ribavirin treatment of infants with respiratory syncytial viral infection. A randomized double-blind study," N. Engl. J. Med. 308(24):1443-1447.

Hall et al., 1975, "Nosocomial respiratory syncytial virus infections," N. Engl. J. Med. 293(26):1343-1346.

Haynes et al., 2002, "Neutralizing anti-F glycoprotein and anti-substance P antibody treatment effectively reduces infection and inflammation associated with respiratory syncytial virus infection," J. Virol. 76(14):6873-6881.

Johnson et al., 1999, "A direct comparison of the activities of two humanized respiratory syncytial virus monoclonal antibodies: MEDI-493 and RSHZ19," J. Infect. Dis. 180(1):35-40.

Karlsson et al., 1997, "Experimental design for kinetic analysis of protein-protein interactions with surface plasmon resonance biosensors," J Immunol. Meth.

Knappik et al., 2000, "Fully synthetic human combinatorial antibody libraries (HuCAL) based on modular consensus frameworks and CDRs randomized with trinucleotides," Academic Press, pp. 57-86.

Liu et al., 1987, "Expression of mouse::human immunoglobulin heavy-chain cDNA in lymphoid cells," Gene 54(1):33-40.

LoBuglio et al., 1989, "Mouse/human chimeric monoclonal antibody in man: kinetics and immune response,"Proc. Natl. Acad. Sci. USA 86(11):4220-4224.

Morrison et al., 1985, "Transfectomas provide novel chimeric antibodies," Science 229(4719):1202-1207.

Morrison et al., 1984, "Chimeric human antibody molecules: mouse antigen-binding domains with human constant region domains," Proc. Natl. Acad. Sci. USA 81(21):6851-6855.

Myszka et al., 1999, "Survey of the 1998 optical biosensor literature," J. Mol. Recog.

Newman et al., 1992, "'Primitization' of recombinant antibodies for immunotherapy of human diseases: A Macaque/Hunab chimeric antibody against human CD4," 10:1455-1460.

Prince et al., 1996, "Treatment of parainfluenza virus type 3 bronchiolitis and pneumonia in a cotton rat model using topical antibody and glucocorticosteroid," J. Infect. Dis. pp. 598-608.

Raman et al., 1992, "Diffusion-limited rates for monoclonal antibody binding to cytochrome," Biochem.

Roost et al., 1995, "Early high-affinity neutralizing anti-viral IgG responses without further overall improvements of affinity," PNAS USA 92:1257-1261.

Rosok et al., 1995, "A combinatorial library strategy for the rapid humanization of anticarcinoma BR 96 Fab," JBC 271(27):22611-22618.

Rudikoff et al., 1982, "Single amino acid substitution altering antigen-binding specificity," Proc. Natl. Acad. Sci. USA 79(6):1979-1983.

Sahagan et al., 1986, "A genetically engineered murine/human chimeric antibody retains specificity for human tumor-associated antigen," J. Immunol. 137(3):1066-1074.

Schier et al., 1996, "Isolation of picomolar affinity anti-c-erbB-2 single-chain Fv by molecular evolution of the complementarity determining regions in the center of the antibody binding site," J. Mol. Biol. 263(4):551-567.

Steplewski et al., 1988, "Biological activity of human-mouse IgG1, IgG2, IgG3, and IgG4 chimeric monoclonal antibodies with antitumor specificity," Proc. Natl. Acad. Sci. USA 85(13):4852-4856.

Sun et al., 1987, "Chimeric antibody with human constant regions and mouse variable regions directed against carcinoma-associated antigen 17-1A," Proc. Natl. Acad. Sci. USA 84(1):214-218.

Takeda et al., 1985, "Construction of chimaeric processed immunoglobulin genes containing mouse variable and human constant region sequences," Nature 314(6010):452-454.

Talwar et al., 1976, "Isoimmunization against human chorionic gonadotropin with conjugates of processed beta-subunit of the hormone and tetanus toxoid," Proc. Natl. Acad. Sci. USA 73(1):218-222.

van Wyke et al., 1985, "Antigenic variation in the hemagglutinin-neuraminidase protein of human parainfluenza type 3 virus," Virology 143(2):569-582.

Wald et al., 1988, "In re ribavirin: a case of premature adjudication?" J. Pediatr. 112(1):154-158.

Wright et al., 1982, "Administration of a highly attenuated, live respiratory syncytial virus vaccine to adults and children," Infect. Immun. 37(1):397-400.

Wu et al., 1998, "Stepwise in vitro affinity maturation of Vitaxin, an avb-specific humanized mAb," PNAS 95:6037-6042.

Geneseq Database, Accession No. AAW70933, entry date Oct. 1998 from patent No. FR2758331-A1 of Bourgeois et al.

Barbas et al ., "Selection and evolution of high-affinity human anti-viral antibodies," Trends in Biotechnology 14(7):230-234 (1996).

Bentley and Rabbits, 1980, "Human immunoglobulin variable region genes—DNA Sequences of Two V Kappa Genes and a Pseudogene", Nature 288: 730-733.

Chamat et al., "Human monoclonal antibodies isolated from spontaneous Epstein-Barr Virus—transformed tumors of Hu-SPL-SCID mice and specific for fusion protein display broad neutralizing activity toward respiratory syncytial virus," Journal of Infections Diseases 180:268-277 (1999).

Chmura et al., PNAS (Jul. 17, 2001) 98(15):8480-8484.

Hefta et al, "Kinetic and affinity constants of epitope specific anti-carcinembryonic antigen (CEA) monoclonal antibodies for CEA and engineered CEA domain constructs," Immunotechnology 4:49-57 (1998).

MedImmune, SYNAGIS (registered trademark) package insert, revised Oct. 23, 2002.

Myszka et al., "Kinetic analysis of a protein antigen-antibody interaction limited by mass transport on an optical biosensor," Elsevier Science, pp. 127-137 (1997).

Roguska et al., "Humanization of murine monoclonal antibodies through variable domain resurfacing," Proceedings of the National Academy of Sciences of the United States of America 91(3):969-973 (1994).

U.S. Census Bureau, Age Data, website updated May 12, 2004, http://www.census.gov/population/www/socdemo/age.html.

U.S. Department of Commerce, Economics and Statistics Administration, Bureau of the Census, We the American Elderly, Sep. 1993.

Wu et al., "Humanization of a murine monoclonal antibody by simultaneous optimization of framework and CDR residues," Journal of Molecular Biology 294(1):151-162 (1999).

Yang et al., "CDR walking mutagenesis for the affinity maturation of a potent human anit-HIV-1 antibody into the picomolar range," Journal of Molecular Biology, Article No: J. Mol. Biol., pp. 254, 392-403, Sep. 5, 1995.

Arbiza et al., "Characterization of two antigenic sites recognized by neutralizing monoclonal antibodies directed against the fusion glycoprotein of human respiratory syncytial virus," Journal of General Virology 73: 2225-2234 (1992).

Balint and Larrick, 1993, "Antibody engineering by parsimonious mutagenesis." Gene. 137(1):109-118.

Bourgeois et al., "New peptides recognizing viral epitope with tropism to mucosa—useful for, e.g. diagnosing, preventing and treating viral infection(s)." GENESEQ database entry for Accession No. AAW70933; Oct. 14, 1998 and alignment with Seq ID No. 12 of U.S. Appl. No. 09/771,415.

Cruse and Lewis, 1995, Illustrated Dictionary of Immunology, Boca Raton: CRC Press, pp. 18-19.

Dorland's Illustrated Medical Dictionary, 1994, 28$^{th}$ ed., Philadelphia: WB Saunders p. 874.

Egan et al., 1999, "Effect of Sch 55700, a humanized monoclonal antibody to human interleukin-5, on eosinophilic responses and bronchial hyperreactivity." Arzneimittel-forschung. 49(9):779-790.

Garcia-Barreno, B. et al., "Marked Differences in the Antigenic Structure of Human Respiratory Syncytial Virus F and G Glycoproteins," Journal of Virology 925-932 (1989).

Greenspan et al., 1999, Nature Biotechnology 17:936-937.

Love et al., 1993, "How the anti-(metal chelate) antibody CHA255 is specific for the metal ion of its antigen: X-ray structures for two Fab'/hapten complexes with different metals in the chelate." Biochemistry. 32(41):10950-10959.

Myszka, 1999 "Survey of the 1998 optical biosensor literature," Journal of Molecular Recognition 12:390-408.

Newman et al., 1992 "Primatization of recombinant antibodies for immunotherapy of human diseases: a macaque/hunab chimeric antibody against human CD4," Biotechnology 10:1455-1460.

Palomo, C. et al., "Induction of a Neutralizing Immune Response to Human Respiratory Syncytial Virus with Anti-Idiotypic Antibodies" Journal of Virology 64(9): 4199-4206 (1990).

Talwar et al., 1978 Proc. Natl. Acad. Sci. U.S.A. 73(1):218-222.

Whitlow et al., 1995, "1.85 A structure of anti-fluorescein 4-4-20 Fab." Protein Eng. 8(8):749-761.

Wu et al., "Ultra-potent Antibodies Against Respiratory Syncytial Virus: Effects of Binding Kinetics and binding Valence on Viral Neutralization," Journal of Molecular Biology 350: 126-144 (2005).

Gilchrist S., et al. 1994 "National surveillance for respiratory syncytial virus, United States, 1985-1990," J. Infect. Dis. 170:986-990.

Nguyen et al., 2000 "Efficient generation of respiratory syncytial virus (RSV)-neutralizing human MoAbs via human peripheral blood lymphocyte (hu-PBL-)SCID mice and scFv phage display libraries," Clin. Exp. Immunol. 122:85-93.

Sakurai, et al., 1999, "Human antibody responses to mature and immature forms of viral envelope in respiratory syncytial virus infection: significance for subunit vaccines." J. Virol. 73(4):2956-2962.

Schier et al., 1996, "Isolation of high-affinity monomeric human anti-c-erbB-2 single chain Fv using affinity-driven selection." J. Mol. Biol. 255(1):28-43.

Verma et al., 1997, "Gene Theapy—promises, problems, and prospects," Nature 389:239-242.

Orkin et al., Dec. 1995, "Report and recommendations of the panel to assess the NIH investment in research on gene therapy," available from http://www.nih.gov/news/panelrep.html.

U.S. Appl. No. 09/724,396—Office Action dated Mar. 26, 2002.
U.S. Appl. No. 09/724,396—Office Action dated Dec. 3, 2002.
U.S. Appl. No. 09/724,396—Office Action dated Jun. 3, 2003.
U.S. Appl. No. 09/724,396—Office Action dated Jul. 28, 2003.
U.S. Appl. No. 09/724,396—Office Action dated Apr. 5, 2004.
U.S. Appl. No. 09/724,531 (U.S. Patent No. 7,229,619)—Office Action dated Feb. 21, 2003.
U.S. Appl. No. 09/724,531 (U.S. Patent No. 7,229,619)—Office Action dated Oct. 21, 2003.
U.S. Appl. No. 09/724,531 (U.S. Patent No. 7,229,619)—Office Action dated Jun. 4, 2004.
U.S. Appl. No. 09/724,531 (U.S. Patent No. 7,229,619)—Office Action dated Feb. 9, 2005.
U.S. Appl. No. 09/724,531 (U.S. Patent No. 7,229,619)—Office Action dated Jun. 15, 2005.
U.S. Appl. No. 09/724,531 (U.S. Patent No. 7,229,619)—Office Action dated Apr. 4, 2006.
U.S. Appl. No. 09/724,531 (U.S. Patent No. 7,229,619)—Office Action dated Aug. 22, 2006.
U.S. Appl. No. 09/724,531 (U.S. Patent No. 7,229,619)—Office Action / Notice of Allowability dated Jan. 30, 2007.
U.S. Appl. No. 09/996,288 (U.S. Patent No. 6,818,216)—Office Action dated Jul. 14, 2003.
U.S. Appl. No. 09/996,288 (U.S. Patent No. 6,818,216)—Office Action dated Jan. 29, 2004.
U.S. Appl. No. 09/996,288 (U.S. Patent No. 6,818,216)—Office Action / Notice of Allowability dated Jun. 30, 2004.
U.S. Appl. No. 09/996,265 (U.S. Patent No. 6,855,493)—Office Action dated Aug. 12, 2003.
U.S. Appl. No. 09/996,265 (U.S. Patent No. 6,855,493)—Office Action / Notice of Allowability dated Mar. 31, 2004.
U.S. Appl. No. 09/996,265 (U.S. Patent No. 6,855,493)—Office Action / Supplemental Notice of Allowability dated Jul. 13, 2004.
U.S. Appl. No. 10/403,180 (U.S. Patent No. 7,179,900)—Office Action dated Apr. 4, 2005.
U.S. Appl. No. 10/403,180 (U.S. Patent No. 7,179,900)—Office Action dated Oct. 19, 2005.
U.S. Appl. No. 10/403,180 (U.S. Patent No. 7,179,900)—Office Action dated Mar. 30, 2006.
U.S. Appl. No. 10/403,180 (U.S. Patent No. 7,179,900)—Office Action / Notice of Allowability dated Sep. 6, 2006.
U.S. Appl. No. 10/900,230 (U.S. Publ. No. 2005/0002926)—Office Action dated Jan. 24, 2006.
U.S. Appl. No. 10/900,230 (U.S. Publ. No. 2005/0002926)—Office Action dated Jun. 30, 2006.
U.S. Appl. No. 10/900,230 (U.S. Publ. No. 2005/0002926)—Office Action dated Dec. 26, 2006.
U.S. Appl. No. 10/900,230 (U.S. Publ. No. 2005/0002926)—Office Action dated Jun. 27, 2007.
U.S. Appl. No. 10/900,230 (U.S. Publ. No. 2005/0002926)—Office Action dated Feb. 21, 2008.
U.S. Appl. No. 10/900,230 (U.S. Publ. No. 2005/0002926)—Office Action dated Sep. 18, 2008.
U.S. Appl. No. 10/962,285 (U.S. Patent No. 7,323,172)—Office Action dated Oct. 26, 2006.
U.S. Appl. No. 10/962,285 (U.S. Patent No. 7,323,172)—Office Action dated Apr. 13, 2007.
U.S. Appl. No. 10/962,285 (U.S. Patent No. 7,323,172)—Office Action / Notice of Allowability dated Sep. 6, 2007.
U.S. Appl. No. 11/263,230 (U.S. Publ. No. 2006/0115485)—Office Action dated Jan. 9, 2008.
U.S. Appl. No. 11/263,230 (U.S. Publ. No. 2006/0115485)—Office Action dated Oct. 2, 2008.
U.S. Appl. No. 09/796,848 (U.S. Publ. No. 2002/0098189)—Office Action dated Jun. 18, 2002.
U.S. Appl. No. 09/796,848 (U.S. Publ. No. 2002/0098189)—Office Action dated Dec. 29, 2003.
U.S. Appl. No. 09/796,848 (U.S. Publ. No. 2002/0098189)—Office Action dated Oct. 29, 2004.
U.S. Appl. No. 09/796,848 (U.S. Publ. No. 2002/0098189)—Office Action dated Jul. 13, 2005.
U.S. Appl. No. 09/796,848 (U.S. Publ. No. 2002/0098189)—Office Action dated Apr. 4, 2006.
U.S. Appl. No. 09/796,848 (U.S. Publ. No. 2002/0098189)—Office Action dated Jul. 27, 2007.
U.S. Appl. No. 09/796,848 (U.S. Publ. No. 2002/0098189)—Office Action dated Apr. 14, 2008.
U.S. Appl. No. 09/771,415 (U.S. Patent No. 6,656,467)—Office Action dated Jun. 18, 2002.
U.S. Appl. No. 09/771,415 (U.S. Patent No. 6,656,467)—Office Action dated Feb. 10, 2003.
U.S. Appl. No. 09/771,415 (U.S. Patent No. 6,656,467)—Office Action / Notice of Allowability dated May 6, 2003.
U.S. Appl. No. 10/657,363 (U.S. Publ. No. 2004/0098189)—Office Action dated May 30, 2007.
U.S. Appl. No. 10/657,363 (U.S. Publ. No. 2004/0098189)—Office Action dated Dec. 14, 2007.
DALL'ACQUA Declaration (dated Jun. 16, 2008)—Filed in U.S. Appl. No. 10/657,363 (U.S. Publ. No. 2004/0098189) on Jun. 16, 2008.
U.S. Appl. No. 10/020,354 (U.S. Patent No. 7,083,784)—Office Action dated Apr. 7, 2004.
U.S. Appl. No. 10/020,354 (U.S. Patent No. 7,083,784)—Office Action dated Nov. 17, 2004.
U.S. Appl. No. 10/020,354 (U.S. Patent No. 7,083,784)—Office Action dated Jun. 1, 2005.
U.S. Appl. No. 10/020,354 (U.S. Patent No. 7,083,784)—Office Action / Notice of Allowability dated Dec. 15, 2005.
DALL'ACQUA Declaration (dated Oct. 3, 2005)—Filed in U.S. Appl. No. 10/020,354 (U.S. Patent No. 7,083,784) on Oct. 8, 2005.
U.S. Appl. No. 11/397,328 (U.S. Publ. No. 2006/0198840)—Office Action dated Oct. 18, 2007.
U.S. Appl. No. 11/397,328 (U.S. Publ. No. 2006/0198840)—Office Action / Notice of Allowability dated Aug. 7, 2008.
U.S. Appl. No. 10/461,904 (U.S. Patent No. 7,132,100)—Office Action dated Dec. 14, 2004.
U.S. Appl. No. 10/461,904 (U.S. Patent No. 7,132,100)—Office Action dated Nov. 25, 2005.
U.S. Appl. No. 10/461,904 (U.S. Patent No. 7,132,100)—Office Action / Notice of Allowability dated May 2, 2006.
U.S. Appl. No. 11/362,267 (U.S. Patent No. 7,294,336)—Office Action dated May 4, 2007.
U.S. Appl. No. 11/362,267 (U.S. Patent No. 7,294,336)—Office Action / Notice of Allowability dated Aug. 6, 2007.
U.S. Appl. No. 10/461,863 (U.S. Patent No. 7,425,618)—Office Action dated Dec. 18, 2006.
U.S. Appl. No. 10/461,863 (U.S. Patent No. 7,425,618)—Office Action dated Jun. 11, 2007.
U.S. Appl. No. 10/461,863 (U.S. Patent No. 7,425,618)—Office Action / Notice of Allowability dated Nov. 19, 2007.

A

DIQMTQSPST LSASVGDRVT ITC<u>KCQLSVGYMH</u> WYQQKPG    40
                                  *CDR L1*

KAPKLLIY <u>DTSKLAS</u> GVPSR FSGSGSGTEF TLTISSLQPD    80
         *CDR L2*

DFATYYC <u>FQGSGYPFT</u> FGGGTKLEIK    106
        *CDR L3*

B

QVTLRESGPA LVKPTQTLTL TCTFSGFSLS <u>TSGMSVG</u> WIR    40
                                      *CDR H1*

QPPGKALEWL A <u>DIWWDDKKDYNPSLKS</u> RLT ISKDTSKNQV    80
             *CDR H2*

VLKVTNMDPA DTATYYCAR <u>SMITNWYFDV</u> W GAGTTVTVSS    120
                            *CDR H3*

FIG. 1

A

DIQMTQSPST LSASVGDRVT ITC<u>SASSSVGYMH</u> WYQQKPG   40
                                  *CDR L1*

KAPKLLIY <u>DTSKLAS</u> GVPSR FSGSGSGTEF TLTISSLQPD   80
        *CDR L2*

DFATYYC <u>FQGSGYPFT</u> FGGG TKVEIK   106
       *CDR L3*

B

QVTLRESGPA LVKPTQTLTL TCTFSGFSLS <u>TSGMSVG</u> WIR   40
                                       *CDR H1*

QPPGKALEWL A <u>DIWWDDKKDYNPSLKS</u> RLT ISKDTSKNQV   80
             *CDR H2*

VLKVTNMDPA DTATYYCAR <u>SMITNWYFDV</u> WGQGTTVTVSS   120
                           *CDR H3*

FIG. 2

US 7,553,489 B2

METHODS OF ADMINISTERING/DOSING ANTI-RSV ANTIBODIES FOR PROPHYLAXIS AND TREATMENT

CROSS-REFERENCE TO RELATED APPLICATIONS:

This application is a continuation of U.S. Ser. No. 10/403,180 (U.S. Pat. No. 7,179,900), filed Mar. 31, 2003, which claims priority to U.S. provisional application Ser. No. 60/368,729, filed Mar. 29, 2002, and is a continuation-in-part of U.S. application Ser. Nos. 09/996,288 (now U.S. Pat. No. 6,818,216) and 09/996,265 (now U.S. Pat. No. 6,855,493), both filed Nov. 28, 2001, and both of which are continuations-in-part of U.S. application Ser. Nos. 09/724,531 (U.S. Pat. No. 7,229,619) and 09/724,396 (abandoned), filed Nov. 28, 2000, each of which is incorporated herein by reference in its entirety.

1. INTRODUCTION

The present invention relates to compositions comprising antibodies or fragments thereof that immunospecifically bind to a RSV antigen and methods for preventing, treating or ameliorating symptoms associated with respiratory syncytial virus (RSV) infection utilizing said compositions. In particular, the present invention relates to methods for preventing, treating or ameliorating symptoms associated with RSV infection, said methods comprising administering to a human subject an effective amount of one or more antibodies or fragments thereof that immunospecifically bind to a RSV antigen, wherein a certain serum titer of said antibodies or antibody fragments is achieved in said human subject. The present invention also relates to detectable or diagnostic compositions comprising antibodies or fragments thereof that immunospecifically bind to a RSV antigen and methods for detecting or diagnosing RSV infection utilizing said compositions.

2. BACKGROUND OF THE INVENTION

Respiratory syncytial virus (RSV) is the leading cause of serious lower respiratory tract disease in infants and children (Feigen et al., eds., 1987, *In: Textbook of Pediatric Infectious Diseases*, W B Saunders, Philadelphia at pages 1653-1675; New Vaccine Development, Establishing Priorities, Vol. 1, 1985, National Academy Press, Washington DC at pages 397-409; and Ruuskanen et al., 1993, Curr. Probl. Pediatr. 23:50-79). The yearly epidemic nature of RSV infection is evident worldwide, but the incidence and severity of RSV disease in a given season vary by region (Hall, C. B., 1993, Contemp. Pediatr. 10:92-110). In temperate regions of the northern hemisphere, it usually begins in late fall and ends in late spring. Primary RSV infection occurs most often in children from 6 weeks to 2 years of age and uncommonly in the first 4 weeks of life during nosocomial epidemics (Hall et al., 1979, New Engl. J. Med. 300:393-396). Children at increased risk from RSV infection include preterm infants (Hall et al., 1979, New Engl. J. Med. 300:393-396) and children with bronchopulmonary dysplasia (Groothuis et al., 1988, Pediatrics 82:199-203), congenital heart disease (MacDonald et al., New Engl. J. Med. 307:397-400), congenital or acquired immunodeficiency (Ogra et al., 1988, Pediatr. Infect. Dis. J. 7:246-249; and Pohl et al., 1992, J. Infect. Dis. 165:166-169), and cystic fibrosis (Abman et al., 1988, J. Pediatr. 113:826-830). The fatality rate in infants with heart or lung disease who are hospitalized with RSV infection is 3%-4% (Navas et al., 1992, J. Pediatr. 121:348-354).

RSV infects adults as well as infants and children. In healthy adults, RSV causes predominantly upper respiratory tract disease. It has recently become evident that some adults, especially the elderly, have symptomatic RSV infections more frequently than had been previously reported (Evans, A. S., eds., 1989, Viral Infections of Humans. Epidemiology and Control, 3$^{rd}$ ed., Plenum Medical Book, New York at pages 525-544). Several epidemics also have been reported among nursing home patients and institutionalized young adults (Falsey, A. R., 1991, Infect. Control Hosp. Epidemiol. 12:602-608; and Garvie et al., 1980, Br. Med. J. 281:1253-1254). Finally, RSV may cause serious disease in immunosuppressed persons, particularly bone marrow transplant patients (Hertz et al., 1989, Medicine 68:269-281).

Treatment options for established RSV disease are limited. Severe RSV disease of the lower respiratory tract often requires considerable supportive care, including administration of humidified oxygen and respiratory assistance (Fields et al., eds, 1990, Fields Virology, 2$^{nd}$ ed., Vol. 1, Raven Press, New York at pages 1045-1072). The only drug approved for treatment of infection is the antiviral agent ribavirin (American Academy of Pediatrics Committee on Infectious Diseases, 1993, Pediatrics 92:501-504). It has been shown to be effective in the treatment of RSV pneumonia and bronchiolitis, modifying the course of severe RSV disease in immunocompetent children (Smith et al., 1991, New Engl. J. Med. 325:24-29). However, ribavirin has had limited use because it requires prolonged aerosol administration and because of concerns about its potential risk to pregnant women who may be exposed to the drug during its administration in hospital settings.

While a vaccine might prevent RSV infection, no vaccine is yet licensed for this indication. A major obstacle to vaccine development is safety. A formalin-inactivated vaccine, though immunogenic, unexpectedly caused a higher and more severe incidence of lower respiratory tract disease due to RSV in immunized infants than in infants immunized with a similarly prepared trivalent parainfluenza vaccine (Kim et al., 1969, Am. J. Epidemiol. 89:422-434; and Kapikian et al., 1969, Am. J. Epidemiol. 89:405-421). Several candidate RSV vaccines have been abandoned and others are under development (Murphy et al., 1994, Virus Res. 32:13-36), but even if safety issues are resolved, vaccine efficacy must also be improved. A number of problems remain to be solved. Immunization would be required in the immediate neonatal period since the peak incidence of lower respiratory tract disease occurs at 2-5 months of age. The immaturity of the neonatal immune response together with high titers of maternally acquired RSV antibody may be expected to reduce vaccine immunogenicity in the neonatal period (Murphy et al., 1988, J. Virol. 62:3907-3910; and Murphy et al., 1991, Vaccine 9:185-189). Finally, primary RSV infection and disease do not protect well against subsequent RSV disease (Henderson et al., 1979, New Engl. J. Med. 300:530-534).

Currently, the only approved approach to prophylaxis of RSV disease is passive immunization. Initial evidence suggesting a protective role for IgG was obtained from observations involving maternal antibody in ferrets (Prince, G. A., Ph.D. diss., University of California, Los Angeles, 1975) and humans (Lambrecht et al, 1976, J. Infect. Dis. 134:211-217; and Glezen et al., 1981, J. Pediatr. 98:708-715). Hemming et al. (Morell et al., eds., 1986, Clinical Use of Intravenous Immunoglobulins, Academic Press, London at pages 285-294) recognized the possible utility of RSV antibody in treatment or prevention of RSV infection during studies involving the pharmacokinetics of an intravenous immune globulin (IVIG) in newborns suspected of having neonatal sepsis.

They noted that 1 infant, whose respiratory secretions yielded RSV, recovered rapidly after IVIG infusion. Subsequent analysis of the IVIG lot revealed an unusually high titer of RSV neutralizing antibody. This same group of investigators then examined the ability of hyperimmune serum or immune globulin, enriched for RSV neutralizing antibody, to protect cotton rats and primates against RSV infection (Prince et al., 1985, Virus Res. 3:193-206; Prince et al., 1990, J. Virol. 64:3091-3092; Hemming et al., 1985, J. Infect. Dis. 152: 1083-1087; Prince et al., 1983, Infect. Immun. 42:81-87; and Prince et al., 1985, J. Virol. 55:517-520). Results of these studies suggested that RSV neutralizing antibody given prophylactically inhibited respiratory tract replication of RSV in cotton rats. When given therapeutically, RSV antibody reduced pulmonary viral replication both in cotton rats and in a nonhuman primate model. Furthermore, passive infusion of immune serum or immune globulin did not produce enhanced pulmonary pathology in cotton rats subsequently challenged with RSV.

Recent clinical studies have demonstrated the ability of this passively administered RSV hyperimmune globulin (RSV IVIG) to protect at-risk children from severe lower respiratory infection by RSV (Groothius et al., 1993, New Engl. J. Med. 329:1524-1530; and The PREVENT Study Group, 1997, Pediatrics 99:93-99). While this is a major advance in preventing RSV infection, this treatment poses certain limitations in its widespread use. First, RSV IVIG must be infused intravenously over several hours to achieve an effective dose. Second, the concentrations of active material in hyperimmune globulins are insufficient to treat adults at risk or most children with comprised cardiopulmonary function. Third, intravenous infusion necessitates monthly hospital visits during the RSV season. Finally, it may prove difficult to select sufficient donors to produce a hyperimmune globulin for RSV to meet the demand for this product. Currently, only approximately 8% of normal donors have RSV neutralizing antibody titers high enough to qualify for the production of hyperimmune globulin.

One way to improve the specific activity of the immunoglobulin would be to develop one or more highly potent RSV neutralizing monoclonal antibodies (MAbs). Such MAbs should be human or humanized in order to retain favorable pharmacokinetics and to avoid generating a human antimouse antibody response, as repeat dosing would be required throughout the RSV season. Two glycoproteins, F and G, on the surface of RSV have been shown to be targets of neutralizing antibodies (Fields et al., 1990, supra; and Murphy et al., 1994, supra). These two proteins are also primarily responsible for viral recognition and entry into target cells; G protein binds to a specific cellular receptor and the F protein promotes fusion of the virus with the cell. The F protein is also expressed on the surface of infected cells and is responsible for subsequent fusion with other cells leading to syncytia formation. Thus, antibodies to the F protein may directly neutralize virus or block entry of the virus into the cell or prevent syncytia formation. Although antigenic and structural differences between A and B subtypes have been described for both the G and F proteins, the more significant antigenic differences reside on the G glycoprotein, where amino acid sequences are only 53% homologous and antigenic relatedness is 5% (Walsh et al., 1987, J. Infect. Dis. 155:1198-1204; and Johnson et al., 1987, Proc. Natl. Acad. Sci. USA 84:5625-5629). Conversely, antibodies raised to the F protein show a high degree of cross-reactivity among subtype A and B viruses. Beeler and Coelingh (1989, J. Virol. 7:2941-2950) conducted an extensive analysis of 18 different murine MAbs directed to the RSV F protein. Comparison of the biologic and biochemical properties of these MAbs resulted in the identification of three distinct antigenic sites (designated A, B, and C). Neutralization studies were performed against a panel of RSV strains isolated from 1956 to 1985 that demonstrated that epitopes within antigenic sites A and C are highly conserved, while the epitopes of antigenic site B are variable.

A humanized antibody directed to an epitope in the A antigenic site of the F protein of RSV, SYNAGIS®, is approved for intramuscular administration to pediatric patients for prevention of serious lower respiratory tract disease caused by RSV at recommended monthly doses of 15 mg/kg of body weight throughout the RSV season (November through April in the northern hemisphere). SYNAGIS® is a composite of human (95%) and murine (5%) antibody sequences. See, Johnson et al., 1997, J. Infect. Diseases 176: 1215-1224 and U.S. Pat. No. 5,824,307, the entire contents of which are incorporated herein by reference. The human heavy chain sequence was derived from the constant domains of human $IgG_1$ and the variable framework regions of the VH genes or Cor (Press et al., 1970, Biochem. J. 117:641-660) and Cess (Takashi et al., 1984, Proc. Natl. Acad. Sci. USA 81:194-198). The human light chain sequence was derived from the constant domain of $C_\kappa$ and the variable framework regions of the VL gene K104 with $J_\kappa$–4 (Bentley et al., 1980, Nature 288:5194-5198). The murine sequences derived from a murine monoclonal antibody, Mab 1129 (Beeler et al., 1989, J. Virology 63:2941-2950), in a process which involved the grafting of the murine complementarity determining regions into the human antibody frameworks.

Although SYNAGIS® has been successfully used for the prevention of RSV infection in pediatric patients, multiple intramuscular doses of 15 mg/kg of SYNAGIS™ is required to achieve a prophylactic effect. In pediatric patients less than 24 months of age, the mean half-life of SYNAGIS® has been shown to be 20 days and monthly intramuscular doses of 15 mg/kg have been shown to result in a mean±standard derivation 30 day serum titer of 37±21 µg/ml after the first injection, 57±41 µg/ml after the second injection, 68±51 µg/ml after the third injection, and 72±50 µg/ml after the fourth injection (The IMpact RSV Study Group, 1998, Pediatrics 102:531-537). Serum concentrations of greater than 30 µg/ml have been shown to be necessary to reduce pulmonary RSV replication by 100 fold in the cotton rat model of RSV infection. However, the administration of multiple intramuscular doses of 15 mg/kg of antibody is inconvenient for the patient. Thus, a need exists for antibodies that immunospecifically bind to a RSV antigen, which are highly potent, have an improved pharmacokinetic profile, and thus have an overall improved therapeutic profile. Further, a need exists for antibodies that immunospecifically bind to a RSV antigen which require less frequent administration.

Citation or discussion of a reference herein shall not be construed as an admission that such is prior art to the present invention.

3. SUMMARY OF THE INVENTION

The present invention is based, in part, on the development of methods for achieving or inducing a prophylactically or therapeutically effective serum titer of an antibody or fragment thereof that immunospecifically binds to a respiratory syncytial virus (RSV) antigen in a mammal by passive immunization with such an antibody or fragment thereof, which methods require lower dosages and/or less frequent administration than previously known methods. The present invention is also based, in part, on the identification of antibodies with higher affinities for a RSV antigen which result in increased efficacy for prophylactic or therapeutic uses such that lower serum titers are prophylactically or therapeutically effective, thereby permitting administration of lower dosages and/or reduced frequency of administration.

The present invention provides methods of preventing, neutralizing, treating and ameliorating one or more symptoms associated with RSV infection in a subject comprising administering to said subject one or more antibodies or fragments thereof which immunospecifically bind to one or more RSV antigens with high affinity and/or high avidity. Because a lower serum titer of such antibodies or antibody fragments is therapeutically or prophylactically effective than the effective serum titer of known antibodies, lower doses of said antibodies or antibody fragments can be used to achieve a serum titer effective for the prevention, neutralization, treatment and the amelioration of symptoms associated with a RSV infection. The use of lower doses of antibodies or fragments thereof which immunospecifically bind to one or more RSV antigens reduces the likelihood of adverse effects. Further, the high affinity and/or high avidity of the antibodies of the invention or fragments thereof enable less frequent administration of said antibodies or antibody fragments than previously thought to be necessary for the prevention, neutralization, treatment or the amelioration of symptoms associated with a RSV infection.

The present invention also provides antibodies which immunospecifically bind to one or more RSV antigens and have increased in vivo half-lives relative to known antibodies such as, e.g., SYNAGIS®. In particular, the present invention encompasses antibodies which immunospecifically bind to one or more RSV antigens and have increased in vivo half-lives relative to known antibodies (e.g., SYNAGIS®), said increased half-lives resulting from one or more modifications (e.g., substitutions, deletions, or insertions) in amino acid residues identified to be involved in the interaction of the Fc domain of said antibodies and the FcRn receptor. The present invention also encompasses pegylated antibodies and fragments thereof which immunospecifically bind to one or more RSV antigens and have increased in vivo half-lives relative to known antibodies such as, e.g., SYNAGIS®. The increased in vivo half-lives of antibodies or fragments thereof which immunospecifically bind to one or more RSV antigens reduce the dosage and/or frequency of administration of said antibodies or fragments thereof to a subject.

The invention encompasses sustained release formulations for the administration of one or more antibodies or fragments thereof which immunospecifically bind to one or more RSV antigens to a subject. The sustained release formulations reduce the dosage and/or frequency of administration of said antibodies or antibody fragments to a subject. Further, the sustained release formulations may be administered to maintain a therapeutically or prophylactically effective serum titer which does not exceed a certain maximum serum titer for a certain period of time.

The present invention encompasses methods of delivering one or more antibodies or fragments thereof which immunospecifically bind to one or more RSV antigens directly to the site of RSV infection. In particular, the invention encompasses pulmonary delivery of one or more antibodies or fragments thereof which immunospecifically bind to one or more RSV antigens. The improved methods of delivering of one or more antibodies or fragments thereof which immunospecifically bind to one or more RSV antigens reduce the dosage and/or frequency of administration of said antibodies or antibody fragments to a subject.

The present invention provides antibodies or fragments thereof which immunospecifically bind to one or more RSV antigens and have an association rate constant or $k_{on}$ rate (antibody (Ab)+ antigen (Ag) $\xrightarrow{k_{on}}$ Ab-Ag) of at least $10^5$ $M^{-1}s^{-1}$, at least $5\times10^5$ $M^{-1}s^{-1}$, at least $10^6$ $M^{-1}s^{-1}$, at least $5\times10^6$ $M^{-1}s^{-1}$, at least $10^7$ $M^{-1}s^{-1}$, at least $5\times10^7$ $M^{-1}s^{-1}$, or at least $10^8$ $M^{-1}s^{-1}$. In particular, the present invention provides compositions for use in the prevention, treatment or amelioration of one or more symptoms associated with a RSV infection, said compositions comprising one or more antibodies or fragments thereof which immunospecifically bind to one or more RSV antigens and have an a $k_{on}$ rate of at least $10^5$ $M^{-1}s^{-1}$, at least $5\times10^5$ $M^{-1}s^{-1}$, at least $10^6$ $M^{-1}s^{-1}$, at least $5\times10^6$ $M^{-1}s^{-1}$, at least $10^7$ $M^{-1}s^{-1}$, at least $5\times10^7$ $M^{-1}s^{-1}$, or at least $10^8$ $M^{-1}s^{-1}$.

The present invention provides antibodies or fragments thereof which immunospecifically bind to one or more RSV antigens and have a $k_{off}$ rate (antibody (Ab)+antigen (Ag) $\xrightarrow{K_{off}}$ Ab-Ag) of less than $10^{-1}$ $s^{-1}$, less than $5\times10^{-1}$ $s^{-1}$, less than $10^{-2}$ $s^{-1}$, less than $5\times10^{-2}$ $s^{-1}$, less than $10^{-3}$ $s^{-1}$, less than $5\times10^{-3}$ $s^{-1}$, less than $10^{-4}$ $s^{-1}$, less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than $10^{-7}$ $s^{-1}$, less than $5\times10^{-7}$ $s^{-1}$, less than $10^{-8}$ $s^{-1}$, less than $5\times10^{-8}s^{-1}$, less than $10^{-9}$ $s^{-1}$, less than $5\times10^{-9}$ $s^{-1}$, or less than $10^{-10}$ $s^{-1}$. In particular, the present invention provides compositions for use in the prevention, treatment or amelioration of one or more symptoms associated with a RSV infection, said compositions comprising one or more antibodies or fragments thereof which immunospecifically bind to one or more RSV antigens and have a $k_{off}$ rate of less than $10^{-1}$ $s^{-1}$, less than $5\times10^{-1}$ $s^{-1}$, less than $10^{-2}$ $s^{-1}$, less than $5\times10^{-2}$ $s^{-1}$, less than $10^{-3}$ $s^{-1}$, less than $5\times10^{-3}$ $s^{-1}$, less than $10^{-4}$ $s^{-1}$, less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than $10^{-7}$ $s^{-1}$, less than $5\times10^{-7}$ $s^{-1}$, less than $10^{-8}$ $s^{-1}$, less than $5\times10^{-8}$ $s^{-1}$, less than $10^{-9}$ $s^{-1}$, less than $5\times10^{-9}$ $s^{-1}$, or less than $10^{-10}$ $s^{-1}$.

The present invention also provides antibodies or fragments thereof which immunospecifically bind to one or more RSV antigens and have an affinity constant or $K_a$ ($k_{on}/k_{off}$) of at least $10^2$ $M^{-1}$, at least $5\times10^2$ $M^{-1}$, at least $10^3$ $M^{-1}$, at least $5\times10^3$ $M^{-1}$, at least $10^4$ $M^{-1}$, at least $5\times10^4$ $M^{-1}$, at least $10^5$ $M^{-1}$, at least $5\times10^5$ $M^{-1}$, at least $10^6$ $M^{-1}$, at least $5\times10^6$ $M^{-1}$, at least $10^7$ $M^{-1}$, at least $5\times10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, at least $5\times10^{12}$ $M^{-1}$, at least $10^{13}$ $M^{-1}$, at least $5\times10^{13}$ $M^{-1}$, at least $10^{14}$ $M^{-1}$, at least $5\times10^{14}$ $M^{-1}$, at least $10^{15}$ $M^{-1}$, or at least $5\times10^{15}$ $M^{-1}$. In particular, the present invention provides compositions for use in the prevention, treatment or amelioration of one or more symptoms associated with a RSV infection, said compositions comprising one or more antibodies or fragments thereof which immunospecifically bind to one or more RSV antigens and have a $K_a$ of at least $10^2$ $M^{-1}$, at least $5\times10^2$ $M^{-1}$, at least $10^3$ $M^{-1}$, at least $5\times10^3$ $M^{-1}$, at least $10^4$ $M^{-1}$, at least $5\times10^4$ $M^{-1}$, at least $10^5$ $M^{-1}$, at least $5\times10^5$ $M^{-1}$, at least $10^6$ $M^{-1}$, at least $5\times10^6$ $M^{-1}$, at least $10^7$ $M^{-1}$, at least $5\times10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, at least $5\times10^{12}$ $M^{-1}$, at least $10^{13}$ $M^{-1}$, at least $5\times10^{13}$ $M^{-1}$, at least $10^{14}$ $M^{-1}$, at least $5\times10^{14}$ $M^{-1}$, at least $10^{15}$ $M^{-1}$, or at least $5\times10^{15}$ $M^{-1}$.

The present invention provides antibodies or fragments thereof which immunospecifically bind to one or more RSV antigens and have an apparent dissociation constant of less than 1.5 nmol/L, less than 1.25 nmol/L, less than 1 nmol/L, less than 0.95 nmol/L, less than 0.85 nmol/L, less than 0.75 nmol/L, less than 0.7 nmol/L, less than 0.65 nmol/L, or less than 5 nmol/L as determined by a sandwich ELISA. In particular, the present invention provides compositions for use in the prevention, treatment or amelioration of one or more symptoms associated with a RSV infection, said compositions comprising one or more antibodies or fragments thereof which immunospecifically bind to one or more RSV antigens and have an apparent dissociation constant of less than 1.5 nmol/L, less than 1.25 nmol/L, less than 1 nmol/L, less than 0.95 nmol/L, less than 0.85 nmol/L, less than 0.75 nmol/L, less than 0.7 nmol/L, less than 0.65 nmol/L, or less than 5 nmol/L as determined by a sandwich ELISA.

The present invention provides antibodies or fragments thereof which immuospecifically bind to one or more RSV antigens and have an apparent dissociation constant of less than 1.75 nmol/L, less than 1.5 nmol/L, less than 1.25 nmol/L, less than 1 nmol/L, less than 0.95 nmol/L, less than 0.85 nmol/L, less than 0.75 nmol/L, less than 0.7 nmol/L, less than 0.65 nmol/L, or less than 5 nmol/L as measured by surface plasmon resonance (SPR) using a BlAcore sensor. In particular, the present invention provides compositions for use in the prevention, treatment or amelioration of one or more symptoms associated with a RSV infection, said compositions comprising one or more antibodies or fragments thereof which immunospecifically bind to one or more RSV antigens and have an apparent dissociation constant of less than 1.75 nmol/L, less than 1.5 nmol/L, less than 1.25 mnol/L, less than 1 nmol/L, less than 0.95 nmol/L, less than 0.85 nmol/L, less than 0.75 nmol/L, less than 0.7 nmol/L, less than 0.65 nmol/L, or less than 5 nmol/L as measured by surface plasmon resonance (SPR) using a BlAcore sensor.

The present invention provides antibodies or fragments thereof which immunospecifically bind to one or more RSV antigens and have a median effective concentration ($EC_{50}$) of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay. In particular, the present invention provides compositions for use in the prevention, treatment or amelioration of one or more symptoms associated with a RSV infection, said compositions comprising one or more antibodies or fragments thereof which immunospecifically bind to one or more RSV antigens and have an $EC_{50}$ of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay.

The present invention also provides antibodies or fragments thereof comprising a VH domain having the amino acid sequence of any VH domain listed in Table 2 and compositions comprising said antibodies or antibody fragments for use in the prevention, treatment or amelioration of one or more symptoms associated with a RSV infection. The present invention also provides antibodies or fragments thereof comprising one or more VH complementarity determining regions (CDRs) having the amino acid sequence of one or more VH CDRs listed in Table 2 and/or Table 3 and compositions comprising said antibodies or antibody fragments for use in the prevention, treatment or amelioration of one or more symptoms associated with a RSV infection. The present invention also provides antibodies or fragments thereof comprising a VL domain having the amino acid sequence of any VL domain listed in Table 2. The present invention also provides antibodies or fragments thereof comprising one or more VL CDRs having the amino acid sequence of one or more VL CDRs listed in Table 2 and/or Table 3 and compositions comprising said antibodies or antibody fragments for use in the prevention, treatment or amelioration of one or more symptoms associated with a RSV infection. The present invention further provides antibodies comprising a VH domain and a VL domain having the amino acid sequence of any VH domain and VL domain listed in Table 2 and compositions comprising said antibodies or antibody fragments for use in the prevention, treatment or amelioration of one or more symptoms associated with a RSV infection. The present invention further provides antibodies comprising one or more VH CDRs and one or more VL CDRs having the amino acid sequence of one or more VH CDRs and one or more VL CDRs listed in Table 2 and/or 3 and compositions comprising said antibodies or antibody fragments for use in the prevention, treatment or amelioration of one or more symptoms associated with a RSV infection. In the above embodiments, preferably the antibody binds immunospecifically to a RSV antigen.

The present invention also encompasses methods for achieving a serum titer of at least 40 μg/ml of one or more antibodies or fragments thereof that immunospecifically bind to one or more RSV antigens in a mammal, preferably a primate and most preferably a human. In particular, the present invention provides methods for achieving a serum titer of at least 40 μg/ml (preferably at least 75 μg/ml, more preferably at least 100 μg/ml, and most preferably at least 150 μg/ml) of an antibody or fragment thereof that immunospecifically binds to a RSV antigen in a non-primate mammal, comprising administering a dose of less than 2.5 mg/kg (preferably 1.5 mg/kg or less) of the antibody or antibody fragment to the non-primate mammal and measuring the serum titer of the antibody or antibody fragment at least 1 day after administering the dose to the non-primate mammal. The present invention also provides methods for achieving a serum titer of at least 150 μg/ml (preferably at least 200 μg/ml) of an antibody or fragment thereof that immunospecifically binds to a RSV antigen in a non-primate mammal, comprising administering a dose of approximately 5 mg/kg of the antibody or antibody fragment to the non-primate mammal and measuring the serum titer of the antibody or antibody fragment at least 1 day after the administration of the dose to the non-primate mammal.

The present invention also provides methods for achieving a serum titer of at least 40 μg/ml of an antibody or fragment thereof that immunospecifically binds to a RSV antigen in a primate, comprising administering a first dose of 10 μg/kg (preferably 5 μg/kg or less and more preferably 1.5 μg/kg or less) of the antibody or antibody fragment to the primate and measuring the serum titer of the antibody or antibody fragment 20 days (preferably 25, 30, 35 or 40 days) after administrating the first dose to the primate and prior to the administration of any subsequent dose. The present invention also provides methods for achieving a serum titer of at least 75 μg/ml (preferably at least 100 μg/ml, at least 150 μg/ml, or at least 200 μg/ml) of an antibody or fragment thereof that immunospecifically binds to a RSV antigen in a primate, comprising administering a first dose of approximately 15 mg/kg of the antibody or antibody fragment to the primate and measuring the serum titer of the antibody or antibody fragment 20 days (preferably 25, 30, 35 or 40 days) after administering the first dose to the primate but prior to any subsequent dose.

The present invention provides methods for maintaining a serum titer of at least 30 μg/ml, preferably at least 40 μg/ml, at least 50 μg/ml, at least 75 μg/ml, at least 100 μg/ml, at least 125 μg/ml or at least 150 μg/ml of an antibody or a fragment thereof that immunospecifically binds to a RSV antigen in a mammal, preferably a primate, said methods comprising administering to said mammal a first dose of a prophylactically or therapeutically effective amount of said antibody or antibody fragment and administering to said mammal one or more subsequent doses of a prophylactically or therapeutically effective amount of said antibody or antibody fragment to maintain a serum titer of at least 30 [μg/ml, preferably at least 40 μg/ml, at least 50 μg/ml, at least 75 μg/ml, at least 100 μg/ml, at least 125 μg/ml or at least 150 μg/ml of said antibody or antibody fragment. In a specific embodiment, the invention provides a method for maintaining a serum titer of at least 30 μg/ml, preferably at least 40 μg/ml, at least 50 μg/ml, at least 75 μg/ml, at least 100 μg/ml, at least 125 μg/ml or at least 150 μg/ml of an antibody or a fragment thereof that immunospecifically binds to a RSV antigen in a mammal, preferably a primate, said methods comprising: (a) administering to said mammal a first dose of a prophylactically or therapeutically effective amount of said antibody or antibody fragment; (b) assessing the serum titer of said antibody or antibody fragment; and (c) administering to said mammal one or more subsequent doses of a prophylactically or therapeutically effective amount of said antibody or antibody fragment to maintain a serum titer of at least 30 μg/ml, preferably at least 40 μg/ml, at least 50 μg/ml, at least 75 μg/ml, at least 100 μg/ml, at least 125 μg/ml or at least 150 μg/ml of said antibody or antibody fragment. In accordance with this embodiment, the serum titer of said antibody or antibody fragment in said mammal can be determined by methods well known to one of skill in the art (e.g., immunoassays).

The present invention also provides methods for preventing, treating, or ameliorating one or more symptoms associated with a RSV infection in a human subject, said methods comprising administering to said human subject at least a first dose of approximately 15 mg/kg of an antibody or fragment thereof that immunospecifically binds to a RSV antigen so that said human subject has a serum antibody titer of at least 75 μg/ml, preferably at least 100 μg/ml, at least 150 μg/ml, or at least 200 μg/ml 30 days after the administration of the first dose of the antibody or antibody fragment and prior to the administration of a subsequent dose. The present invention also provides methods for preventing, treating or ameliorating one or more symptoms associated with a RSV infection in a human subject, said methods comprising administering to said human subject at least a first dose of less than 15 mg/kg (preferably 10 mg/kg or less, more preferably 5 mg/kg or less, and most preferably 1.5 mg/kg or less) of an antibody or fragment thereof that immunospecifically binds to a RSV antigen so that said human subject has a serum antibody titer of at least 75 μg/ml, preferably at least 100 μg/ml, at least 150 μg/ml, or at least 200 μg/ml 30 days after the administration of the first dose of the antibody or antibody fragment and prior to the administration of a subsequent dose. The present invention further provides methods for preventing, treating or ameliorating one or more symptoms associated with a RSV infection in a human subject, said methods comprising administering to said human subject a first dose of an antibody or fragment thereof that immunospecifically binds to a RSV antigen such that a prophylactically or therapeutically effective serum titer of less than 10 μg/ml is achieved no more than 30 days after administering the antibody or antibody fragment.

The present invention also provides methods for preventing, treating, or ameliorating one or more symptoms associated with a RSV infection in a mammalian subject, said methods comprising administering to said subject a first dose of a prophylactically or therapeutically effective amount of said antibody or antibody fragment and administering to said subject one or more subsequent doses of a prophylactically or therapeutically effective amount of said antibody or antibody fragment to maintain a serum titer of at least 30 μg/ml, preferably at least 40 μg/ml, at least 50 μg/ml, at least 75 μg/ml, at least 100 μg/ml, at least 125 μg/ml or at least 150 μg/ml of said antibody or antibody fragment. In a specific embodiment, the invention provides a method for preventing, treating, or ameliorating one or more symptoms associated with a RSV infection in a mammalian subject, said method comprising: (a) administering to said subject a first dose of a prophylactically or therapeutically effective amount of said antibody or antibody fragment; (b) assessing the serum titer of said antibody or antibody fragment; and (c) administering to said subject one or more subsequent doses of a prophylactically or therapeutically effective amount of said antibody or antibody fragment to maintain a serum titer of at least 30 μg/ml, preferably at least 40 μg/ml, at least 50 μg/ml, at least 75 μg/ml, at least 100 μg/ml, at least 125 μg/ml or at least 150 μg/ml of said antibody or antibody fragment. In accordance with this embodiment, the serum titer of said antibody or antibody fragment in said subject can be determined by methods well known to one of skill in the art (e.g., immunoassays).

The present invention provides methods for achieving a therapeutically or prophylactically effective serum titer in a mammal, said methods comprising administering to said mammal an antibody or fragment thereof which immunospecifically binds to a RSV antigen and which has a $k_{on}$ rate (antibody (Ab)+antigen (Ag) $\xrightarrow{k_{on}}$ Ab-Ag) of at least $2.5 \times 10^{-5} M^{-1} s^{-1}$, preferably at least $3 \times 10^5 M^{-1} s^{-1}$, at least $5 \times 10^5 M^{-1} s^{-1}$, at least $10^6 M^{-1} s^{-1}$, at least $5 \times 10^6 M^{-1} s^{-1}$, at least $10^7 M^{-1} s^{-1}$, at least $5 \times 10^7 M^{-1} s^{-1}$ or at least $10^8 M^{-1} s^{-1}$. In particular, the present invention provides methods for achieving a therapeutically or prophylactically effective serum titer, wherein said effective serum titer is less than 30 μg/ml (and is preferably at least 2 μg/ml, more preferably at least 4 μg/ml, and most preferably at least 6 μg/ml) after a certain number of days (for example, but not limited to, 20, 25, 30 or 35 days) without any other dosing within that period, comprising administering to a mammal an antibody or fragment thereof which immunospecifically binds to a RSV antigen and which has a $k_{on}$ rate of at least $2.5 \times 10^5 M^{-1} s^{-1}$, preferably at least $3 \times 10^5 M^{-1} s^{-1}$, at least $5 \times 10^5 M^{-1} s^{-1}$, at least $10^6 M^{-1} s^{-1}$, at least $5 \times 10^6 M^{-1} s^{-1}$, at least $10^7 M^{-1} s^{-1}$, at least $5 \times 10^7 M^{-1} s^{-1}$, or at least $10^8 M^{-1} s^{-1}$. Preferably, the antibody or antibody fragment has a higher $k_{on}$ rate than SYNAGIS®.

The present invention also provides methods of neutralizing RSV using an antibody or fragment thereof which immunospecifically bind to a RSV antigen and which has a $k_{on}$ rate of at least $2.5 \times 10^5 M^{-1} s^{-1}$, preferably at least $3 \times 10^5 M^{-1} s^{-1} s^{-1}$, at least $5 \times 10^5 M^{-1} s^{-1}$, at least $10^6 M^{-1} s^{-1}$, at least $5 \times 10^6 M^{-1} s^{-1}$, at least $10^7 M^{-1} s^{-1}$, at least $5 \times 10^7 M^{-1} s^{-1}$, or at least $10^8 M^{-1} s^{-1}$ to achieve a prophylactically or therapeutically effective serum titer, wherein said effective serum titer is less than 30 μg/ml (and is preferably at least 2 μg/ml, more preferably at least 4 μg/ml, and most preferably at least 6 μg/ml) 20, 25, 30, or 35 days after administration without any other dosage administration. Preferably, the antibody or antibody fragment has a higher $k_{on}$ rate than SYNAGIS®.

The present invention also provides methods for preventing, treating or ameliorating one or more symptoms associated with a RSV infection in a mammal, preferably a human, said methods comprising administering to said mammal, a dose of less than 15 mg/kg (preferably 5 mg/kg or less, more preferably 3 mg/kg or less, and most preferably 1.5 mg/kg or less) of an antibody or fragment thereof which immunospecifically binds to a RSV antigen and has a $k_{on}$ rate of at least $2.5 \times 10^5$ $M^{-1}s^{-1}$, preferably at least $3 \times 10^5$ $M^{-1}s^{-1}$, at least $5 \times 10^5$ $M^{-1}s^{-1}$, at least $10^6$ $M^{-1}s^{-1}$, at least $5 \times 10^6$ $M^{-1}s^{-1}$, at least $10^7$ $M^{-1}s^{-1}$, at least $5 \times 10^7$ $M^{-1}s^{-1}$, or at least $10^8$ $M^{-1}s^{-1}$. Preferably, the antibody or antibody fragment has a higher $k_{on}$ rate for the RSV F glycoprotein than SYNAGIS®.

The present invention also provides methods for achieving a therapeutically or prophylactically effective serum titer in a mammal, said methods comprising administering to said mammal an antibody or fragment thereof which immunospecifically binds to a RSV antigen and which has a $K_{off}$ rate (antibody (Ab)+antigen (Ag) $\xrightleftharpoons[]{K_{off}}$ Ab-Ag) of less than $6.5 \times 10^{-4}$ $sec^{-1}$, less than $5 \times 10^{-4}$ $sec^{-1}$, less than $3 \times 10^{-4}$ $sec^{-1}$, less than $2 \times 10^{-4}$ $sec^{-1}$, less than $1 \times 10^{-4}$ $sec^{-1}$, or less than $5 \times 10^{-3}$ $sec^{-1}$. In particular, the present invention provides methods for achieving a therapeutically or prophylactically effective serum titer, wherein said effective serum titer is less than 30 μg/ml (and is preferably at least 2 μg/ml, more preferably at least 4 μg/ml, and most preferably at least 6 μg/ml) after a certain number of days (for example, but not limited to, 20, 25, 30 or 35 days) without any other dosing within that period, comprising administering to a mammal an antibody or fragment thereof which immunospecifically binds to a RSV antigen and which has a $K_{off}$ rate of less than $6.5 \times 10^{-4}$ $sec^{-1}$, less than $5 \times 10^{-4}$ $sec^{-1}$, less than $3 \times 10^{-4}$ $sec^{-1}$, less than $2 \times 10^{-4}$ $sec^{-1}$, less than $1 \times 10^{-4}$ $sec^{-1}$, or less than $3 \times 10^{-3}$ $sec^{-1}$. Preferably, the antibody or fragment thereof has a lower $K_{off}$ rate than SYNAGIS®.

The present invention also provides methods of neutralizing RSV using an antibody or antibody fragment thereof which immunospecifically binds to a RSV antigen and which has a $K_{off}$ rate of less than $6.5 \times 10^{-4}$ $sec^{-1}$, less than $5 \times 10^{-4}$ $sec^{-1}$, less than $3 \times 10^{-4}$ $sec^{-1}$, less than $2 \times 10^{-4}$ $sec^{-1}$, less than $1 \times 10^{-4}$ $sec^{-1}$, or less than $5 \times 10^{-1}$ $sec^{-1}$ to achieve a prophylactically or therapeutically effective serum titer, wherein said effective serum titer is less than 30 μg/ml (and is preferably at least 2 μg/ml, more preferably at least 4 μg/ml, and most preferably at least 6 μg/ml) 20, 25, 30, or 35 days after administration without any other dosage administration. Preferably, the antibody or antibody fragment has a lower $K_{off}$ than SYNAGIS®.

The present invention also provides methods for preventing, treating, or ameliorating one or more symptoms associated with a RSV infection in a mammal, preferably a human, said methods comprising administering to a said mammal a dose of less than 15 mg/kg (preferably 5 mg/kg or less, more preferably 3 mg/kg or less, and most preferably 1.5 mg/kg or less) of an antibody or a fragment thereof which immunospecifically binds to a RSV antigen and which has a $K_{off}$ rate of less than $6.5 \times 10^{-4}$ $sec^{-1}$, less than $5 \times 10^{-4}$ $sec^{-1}$, less than $3 \times 10^{-4}$ $sec^{-1}$, less than $2 \times 10^{-4}$ $sec^{-1}$, less than $1 \times 10^{-4}$ $sec^{-1}$, or less than $5 \times 10^{-3}$ $sec^{-1}$. Preferably, the antibody or antibody fragment has a lower $K_{off}$ rate than SYNAGIS®.

The present invention also provides methods for achieving a therapeutically or prophylactically effective serum titer in a mammal, said methods comprising administering to said mammal an antibody or fragment thereof which immunospecifically binds to a RSV antigen and which has an $EC_{50}$ of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay. In particular, the present invention provides methods for achieving a therapeutically or prophylactically effective serum titer, wherein said effective serum titer is less than 30 μg/ml (and is preferably at least 2 μg/ml, more preferably at least 4 μg/ml, and most preferably at least 6 μg/ml) after a certain number of days (for example, but not limited to, 20, 25, 30 or 35 days) without any other dosing within that period, comprising administering to a mammal an antibody or fragment thereof which immunospecifically binds to a RSV antigen and which has an $EC_{50}$ of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay. Preferably, the antibody or antibody fragment has a lower $EC_{50}$ than SYNAGIS®.

The present invention also provides methods of neutralizing RSV using an antibody or fragment thereof which immunospecifically binds to a RSV antigen and which has an $EC_{50}$ of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay to achieve a prophylactically or therapeutically effective serum titer, wherein said effective serum titer is less than 30 μg/ml (and is preferably at least 2 μg/ml, more preferably at least 4 μg/ml, and most preferably at least 6 μg/ml) 20, 25, 30, or 35 days after administration without any other dosage administration. Preferably, the antibody or antibody fragment has a lower $EC_{50}$ than SYNAGIS®.

The present invention also provides methods for preventing, treating or ameliorating one or more symptoms associated with a RSV infection in a mammal, preferably a human, said methods comprising administering to said mammal a dose of less than 15 mg/kg (preferably 5 mg/kg or less, more preferably 3 mg/kg or less, and most preferably 1.5 mg/kg or less) of an antibody or a fragment thereof which immunospecifically binds to a RSV antigen and which has an $EC_{50}$ of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay. Preferably, the antibody or antibody fragment has a lower $EC_{50}$ than SYNAGIS®.

The present invention provides methods for achieving a therapeutically or prophylactically effective serum titer in a mammal, said methods comprising administering to said mammal an antibody or fragment thereof which immunospecifically binds to a RSV antigen and which has an affinity constant ($K_a$) for a RSV antigen of at least $2 \times 10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, at least $5 \times 10^{12}$ $M^{-1}$, at least $10^{13}$ $M^{-1}$, at least $5 \times 10^{13}$ $M^{-1}$, at least $10^{14}$ $M^{-1}$, at least $5 \times 10^{14}$ $M^{-1}$, at least $10^{15}$ $M^{-1}$, or at least $5 \times 10^{15}$ $M^{-1}$. In particular, the present invention also provides methods for achieving a therapeutically or prophylactically effective serum titer, wherein said effective serum titer is less than 30 μg/ml (and is preferably at least 2 μg/ml, more preferably at least 4 μg/ml, and most preferably at least 6 μg/ml) after a certain number of days (for example, but not limited to, 20, 25, 30 or 35 days) without any other dosing within that period, comprising administering to a mammal an antibody or fragment thereof that has an affinity constant ($K_a$) for a RSV antigen of at least $2 \times 10^8$ $M^{-1}$, at least $2.5 \times 10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, at least $5 \times 10^{12}$ $M^{-1}$, at least $10^{13}$ $M^{-1}$, at least $5 \times 10^{13}$ $M^{-1}$, at least $10^{14}$ $M^{-1}$, at least $5 \times 10^{14}$ $M^{-1}$, at least $10^{15}$ $M^{-1}$, or at least $5\times10^{15}$ M$^{-1}$. Preferably, the antibody or antibody fragment has a higher affinity for a RSV F glycoprotein than SYNAGIS®.

The present invention also provides methods of achieving a therapeutically or prophylactically effective serum titer, wherein said effective serum titer is less than 30 μg/ml (and is preferably at least 2 μg/ml, more preferably at least 4 μg/ml, and most preferably at least 6 μg/ml) after a certain number of days (for example, but not limited to, 20, 25, 30 or 35 days) without any other dosing within that period, comprising administering to a mammal an antibody or fragment thereof which immunospecifically binds to a RSV antigen with a higher avidity than known antibodies such as, e.g., SYNAGIS®.

The present invention also provides methods of neutralizing RSV using an antibody or fragment thereof that has an affinity constant ($K_a$) for a RSV antigen of at least $2\times10^8$ M$^{-1}$, at least $2.5\times10^8$ M$^{-1}$, at least $5\times10^8$ M$^{-1}$, at least $10^9$ M$^{-1}$, at least $5\times10^9$ M$^{-1}$, at least $10^{10}$ M$^{-1}$, at least $5\times10^{10}$ M$^{-1}$, at least $10^{11}$ M$^{-1}$, at least $5\times10^{11}$ M$^{-1}$, at least $10^{12}$ M$^{-1}$, at least $5\times10^{12}$ M$^{-1}$, at least $10^{13}$ M$^{-1}$, at least $5\times10^{13}$ M$^{-1}$, at least $10^{14}$ M$^{-1}$, at least $5\times10^{14}$ M$^{-1}$, at least $10^{15}$ M$^{-1}$, or at least $5\times10^{15}$ M$^{-1}$ to achieve a prophylactically or therapeutically effective serum titer, wherein said effective serum titer is less than 30 μg/ml (and is at least 2 μg/ml and more preferably at least 6 μg/ml) 20, 25, 30, or 35 days after administration without any other dosage administration. Preferably, the antibody or antibody fragment has a higher affinity for the RSV F glycoprotein than SYNAGIS®. The present invention also provides methods of neutralizing RSV using an antibody or fragment thereof that has a higher avidity than known antibodies such as, e.g., SYNAGIS®.

The present invention also provides methods for preventing, treating or ameliorating one or more symptoms associated with a RSV infection in a mammal, preferably a human, said methods comprising administering to said mammal a dose of less than 15 mg/kg (preferably 5 mg/kg or less, more preferably 3 mg/kg or less, and most preferably 1.5 mg/kg or less) of an antibody or fragment thereof that has an affinity constant ($K_a$) for a RSV antigen of at least $2\times10^8$ M$^{-1}$, at least $2.5\times10^8$ M$^{-1}$, at least $5\times10^8$ M$^{-1}$, at least $10^9$ M$^{-1}$, at least $5\times10^9$ M$^{-1}$, at least $10^{10}$ M$^{-1}$, at least $5\times10^{10}$ M$^{-1}$, at least $10^{11}$ M$^{-1}$, at least $5\times10^{11}$ M$^{-1}$, at least $10^{12}$ M$^{-1}$, at least $5\times10^{12}$ M$^{-1}$, at least $10^{13}$ M$^{-1}$, at least $5\times10^{13}$ M$^{-1}$, at least $10^{14}$ M$^{-1}$, at least $5\times10^{14}$ M$^{-1}$, at least $10^{15}$ M$^{-1}$, or at least $5\times10^{15}$ M$^{-1}$. Preferably, the antibody or antibody fragment has a higher affinity for the RSV F glycoprotein than SYNAGIS®.

The present invention also provides methods for preventing, treating or ameliorating one or more symptoms associated with a RSV infection in a mammal, preferably a human, said methods comprising administering to said mammal a first dose of less than 15 mg/kg (preferably 5 mg/kg or less, more preferably 3 mg/kg or less, and most preferably 1.5 mg/kg or less) of an antibody or fragment thereof that has a higher avidity than known antibodies such as, e.g., SYNAGIS®.

The present invention encompasses methods for preventing, treating or ameliorating one or more symptoms associated with a RSV infection in a mammal, preferably a human, comprising administering to said mammal a first dose of a prophylactically or therapeutically effective amount of one or more antibodies or fragments thereof that immunospecifically bind to one or more RSV antigens with higher avidity and/or higher affinity than known antibodies such as, e.g., SYNAGIS®, wherein said effective amount is less than 15 mg/kg (preferably 5 mg/kg or less, more preferably 3 mg/kg or less, and most preferably 1.5 mg/kg or less) of said antibodies or antibody fragments which dose results in a serum titer of less than 30 μg/ml (which is preferably at least 2 μg/ml, more preferably at least 4 μg/ml, and most preferably at least 6 μg/ml) at least 20 days (preferably at least 25, at least 30, or at least 35 days) after the administration of the first dose and prior to the administration of a subsequent dose. In particular, the present invention provides methods for preventing, treating, or ameliorating one or more symptoms associated with a RSV infection in a human subject, comprising administering to said human subject a first dose of less than 5 mg/kg (preferably 3 mg/kg or less, and most preferably 1.5 mg/kg) of an antibody or fragment thereof that immunospecifically binds to a RSV antigen with higher avidity and/or higher affinity than known antibodies such as, e.g., SYNAGIS® (e.g., an affinity of at least $2\times10^8$ M$^{-1}$, at least $2.5\times10^8$ M$^{-1}$, at least $5\times10^8$ M$^{-1}$, at least $10^9$ M$^{-1}$, at least $5\times10^9$ M$^{-1}$, at least $10^{10}$ M$^{-1}$, at least $5\times10^{10}$ M$^{-1}$, at least $10^{11}$ M$^{-1}$, at least $5\times10^{11}$ M$^{-1}$, at least $10^{12}$ M$^{-1}$, or at least $5\times10^{12}$ M$^{-1}$) so that said human subject has a serum antibody titer of less than 30 μg/ml (which is preferably at least 2 μg/ml, more preferably at least 4 μg/ml, and most preferably at least 6 μg/ml) at least 20 days (preferably at least 25, at least 30, or at least 35 days) after the administration of the first dose of the antibody or antibody fragment and prior to the administration of a subsequent dose.

The present invention also provides methods for preventing, treating or ameliorating one or more symptoms associated with a RSV infection in a mammal, said methods comprising administering to said mammal a first dose of one or more antibodies or fragments thereof comprising a VH domain having an amino acid sequence of any VH domain listed in Table 2 to achieve a therapeutically or prophylactically effective serum titer, wherein said effective serum titer is less than 30 μg/ml (and is preferably at least 2 μg/ml, more preferably at least 4 μg/ml, and most preferably at least 6 μg/ml) after a certain number of days (for example, but not limited to, 20, 25, 30 or 35 days) without any other dosing within that period. The present invention also provides methods for preventing, treating or ameliorating one or more symptoms associated with a RSV infection in a mammal, said methods comprising administering to said mammal a first dose of one or more antibodies or fragments thereof comprising one or more VH complementarity determining regions (CDRs) having the amino acid sequence of one or more VH CDRs listed in Table 2 and/or Table 3 to achieve a therapeutically or prophylactically effective serum titer, wherein said effective serum titer is less than 30 μg/ml (and is preferably at least 2 μg/ml, more preferably at least 4 μg/ml, and most preferably at least 6 μg/ml) after a certain number of days (for example, but not limited to, 20, 25, 30 or 35 days) without any other dosing within that period. Preferably, said antibodies or antibody fragments immunospecifically bind to a RSV antigen.

The present invention also provides methods for preventing, treating or ameliorating one or more symptoms associated with a RSV infection in a mammal, said methods comprising administering to said mammal a first dose of one or more antibodies or fragments thereof comprising a VL domain having the amino acid sequence of any VL domain listed in Table 2 to achieve a therapeutically or prophylactically effective serum titer, wherein said effective serum titer is less than 30 μg/ml (and is preferably at least 2 μg/ml, more preferably at least 4 μg/ml, and most preferably at least 6 μg/ml) after a certain number of days (for example, but not limited to, 20, 25, 30 or 35 days) without any other dosing within that period. The present invention also provides methods for preventing, treating or ameliorating one or more symptoms associated with a RSV infection in a mammal, said methods comprising administering to said mammal a first dose of one or more antibodies or fragments thereof comprising one or more VL CDRs having the amino acid sequence of one or more VL CDRs listed in Table 2 and/or Table 3 to achieve a therapeutically or prophylactically effective serum titer, wherein said effective serum titer is less than 30 µg/ml (and is preferably at least 2 µg/ml, more preferably at least 4 µg/ml, and most preferably at least 6 µg/ml) after a certain number of days (for example, but not limited to, 20, 25, 30 or 35 days) without any other dosing within that period. Preferably, said antibodies or antibody fragments immunospecifically bind to a RSV antigen.

The present invention also provides methods for preventing, treating or ameliorating one or more symptoms associated with a RSV infection in a mammal, said methods comprising administering to said mammal a first dose of one or more antibodies or fragments thereof comprising a VH domain and a VL domain having the amino acid sequence of any VH domain and VL domain listed in Table 2 to achieve a therapeutically or prophylactically effective serum titer, wherein said effective serum titer is less than 30 µg/ml (and is preferably at least 2 µg/ml, more preferably at least 4 µg/ml, and most preferably at least 6 µg/ml) after a certain number of days (for example, but not limited to, 20, 25, 30 or 35 days) without any other dosing within that period. The present invention also provides methods for preventing, treating or ameliorating one or more symptoms associated with a RSV infection in a mammal, said methods comprising administering to said mammal a first dose of one or more antibodies or fragments thereof comprising one or more VH CDRs and one or more VL CDRs having the amino acid sequence of one or more VH CDRs and one or more VL CDRs listed in Table 2 and/or 3 to achieve a therapeutically or prophylactically effective serum titer, wherein said effective serum titer is less than 30 µg/ml (and is preferably at least 2 µg/ml, more preferably at least 4 µg/ml, and most preferably at least 6 µg/ml) after a certain number of days (for example, but not limited to, 20, 25, 30 or 35 days) without any other dosing within that period. Preferably, said antibodies or antibody fragments immunospecifically bind to a RSV antigen.

In a specific embodiment, the present invention provides methods for preventing, treating or ameliorating one or more symptoms associated with a RSV infection in a mammal, said methods comprising administering to said mammal a first dose of one or more antibodies or fragments thereof comprising a VH domain having an amino acid sequence of SEQ ID NO:7, 9, 17, 24, 28, 33, 36, 40, 44, 48, 51, 67, or 78 and/or a VL domain having an amino acid sequence of SEQ ID NO:8, 11, 13, 21, 26, 30, 34, 38, 42, 46, 49, 52, 54, 56, 58, 60, 62, 64, 65, 68, 70, 71, 74 or 76 to achieve a therapeutically or prophylactically effective serum titer, wherein said effective serum titer is less than 30 µg/ml (and is preferably at least 2 µg/ml, more preferably at least 4 µg/ml, and most preferably at least 6 µg/ml) after a certain number of days (for example, but not limited to, 20, 25, 30 or 35 days) without any other dosing within that period. In a preferred embodiment, the present invention provides methods for preventing, treating or ameliorating one or more symptoms associated with a RSV infection in a mammal, said methods comprising administering to said mammal a first dose of one or more antibodies or fragments thereof comprising a VH domain having an amino acid sequence of SEQ ID NO:9, 17, 24, 28, 33, 36, 40, 44, 48, 51, 55, 67 or 78 and/or a VL domain having an amino acid sequence of SEQ ID NO:13, 21, 26, 30, 34, 38, 42, 46, 49, 52, 54, 56, 58, 60, 62, 64, 65, 68, 70, 71, 74 or 76 to achieve a therapeutically or prophylactically effective serum titer, wherein said effective serum titer is less than 30 µg/ml (and is preferably at least 2 µg/ml, more preferably at least 4 µg/ml, and most preferably at least 6 µg/ml) after a certain number of days (for example, but not limited to, 20, 25, 30 or 35 days) without any other dosing within that period. In another embodiment, the present invention provides methods for preventing, treating or ameliorating one or more symptoms associated with a RSV infection in a mammal, said methods comprising administering to said mammal a first dose of one or more antibodies or fragments thereof comprising a VH CDR3 having an amino acid sequence of SEQ ID NO:3, 12, 20, 29, or 79 and a VL CDR3 having an amino acid sequence of SEQ ID NO:6, 16 or 61 to a therapeutically or prophylactically effective serum titer, wherein said effective serum titer is less than 30 µg/ml (and is preferably at least 2 µg/ml, more preferably at least 4 µg/ml, and most preferably at least 6 µg/ml) after a certain number of days (for example, but not limited to, 20, 25, 30 or 35 days) without any other dosing within that period.

The present invention also provides compositions comprising one or more antibodies or fragments thereof which immunospecifically bind to one or more RSV antigens and which have increased in vivo half-lives compared to known anti-RSV antibodies as a result of, e.g., one or more modifications in amino acid residues identified to be involved in the interaction between the Fc domain of said antibodies or antibody fragments and the FcRn receptor. In one embodiment, a composition of the invention comprises HL-SYNAGIS or an antigen-binding fragment thereof. In another embodiment, a composition of the invention comprises one or more antibodies or fragments thereof which immunospecifically bind to one or more RSV antigens with a higher avidity and/or a higher affinity than known antibodies such as, e.g., SYNAGIS® (e.g., antibodies or antibody fragments with an affinity of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $5\times10^{12}$ $M^{-1}$ for a RSV antigen) and which comprise an Fc domain with increased affinity for the FcRn receptor relative to the Fc domain of SYNAGIS®. In accordance with this embodiment, the increased affinity of the Fc domain of said antibodies or antibody fragments results in an in vivo half-life of said antibodies or antibody fragments of at least 25 days, preferably at least 30 days, more preferably at least 30 days, and most preferably at least 40 days. In another embodiment, a composition of the invention comprises HL-SYNAGIS or an antigen-binding fragment thereof and one or more antibodies or fragments thereof which immunospecifically bind to one or more RSV antigens and which comprise an Fc domain with increased affinity for the FcRn receptor relative to the Fc domain of SYNAGIS®.

The present invention also provides compositions comprising one or more pegylated antibodies or fragments thereof which immunospecifically bind to one or more RSV antigens. In one embodiment, a composition of the invention comprises pegylated SYNAGIS® or a fragment thereof. In another embodiment, a composition of the invention comprises one or more pegylated antibodies or fragments thereof that immunospecifically bind to one or more RSV antigens with higher avidity and/or higher affinity than known antibodies such as, e.g., SYNAGIS®. In yet another embodiment, a composition of the invention comprises pegylated SYNAGIS® or an antigen-binding fragment thereof and one or more pegylated antibodies or fragments thereof that immunospecifically bind to one or more RSV antigens with higher avidity and/or higher affinity than known antibodies such as, e.g., SYNAGIS®.

The present invention also provides compositions comprising one or more pegylated antibodies or fragments thereof which comprise an Fc domain with increased affinity for the FcRn receptor relative to the Fc domain of SYNAGIS®. In one embodiment, a composition of the invention comprises a pegylated HL-SYNAGIS or an antigen-binding fragment thereof. In another embodiment, a composition of the invention comprises one or more pegylated antibodies or fragments thereof which immunospecifically bind to one or more RSV antigens with a higher avidity and/or a higher affinity than known such as, e.g., SYNAGIS® and which comprise an Fc domain with increased affinity for the FcRn receptor relative to the Fc domain of SYNAGIS®

The present invention encompasses methods for preventing, treating or ameliorating one or more symptoms associated with a RSV infection in a mammal, preferably a human, comprising administering to said mammal a first dose of a prophylactically or therapeutically effective amount of HL-SYNAGIS or an antigen-binding fragment thereof, wherein said effective amount is approximately 15 mg/kg of said antibodies or fragments thereof which dose results in a serum titer of at least 30 µg/ml at least 30 days after the administration of the first dose and prior to the administration of a subsequent dose. In particular, the present invention provides methods for preventing, treating or ameliorating one or more symptoms associated with a RSV infection in a human subject, comprising administering to said human subject a first dose of 15 mg/kg of HL-SYNAGIS or an antigen-binding fragment thereof so that said human subject has a serum antibody titer of at least 30 µg/ml at least 30 days after the administration of the first dose of the antibody or antibody fragment and prior to the administration of a subsequent dose.

The present invention also encompasses methods for preventing, treating or ameliorating one or more symptoms associated with a RSV infection in a mammal, preferably a human, comprising administering to said mammal a first dose of a prophylactically or therapeutically effective amount of one or more antibodies or fragments thereof which have increased in vivo half-lives and which immunospecifically bind to one or more RSV antigens with higher avidity and/or higher affinity than known antibodies such as, e.g., SYNAGIS® (e.g., antibodies or antibody fragments with an affinity of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $5\times10^{12}$ $M^{-1}$ for a RSV antigen), wherein said effective amount is less than 15 mg/kg (preferably 5 mg/kg or less, more preferably 3 mg/kg or less, and most preferably 1.5 mg/kg or less) of said antibodies or fragments thereof which dose results in a serum titer of less than 30 µg/ml (which is preferably at least 2 µg/ml, more preferably at least 4 µg/ml, and most preferably at least 6 µg/ml) at least 20 days (preferably at least 25, at least 30, or at least 35 days) after the administration of the first dose and prior to the administration of a subsequent dose. In particular, the present invention provides methods for preventing, treating or ameliorating one or more symptoms associated with a RSV infection in a human subject, comprising administering to said human subject a first dose of less than 5 mg/kg (preferably 1.5 mg/kg or less) of an antibody or a fragment thereof which has an increased in vivo half-life and which immunospecifically binds to a RSV antigen with higher avidity and/or higher affinity than known antibodies such as, e.g., SYNAGIS® (e.g., antibodies or antibody fragments with an affinity of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $5\times10^{12}$ $M^{-1}$ for a RSV antigen) so that said human subject has a serum antibody titer of less than 30 µg/ml (which is preferably at least 2 µg/ml, more preferably at least 4 µg/ml, and most preferably at least 6 µg/ml) at least 25 days (preferably at least 30, at least 35, or at least 40 days) after the administration of the first dose of the antibody or antibody fragment and prior to the administration of a subsequent dose.

The present invention provides sustained release formulations comprising one or more antibodies or fragments thereof that immunospecifically bind to one or more RSV antigens. In one embodiment, a sustained release formulation comprises SYNAGIS® or a fragment thereof. In another embodiment, a sustained release formulation comprises one or more antibodies or fragments thereof that immunospecifically bind to one or more RSV antigens with higher avidity and/or higher affinity than known antibodies such as, e.g., SYNAGIS® (e.g., antibodies or antibody fragments with an affinity of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $5\times10^{12}$ $M^{-1}$ for a RSV antigen). In another embodiment, a sustained release formulation comprises SYNAGIS® or an antigen-binding fragment thereof and one or more antibodies or fragments thereof that immunospecifically bind to one or more RSV antigens with higher avidity and/or higher affinity than known antibodies such as, e.g., SYNAGIS® (e.g., antibodies or antibody fragments with an affinity of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $5\times10^{12}$ $M^{-1}$, for a RSV antigen). In another embodiment, HL-SYNAGIS or an antigen-binding fragment thereof is formulated in as sustained release formulation. In yet another embodiment, antibodies or fragments thereof which have higher avidity and/or higher affinity for one or more RSV antigens than known antibodies such as, e.g., SYNAGIS® (e.g., antibodies or antibody fragments with an affinity of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $5\times10^{12}$ $M^{-1}$ for a RSV antigen) and which comprises an Fc domain with increased affinity for the FcRn receptor relative to the Fc domain of SYNAGIS® are formulated in sustained release formulations.

The present invention also provides methods for preventing, treating or ameliorating one or more symptoms associated with a RSV infection in a mammal, preferably a human, comprising administering to said mammal a first dose of a prophylactically or therapeutically effective amount of one or more antibodies or fragments thereof that immunospecifically bind to one or more RSV antigens in a sustained release formulation, wherein said effective amount is a dose of 15 mg/kg or less of said antibodies or fragments thereof, which dose, preferably results in a serum titer of at least 2 µg/ml (preferably at least 5 µg/ml, at least 10 µg/ml, at least 20 µg/ml, at least 30 µg/ml, or at least 40 µg/ml) for at least 20 days (preferably at least 25, 30, 35 or 40 days) after the administration of the first dose and prior to the administration of a subsequent dose.

In one embodiment, a mammal, preferably a human, is administered a first dose of a prophylactically or therapeutically effective amount of SYNAGIS® or an antigen-binding fragment thereof in a sustained release formulation, wherein said effective amount is a dose of approximately 15 µg/kg of SYNAGIS® or an antigen-binding fragment thereof which dose results in a serum titer of at least 20 μg/ml (preferably at least 30 μg/ml, more preferably at least 40 μg/ml, and most preferably at least 50 μg/ml) for at least 30 days (preferably at least 35 days, more preferably at least 40 days, and most preferably at least 45 days) after the administration of the first dose and prior to the administration of a subsequent dose. In a preferred embodiment, a mammal, preferably a human, is administered a first dose of a prophylactically or therapeutically effective amount of SYNAGIS® or an antigen-binding fragment thereof in a sustained release formulation, wherein said effective amount is a dose of 15 μg/kg or less of SYNAGIS® or an antigen-binding fragment thereof which dose results in a serum titer of 20 μg/ml (preferably at least 30 μg/ml, more preferably at least 40 μg/ml, and most preferably at least 50 μg/ml) at least 30 days (preferably at least 35 days, more preferably at least 40 days, and most preferably at least 45 days) after the administration of the first dose and prior to the administration of a subsequent dose.

In another embodiment, a mammal, preferably a human, is administered a first dose of a prophylactically or therapeutically effective amount of one or more antibodies or fragments thereof which immunospecifically bind to one or more RSV antigens with higher avidity and/or higher affinity than known antibodies such as, e.g., SYNAGIS® (e.g., antibodies or antibody fragments with an affinity of at least $2 \times 10^8$ $M^{-1}$, at least $2.5 \times 10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, or at least $5 \times 10^{12}$ $M^{-1}$ for a RSV antigen) in a sustained release formulation, wherein said effective amount is a dose of less than 15 mg/kg (preferably 5 mg/kg or less, more preferably 3 mg/kg or less, and most preferably 1.5 mg/kg or less) of said antibodies or antibody fragments which dose results in a serum titer of less than 30 μg/ml (which is preferably at least 2 μg/ml, more preferably at least 4 μg/ml, and most preferably at least 6 μg/ml) for at least 20 days (preferably at least 25, at least 30, at least 35, or at least 40 days) after the administration of the first dose and prior to the administration of a subsequent dose. In a preferred embodiment, a mammal, preferably a human, is administered a first dose of a prophylactically or therapeutically effective amount of one or more antibodies or fragments thereof which immunospecifically bind to one or more RSV antigens with higher avidity and/or higher affinity than known antibodies such as, e.g., SYNAGIS® (e.g., antibodies or antibody fragments with an affinity of at least $2 \times 10^8$ $M^{-1}$, at least $2.5 \times 10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, or at least $5 \times 10^{12}$ $M^{-1}$ for a RSV antigen) in a sustained release formulation, wherein said effective amount is a dose of less than 15 mg/kg of said antibodies or antibody fragments which dose results in a serum titer of 10 μg/ml for at least 20 days (preferably at least 25, at least 30, at least 35 or at least 40 days) after the administration of the first dose and prior to the administration of a subsequent dose. In accordance with this embodiment, the prophylactically or therapeutically effective amount of the dose of the antibodies or antibody fragments is approximately 0.5 mg/kg, preferably 1 mg/kg, 1.5 mg/kg, 3 mg/kg, 5 mg/kg, 7.5 mg/kg, 10 mg/kg, 12 mg/kg, or 14 mg/kg. In another preferred embodiment, a mammal, preferably a human, is administered a first dose of a prophylactically or therapeutically effective amount of one or more antibodies or fragments thereof which immunospecifically bind to one or more RSV antigens with higher avidity and/or higher affinity than known antibodies such as, e.g., SYNAGIS® (e.g., antibodies or antibody fragments with an affinity of at least $2 \times 10^8$ $M^{-1}$, at least $2.5 \times 10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, or at least $5 \times 10^{12}$ $M^{-1}$ for a RSV antigen) in a sustained release formulation, wherein said effective amount is a dose of 1.5 mg/kg of said antibodies or antibody fragments which dose results in a serum titer of 10 μg/ml for at least 20 days (preferably at least 25, at least 30, at least 35, or at least 40 days) after the administration of the first dose and prior to the administration of a subsequent dose.

Additionally, the present invention provides sustained release compositions comprising one or more antibodies or fragments thereof which immunospecifically bind to one or more RSV antigens, which sustained release compositions maintain a certain serum titer in a subject for a certain period of time without exceeding a particular serum titer. In one embodiment, a sustained release formulation comprising SYNAGIS® or an antigen-binding fragment thereof maintains a serum titer in a mammal, preferably a human, of approximately 25 μg/ml (preferably 30 μg/ml, more preferably 40 μg/ml, and most preferably 50 μg/ml) without exceeding a serum titer of approximately 100 μg/ml (preferably 75 μg/ml) for at least 20 days (preferably at least 25, 30, 35, or 40 days). In another embodiment, a sustained release formulation comprising one or more antibodies or fragments thereof which immunospecifically bind to one or more RSV antigens with a higher avidity and/or a higher affinity than previously known antibodies such as, e.g., SYNAGIS®, maintains a serum titer in a mammal, preferably a human, of approximately 2 μg/ml (preferably 6 μg/ml, 10 μg/ml, 20 μg/ml, or 30 μg/ml) without exceeding a serum titer of approximately 40 μg/ml (preferably 75 μg/ml) for at least 20 days (preferably at least 25, 30, 35, or 40 days).

The present invention encompasses methods of preventing, treating or ameliorating one or more symptoms of RSV infection in a mammal, preferably a human, by administering sustained release formulations of one or more antibodies or fragments thereof which immunospecifically bind to one or more RSV antigens and which have increased in vivo half-lives. In one embodiment, a sustained release formulation comprising HL-SYNAGIS or an antigen-binding fragment thereof is administered to a mammal, preferably a human, to prevent, treat, or ameliorate one or more symptoms associated with a RSV infection. In another embodiment, a sustained release formulation comprising one or more antibodies or fragments thereof which have higher avidity and/or higher affinity for one or more RSV antigens than known antibodies such as, e.g., SYNAGIS® (e.g., antibodies or antibody fragments with an affinity of at least $2 \times 10^8$ $M^{-1}$, at least $2.5 \times 10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, or at least $5 \times 10^{12}$ $M^{-1}$ for a RSV antigen) and which comprises an Fc domain with increased affinity for the FcRn receptor relative to the Fc domain of SYNAGIS® are administered to a mammal, preferably a human, to prevent, treat, or ameliorate one or more symptoms associated with a RSV infection.

The present invention also provides pulmonary delivery systems for administering one or more antibodies or fragments thereof which immunospecifically bind to one or more RSV antigens. In particular, the present invention provides compositions for pulmonary delivery, said compositions comprising one or more antibodies or fragments thereof which immunospecifically bind to one or more RSV antigens. SYNAGIS® or an antigen-binding fragment thereof can be incorporated into compositions for pulmonary delivery. HL-SYNAGIS or an antigen-binding fragment thereof can be incorporated into compositions for pulmonary delivery. One or more antibodies or fragments thereof that bind to one or more RSV antigens with higher affinity and/or higher avidity than known antibodies such as, e.g., SYNAGIS® (e.g., antibodies or antibody fragments with an affinity of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $5\times10^{12}$ $M^{-1}$ for a RSV antigen) can be incorporated into compositions for pulmonary delivery. Further, one or more antibodies or fragments thereof which bind to one or more RSV antigens with higher affinity and/or higher avidity than known antibodies such as, e.g., SYNAGIS® (e.g., antibodies or antibody fragments with an affinity of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ M $^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $5\times10^{12}$ $M^{-1}$ for a RSV antigen) and which comprise an Fc domain with increased affinity for the FcRn receptor relative to the Fc domain of SYNAGIS® can be incorporated into compositions for pulmonary delivery.

The present invention also provides methods for preventing, treating or ameliorating one or more symptoms associated with a RSV infection, said methods comprising administering to a mammal, preferably a human, a composition for pulmonary delivery comprising one or more antibodies or fragments thereof which immunospecifically bind to one or more RSV antigens. In particular, the present invention provides methods for preventing, treating or ameliorating one or more symptoms associated with a RSV infection, said methods comprising administering to a mammal, preferably a human, a composition for pulmonary delivery comprising SYNAGIS® or fragments thereof. The present invention also provides methods for preventing, treating or ameliorating one or more symptoms associated with a RSV infection, said methods comprising administering to a mammal, preferably a human, a composition for pulmonary delivery comprising one or more antibodies or fragments thereof which immunospecifically bind to one or more RSV antigens with higher affinity and/or higher avidity than known antibodies such as, e.g., SYNAGIS® (e.g., antibodies or antibody fragments having an affinity of at least $2\times10^8$ M $^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $5\times10^{12}$ $M^{-1}$ for one or more RSV antigens).

In one embodiment, a first dose of a prophylactically or therapeutically effective amount of a composition comprising SYNAGIS® or an antigen-binding fragment thereof is administered to the lungs of a mammal, preferably a human, and results in an antibody concentration of at least 20 ng per mg of lung protein (preferably at least 40 ng/mg, at least 60 ng/mg, at least 80 ng/mg, at least 50 ng/mg, at least 75 ng/mg, at least 100 ng/mg, or at least 150 ng/mg) at least 20 days (preferably at least 25, 30, 35 or 40 days) after the administration of the first dose and prior to the administration of a subsequent dose. Preferably, the prophylactically or therapeutically effective amount is a dose of approximately 0.01 mg/kg, (preferably at least 0.1 mg/kg, at least 1 mg/kg, at least 2 mg/kg, at least 4 mg/kg, at least 5 mg/kg or at least 10 mg/kg) of SYNAGIS® or an antigen-binding fragment thereof.

In another embodiment, a first dose of a prophylactically or therapeutically effective amount of a composition comprising one or more antibodies or fragments thereof which immunospecifically bind to one or more RSV antigens with higher affinity and/or higher avidity than known antibodies such as, e.g., SYNAGIS®, (e.g., antibodies or antibody fragments having an affinity of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $5\times10^{12}$ $M^{-1}$ for one or more RSV antigens) is administered to the lungs of a mammal, preferably a human and results in an antibody concentration of 20 ng per mg of lung protein (preferably at least 40 ng/mg, at least 60 ng/mg, at least 80 ng/mg, at least 50 ng/mg, at least 75 ng/mg, at least 100 ng/mg, or at least 150 ng/mg), at least 200 ng/mg, at least 250 ng/mg, at least 500 ng/mg, at least 750 ng/mg, at least 1 µg/mg, at least 2 µg/mg, at least 5 µg/mg, at least 10 µg/mg, at least 15 µg/mg, or at least 25 µg/mg) at least 20 days (preferably at least 25, 30, 35 or 40 days) at least 20 days (preferably at least 25, at least 30, at least 35 or at least 40 days after the administration of the first dose and prior to the administration of a subsequent dose. Preferably, the prophylactically effective amount is a dose of approximately 0.001 mg/kg, (preferably at least 0.005 mg/kg, at least 0.01 mg/kg, at least 0.05 mg/kg, at least 0.1 mg/kg, at least 1 mg/kg, at least 2 mg/kg, at least 4 mg/kg, at least 5 mg/kg or at least 10 mg/kg) of said antibodies or antibody fragments.

The present invention also provides detectable or diagnostic compositions comprising using antibodies or fragments thereof that immunospecifically bind to a RSV antigen, and methods for detecting or diagnosing a RSV infection utilizing said compositions.

The present invention provides peptides, polypeptides and/or proteins comprising variable and/or hypervariable regions of the antibodies of the invention. In a specific embodiment, the present invention provides peptides, polypeptides and/or proteins comprising a VH or VL domain of an antibody of the invention. In another embodiment, the present invention provides peptides, polypeptides and/or proteins comprising one or more CDRs having the amino acid sequence of any of the CDRs listed in Table 2 or Table 3.

The present invention further provides peptides, polypeptides and/or proteins comprising variable and/or hypervariable regions of the antibodies of the invention. In specific embodiment, the present invention provides compositions comprising one or more peptides, polypeptides and/or proteins comprising a VH or VL domain of antibody of the invention. In another embodiment, the present invention provides compositions comprising one or more peptides, polypeptides and/or proteins comprising one or more CDRs having the amino acid sequence of any one of the CDRs listed in Table 2 or Table 3.

3.1. Definitions

The term "analog" as used herein refers to a polypeptide that possesses a similar or identical function as a RSV polypeptide, a fragment of a RSV polypeptide, an antibody, or antibody fragment but does not necessarily comprise a similar or identical amino acid sequence of a RSV polypeptide, a fragment of a RSV polypeptide, an antibody, or antibody fragment, or possess a similar or identical structure of a RSV polypeptide, a fragment of a RSV polypeptide, an antibody, or antibody fragment. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a RSV polypeptide, a fragment of a RSV polypeptide, an antibody, or antibody fragment described herein; (b) a polypeptide encoded by a nucleotide sequence that hybridizes under stringent conditions to a nucleotide sequence encoding a RSV polypeptide, a fragment of a RSV polypeptide, an antibody, or antibody fragment described herein of at least 5 amino acid residues, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a RSV polypeptide, a fragment of a RSV polypeptide, an antibody, or antibody fragment described herein. A polypeptide with similar structure to a RSV polypeptide, a fragment of a RSV polypeptide, an antibody, or antibody fragment described herein refers to a polypeptide that has a similar secondary, tertiary or quaternary structure of a RSV polypeptide, a fragment of a RSV, an antibody, or antibody fragment described herein. The structure of a polypeptide can determined by methods known to those skilled in the art, including but not limited to, X-ray crystallography, nuclear magnetic resonance, and crystallographic electron microscopy.

The term "derivative" as used herein refers to a polypeptide that comprises an amino acid sequence of a RSV polypeptide, a fragment of a RSV polypeptide, an antibody that immunospecifically binds to a RSV polypeptide, or an antibody fragment that immunospecifically binds to a RSV polypeptide which has been altered by the introduction of amino acid residue substitutions, deletions or additions. The term "derivative" as used herein also refers to a RSV polypeptide, a fragment of a RSV polypeptide, an antibody that immunospecifically binds to a RSV polypeptide, or an antibody fragment that immunospecifically binds to a RSV polypeptide which has been modified, i.e, by the covalent attachment of any type of molecule to the polypeptide. For example, but not by way of limitation, a RSV polypeptide, a fragment of a RSV polypeptide, an antibody, or antibody fragment may be modified, e.g., by glycosylation, acetylation, pegylation, phosphorylation, amidation, derivatization by known protecting/blocking groups, proteolytic cleavage, linkage to a cellular ligand or other protein, etc. A derivative of a RSV polypeptide, a fragment of a RSV polypeptide, an antibody, or antibody fragment may be modified by chemical modifications using techniques known to those of skill in the art, including, but not limited to specific chemical cleavage, acetylation, formylation, metabolic synthesis of tunicamycin, etc. Further, a derivative of a RSV polypeptide, a fragment of a RSV polypeptide, an antibody, or antibody fragment may contain one or more non-classical amino acids. A polypeptide derivative possesses a similar or identical function as a RSV polypeptide, a fragment of a RSV polypeptide, an antibody, or antibody fragment described herein.

The term "effective neutralizing titer" as used herein refers to the amount of antibody which corresponds to the amount present in the serum of animals (human or cotton rat) that has been shown to be either clinically efficacious (in humans) or to reduce virus by 99% in, for example, cotton rats. The 99% reduction is defined by a specific challenge of, e.g., $10^3$ pfu, $10^4$ pfu, $10^5$ pfu, $10^6$ pfu, $10^7$ pfu, $10^8$ pfu, or $10^9$ pfu) of RSV.

The term "epitopes" as used herein refers to portions of a RSV polypeptide having antigenic or immunogenic activity in an animal, preferably a mammal, and most preferably in a human. An epitope having immunogenic activity is a portion of a RSV polypeptide that elicits an antibody response in an animal. An eptiope having antigenic activity is a portion of a RSV polypeptide to which an antibody immunospecifically binds as determined by any method well known in the art, for example, by the immunoassays described herein. Antigenic epitopes need not necessarily be immunogenic.

The term "fragment" as used herein refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of a RSV polypeptide or an antibody that immunospecifically binds to a RSV polypeptide. In certain embodiments, a fragment refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, or at least 50 contiguous amino acid residues of a RSV F glycoprotein. In other embodiments, a fragment refers to a peptide or polypeptide comprising an amino acid of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, or at least 50 contiguous amino acid residues of a VH and/or VL domain of an antibody that immunospecifically binds to a RSV polypeptide. Preferably, a fragment of a RSV polypeptide or a fragment of an antibody that immunospecifically binds to a RSV polypeptide retains at least one function of said RSV polypeptide or antibody.

The term "human infant" as used herein refers to a human 24 months, preferably less than 24 months, less than 16 months, less than 12 months, less than 6 months, less than 3 months, less than 2 months, or less than 1 month of age.

The term "human infant born prematurely" as used herein refers to a human born at less than 40 weeks gestational age, preferably less than 35 weeks gestational age, who is less than 6 months old, preferably less than 3 months old, more preferably less than 2 months old, and most preferably less than 1 month old.

An "isolated" or "purified" antibody or fragment thereof is substantially free of cellular material or other contaminating proteins from the cell or tissue source from which the protein is derived, or substantially free of chemical precursors or other chemicals when chemically synthesized. The language "substantially free of cellular material" includes preparations of an antibody or antibody fragment in which the antibody or antibody fragment is separated from cellular components of the cells from which it is isolated or recombinantly produced. Thus, an antibody or antibody fragment that is substantially free of cellular material includes preparations of antibody or antibody fragment having less than about 30%, 20%, 10%, or 5% (by dry weight) of heterologous protein (also referred to herein as a "contaminating protein"). When the antibody or antibody fragment is recombinantly produced, it is also preferably substantially free of culture medium, i.e., culture medium represents less than about 20%, 10%, or 5% of the volume of the protein preparation. When the antibody or antibody fragment is produced by chemical synthesis, it is preferably substantially free of chemical precursors or other chemicals, i.e., it is separated from chemical precursors or other chemicals which are involved in the synthesis of the protein. Accordingly such preparations of the antibody or antibody fragment have less than about 30%, 20%, 10%, 5% (by dry weight) of chemical precursors or compounds other than the antibody or antibody fragment of interest. In a preferred embodiment, antibodies of the invention or fragments thereof are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a preferred embodiment, nucleic acid molecules encoding antibodies of the invention or fragments thereof are isolated or purified.

The term "fusion protein" as used herein refers to a peptide, polypeptide or protein that comprises an amino acid sequence of an antibody or fragment thereof that immunospecifically binds to a RSV antigen and an amino acid sequence of a heterologous peptide, polypeptide or protein (e.g., a non-anti-RSV antigen antibody). In certain embodiments, a fusion protein retains the ability to immunospecifically bind to an RSV antigen. In other embodiments, a fusion protein does not retain the ability to immunospecifically bind to a RSV antigen.

The term "high potency" as used herein refers to antibodies or fragments thereof that exhibit high potency as determined in various assays for biological activity (e.g., neutralization of RSV) such as those described herein. For example, high potency antibodies of the present invention or fragments thereof have an $EC_{50}$ value less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM as measured by a microneutralization assay described herein. Further, high potency antibodies of the present invention or fragments thereof result in at least a 75%, preferably at least a 95% and more preferably a 99% lower RSV titer in a cotton rat 5 days after challenge with $10^5$ pfu relative to a cotton rat not administered said antibodies or antibody fragments. In certain embodiments of the invention, high potency antibodies of the present invention or fragments thereof exhibit a high affinity and/or high avidity for one or more RSV antigens (e.g., antibodies or antibody fragments having an affinity of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ M-1, or at least $5\times10^{12}$ $M^{-1}$ for one or more RSV antigens).

The term "host" as used herein refers to a mammal, preferably a human.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "patient" as used herein refers to a mammal (e.g., a horse, cow, pig, dog or cat), preferably a primate, and most preferably a human.

The phrases "a peptide, polypeptide or protein comprising a variable or hypervariable region of an antibody of the invention", "a peptide, polypeptide or protein comprising a VH or VL domain of an antibody of the invention", "a peptide, polypeptide or protein comprising one or more CDRs having an amino acid sequence of one or more of the CDRs listed in Table 2 or Table 3", and analogous phrases as used herein refer to fusion proteins.

In certain embodiments of the invention, a "prophylactically effective serum titer" is the serum titer in a mammal, preferably a human, that reduces the incidence of a RSV infection in said mammal. Preferably, the prophylactically effective serum titer reduces the incidence of RSV infections in humans with the greatest probability of complications resulting from RSV infection (e.g., a human with cystic fibrosis, chronic lung disease (e.g,. bronchopulmonary dysplasia), congenital heart disease, congenital immunodeficiency or acquired immunodeficiency, a human who has had a bone marrow transplant, a human who has had a stem cell transplant, a human infant, or an elderly human). In certain other embodiments of the invention, a "prophylactically effective serum titer" is the serum titer in a cotton rat that results in a RSV titer 5 days after challenge with $10^5$ pfu that is 99% lower than the RSV titer 5 days after challenge with $10^5$ pfu of RSV in a cotton rat not administered an antibody or antibody fragment that immunospecifically binds to a RSV antigen.

In certain embodiments of the invention, a "therapeutically effective serum titer" is the serum titer in a mammal, preferably a human, that reduces the severity, the duration and/or the symptoms associated with a RSV infection in said mammal. Preferably, the therapeutically effective serum titer reduces the severity, the duration and/or the number symptoms associated with RSV infections in humans with the greatest probability of complications resulting from a RSV infection (e.g., a human with cystic fibrosis, chronic lung disease (e.g,. bronchopulmonary dysplasia), congenital heart disease, congenital immunodeficiency or acquired immunodeficiency, a human who has had a bone marrow transplant, a human who has had a stem cell transplant, a human infant, or an elderly human). In certain other embodiments of the invention, a "therapeutically effective serum titer" is the serum titer in a cotton rat that results in a RSV titer 5 days after challenge with $10^5$ pfu that is 99% lower than the RSV titer 5 days after challenge with $10^5$ pfu of RSV in a cotton rat not administered an antibody or antibody fragment that immunospecifically binds to a RSV antigen.

As used herein, "HL-SYNAGIS" is SYNAGIS® with one or more modifications in amino acid residues identified to be involved in the interaction between the Fc domain of SYNAGIS® and the FcRn receptor which results in an increase in the in vivo half-life of SYNAGIS® to greater than 21 days. An antigen-binding fragment of HL-SYNAGIS is a fragment of SYNAGIS® which immunospecifically binds to RSV F glycoprotein and has one or more modifications in amino acid residues identified to be involved in the interaction between the Fc domain of SYNAGIS® and the FcRn receptor, wherein said modifications result in an increase in the in vivo half-life of the antigen-binding fragment. In accordance with the invention, HL-SYNAGIS or an antigen-binding fragment thereof has an in vivo half-life of at least 25 days, preferably at least 30 days, more preferably at least 35 days, and most preferably at least 40 days.

The term "RSV antigen" refers to a RSV polypeptide or fragment thereof to which an antibody or antibody fragment immunospecifically binds. An RSV antigen also refers to an analog or derivative of a RSV polypeptide or fragment thereof to which an antibody or antibody fragment immunospecifically binds. In a preferred embodiment, a RSV antigen is a RSV F glycoprotein, a fragment, an analog or a derivative thereof to which an antibody or antibody fragment immunospecifically binds.

The term "serum titer" as used herein refers to an average serum titer in a population of least 10, preferably at least 20, and most preferably at least 40 subjects.

The term "antibodies or fragments that immunospecifically bind to a RSV antigen" as used herein refers to antibodies or fragments thereof that specifically bind to a RSV polypeptide or a fragment of a RSV polypeptide and do not non-specifically bind to other polypeptides. Antibodies or fragments that immunospecifically bind to a RSV polypeptide or fragment thereof may have cross-reactivity with other antigens. Preferably, antibodies or fragments that immunospecifically bind to a RSV polypeptide or fragment thereof do not cross-react with other antigens. Antibodies or fragments that immunospecifically bind to a RSV polypeptide can be identified, for example, by immunoassays or other techniques known to those of skill in the art.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions x 100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., http://www.ncbi.nlm.nih.gov). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

4. DESCRIPTION OF THE FIGURES.

FIGS. 1A-1B show the amino acid sequences of the (A) light chain variable region (SEQ ID NO:260) and (B) heavy chain variable region (SEQ ID NO:261) of a high affinity monoclonal antibody that binds to a RSV antigen the potency of which can be increased by methods described herein or in Applicants' copending applications Ser. Nos. 60/168,426 and 60/186,252. For reference purposes, this is the amino acid sequence of the SYNAGIS® antibody disclosed in Johnson et al, 1997, J. Infect. Dis. 176:1215-1224 and U.S. Pat. No. 5,824,307. Here, the CDR regions are underlined while non-underlined residues form the framework regions of the variable regions of each antibody. In this antibody, the CDRs are derived from a mouse antibody while the framework regions are derived from a human antibody. The constant regions (not shown) are also derived from a human antibody.

FIGS. 2A-2B show the (A) light chain variable region (SEQ ID NO:262) and (B) heavy light chain variable region (SEQ ID NO:263) for an antibody sequence. CDR regions are underlined. This sequence differs from the sequence disclosed in FIGS. 1A-1B in the first 4 residues of VH CDR1, residue 103 of the light chain and residue 112 of the heavy chain.

5. DETAILED DESCRIPTION OF THE INVENTION

The present invention provides methods of preventing, neutralizing, treating and ameliorating one or more symptoms associated with a RSV infection in a subject comprising administering to said subject one or more antibodies which immunospecifically bind to one or more RSV antigens with high affinity and/or high avidity and/or have a longer serum half-life. The high affinity and/or high avidity of the antibodies of the invention enable the use of lower doses of said antibodies than previously thought to be effective for the prevention, neutralization, treatment and the amelioration of symptoms associated with RSV infection. The use of lower doses of antibodies which immunospecifically bind to one or more RSV antigens reduces the likelihood of adverse effects, as well as providing a more effective prophylaxis. Further, the high affinity and/or high avidity of the antibodies of the invention enable less frequent administration of said antibodies than previously thought to be necessary for the prevention, neutralization, treatment and the amelioration of symptoms associated with RSV infection.

The present invention also provides methods of preventing, neutralizing, treating and ameliorating one or more symptoms associated with a RSV infection in a subject comprising administering to said subject one or more antibodies which immunospecifically bind to one or more RSV antigens, said antibodies having a longer half-life than other previously known antibodies.

The present invention also provides improved methods of administering one or more antibodies which immunospecifically bind to one or more RSV antigens to a subject, said methods enable lower doses of said antibodies to be administered to the subject while achieving serum titers effective for the prevention, neutralization, treatment and amelioration of one or more symptoms associated with RSV infection. The present invention encompasses methods of delivering one or more antibodies which immunospecifically bind to one or more RSV antigens directly to the site of RSV infection. In particular, the invention encompasses pulmonary delivery of one or more antibodies which immunospecifically bind to one or more RSV antigens. The improved methods of delivering of one or more antibodies which immunospecifically bind to one or more RSV antigens reduces the dosage and frequency of administration of said antibodies to a subject.

The present invention is based, in part, upon achieving or inducing a serum titer of 1 µg/ml or less, preferably 2 µg/ml or less, 5 µg/ml or less, 6 µg/ml or less, 10 µg/ml or less, 15 µg/ml or less, 20 µg/ml or less, or 25 µg/ml or less of an antibody or fragment thereof that immunospecifically binds to a respiratory syncytial virus (RSV) antigen in a mammal with higher affinity and/or higher avidity than previously known antibodies, while reducing or avoiding adverse affects. Preferably a serum titer or serum titer of 1 µg/ml or less, preferably 2 µg/ml or less, 5 µg/ml or less, 6 µg/ml or less, 10 µg/ml or less, 15 µg/ml or less, 20 µg/ml or less, or 25 µg/ml or less is achieved approximately 20 days (preferably 25, 30, 35 or 40 days) after administration of a first dose of antibodies or fragments thereof which immunospecifically bind to a RSV antigen and without administration of any other doses of said antibodies or fragments thereof.

The present invention provides methods of achieving or inducing a serum titer of at least 30 µg/ml, at least 40 µg/ml, at least 50 µg/ml, at least 75 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml of an antibody or fragment thereof that immunospecifically binds to a respiratory syncytial virus (RSV) antigen in a mammal, while reducing or avoiding adverse affects. Preferably a serum titer or serum titer of at least 30 µg/ml, preferably at least 40 µg/ml, at least 50 µg/ml, at least 75 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml is achieved approximately 30 days after administration of a first dose of antibodies or fragments thereof which immunospecifically bind to a RSV antigen and without administration of any other doses of said antibodies or fragments thereof.

In a specific embodiment, a serum titer in a non-primate mammal of at least 40 µg/ml, preferably at least 80 µg/ml, at least 100 µg/ml, at least 120 µg/ml, at least 150 µg/ml, at least 200 µg/ml, at least 250 µg/ml, or at least 300 µg/ml, of one or more antibodies or fragments thereof that immunospecifically bind to one or more RSV antigens is achieved at least 1 day after administering a dose of less than 2.5 mg/kg, preferably less than 1 mg/kg, or less than 0.5 mg/kg of the antibodies or antibody fragments to the non-primate mammal. In another embodiment, a serum titer in a non-primate mammal of at least 150 µg/ml, preferably at least 200 µg/ml, at least 250 µg/ml, at least 300 µg/ml, at least 350 µg/ml, or at least 400 µg/ml of one or more antibodies or fragments thereof that immunospecifically bind to one or more RSV antigens is achieved at least 1 day after administering a dose of approximately 5 mg/kg of the antibodies or antibody fragments to the non-primate mammal.

In another embodiment, a serum titer in a primate of at least 40 µg/ml, preferably at least 80 µg/ml, at least 100 µg/ml, at least 120 µg/ml, at least 150 µg/ml, at least 200 µg/ml, at least 250 µg/ml, or at least 300 µg/ml of one or more antibodies or fragments thereof that immunospecifically bind to one or more RSV antigens is achieved at least 30 days after administering a first dose of less than 5 mg/kg, preferably less than 3 mg/kg, less than 1 mg/kg, or less than 0.5 mg/kg of the antibodies or fragments thereof to the primate. In yet another embodiment, a serum titer in a primate of at least 200 µg/ml, at least 250 µg/ml, at least 300 µg/ml, at least 350 µg/ml, or at least 400 µg/ml of one or more antibodies or fragments thereof that immunospecifically bind to one or more RSV antigens is achieved at least 30 days after administering a first dose of approximately 15 mg/kg of the antibodies or fragments thereof to the primate. In accordance with these embodiments, the primate is preferably a human.

The present invention provides methods for maintaining a serum titer of at least 30 µg/ml, preferably at least 40 µg/ml, at least 50 µg/ml, at least 75 µg/ml, at least 100 µg/ml, at least 125 µg/ml or at least 150 µg/ml of an antibody or a fragment thereof that immunospecifically binds to a RSV antigen in a mammal, preferably a primate, said methods comprising administering to said mammal a first dose of a prophylactically or therapeutically effective amount of said antibody or antibody fragment and administering to said mammal one or more subsequent doses of a prophylactically or therapeutically effective amount of said antibody or antibody fragment to maintain a serum titer of at least 30 µg/ml, preferably at least 40 µg/ml, at least 50 µg/ml, at least 75 µg/ml, at least 100 µg/ml, at least 125 µg/ml or at least 150 µg/ml of said antibody or antibody fragment. In a specific embodiment, the invention provides a method for maintaining a serum titer of at least 30 µg/ml, preferably at least 40 µg/ml, at least 50 µg/ml, at least 75 µg/ml, at least 100 µg/ml, at least 125 µg/ml or at least 150 µg/ml of an antibody or a fragment thereof that immunospecifically binds to a RSV antigen in a mammal, preferably a primate, said method comprising: (a) administering to said mammal a first dose of a prophylactically or therapeutically effective amount of said antibody or antibody fragment; (b) assessing the serum titer of said antibody or antibody fragment; and (c) administering to said mammal one or more subsequent doses of a prophylactically or therapeutically effective amount of said antibody or antibody fragment to maintain a serum titer of at least 30 µg/ml, preferably at least 40 µg/ml, at least 50 µg/ml, at least 75 µg/ml, at least 100 µg/ml, at least 125 µg/ml or at least 150 µg/ml of said antibody or antibody fragment. In accordance with this embodiment, the serum titer of said antibody or antibody fragment in said mammal can be determined by methods well known to one of skill in the art or described herein (e.g., immunoassays).

The present invention provides methods for preventing, treating, or ameliorating one or more symptoms associated with a RSV infection in a mammal, preferably a human, said methods comprising administering a first dose to said mammal of a prophylactically or therapeutically effective amount of one or more antibodies or fragments thereof that immunospecifically bind to one or more RSV antigens, wherein said effective amount is less than 15 mg/kg of said antibodies or fragments thereof and which results in a serum titer of greater than 40 µg/ml 30 days after the first administration and prior to any subsequent administration. In one embodiment, RSV infection in a human subject is prevented or treated, or one or more symptoms associated with RSV infection is ameliorated by administering a first dose of less than 10 mg/kg, preferably less than 5 mg/kg, less than 3 mg/kg, or less than 1 mg/kg of one or more antibodies or fragments thereof that immunospecifically bind to one or more RSV antigens so that a serum antibody titer of at least 40 µg/ml, preferably at least 80 µg/ml, or at least 120 µg/ml, at least 150 µg/ml, at least 200 µg/ml, at least 250 µg/ml, or at least 300 µg/ml is achieved 30 days after the administration of the first dose of the antibodies or antibody fragments and prior to the administration of a subsequent dose. In another embodiment, RSV infection in a human subject is prevented or treated, or one or more symptoms associated with a RSV infection is ameliorated by administering a first dose of approximately 15 mg/kg of one or more antibodies or fragments thereof that immunospecifically bind to one or more RSV antigens so that a serum antibody titer of at least 75 µg/ml, preferably at least 100 µg/ml, at least 200 µg/ml, at least 250 µg/ml, at least 300 µg/ml, at least 350 µg/ml, or at least 400 µg/ml is achieved 30 days after the administration of the first dose of the antibodies or antibody fragments and prior to the administration of a subsequent dose. In yet another embodiment, RSV infection in a human subject is prevented or treated, or one or more symptoms associated with a RSV infection is ameliorated by administering a first dose of one or more antibodies or fragments thereof that immunospecifically bind to one or more RSV antigens such that a prophylactically or therapeutically effective serum titer of less than 10 µg/ml, preferably less than 5 µg/ml, less than 3 µg/ml, less than 1 µg/ml, or less than 0.5 µg/ml is achieved no more than 30 days after administering the antibodies or antibody fragments. In accordance with this embodiment, the first dose of one or more antibodies or fragments thereof is less than 10 mg/kg, preferably less than 5 mg/kg, less than 1 mg/kg, or less than 0.5 mg/kg.

The present invention also provides methods for preventing, treating, or ameliorating one or more symptoms associated with a RSV infection in a mammalian subject (preferably, a human subject), said methods comprising administering to said subject a first dose of a prophylactically or therapeutically effective amount of said antibody or antibody fragment and administering to said subject one or more subsequent doses of a prophylactically or therapeutically effective amount of said antibody or antibody fragment to maintain a serum titer of at least 30 µg/ml, preferably at least 40 µg/ml, at least 50 µg/ml, at least 75 µg/ml, at least 100 µg/ml, at least 125 µg/ml or at least 150 µg/ml of said antibody or antibody fragment. In a specific embodiment, the invention provides a method for preventing, treating, or ameliorating one or more symptoms associated with a RSV infection in a mammalian subject (preferably a human subject), said method comprising: (a) administering to said subject a first dose of a prophylactically or therapeutically effective amount of said antibody or antibody fragment; (b) assessing the serum titer of said antibody or antibody fragment; and (c) administering to said subject one or more subsequent doses of a prophylactically or therapeutically effective amount of said antibody or antibody fragment to maintain a serum titer of at least 30 µg/ml, preferably at least 40 µg/ml, at least 50 µg/ml, at least 75 µg/ml, at least 100 µg/ml, at least 125 µg/ml or at least 150 µg/ml of said antibody or antibody fragment. In accordance with this embodiment, the serum titer of said antibody or antibody fragment in said subject can be determined by methods well known to one of skill in the art or described herein (e.g., immunoassays).

The present invention provides antibodies or fragments thereof which immunospecifically bind to a RSV antigen with an affinity constant of at least $2\times10^8$ M$^{-1}$, at least $2.5\times10^8$ M$^{-1}$, at least $5\times10^8$ M$^{-1}$, at least $10^9$ M$^{-1}$, at least $5\times10^9$ M$^{-1}$, at least $10^{10}$ M$^{-1}$, at least $5\times10^{10}$ M$^{-1}$, at least $10^{11}$ M$^{-1}$, at least $5\times10^{11}$ M$^{-1}$, at least $10^{12}$ M$^{-1}$, at least $5\times10^{12}$ M$^{-1}$, at least $10^{13}$ M$^{-1}$, at least $5\times10^{13}$ M$^{-1}$, at least $10^{14}$ M$^{-1}$, at least $5\times10^{14}$ M$^{-1}$, at least $10^{15}$ M$^{-1}$, or at least $5\times10^{15}$ M$^{-1}$. Preferably, the antibodies or antibody fragments have a higher affinity for a RSV antigen than SYNAGIS® does for the RSV F glycoprotein. The present invention also provides pharmaceutical compositions comprising one or more antibodies which immunospecifically bind to a RSV antigen with an affinity constant of at least $2\times10^8$ M$^{-1}$, at least $2.5\times10^8$ M$^{-1}$, at least $5\times10^8$ M$^{-1}$, at least $10^9$ M$^{-1}$, at least $5\times10^9$ M$^{-1}$, at least $10^{10}$ M$^{-1}$, at least $5\times10^{10}$ M$^{-1}$, at least $10^{11}$ M$^{-1}$, at least $5\times10^{11}$ M$^{-1}$, at least $10^{12}$ M$^{-1}$, at least $5\times10^{12}$ M$^{-1}$, at least $10^{13}$ M$^{-1}$, at least $5\times10^{13}$ M$^{-1}$, at least $10^{14}$ M$^{-1}$, at least $5\times10^{14}$ M$^{-1}$, at least $10^{15}$ M$^{-1}$, or at least $5\times10^{15}$ M$^{-1}$.

The present invention also provides antibodies or fragments thereof which immunospecifically bind to a RSV antigen with a higher avidity than any previously known antibodies or fragments thereof. Preferably, the antibodies or antibody fragments have higher avidity for a RSV antigen than SYNAGIS® has for the RSV F glycoprotein. The present invention also provides antibodies or fragments thereof that immunospecifically bind to a RSV antigen which have a higher affinity for a RSV antigen than any previously known antibodies or fragments thereof. The present invention also provides pharmaceutical compositions comprising one or more antibodies or fragments thereof which immunospecifically bind to a RSV antigen with a higher avidity than any previously known antibodies or fragments thereof.

The present invention also provides for antibodies or fragments thereof which immunospecifically bind to one or more RSV antigens with an affinity constant of at least $2\times10^8$ M$^{-1}$, at least $2.5\times10^8$ M$^{-1}$, at least $5\times10^8$ M$^{-1}$, at least $10^9$ M$^{-1}$, at least $5\times10^9$ M$^{-1}$, at least $10^{10}$ M$^{-1}$, at least $5\times10^{10}$ M$^{-1}$, at least $10^{11}$ M$^{-1}$, at least $5\times10^{11}$ M$^{-1}$, at least $10^{12}$ M$^{-1}$, at least $5\times10^{12}$ M$^{-1}$, at least $10^{13}$ M$^{-1}$, at least $5\times10^{13}$ M$^{-1}$, at least $10^{14}$ M$^{-1}$, at least $5\times10^{14}$ M$^{-1}$, at least $10^{15}$ M$^{-1}$, or at least $5\times10^{15}$ M$^{-1}$ and which have a higher avidity for one or more RSV antigens than any previously known antibodies or fragments thereof such as, e.g., SYNAGIS®. The present invention further provides pharmaceutical compositions comprising one or more antibodies or fragments thereof which immunospecifically bind to one or more RSV antigens with an affinity constant of at least $2\times10^8$ M$^{-1}$, at least $2.5\times10^8$ M$^{-1}$, at least $5\times10^8$ M$^{-1}$, at least $10^9$ M$^{-1}$, at least $5\times10^9$ M$^{-1}$, at least $10^{10}$ M$^{-1}$, at least $5\times10^{10}$ M$^{-1}$, at least $10^{11}$ M$^{-1}$, at least $5\times10^{11}$ M$^{-1}$, at least $10^{12}$ M$^{-1}$, at least $5\times10^{12}$ M$^{-1}$, at least $10^{13}$ M$^{-1}$, at least $5\times10^{13}$ M$^{-1}$, at least $10^{14}$ M$^{-1}$, at least $5\times10^{14}$ M$^{-1}$, at least $10^{15}$ M$^{-1}$, or at least $5\times10^{15}$ M$^{-1}$ and which have a higher avidity for one or more RSV antigens than any previously known antibodies or fragments thereof such as, e.g., SYNAGIS®.

The present invention provides methods of achieving a certain serum titer (preferably a serum titer 1 µg/ml or less, 2 µg/ml or less, 5 µg/ml or less, 6 µg/ml or less, 10 µg/ml or less, 15 µg/ml or less, 20 µg/ml or less, or 25 µg/ml or less) of antibodies or fragments thereof that immunospecifically bind to one or more RSV antigens in a mammal, said methods comprising administering to said mammal one or more antibodies or fragments thereof that have an affinity constant of at least $2\times10^8$ M$^{-1}$, at least $2.5\times10^8$ M$^{-1}$, at least $5\times10^8$ M$^{-1}$, at least $10^9$ M$^{-1}$, at least $5\times10^9$ M$^{-1}$, at least $10^{10}$ M$^{-1}$, at least $5\times10^{10}$ M$^{-1}$, at least $10^{11}$ M$^{-1}$, at least $5\times10^{11}$ M$^{-1}$, at least $10^{12}$ M$^{-1}$, at least $5\times10^{12}$ M$^{-1}$, at least $10^{13}$ M$^{-1}$, at least $5\times10^{13}$ M$^{-1}$, at least $10^{14}$ M$^{-1}$, at least $5\times10^{14}$ M$^{-1}$, or at least $5\times10^{15}$ M$^{-1}$ for said RSV antigens. Preferably, the antibodies or antibody fragments have a higher affinity for a RSV antigen than SYNAGIS® does for the RSV F glycoprotein.

The present invention also provides methods of achieving a certain serum titer of antibodies or fragments thereof that immunospecifically bind to one or more RSV antigens in a mammal, said methods comprising administering to said mammal one or more antibodies or fragments thereof that have a higher avidity for said RSV antigens than any previously known antibodies or antibody fragments. Preferably, the antibodies or antibody fragments have higher avidity for a RSV antigen than SYNAGIS® has for the RSV F glycoprotein.

The present invention also provides methods of achieving a certain serum titer of antibodies or fragments thereof that immunospecifically bind to one or more RSV antigens in mammal, said methods comprising administering to said mammal one or more antibodies or fragments thereof that have an affinity constant of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, at least $5\times10^{12}$ $M^{-1}$, at least $10^{13}$ $M^{-1}$, at least $5\times10^{13}$ $M^{-1}$, at least $10^{14}$ $M^{-1}$, at least $5\times10^{14}$ $M^{-1}$, at least $10^{15}$ $M^{-1}$, or at least $5\times10^{15}$ $M^{-1}$ for one or more RSV antigens and have a higher avidity than any previously known antibodies or antibody fragments for said RSV antigens.

The present invention also provides methods of neutralizing RSV using antibodies or fragments thereof that immunospecifically bind to one or more RSV antigens and which have an affinity constant of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, at least $5\times10^{12}$ $M^{-1}$, at least $10^{13}$ $M^{-1}$, at least $5\times10^{13}$ $M^{-1}$, at least $10^{14}$ $M^{-1}$, at least $5\times10^{14}$ $M^{-1}$, at least $10^{15}$ $M^{-1}$, or at least $5\times10^{15}$ $M^{-1}$ for said RSV antigens. Preferably, the antibodies or antibody fragments have a higher affinity for a RSV antigen than SYNAGIS® does for the RSV F glycoprotein. The present invention also provides methods of neutralizing RSV using antibodies or fragments thereof that immunospecifically bind to one or more RSV antigens and which have a higher avidity for said RSV antigens than any previously known antibodies or antibody fragments. Preferably, the antibodies or antibody fragments have a higher avidity for a RSV antigen than SYNAGIS® does for the RSV F glycoprotein. The present invention also provides methods of neutralizing RSV using antibodies or fragments thereof that immunospecifically bind to one or more RSV antigens with an affinity constant of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, at least $5\times10^{12}$ $M^{-1}$, at least $10^{13}$ $M^{-1}$, at least $5\times10^{13}$ $M^{-1}$, at least $10^{14}$ $M^{-1}$, at least $5\times10^{14}$ $M^{-1}$, at least $10^{15}$ $M^{-1}$, or at least $5\times10^{15}$ $M^{-1}$ and which have a higher avidity for said RSV antigens than any previously known antibodies or antibody fragments. The higher affinity and/or higher avidity that these antibodies or antibody fragments have for a RSV antigen results in a lower concentration of these antibodies or antibody fragments necessary to achieve neutralization of RSV than previously known.

The present invention also provides methods for preventing, treating or ameliorating one or more symptoms of RSV infection in a mammal, said methods comprising administering to said mammal one or more antibodies or fragments thereof that immunospecifically bind to one or more RSV antigens and which have an affinity constant of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $10^{11}$ $M^{-1}$, at least $5\times10^{11}$ $M^{-1}$, at least $10^{12}$ $M^{-1}$, at least $5\times10^{12}$ $M^{-1}$, at least $10^{13}$ $M^{-1}$, at least $5\times10^{13}$ $M^{-1}$, at least $10^{14}$ $M^{-1}$, at least $5\times10^{14}$ $M^{-1}$, at least $10^{15}$ $M^{-1}$, or at least $5\times10^{15}$ $M^{-1}$ for said RSV antigens. Preferably, the antibodies or antibody fragments have a higher affinity for a RSV antigen than SYNAGIS® does for the RSV F glycoprotein. The present invention also provides of methods preventing, treating or ameliorating one or more symptoms of RSV infection in a mammal, said methods comprising administering to said mammal one or more antibodies or fragments thereof that immunospecifically bind to one or more RSV antigen and which have a higher avidity for said RSV antigen than any previously known antibodies or antibody fragments. Preferably, the antibodies or antibody fragments have a higher avidity for a RSV antigen than SYNAGIS® does for the RSV F glycoprotein. The present invention further provides methods of preventing, treating or ameliorating one or more symptoms of RSV infection in a mammal, said methods comprising administering to said mammal one or more antibodies or fragments thereof that immunospecifically bind to one or more RSV antigens with an affinity constant of at least $2\times10^8$ $M^{-1}$, at least $2.5\times10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, at least $5\times10^{12}$ $M^{-1}$, at least $10^{13}$ $M^{-1}$, at least $5\times10^{13}$ $M^{-1}$, at least $10^{14}$ $M^{-1}$, at least $5\times10^{14}$ $M^{-1}$, at least $10^{15}$ $M^{-1}$, or at least $5\times10^{15}$ $M^{-1}$ for said RSV antigen and which have a higher avidity for said RSV antigens than any previously known antibodies or antibody fragments. The higher affinity and/or higher avidity that these antibodies or antibody fragments have for a RSV antigen results in lower and/or less frequent doses of these antibodies or antibody fragments to achieve a prophylactic or therapeutic effect in a mammal, preferably a human, than previously known.

The present invention provides methods for preventing, treating, or ameliorating one or more symptoms associated with a RSV infection in a mammal, preferably a human, said methods comprising administering a first dose to said mammal of a prophylactically or therapeutically effective amount of one or more antibodies or fragments thereof which immunospecifically bind to one or more RSV antigens with a higher avidity and/or affinity than previously known antibodies such as SYNAGIS®, wherein said effective amount is less than 15 mg/kg of said antibodies or fragments thereof and which results in a serum titer less than 30 µg/ml (which is preferably at least 2 µg/ml, more preferably at least 4 µg/ml, and most preferably at least 6 µg/ml) 30 days after the first administration and prior to any subsequent administration. In one embodiment, RSV infection in a human subject is prevented or treated, or one or more symptoms in a human subject is ameliorated by administering a first dose of less than 10 mg/kg, preferably less than 5 mg/kg, less than 3 mg/kg, less than 1 mg/kg, or less than 0.5 mg/kg of one or more antibodies or fragments thereof that immunospecifically bind to one or more RSV antigens with a higher avidity and/or affinity than previously known antibodies such as SYNAGIS® so that a serum antibody titer of at least 6 µg/ml, preferably at least 10 µg/ml, at least 25 µg/ml, at least 30 µg/ml, at least 40 µg/ml at least 80 µg/ml, or at least 120 µg/ml, at least 150 µg/ml, at least 200 µg/ml, at least 250 µg/ml, or at least 300 µg/ml is achieved 30 days after the administration of the first dose of the antibodies or antibody fragments and prior to the administration of a subsequent dose.

The present invention provides antibodies or fragments thereof comprising a variable heavy ("VH") domain having an amino acid sequence of any VH domain listed in Table 2, and pharmaceutical compositions comprising said antibodies or antibody fragments. The present invention also provides antibodies or fragments thereof comprising one or more VH CDRs having the amino acid sequence of one or more VH CDRs listed in Table 2 and/or Table 3, and pharmaceutical compositions comprising said antibodies or antibody fragments. The present invention also provides antibodies or fragments thereof comprising a variable light ("VL") domain having the amino acid sequence of any VL domain listed in Table 2, and pharmaceutical compositions comprising said antibodies or antibody fragments. The present invention also provides antibodies or fragments thereof comprising one or more VL CDRs having the amino acid sequence of one or more VL CDRs listed in Table 2 and/or Table 3, and pharmaceutical compositions comprising said antibodies or antibody fragments. The present invention also provides antibodies or fragments thereof comprising a VH domain having the amino acid sequence any VH domain listed in Table 2 and a VL domain having the amino acid sequence of any VL domain listed in Table 2, and pharmaceutical compositions comprising said antibodies or antibody fragments. The present invention provides antibodies or fragments thereof comprising one or more VH CDRs having the amino acid sequence one or more VH CDRs listed in Table 2 and/or Table 3 and one or more VL CDRs having the amino acid sequence of one or more VL CDRs listed in Table 2 and/or Table 3. The present invention encompasses pharmaceutical compositions comprising said antibodies or antibody fragments. Preferably, said antibodies or antibody fragments immunospecifically bind to one or more RSV antigens.

The present invention encompasses methods for preventing, treating, neutralizing and ameliorating one or more symptoms using one or more antibodies comprising a variable heavy ("VH") domain having an amino acid sequence of any VH domain listed in Table 2. The present invention also encompasses methods for preventing, treating, neutralizing and ameliorating one or more symptoms using one or more antibodies comprising one or more VH CDRs having the amino acid sequence of one or more VH CDRs listed in Table 2 and/or Table 3. The present invention also encompasses methods for preventing, treating, neutralizing and ameliorating one or more symptoms using one or more antibodies comprising a variable light ("VL") domain having the amino acid sequence of any VL domain listed in Table 2. The present invention also encompasses methods for preventing, treating, neutralizing and ameliorating one or more symptoms using one or more antibodies comprising one or more VL CDRs having the amino acid sequence of one or more VL CDRs listed in Table 2 and/or Table 3. The present invention also encompasses methods for preventing, treating, neutralizing and ameliorating one or more symptoms using one or more antibodies comprising a VH domain having the amino acid sequence any VH domain listed in Table 2 and a VL domain having the amino acid sequence of any VL domain listed in Table 2. The present invention further encompasses methods for preventing, treating, neutralizing and ameliorating one or more symptoms using one or more antibodies comprising one or more VH CDRs having the amino acid sequence one or more VH CDRs listed in Table 2 and/or Table 3 and one or more VL CDRs having the amino acid sequence of one or more VL CDRs listed in Table 2 and/or Table 3. Preferably, said antibodies or antibody fragments immunospecifically bind to one or more RSV antigens.

The present invention encompasses antibodies or fragments thereof that immunospecifically bind to one or more RSV antigens with increased in vivo half-lives. In particular, the present invention encompasses HL-SYNAGIS and antigen-binding fragments thereof. The present invention also encompasses novel antibodies or fragments thereof described herein which immunospecifically bind to one or more RSV antigens and have an Fc domain with a higher affinity for the FcRn receptor than the Fc domain of SYNAGIS®.

The present invention also encompasses methods for the prevention, neutralization, treatment or amelioration of one or more symptoms associated with a RSV infection using antibodies or fragments thereof that immunospecifically bind to one or more RSV antigens with increased in vivo half-lives. In particular, the invention encompasses methods for the prevention, neutralization, treatment or amelioration of one or more symptoms associated with a RSV infection using HL-SYNAGIS or an antigen-binding fragment thereof The invention also encompasses methods for the prevention, neutralization, treatment or amelioration of one or more symptoms associated with a RSV infection using novel antibodies or fragments thereof described herein which immunospecifically bind to one or more RSV antigens and have an Fc domain with a higher affinity for the FcRn receptor than the Fc domain of SYNAGIS®.

The present invention provides sustained release formulations of antibodies or fragments thereof that immunospecifically bind to one or more RSV antigens for the prevention, neutralization, treatment or amelioration of one or more symptoms associated with a RSV infection. In particular, the present invention provides sustained release formulations of SYNAGIS® or fragments thereof for the prevention, neutralization, treatment or amelioration of one or more symptoms associated with a RSV infection. The present invention also provides sustained release formulations of one or more novel antibodies or fragments thereof described herein which immunospecifically bind to one or more RSV antigens for the prevention, neutralization, treatment or amelioration of one or more symptoms associated with a RSV infection.

The present invention also provides methods of administering compositions comprising antibodies or fragments thereof which immunospecifically bind to one or more RSV antigens to the site of a RSV infection in a subject. In particular, the present invention provides compositions comprising one or more antibodies or fragments thereof for pulmonary delivery to a subject.

The present invention provides compositions comprising one or more antibodies or fragments thereof that immunospecifically bind to one or more RSV antigens, and methods for detecting or diagnosing a RSV infection utilizing said antibodies or antibody fragments.

5.1. Antibodies

It should be recognized that antibodies that immunospecifically bind to a RSV antigen are known in the art. For example, SYNAGIS® is a humanized monoclonal antibody presently used for the prevention of RSV infection in pediatric patients. The present invention encompasses novel formulations for administration of SYNAGIS® and other known anti-RSV antibodies and novel doses of SYNAGIS® and other known anti-RSV antibodies, as discussed herein.

In addition, the invention encompasses novel antibodies, fragments and other biological or macromolecules which immunospecifically bind to one or more RSV antigens. With respect to these novel agents, the invention further encompasses novel modes of administration, doses, dosing and uses based, in part, upon their unique therapeutic profiles and potency.

Set forth below, is a more detailed description of the antibodies encompassed within the various aspects of the invention.

The present invention provides antibodies or fragments thereof that immunospecifically bind to one or more RSV antigens. The present invention provides antibodies or fragments thereof that immunospecifically bind to one or more RSV antigens. Preferably, the antibodies of the invention or fragments thereof immunospecifically bind to one or more RSV antigens regardless of the strain of RSV. In a specific embodiment, the antibodies of the invention or fragments thereof immunospecifically bind to an RSV antigen of RSV subtype A and/or RSV subtype B. The present invention also provides antibodies or fragments thereof that differentially or preferentially bind to RSV antigens from one strain of RSV versus another RSV strain. In a specific embodiment, the antibodies of the invention or fragments thereof immunospecifically bind to the RSV F glycoprotein, G glycoprotein or SH protein. In a preferred embodiment, the antibodies present invention or fragments thereof immunospecifically bind to the RSV F glycoprotein. In another preferred embodiment, the antibodies of the present invention or fragments thereof bind to the A, B, or C antigenic sites of the RSV F glycoprotein.

Antibodies of the invention include, but are not limited to, monoclonal antibodies, multispecific antibodies, human antibodies, humanized antibodies, chimeric antibodies, single domain antibodies, carmelised single domain antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies of the invention), and epitope-binding fragments of any of the above. In particular, antibodies of the present invention include immunoglobulin molecules and immunologically active portions of immunoglobulin molecules, i.e., molecules that contain an antigen binding site that immunospecifically binds to a RSV antigen. The immunoglobulin molecules of the invention can be of any type (e.g., IgG, IgE, IgM, IgD, IgA and IgY), class (e.g., $IgG_1$, $IgG_2$, $IgG_3$, $IgG_4$, $IgA_1$, and $IgA_2$) or subclass of immunoglobulin molecule.

The antibodies of the invention may be from any animal origin including birds and mammals (e.g., human, murine, donkey, sheep, rabbit, goat, guinea pig, camel, llama, horse, or chicken). Preferably, the antibodies of the invention are human or humanized monoclonal antibodies. As used herein, "human" antibodies include antibodies having the amino acid sequence of a human immunoglobulin and include antibodies isolated from human immunoglobulin libraries or from mice that express antibodies from human genes.

The antibodies of the present invention may be monospecific, bispecific, trispecific or of greater multispecificity. Multispecific antibodies may be specific for different epitopes of a RSV polypeptide or may be specific for both a RSV polypeptide as well as for a heterologous epitope, such as a heterologous polypeptide or solid support material. See, e.g., PCT publications WO 93/17715, WO 92/08802, WO 91/00360, and WO 92/05793; Tutt, et al., J. Immunol. 147: 60-69 (1991); U.S. Pat. Nos. 4,474,893, 4,714,681, 4,925, 648, 5,573,920, and 5,601,819; and Kostelny et al., J. Immunol. 148:1547-1553 (1992).

The present invention provides for antibodies or fragments thereof that exhibit a high potency in an assay described herein. High potency antibodies or fragments thereof can be produced by methods disclosed in copending U.S. patent application Ser. Nos. 60/168,426 and 60/186,252 and methods described herein. For example, high potency antibodies can be produced by genetically engineering appropriate antibody gene sequences and expressing the antibody sequences in a suitable host. The antibodies produced can be screened to identify antibodies with, e.g., high $k_{on}$ values in a BIAcore assay.

The present invention provides for antibodies or fragments thereof that have a high binding affinity for one or more RSV antigens. In a specific embodiment, an antibody of the present invention or fragment thereof has an association rate constant or $k_{on}$ rate (antibody (Ab)+antigen (Ag) $\xrightarrow{k_{on}}$ Ab-Ag) of at least $10^5$ $M^{-1}s^{-1}$, at least $5\times10^5$ $M^{-1}s^{-1}$, at least $10^6$ $M^{-1}s^{-1}$, at least $5\times10^6$ $M^{-1}s^{-1}$, at least $10^7$ $M^{-1}s^{-1}$, at least $5\times10^7$ $M^{-1}s^{-1}$, or at least $10^8$ $M^{-1}s^{-1}$. In a preferred embodiment, an antibody of the present invention or fragment thereof has a $k_{on}$ of at least $2\times10^5$ $M^{-1}s^{-1}$, at least $5\times10^5$ $M^{-1}s^{-1}$, at least $10^6$ $M^{-1}s^{-1}$, at least $5\times10^6$ $M^{-1}s^{-1}$, at least $10^7$ $M^{-1}s^{-1}$, at least $5\times10^7$ $M^{-1}s^{-1}$, or at least $10^8$ $M^{-1}s^{-1}$.

In another embodiment, an antibody of the present invention or fragment thereof has a $k_{off}$ rate (antibody (Ab)+antigen (Ag) $\xrightarrow{k_{off}}$ Ab-Ag) of less than $10^{-1}$ $s^{-1}$, less than $5\times10^{-1}$ $s^{-1}$, less than $10^{-2}$ $s^{-1}$, less than $5\times10^{-2}$ $s^{-1}$, less than $10^{-3}$ $s^{-1}$, less than $5\times10^{-3}$ $s^{-1}$, less than $10^{-4}$ $s^{-1}$, less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than $10^{-7}$ $s^{-1}$, less than $5\times10^{-7}$ $s^{-1}$, less than $10^{-8}$ $s^{-1}$, less than $5\times10^{-8}$ $s^{-1}$, less than $10^{-9}$ $s^{-1}$, less than $5\times10^{-9}$ $s^{-1}$, or less than $10^{-10}$ $s^{-1}$. In a preferred embodiment, an antibody of the present invention or fragment thereof has a $k_{off}$ of less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than $10^{-7}$ $s^{-1}$, less than $5\times10^{-7}$ $s^{-1}$, less than $10^{-8}$ $s^{-1}$, less than $5\times10^{-8}$ $s^{-1}$, less than $10^{-9}$ $s^{-1}$, less than $5\times10^{-9}$ $s^{-1}$, or less than $10^{-10}$ $s^{-1}$.

In another embodiment, an antibody of the present invention or fragment thereof has an affinity constant or $K_a$ ($k_{on}/k_{off}$) of at least $10^2$ $M^{-1}$, at least $5\times10^2$ $M^{-1}$, at least $10^3$ $M^{-1}$, at least $5\times10^3$ $M^{-1}$, at least $10^4$ $M^{-1}$, at least $5\times10^4$ $M^{-1}$, at least $10^5$ $M^{-1}$, at least $5\times10^5$ $M^{-1}$, at least $10^6$ $M^{-1}$, at least $5\times10^6$ $M^{-1}$, at least $10^7$ $M^{-1}$, at least $5\times10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, at least $5\times10^{12}$ $M^{-1}$, at least $10^{13}$ $M^{-1}$, at least $5\times10^{13}$ $M^{-1}$, at least $10^{14}$ $M^{-1}$, at least $5\times10^{14}$ $M^{-1}$, at least $10^{15}$ $M^{-1}$, or at least $5\times10^{15}$ $M^{-1}$. In yet another embodiment, an antibody or fragment thereof has a dissociation constant or $K_d$ ($k_{off}/k_{on}$) of less than $10^{-2}$ M, less than $5\times10^{-2}$ M, less than $10^{-3}$ M, less than $5\times10^{-3}$ M, less than $10^{-4}$ M, less than $5\times10^{-4}$ M, less than $10^{-5}$ M, less than $5\times10^{-5}$ M, less than $10^{-6}$ M, less than $5\times10^{-6}$ M, less than $10^{-7}$ M, less than $5\times10^{-7}$ M, less than $10^{-8}$ M, less than $5\times10^{-8}$ M, less than $10^{-9}$ M, less than $5\times10^{-9}$ M, less than $10^{-10}$ M, less than $5\times10^{-10}$ M, less than $10^{-11}$ M, less than $5\times10^{-11}$ M, less than $10^{-12}$ M, less than $5\times10^{-12}$ M, less than $10^{-13}$ M, less than $5\times10^{-13}$ M, less than $10^{-14}$ M, less than $5\times10^{-14}$ M, less than $10^{-15}$ M, or less than $5\times10^{-15}$ M.

The present invention provides antibodies or fragment thereof that have a median effective concentration ($EC_{50}$) of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay. The median effective concentration is the concentration of antibody or antibody fragments that neutralizes 50% of the RSV in an in vitro microneutralization assay. In a preferred embodiment, antibody of the invention or fragment thereof has an $EC_{50}$ of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay.

In a specific embodiment, an antibody of the present invention is SYNAGIS® or an antibody-binding fragment thereof (e.g., one or more complementarity determining regions (CDRs) of SYNAGIS®). The amino acid sequence of SYNAGIS® is disclosed, e.g., in Johnson et al., 1997, J. Infectious Disease 176:1215-1224, and U.S. Pat. No. 5,824,307, each of which is incorporated herein by reference in its entirety. In alternative embodiment, an antibody of the present invention or fragment thereof is not SYNAGIS® or a fragment of SYNAGIS®, i.e., is not an antibody comprising a VH domain of SEQ ID NO:7 and/or a VL domain of SEQ ID NO:8.

The present invention provides for antibodies or fragments thereof that immunospecifically bind to one or more RSV antigens, said antibodies or antibody fragments comprising the amino acid sequence of SYNAGIS® with one or more amino acid residue substitutions in the variable light (VL) domain and/or variable heavy (VH) domain depicted in FIG. 1. The present invention also provides for antibodies or fragments thereof that immunospecifically bind to one or more RSV antigens, said antibodies or antibody fragments comprising the amino acid sequence of SYNAGIS® with one or more amino acid residue substitutions in one or more VL CDRs and/or one or more VH CDRs. In a specific embodiment, an antibody or fragment thereof comprises the amino acid sequence of SYNAGIS® with one or more amino acid residue substitutions of the amino acid residues indicated in bold face and underlining in Table 1. In accordance with this embodiment, the amino acid residue substitutions can be conservative or non-conservative. The antibody or antibody fragment generated by introducing substitutions in the VH domain, VH CDRs, VL domain and/or VL CDRs of SYNAGIS® can be tested in vitro and in vivo, for example, for its ability to bind to RSV F antigen, for its ability to neutralize RSV, or for its ability to prevent, treat or ameliorate one or more symptoms associated with a RSV infection.

TABLE 1

CDR Sequences Of SYNAGIS ®

| CDR | Sequence | SEQ ID NO: |
|---|---|---|
| VH1 | TSGMSVG | 1 |
| VH2 | DIWWDDKKDYNPSLKS | 2 |
| VH3 | SMITNWYFDV | 3 |
| VL1 | KCQLSVGYMH | 4 |
| VL2 | DTSKLAS | 5 |
| VL3 | FQGSGYPFT | 6 |

Bold faced & underlined amino acid residues are preferred residues which should be substituted.

In a specific embodiment, an antibody of the present invention is SYNAGIS®, AFFF, P12f2, P12f4, P11d4, Ale9, A12a6, A13c4, A17d4, A4B4, A8c7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S, each of which immunospecifically binds to a RSV F glycoprotein or a fragment thereof. Preferably, an antibody of the present invention is AFFF, P12f2, P12f4, P11d4, Ale9, A12a6, A13c4, A17d4, A4B4, A8c7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S. In another embodiment, an antibody is a Fab fragment of SYNAGIS®, AFFF, P12f2, P12f4, P11d4, Ale9, A12a6, A13c4, A17d4, A4B4, A8c7, A4B4(1), A4B4L1FR-S28R, or A4B4-F52S.

AFFF, P12f2, P12f4, P11d4, Ale9, A12a6, A13c4, A17d4, A8C7, IX-493L1FR, H3-3F4, M3H9, Y10H6, DG, AFFF(1), 6H8, L1-7E5, L2-15B10, A13a11, and A1h5 comprise the framework region and constant regions of SYNAGIS®. A4B4, A4B4(1), A4B4L1FR-S28R, and A4B4-F52S comprise the framework region and constant regions of SYNAGIS® with the exception that there is a valine at position 103, numbered as shown in FIG. 2A, and a-glutamine at position 112, numbered as shown in FIG. 2B. In certain embodiments, A4B4, A4B4(1), A4B4L1FR-S28R, and A4B4-F52S comprise the framework region and constant regions of SYNAGIS®.

In another embodiment, the present invention provides for an antigen-binding fragment of AFFF, P12f2, P12f4, P11d4, Ale9, A12a6, A13c4, A17d4, A4B4, A8c7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S. In another embodiment, the present invention provides for one or more antibodies or fragments thereof that immunospecifically bind to one or more RSV antigens, said antibodies or antibody fragments comprising a VH chain and/or VL chain having the amino acid sequence of a VH chain and/or VL chain of AFFF, P12f2, P12f4, P11d4, Ale9, A12a6, A13c4, A17d4, A4B4, A8c7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S. In another embodiment, the present invention provides for one or more antibodies or fragments thereof that immunospecifically bind to one or more RSV antigens, said antibodies or antibody fragments comprising a VH domain and/or VL domain having the amino acid sequence of a VH domain and/or VL domain of AFFF, P12f2, P12f4, P11d4, Ale9, A12a6, A13c4, A17d4, A4B4, A8c7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S. In another embodiment, the present invention provides for antibodies or fragments thereof that immunospecifically bind to one or more RSV antigens, said antibodies or antibody fragments comprising one or more CDRs having the amino acid sequence of one or more CDRs of AFFF, P12f2, P12f4, P11d4, Ale9, A12a6, A13c4, A17d4, A4B4, A8c7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S. In yet another embodiment, the present invention provides for one or more antibodies or fragments thereof that immunospecifically bind to one or more RSV antigens, said antibodies or antibody fragments comprising a combination of VH CDRs and/or VL CDRs having the amino acid sequence of VH CDRs and/or VL CDRs of AFFF, P12f2, P12f4, P11d4, Ale9, A12a6, A13c4, A17d4, A4B4, A8c7, IX-493L1FR, H3-3F4, M3H9, Y10H6, DG, AFFF(1), 6H8, L1-7E5, L2-15B10, A13a11, A1h5, A4B4(1), A4B4L1FR-S28R, and/or A4B4-F52S.

The present invention provides antibodies or fragments thereof that immunospecifically bind to one or more RSV antigens, said antibodies or antibody fragments comprising a variable heavy ("WH") chain having an amino acid sequence of any one of the VH chains listed in Table 2. The present invention also provides antibodies or fragments thereof that immunospecifically bind to one or more RSV antigens, said antibodies or antibody fragments comprising a VH domain having an amino acid sequence of any one of the VH domains listed in Table 2. In certain embodiments of the invention, an antibody or fragment thereof comprising a VH domain having an amino acid of any of one of the VH domains listed in Table 2 is not SYNAGIS®. The present invention also provides antibodies or fragments thereof that immunospecifically bind to one or more RSV antigens, said antibodies or fragments comprising a VH complementarity determining region ("CDR") having an amino acid sequence of any on one of the VH CDRs listed in Table 2 and/or Table 3. In certain embodiments of the invention, an antibody or fragment thereof comprising a VH CDR having an amino acid of any of one of the VH CDRs listed in Table 2 and/or Table 3 is not SYNAGIS®.

TABLE 2

Antibodies & Fragments Thereof

| Antibody Name | VH Chain | VH Domain | VH CDR1 | VH CDR2 | VH CDR3 | VL Chain | VL Domain | VL CDR1 | VL CDR2 | VL CDR3 |
|---|---|---|---|---|---|---|---|---|---|---|
| **SYNAGIS | SEQ ID NO: 208 | SEQ ID NO:7 | TSGMSVG (SEQ ID NO:1) | DIWWDDKKDY NPSLKS (SEQ ID NO:2) | SMITNWYFDV (SEQ ID NO:3) | SEQ ID NO: 209 | SEQ ID NO:8 | KCQLSVGYMH (SEQ ID NO:4) | DTSKLAS (SEQ ID NO:5) | FQGSGYPFT (SEQ ID NO:6) |
| *AFFF | SEQ ID NO: 210 | SEQ ID NO:9 | TAGMSVG (SEQ ID NO:10) | DIWWDDKKDYN PSLKS (SEQ ID NO:2) | SMITNFYFDV (SEQ ID NO:12) | SEQ ID NO: 211 | SEQ ID NO:13 | SASSSVGYMH (SEQ ID NO:14) | DTFKLAS (SEQ ID NO:15) | FQF**SGYPFT (SEQ ID NO:16) |
| *P12f2 | SEQ ID NO: 212 | SEQ ID NO:17 | TPGMSVG (SEQ ID NO:18) | DIWWDDKKHYN PSLKD (SEQ ID NO:19) | DMIFNFYFDV (SEQ ID NO:20) | SEQ ID NO: 213 | SEQ ID NO:21 | SLSSRVGYMH (SEQ ID NO:22) | DTFYLSS** (SEQ ID NO:23) | FQGSGYPFT (SEQ ID NO:6) |
| *P12f4 | SEQ ID NO: 214 | SEQ ID NO:24 | TPGMSVG (SEQ ID NO:18) | DIWWDGKKHYN PSLKD (SEQ ID NO:25) | DMIFNFYFDV (SEQ ID NO:20) | SEQ ID NO: 215 | SEQ ID NO:26 | SLSSRVGYMH (SEQ ID NO:22) | DTRGLPS** (SEQ ID NO:27) | FQGSGYPFT (SEQ ID NO:6) |
| *P11d4 | SEQ ID NO: 216 | SEQ ID NO:28 | TPGMSVG (SEQ ID NO:18) | DIWWDGKKHYN PSLKD (SEQ ID NO:25) | DMIFNWYFDV (SEQ ID NO:29) | SEQ ID NO: 217 | SEQ ID NO:30 | SPSSRVGYMH (SEQ ID NO:31) | DTMRLAS** (SEQ ID NO:32) | FQGSGYPFT (SEQ ID NO:6) |
| *A1e9 | SEQ ID NO: 218 | SEQ ID NO:33 | TAGMSVG (SEQ ID NO:10) | DIWWDGKKHYN PSLKD (SEQ ID NO:25) | DMIFNWYFDV (SEQ ID NO:29) | SEQ ID NO: 219 | SEQ ID NO:34 | SLSSRVGYMH (SEQ ID NO:22) | DTFKLSS** (SEQ ID NO:35) | FQGSGYPFT (SEQ ID NO:6) |
| *A12a6 | SEQ ID NO: 220 | SEQ ID NO:36 | TAGMSVG (SEQ ID NO:10) | DIWWDGKKDYN PSLKD (SEQ ID NO:37) | DMIFNFYFDV (SEQ ID NO:20) | SEQ ID NO: 221 | SEQ ID NO:38 | SASSRVGYMH (SEQ ID NO:39) | DTFKLSS** (SEQ ID NO:35) | FQGSGYPFT (SEQ ID NO:6) |
| *A13c4 | SEQ ID NO: 222 | SEQ ID NO:40 | TAGMSVG (SEQ ID NO:10) | DIWWDGKKSYN PSLKD (SEQ ID NO:41) | DMIFNFYFDV (SEQ ID NO:20) | SEQ ID NO: 223 | SEQ ID NO:42 | SLSSRVGYMH (SEQ ID NO:22) | DTMYQSS** (SEQ ID NO:43) | FQGSGYPFT (SEQ ID NO:6) |
| *A17d4 | SEQ ID NO: 224 | SEQ ID NO:44 | TAGMSVG (SEQ ID NO:10) | DIWWDDKKSY NPSLKD (SEQ ID NO:45) | DMIFNFYFDV (SEQ ID NO:20) | SEQ ID NO: 225 | SEQ ID NO:46 | LPSSRVGYMH (SEQ ID NO:47) | DTMYQSS** (SEQ ID NO:43) | FQGSGYPFT (SEQ ID NO:6) |
| *A4B4 | SEQ ID NO: 226 | SEQ ID NO:48 | TAGMSVG (SEQ ID NO:10) | DIWWDDKKHY NPSLKD (SEQ ID NO:19) | DMIFNFYFDV (SEQ ID NO:20) | SEQ ID NO: 227 | SEQ ID NO:49 | SASSRVGYMH (SEQ ID NO:39) | DTFFLDS** (SEQ ID NO:50) | FQGSGYPFT (SEQ ID NO:6) |
| *A8c7 | SEQ ID NO: 228 | SEQ ID NO:51 | TAGMSVG (SEQ ID NO:10) | DIWWDDKKSY NPSLKD (SEQ ID NO:45) | DMIFNFYFDV (SEQ ID NO:29) | SEQ ID NO: 229 | SEQ ID NO:52 | SPSSRVGYMH (SEQ ID NO:31) | DTRYQSS** (SEQ ID NO:53) | FQGSGYPFT (SEQ ID NO:6) |
| *IX-493L1FR | SEQ ID NO: 230 | SEQ ID NO:7 | TSGMSVG (SEQ ID NO:1) | DIWWDDKKDYN PSLKS (SEQ ID NO:2) | SMITNWYFDV (SEQ ID NO:3) | SEQ ID NO: 231 | SEQ ID NO:54 | SASSSVGYMH (SEQ ID NO:14) | DTSKLAS (SEQ ID NO:5) | FQGSGYPFT (SEQ ID NO:6) |
| *H3-3F4 | SEQ ID NO: 232 | SEQ ID NO:55 | TAGMSVG (SEQ ID NO:10) | DIWWDDKKDYN PSLKS (SEQ ID NO:2) | DMIFNWYFDV (SEQ ID NO:29) | SEQ ID NO: 233 | SEQ ID NO:56 | SASSSVGYMH (SEQ ID NO:14) | DTFKLAS (SEQ ID NO:15) | FQGSGYPFT (SEQ ID NO:6) |
| *M3H9 | SEQ ID NO: 234 | SEQ ID NO:55 | TAGMSVG (SEQ ID NO:10) | DIWWDDKKDYN PSLKS (SEQ ID NO:2) | DMIFNWYFDV (SEQ ID NO:29) | SEQ ID NO: 235 | SEQ ID NO:70 | SASSSVGYMH (SEQ ID NO:14) | DTYKQTS (SEQ ID NO:57) | FQGSGYPFT (SEQ ID NO:6) |
| *Y10H6 | SEQ ID NO: 236 | SEQ ID NO:55 | TAGMSVG (SEQ ID NO:10) | DIWWDDKKDYN PSLKS (SEQ ID NO:2) | DMIFNWYFDV (SEQ ID NO:29) | SEQ ID NO: 237 | SEQ ID NO:58 | SASSSVGYMH (SEQ ID NO:14) | DTRYLSS (SEQ ID NO:59) | FQGSGYPFT (SEQ ID NO:6) |

TABLE 2-continued

Antibodies & Fragments Thereof

| Antibody Name | VH Chain | VH Domain | VH CDR1 | VH CDR2 | VH CDR3 | VL Chain | VL Domain | VL CDR1 | VL CDR2 | VL CDR3 |
|---|---|---|---|---|---|---|---|---|---|---|
| *DG | SEQ ID NO: 238 | SEQ ID NO:78 | TAGMSVG (SEQ ID NO:10) | DIWWDDKKDYN PSLKS (SEQ ID NO:2) | DMITNFYFDV (SEQ ID NO:79) | SEQ ID NO: 239 | SEQ ID NO:56 | SASSSVGYMH (SEQ ID NO:14) | DTFKLAS (SEQ ID NO:15) | FQGSGYPFT (SEQ ID NO:6) |
| AFFF(1) | SEQ ID NO: 240 | SEQ ID NO:9 | TAGMSVG (SEQ ID NO:10) | DIWWDDKKDYN PSLKS (SEQ ID NO:2) | SMITNFYFDV (SEQ ID NO:12) | SEQ ID NO: 241 | SEQ ID NO:60 | SASSSVGYMH (SEQ ID NO:14) | DTFKLAS (SEQ ID NO:15) | FQGSFYPFT (SEQ ID NO:61) |
| *6H8 | SEQ ID NO: 242 | SEQ ID NO:78 | TAGMSVG (SEQ ID NO:10) | DIWWDDKKDYN PSLKS (SEQ ID NO:2) | DMITNFYFDV (SEQ ID NO:79) | SEQ ID NO: 243 | SEQ ID NO:62 | SASSSVGYMH (SEQ ID NO:14) | DTFKLTS (SEQ ID NO:63) | FQGSGYPFT (SEQ ID NO:6) |
| *L1-7E5 | SEQ ID NO: 244 | SEQ ID NO:78 | TAGMSVG (SEQ ID NO:10) | DIWWDDKKDYN PSLKS (SEQ ID NO:2) | DMITNFYFDV (SEQ ID NO:79) | SEQ ID NO: 245 | SEQ ID NO:64 | SASSRVGYMH (SEQ ID NO:39) | DTF**KLAS (SEQ ID NO:15) | FQGSGYPFT (SEQ ID NO:6) |
| *L2-15B10 | SEQ ID NO: 246 | SEQ ID NO:78 | TAGMSVG (SEQ ID NO:10) | DIWWDDKKDYN PSLKS (SEQ ID NO:2) | DMITNFYFDV (SEQ ID NO:79) | SEQ ID NO: 247 | SEQ ID NO:65 | SASSSVGYMH (SEQ ID NO:14) | DTFRLAS (SEQ ID NO:66) | FQGSGYPFT (SEQ ID NO:6) |
| *A13a11 | SEQ ID NO: 248 | SEQ ID NO:67 | TAGMSVG (SEQ ID NO:10) | DIWWDDKKHYN PSLKD (SEQ ID NO:19) | DMIFNWYFDV (SEQ ID NO:29) | SEQ ID NO: 249 | SEQ ID NO:68 | SPSSRVGYMH (SEQ ID NO:31) | DTYRHS**S (SEQ ID NO:69) | FQGSGYPFT (SEQ ID NO:6) |
| *A1h5 | SEQ ID NO: 250 | SEQ ID NO:33 | TAGMSVG (SEQ ID NO:10) | DIWWGKKHYN PSLKD (SEQ ID NO:25) | DMIFNWYFDV (SEQ ID NO:29) | SEQ ID NO: 251 | SEQ ID NO:71 | SLSSSVGYMH (SEQ ID NO:72) | DTFFHRS (SEQ ID NO:73) | FQGSGYPFT (SEQ ID NO:6) |
| A4B4(I) | SEQ ID NO: 252 | SEQ ID NO:48 | TAGMSVG (SEQ ID NO:10) | DIWWDDKKHY NPSLKD (SEQ ID NO:19) | DMIFNFYFDV (SEQ ID NO:20) | SEQ ID NO: 253 | SEQ ID NO:74 | SASSRVGYM H (SEQ ID NO:39) | DTLLLD**S (SEQ ID NO:75) | FQGSGYPFT (SEQ ID NO:6) |
| *A4B4L1F R-S28R | SEQ ID NO: 254 | SEQ ID NO:48 | TAGMSVG (SEQ ID NO:10) | DIWWDDKKHY NPSLKD (SEQ ID NO:19) | DMIFNFYFDV (SEQ ID NO:20) | SEQ ID NO: 255 | SEQ ID NO:11 | SASSRVGYM H (SEQ ID NO:39) | DTSKLAS (SEQ ID NO:5) | FQGSGYPFT (SEQ ID NO:6) |
| *A4B4-F52S | SEQ ID NO: 256 | SEQ ID NO:48 | TAGMSVG (SEQ ID NO:10) | DIWWDDKKHYN PSLKD (SEQ ID NO:19) | DMIFNFYFDV (SEQ ID NO:20) | SEQ ID NO: 257 | SEQ ID NO:76 | SASSRVGYMH (SEQ ID NO:39) | DTSFLDS (SEQ ID NO:77) | FQGSGYPFT (SEQ ID NO:6) |

Bold faced & underlined amino acid residues are the residues which differ from the amino acid sequence in SYNAGIS ®; Fab fragment produced (*); Monoclonal antibody produced (); Fab fragment & monoclonal antibody produced (*)

TABLE 3

CDR Sequences

| VH CDR1 | VH CDR2 | VH CDR3 | VL CDR1 | VL CDR2 | VL CDR3 |
|---|---|---|---|---|---|
| TSGMSVG (SEQ ID NO:1) | DIWWDDKKDYNPSLKS (SEQ ID NO:2) | SMITNWYFDV (SEQ ID NO:3) | KCQLSVGYMH (SEQ ID NO:4) | DTSKLAS (SEQ ID NO:5) | FQGSGYPFT (SEQ ID NO:6) |
| TPGMSVG (SEQ ID NO:18) | DIWWDDKKHYNPSLKD (SEQ ID NO:19) | DMITNFYFDV (SEQ ID NO:29) | KCQSSVGYMH (SEQ ID NO:80) | DTSYLAS (SEQ ID NO:81) | FQFSGYPFT (SEQ ID NO:6) |
| TAGMSVG (SEQ ID NO:10) | DIWWDDKKHYNPSLKS (SEQ ID NO:82) | DMITNWYFDV (SEQ ID NO:83) | KCQSRVGYMH (SEQ ID NO:84) | DTSYLSS (SEQ ID NO:85) | FQGSF**YPFT (SEQ ID NO:61) |
| | DIWWDDKKDYNPSLKD (SEQ ID NO:86) | DMIFNWYFDV (SEQ ID NO:29) | KCQLRVGYMH (SEQ ID NO:87) | DTKKLSS (SEQ ID NO:88) | |
| | DIWWDDKKHYNPSLKS (SEQ ID NO:91) | DMIFNFYFDV (SEQ ID NO:20) | KLQLSVGYMH (SEQ ID NO:89) | DTFYLS**S (SEQ ID NO:90) | |
| | DIWWDDKKDYNPSLKD (SEQ ID NO:93) | SMITNFYFDV (SEQ ID NO:12) | KLQSSVGYMH (SEQ ID NO:92) | DTFKLAS (SEQ ID NO:15) | |

TABLE 3-continued

CDR Sequences

| VH CDR1 | VH CDR2 | VH CDR3 | VL CDR1 | VL CDR2 | VL CDR3 |
|---------|---------|---------|---------|---------|---------|
| | DIWWDGKKHYNPSLKD (SEQ ID NO:25) | SMIFNWYFDV (SEQ ID NO:94) | KLQSRVGYMH (SEQ ID NO:95) | DTFKLSS (SEQ ID NO:96) | |
| | DIWWDGKKDYNPSLKS (SEQ ID NO:100) | SMIFNFYFDV (SEQ ID NO:97) | KLQLRVGYMH (SEQ ID NO:98) | DTFYLAS (SEQ ID NO:99) | |
| | DIWWDGKKDYNPSLKD (SEQ ID NO:103) | | KLSLSVGYMH (SEQ ID NO:101) | DTSKLPS (SEQ ID NO:102) | |
| | DIWWDGKKHYNPSLKS (SEQ ID NO:106) | | KLSSSVGYMH (SEQ ID NO:104) | DTSGLAS (SEQ ID NO:105) | |
| | DIWWDDKKSYNPSLKS (SEQ ID NO:109) | | KLSSRVGYMH **(SEQ ID NO:107) | DTSGLPS (SEQ ID NO:108) | |
| | DIWWDDKKSYNPSLKD (SEQ ID NO:111) | | KLSLRVGYMH (SEQ ID NO:110) | DTRGLPS (SEQ ID NO:27) | |
| | DIWWDGKKSYNPSLKS (SEQ ID NO:114) | | KCSLSVGYMH (SEQ ID NO:112) | DTRKLAS (SEQ ID NO:113) | |
| | DIWWDGKKSYNPSLKD (SEQ ID NO:41) | | KCSSSVGYMH (SEQ ID NO:115) | DTRGLAS (SEQ ID NO:116) | |
| | | | KCSSRVGYMH (SEQ ID NO:117) | DTRKLPS (SEQ ID NO:118) | |
| | | | KCSLRVGYMH (SEQ ID NO:119) | DTMRLAS (SEQ ID NO:32) | |
| | | | SLSLSVGYMH (SEQ ID NO:120) | DTMKLAS (SEQ ID NO:121) | |
| | | | SLSSSVGYMH (SEQ ID NO:122) | DTSRLAS (SEQ ID NO:123) | |
| | | | SLSSRVGYMH (SEQ ID NO:22) | DTSLLAS (SEQ ID NO:124) | |
| | | | SLSLRVGYMH (SEQ ID NO:125) | DTSLLDS (SEQ ID NO:126) | |
| | | | SCQLSVGYMH (SEQ ID NO:127) | DTSKLDS (SEQ ID NO:128) | |
| | | | SCQSSVGYMH (SEQ ID NO:129) | DTLLLDS (SEQ ID NO:75) | |
| | | | SCQSRVGYMH (SEQ ID NO:130) | DTLKLDS (SEQ ID NO:131) | |
| | | | SCQLRVGYMH (SEQ ID NO:132) | DTLLLAS (SEQ ID NO:133) | |
| | | | SLQLSVGYMH (SEQ ID NO:134) | DTLKLAS (SEQ ID NO:135) | |
| | | | SLQSSVGYMH (SEQ ID NO:136) | DTSKLSS (SEQ ID NO:137) | |
| | | | SLQSRVGYMH (SEQ ID NO:138) | DTSKQAS (SEQ ID NO:139) | |
| | | | SLQLRVGYMH (SEQ ID NO:140) | DTSKQSS (SEQ ID NO:141) | |
| | | | SCSLSVGYMH (SEQ ID NO:142) | DTSYLAS (SEQ ID NO:143) | |
| | | | SCSSSVGYMH (SEQ ID NO:144) | DTSYLSS (SEQ ID NO:145) | |
| | | | SCSSRVGYMH (SEQ ID NO:146) | DTSYQAS (SEQ ID NO:147) | |

TABLE 3-continued

CDR Sequences

| VH CDR1 | VH CDR2 | VH CDR3 | VL CDR1 | VL CDR2 | VL CDR3 |
|---------|---------|---------|---------|---------|---------|
| | | | SCSLRVGYMH (SEQ ID NO:148) | DTSYQSS (SEQ ID NO:149) | |
| | | | KPSSRVGYMH (SEQ ID NO:150) | DTMYQAS (SEQID NO:151) | |
| | | | KPSLRVGYMH (SEQ ID NO:152) | DTMYQSS (SEQ ID NO:43) | |
| | | | KPSSSVGYMH (SEQ ID NO:153) | DTMKQAS (SEQ ID NO:154) | |
| | | | KPSLSVGYMH (SEQ ID NO:155) | DTMKQSS (SEQ ID NO:156) | |
| | | | KPQSRVGYMH (SEQ ID NO:157) | DTMYLAS (SEQ ID NO:158) | |
| | | | KPQLRVGYMH (SEQ ID NO:159) | DTMYLSS (SEQ ID NO:160) | |
| | | | KPQSSVGYMH (SEQ ID NO:161) | DTMKLAS (SEQ ID NO:162) | |
| | | | KPQLSVGYMH (SEQ ID NO:163) | DTMKLSS (SEQ ID NO:164) | |
| | | | SPSSRVGYMH (SEQ ID NO:31) | DTSKLSS (SEQ ID NO:165) | |
| | | | SPSLRVGYMH (SEQ ID NO:166) | DTRYQAS (SEQ ID NO:167) | |
| | | | SPSSSVGYMH (SEQ ID NO:168) | DTRYQSS (SEQ ID NO:53) | |
| | | | SPSLSVGYMH (SEQ ID NO:169) | DTRKQAS (SEQ ID NO:170) | |
| | | | SPQSRVGYMH (SEQ ID NO:171) | DTRKQSS (SEQ ID NO:172) | |
| | | | SPQLRVGYMH (SEQ ID NO:173) | DTRKLAS (SEQ ID NO:174) | |
| | | | SPQSSVGYMH (SEQ ID NO:175) | DTRKLSS (SEQ ID NO:176) | |
| | | | SPQLSVGYMH (SEQ ID NO:177) | DTRYLAS (SEQ ID NO:178) | |
| | | | KAQSRVGYMH (SEQ ID NO:179) | DTRYLSS (SEQ ID NO:59) | |
| | | | KAQLRVGYMH (SEQ ID NO:180) | DTFFLDS (SEQ ID NO:50) | |
| | | | KAQSSVGYMH (SEQ ID NO:181) | DTSFLDS (SEQ ID NO:77) | |
| | | | KAQLSVGYMH (SEQ ID NO:182) | | |
| | | | KASSRVGYMH (SEQ ID NO:183) | | |
| | | | KASLRVGYMH (SEQ ID NO:184) | | |
| | | | KASSSVGYMH (SEQ ID NO:185) | | |
| | | | KASLSVGYMH (SEQ ID NO:186) | | |

TABLE 3-continued

CDR Sequences

| VH CDR1 | VH CDR2 | VH CDR3 | VL CDR1 | VL CDR2 | VL CDR3 |
|---------|---------|---------|---------|---------|---------|
| | | | SASSRVGYMH (SEQ ID NO:39) | | |
| | | | SASLRVGYMH (SEQ ID NO:187) | | |
| | | | SASSSVGYMH (SEQ ID NO:14) | | |
| | | | SASLSVGYMH (SEQ ID NO:188) | | |
| | | | SAQSRVGYMH (SEQ ID NO:189) | | |
| | | | SAQLRVGYMH (SEQ ID NO:190) | | |
| | | | SAQSSVGYMH (SEQ ID NO:191) | | |
| | | | LPSSRVGYMH (SEQ ID NO:47) | | |
| | | | LPSLSVGYMH (SEQ ID NO:192) | | |
| | | | LPSSSVGYMH (SEQ ID NO:193) | | |
| | | | LPSLRVGYMH (SEQ ID NO:194) | | |
| | | | LCSSRVGYMH (SEQ ID NO:195) | | |
| | | | LCSLSVGYMH (SEQ ID NO:196) | | |
| | | | LCSSSVGYMH (SEQ ID NO:197) | | |
| | | | LCSLRVGYMH (SEQ ID NO:198) | | |
| | | | LPQSRVGYMH (SEQ ID NO:199) | | |
| | | | LPQLSVGYMH (SEQ ID NO:200) | | |
| | | | LPQSSVGYMH (SEQ ID NO:201) | | |
| | | | LPQLRVGYMH (SEQ ID NO:202) | | |
| | | | LCQSRVGYMH (SEQ ID NO:203) | | |
| | | | LCQLSVGYMH (SEQ ID NO:204) | | |
| | | | LCQSSVGYMH (SEQ ID NO:205) | | |
| | | | LCQLRVGYMH (SEQ ID NO:206) | | |
| | | | SAQLSVGYMH (SEQ ID NO:207) | | |

In one embodiment of the present invention, antibodies or fragments thereof comprise a VH CDR1 having the amino acid sequence of SEQ ID NO:1, SEQ ID NO:10 or SEQ ID NO:18. In another embodiment, antibodies or fragments thereof comprise a VH CDR2 having the amino acid sequence of SEQ ID NO:2, SEQ ID NO:19, SEQ ID NO:25, SEQ ID NO:37, SEQ ID NO:41 or SEQ ID NO:45. In another embodiment, antibodies comprise a VH CDR3 having the amino acid sequence of SEQ ID NO:3, SEQ ID NO:12, SEQ ID NO:20, SEQ ID NO:29 or SEQ ID NO:79. In a preferred embodiment, antibodies or fragments thereof comprise a VH CDR1 having the amino acid sequence of SEQ ID NO:1, SEQ ID NO:10 or SEQ ID NO:18, a VH CDR2 having the amino acid sequence of SEQ ID NO:2, SEQ ID NO:19, SEQ ID NO:25, SEQ ID NO:37 or SEQ ID NO:41, SEQ ID NO:45, and a VH CDR3 having the amino acid sequence of SEQ ID NO:3, SEQ ID NO:12, SEQ ID NO:20, SEQ ID NO:29 or SEQ ID NO:79.

The present invention also provides antibodies or fragments thereof that immunospecifically bind to one or more RSV antigens, said antibodies or antibody fragments comprising a variable light ("VL") domain having an amino acid sequence of any one of the VL domains listed in Table 2. The present invention also provides antibodies or fragments thereof that immunospecifically bind to one or more RSV antigens, said antibodies or fragments comprising a VL CDR having an amino acid sequence of any one of the VL CDRs listed in Table 2 and/or Table 3.

In one embodiment of the present invention, antibodies or fragments thereof comprise a VL CDR1 having the amino acid sequence of SEQ ID NO:4, SEQ ID NO:14, SEQ ID NO:22, SEQ ID NO:31, SEQ ID NO:39, or SEQ ID NO:47. In another embodiment, antibodies or fragments thereof comprise a VL CDR2 having the amino acid sequence of SEQ ID NO:5, SEQ ID NO:15, SEQ ID NO:23, SEQ ID NO:27, SEQ ID NO:32, SEQ ID NO:35, SEQ ID NO:43, SEQ ID NO:50, SEQ ID NO:53, SEQ ID NO:57, SEQ ID NO:59, SEQ ID NO:63, SEQ ID NO:66, SEQ ID NO:69, SEQ ID NO:73, SEQ ID NO:75 or SEQ ID NO:77. In another embodiment, antibodies or fragments thereof comprise a VL CDR3 having the amino acid sequence of SEQ ID NO:6, SEQ ID NO:16 or SEQ ID NO:61. In a preferred embodiment, antibodies or fragments thereof comprise a VL CDR1 having the amino acid sequence of SEQ ID NO:4, SEQ ID NO:14, SEQ ID NO:22, SEQ ID NO:31, SEQ ID NO:39, or SEQ ID NO:47, a VL CDR2 having the amino acid sequence of SEQ ID NO:5, SEQ ID NO:15, SEQ ID NO:23, SEQ ID NO:27, SEQ ID NO:32, SEQ ID NO:35, SEQ ID NO:43, SEQ ID NO:50, SEQ ID NO:53, SEQ ID NO:57, SEQ ID NO:59, SEQ ID NO:63, SEQ ID NO:66, SEQ ID NO:69, SEQ ID NO:73, SEQ ID NO:75 or SEQ ID NO:77, and a VL CDR3 having the amino acid sequence of SEQ ID NO:6, SEQ ID NO:16 or SEQ ID NO:61.

The present invention also provides antibodies or fragments thereof that immunospecifically bind to one or more RSV antigens, said antibodies or antibody fragments comprising a VH domain disclosed herein combined with a VL domain disclosed herein, or other VL domain. The present invention further provides antibodies or fragments thereof that immunospecifically bind to one or more RSV antigens, said antibodies or fragments comprising a VL domain disclosed herein combined with a VH domain disclosed herein, or other VH domain. In a preferred embodiment, antibodies or fragments thereof that immunospecifically bind to a RSV antigen comprise a VH domain having the amino acid sequence of SEQ ID NO:7, SEQ ID NO:9, SEQ ID NO:17, SEQ ID NO:24, SEQ ID NO:28, SEQ ID NO:33, SEQ ID NO:36, SEQ ID NO:40, SEQ ID NO:44, SEQ ID NO:48, SEQ ID NO:51, SEQ ID NO:55, SEQ ID NO:67 or SEQ ID NO:78 and a VL domain having the amino acid sequence of SEQ ID NO:8, SEQ ID NO:13, SEQ ID NO:21, SEQ ID NO:26, SEQ ID NO:30, SEQ ID NO:34, SEQ ID NO:38, SEQ ID NO:42, SEQ ID NO:46, SEQ ID NO:49, SEQ ID NO:52, SEQ ID NO:54, SEQ ID NO:56, SEQ ID NO:58, SEQ ID NO:60, SEQ ID NO:62, SEQ ID NO:64, SEQ ID NO:65, SEQ ID NO:68, SEQ ID NO:70, SEQ ID NO:71, SEQ ID NO:74 or SEQ ID NO:76.

The present invention also provides antibodies or fragments thereof comprising one or more VH CDRs and one or more VL CDRs listed in Table 2 and/or Table 3. In particular, the invention provides for an antibody or fragment thereof comprising a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof of the VH CDRs and VL CDRs listed in Table 2. The invention also provides for an antibody or fragment thereof comprising a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof of the VH CDRs and VL CDRs listed in Table 3. The invention also provides for an antibody or fragment thereof comprising a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof of the VH CDRs and VL CDRs listed in Table 2 and Table 3.

In one embodiment, an antibody or fragment thereof comprises a VH CDR1 having the amino acid sequence of SEQ ID NO:1, SEQ ID NO:10 or SEQ ID NO:18 and a VL CDR1 having the amino acid sequence of SEQ ID NO:4, SEQ ID NO:14, SEQ ID NO:22, SEQ ID NO:31, SEQ ID NO:39, or SEQ ID NO:47. In another embodiment, an antibody of the present invention or fragment thereof comprises a VH CDR1 having the amino acid sequence of SEQ ID NO:1, SEQ ID NO:10 or SEQ ID NO:18 and a VL CDR2 having the amino acid sequence of SEQ ID NO:5, SEQ ID NO:15, SEQ ID NO:23, SEQ ID NO:27, SEQ ID NO:32, SEQ ID NO:35, SEQ ID NO:43, SEQ ID NO:50, SEQ ID NO:53, SEQ ID NO:57, SEQ ID NO:59, SEQ ID NO:63, SEQ ID NO:66, SEQ ID NO:69, SEQ ID NO:73, SEQ ID NO:75, or SEQ ID NO:77. In another embodiment, an antibody of the present invention or fragment thereof comprises a VH CDR1 having the amino acid sequence of SEQ ID NO:1, SEQ ID NO:10 or SEQ ID NO:18 and a VL CDR3 having the amino acid sequence of SEQ ID NO:6, SEQ ID NO:16 or SEQ ID NO:61.

In another embodiment, an antibody of the present invention or fragment thereof comprises a VH CDR2 having the amino acid sequence of SEQ ID NO:2, SEQ ID NO:19, SEQ ID NO:25, SEQ ID NO:37, SEQ ID NO:41 or SEQ ID NO:45 and a VL CDR1 having the amino acid sequence of SEQ ID NO:4, SEQ ID NO:14, SEQ ID NO:22, SEQ ID NO:31, SEQ ID NO:39 or SEQ ID NO:47. In another embodiment, an antibody of the present invention or fragment thereof comprises a VH CDR2 having the amino acid sequence of SEQ ID NO:2, SEQ ID NO:19, SEQ ID NO:25, SEQ ID NO:37, SEQ ID NO:41 or SEQ ID NO:45 and a VL CDR2 having the amino acid sequence of SEQ ID NO:5, SEQ ID NO:15, SEQ ID NO:23, SEQ ID NO:27, SEQ ID NO:32, SEQ ID NO:35, SEQ ID NO:43, SEQ ID NO:50, SEQ ID NO:53, SEQ ID NO:57, SEQ ID NO:59, SEQ ID NO:63, SEQ ID NO:66, SEQ ID NO:69, SEQ ID NO:73, SEQ ID NO:75, or SEQ ID NO:77. In another embodiment, an antibody of the present invention or fragment thereof comprises a VH CDR2 having the amino acid sequence of SEQ ID NO:2, SEQ ID NO:19, SEQ ID NO:25, SEQ ID NO:37, SEQ ID NO:41 or SEQ ID NO:45 and a VL CDR3 having the amino acid sequence of SEQ ID NO:6, SEQ ID NO:16, or SEQ ID NO:61.

In another embodiment, an antibody of the present invention or fragment thereof comprises a VH CDR3 having the amino acid sequence of SEQ ID NO:3, SEQ ID NO:12, SEQ ID NO:20, SEQ ID NO:29 or SEQ ID NO:79 and a VL CDR1 having the amino acid sequence of SEQ ID NO:4, SEQ ID NO:14, SEQ ID NO:22, SEQ ID NO:31, SEQ ID NO:39 or SEQ ID NO:47. In another embodiment, an antibody of the present invention or fragment thereof comprises a VH CDR3 having the amino acid sequence of SEQ ID NO:3, SEQ ID NO:12, SEQ ID NO:20, SEQ ID NO:29 or SEQ ID NO:79 and a VL CDR having the amino acid sequence of SEQ ID NO:5, SEQ ID NO:15, SEQ ID NO:23, SEQ ID NO:27, SEQ ID NO:32, SEQ ID NO:35, SEQ ID NO:43, SEQ ID NO:50, SEQ ID NO:53, SEQ ID NO:57, SEQ ID NO:59, SEQ ID NO:63, SEQ ID NO:66, SEQ ID NO:69, SEQ ID NO:73, SEQ ID NO:75, or SEQ ID NO:77. In a preferred embodiment, an antibody of the present invention or fragment thereof comprises a VH CDR3 having the amino acid sequence of SEQ ID NO:3, SEQ ID NO:12, SEQ ID NO:20, SEQ ID NO:29 or SEQ ID NO:79 and a VL CDR3 having the amino acid sequence of SEQ ID NO:6, SEQ ID NO:16, or SEQ ID NO:61.

The present invention also provides for nucleic acid molecules, generally isolated, encoding an antibody of the invention or fragment thereof. In a specific embodiment, isolated nucleic acid molecules of the invention encode for SYNAGIS®, AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S. Preferably, isolated nucleic acid molecules of the invention encode for AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L-1-7E5, L2-15B10, A13a11, A1h5, A4B4 (1), A4B4L1FR-S28R, or A4B4-F52S. In another embodiment, isolated nucleic acid molecules of the invention encode for an antigen-binding fragment of SYNAGIS®, AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S.

In another embodiment, an isolated nucleic acid molecule(s) of the invention encodes an antibody or fragment thereof comprising a VH domain having an amino acid sequence of any one of the VH domains listed in Table 2. In another embodiment, an isolated nucleic acid molecule(s) of the invention encodes an antibody or fragment thereof comprising a VH CDR1 having an amino acid sequence of any one of the VH CDR1s listed in Table 2 or Table 3. In another embodiment, an isolated nucleic acid molecule(s) of the invention encodes an antibody or fragment thereof comprising a VH CDR2 having an amino acid sequence of any one of the VH CDR2s listed in Table 2 or Table 3 In yet another embodiment, an isolated nucleic acid molecule(s) of the invention encodes an antibody or fragment thereof comprising a VH CDR3 having an amino acid sequence of any one of the VH CDR3s listed in Table 2 or Table 3.

In another embodiment, an isolated nucleic acid molecule(s) of the invention encodes an antibody or fragment thereof comprising a VL domain having an amino acid sequence of any one of the VL domains listed in Table 2. In another embodiment, an isolated nucleic acid molecule(s) of the present invention encodes an antibody or fragment thereof comprising a VL CDR1 having amino acid sequence of any one of the VL CDR1s listed in Table 2 or Table 3. In another embodiment, an isolated nucleic acid molecule(s) of the present invention encodes an antibody or fragment thereof comprising a VL CDR2 having an amino acid sequence of any one of the VL CDR2s listed in Table 2 or Table 3. In yet another embodiment, an isolated nucleic acid molecule(s) of the present invention encodes an antibody or fragment thereof comprising a VL CDR3 having an amino acid sequence of any one of the VL CDR3s listed in Table 2 or Table 3.

In another embodiment, a nucleic acid molecule(s) of the invention encodes an antibody or fragment thereof comprising a VH domain having an amino acid sequence of any one of the VH domains listed in Table 2 and a VL domain having an amino acid sequence of any one of the VL domains listed in Table 2. In another embodiment, a nucleic acid molecule(s) of the invention encodes an antibody or fragment thereof comprising a VH CDR1, a VL CDR1, a VH CDR2, a VL CDR2, a VH CDR3, a VL CDR3, or any combination thereof having an amino acid sequence listed in Table 2. In another embodiment, a nucleic acid molecule(s) of the invention encodes an antibody or fragment thereof comprising a VH CDR1, a VL CDR1, a VH CDR2, a VL CDR2, a VH CDR3, a VL CDR3, or any combination thereof having an amino acid sequence listed in Table 3. In another embodiment, a nucleic acid molecule(s) of the invention encodes an antibody or fragment thereof comprising a VH CDR1, a VL CDR1, a VH CDR2, a VL CDR2, a VH CDR3, a VL CDR3, or any combination thereof having an amino acid sequence listed in Table 2 and Table 3.

The present invention also provides antibodies or fragments thereof comprising derivatives of the VH domains, VH CDRs, VL domains, and VL CDRs described herein that immunospecifically bind to an RSV antigen. The present invention also provides antibodies or fragments thereof comprising derivatives of SYNAGIS®, AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S, wherein said antibodies or fragments thereof immunospecifically bind to one or more RSV antigens. Standard techniques known to those of skill in the art can be used to introduce mutations in the nucleotide sequence encoding a molecule of the invention, including, for example, site-directed mutagenesis and PCR-mediated mutagenesis which results in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In a specific embodiment, an antibody or fragment thereof that immunospecifically binds to a RSV antigen comprises a nucleotide sequence that hybridizes to the nucleotide sequence(s) encoding SYNAGIS®, AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S under stringent conditions, e.g., hybridization to filter-bound DNA in 6× sodium chloride/sodium citrate (SSC) at about 45 C followed by one or more washes in 0.2×SSC/0.1% SDS at about 50-65 C, under highly stringent conditions, e.g., hybridization to filter-bound nucleic acid in 6×SSC at about 45 C followed by one or more washes in 0.1×SSC/0.2% SDS at about 68 C, or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3).

In another embodiment, an antibody or fragment thereof that immunospecifically binds to a RSV antigen comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of SYNAGIS®, AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S.

In a specific embodiment, an antibody or fragment thereof that immunospecifically binds to a RSV antigen comprises an amino acid sequence of a VH domain or an amino acid sequence a VL domain encoded by a nucleotide sequence that hybridizes to the nucleotide sequence encoding any one of the VH or VL domains listed in Table 2 under stringent conditions, e.g., hybridization to filter-bound DNA in 6× sodium chloride/sodium citrate (SSC) at about 45 C followed by one or more washes in 0.2×SSC/0.1% SDS at about 50-65 C, under highly stringent conditions, e.g., hybridization to filter-bound nucleic acid in 6×SSC at about 45 C followed by one or more washes in 0.1×SSC/0.2% SDS at about 68 C, or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3). In another embodiment, an antibody or fragment thereof that immunospecifically binds to a RSV antigen comprises an amino acid sequence of a VH CDR or an amino acid sequence of a VL CDRs encoded by a nucleotide sequence that hybridizes to the nucleotide sequence encoding any one of the VH CDRs or VL CDRs listed in Table 2 or Table 3 under stringent conditions e.g., hybridization to filter-bound DNA in 6× sodium chloride/sodium citrate (SSC) at about 45 C followed by one or more washes in 0.2×SSC/0.1% SDS at about 50-65 C, under highly stringent conditions, e.g., hybridization to filter-bound nucleic acid in 6×SSC at about 45 C followed by one or more washes in 0.1×SSC/0.2% SDS at about 68 C, or under other stringent hybridization conditions which are known to those of skill in the art. In yet another embodiment, an antibody or fragment thereof that immunospecifically binds to a RSV antigen comprises an amino acid sequence of a VH CDR and an amino acid sequence of a VL CDR encoded by nucleotide sequences that hybridizes to the nucleotide sequences encoding any one of the VH CDRs and VL CDRs, respectively, listed in Table 2 or Table 3 under stringent conditions, e.g., hybridization to filter-bound DNA in 6× sodium chloride/sodium citrate (SSC) at about 45 C followed by one or more washes in 0.2×SSC/0.1% SDS at about 50-65 C, under highly stringent conditions, e.g., hybridization to filter-bound nucleic acid in 6×SSC at about 45 C followed by one or more washes in 0.1×SSC/0.2% SDS at about 68 C, or under other stringent hybridization conditions which are known to those of skill in the art.

In another embodiment, an antibody or fragment thereof that immunospecifically binds to a RSV antigen comprises an amino acid sequence of a VH domain that is at least 35%, at least 40%, at least 45%, at least 50%, at least 55%, at least 60%, at least 65%, at least 70%, at least 75%, at least 80%, at least 85%, at least 90%, at least 95%, or at least 99% identical to any one of the VH domains listed in Table 2. In another embodiment, an antibody or fragment thereof that immunospecifically binds to a RSV antigen comprises an amino acid sequence of one or more VH CDRs that are at least 35%, at least 40%, at least 45%, at least 50%, at least 55%, at least 60%, at least 65%, at least 70%, at least 75%, at least 80%, at least 85%, at least 90%, at least 95%, or at least 99% identical to any of the VH CDRs listed in Table 2 or Table 3.

In another embodiment, an antibody or fragment thereof that immunospecifically binds to a RSV antigen comprises an amino acid sequence of a VL domain that is at least 35%, at least 40%, at least 45%, at least 50%, at least 55%, at least 60%, at least 65%, at least 70%, at least 75%, at least 80%, at least 85%, at least 90%, at least 95%, or at least 99% identical to any one of the VL domains listed in Table 2. In another embodiment, an antibody or fragment thereof that immunospecifically binds to a RSV antigen comprises an amino acid sequence of one or more VL CDRs that are at least 35%, at least 40%, at least 45%, at least 50%, at least 55%, at least 60%, at least 65%, at least 70%, at least 75%, at least 80%, at least 85%, at least 90%, at least 95%, or at least 99% identical to any of the VL CDRs listed in Table 2 or Table 3.

In another embodiment, an antibody or fragment thereof that immunospecifically binds to a RSV antigen comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence of SYNAGIS®, AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S The present invention also encompasses antibodies or fragments thereof that compete with an antibody or Fab fragment listed in Table 2 for binding to a RSV antigen. In particular, the present invention encompasses antibodies or fragments thereof that compete with SYNAGIS® or an antigen-binding fragment thereof for binding to the RSV F glycoprotein. The present invention also encompasses VL domains, VH domains, VL CDRs, and VH CDRs that compete with a VL domain, VH domain, VL CDR, or VH CDR listed in Table 2 for binding to a RSV antigen. Further, the present invention encompasses VL CDRs and VL CDRs that compete with a VL CDR or VH CDR listed in Table 3 for binding to a RSV antigen.

The present invention encompasses single domain antibodies, including camelised single domain antibodies. The present invention provides single domain antibodies comprising two VH domains having the amino acid sequence of any of the VH domains listed in Table 2 with modifications such that single domain antibodies are formed. The present invention also provides single domain antibodies comprising two VH domains comprising one or more of the VH CDRs listed in Table 2 or Table 3.

The antibodies of the invention include derivatives that are modified, i.e, by the covalent attachment of any type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The present invention also provides antibodies of the invention or fragments thereof that comprise a framework region known to those of skill in the art. Preferably, the framework region of an antibody of the invention or fragment thereof is human. In a specific embodiment, an antibody of the invention or fragment thereof comprises the framework region of SYNAGIS®.

The present invention also provides antibodies of the invention or fragments thereof that comprise constant regions known to those of skill in the art. Preferably, the constant regions of an antibody of the invention or fragment thereof are human. In a specific embodiment, an antibody of the invention or fragment thereof comprises the constant regions of SYNAGIS®.

The present invention also provides for antibodies or fragments thereof that have half-lives in a mammal, preferably a human, of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present invention or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor (see, e.g., PCT Publication No. WO 97/34631, which is incorporated herein by reference in its entirety). Such antibodies or fragments thereof can be tested for binding activity to RSV antigens as well as for in vivo efficacy using methods known to those skilled in the art, for example, by immunoassays described herein.

Further, antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography. PEG-derivatizated antibodies or fragments thereof can be tested for binding activity to RSV antigens as well as for in vivo efficacy using methods known to those skilled in the art, for example, by immunoassays described herein.

The present invention also encompasses antibodies or fragments thereof which immunospecifically bind to one or more RSV antigens, said antibodies or antibody fragments comprising the amino acid sequence of SYNAGIS® with mutations (e.g., one or more amino acid substitutions) in the framework regions. In certain embodiments, antibodies or fragments thereof which immunospecifically bind to one or more RSV antigens comprise the amino acid sequence of SYNAGIS® with one or more amino acid residue substitutions in the framework regions of the VH and/or VL domains depicted in FIG. 1. In a specific embodiment, antibodies or fragments thereof which immunospecifically bind to one or more RSV antigens comprise the framework regions depicted in FIG. 2.

The present invention also encompasses antibodies or fragments thereof which immunospecifically bind to one or more RSV antigens, said antibodies or fragments thereof comprising the amino acid sequence of SYNAGIS® with mutations (e.g., one or more amino acid residue substitutions) in the variable and framework regions.

The present invention provides for fusion proteins comprising an antibody or fragment thereof that immunospecifically binds to a RSV antigen and a heterologous polypeptide. Preferably, the heterologous polypeptide that the antibody or antibody fragment is fused to is useful for targeting the antibody to respiratory epithelial cells.

The present invention provides peptides, polypeptides and/or proteins comprising one or more variable or hypervariable regions of the antibodies described herein. Preferably, peptides, polypeptides or proteins comprising one or more variable or hypervariable regions of antibodies of the invention further comprise a heterologous amino acid sequence. In certain embodiments, such a heterologous amino acid sequence comprises at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 40 contiguous amino acid residues, at least 50 contiguous amino acid residues, at least 75 contiguous amino acid residues, at least 100 contiguous amino acid residues or more contiguous amino acid residues. Such peptides, polypeptides and/or proteins may be referred to as fusion proteins.

In a specific embodiment, peptides, polypeptides or proteins comprising one or more variable or hypervariable regions of the antibodies of the invention are 10 amino acid residues, 15 amino acid residues, 20 amino acid residues, 25 amino acid residues, 30 amino acid residues, 35 amino acid residues, 40 amino acid residues, 45 amino acid residues, 50 amino acid residues, 75 amino acid residues, 100 amino acid residues, 125 amino acid residues, 150 amino acid residues or more amino acid residues in length. In certain embodiments, peptides, polypeptides, or proteins comprising one or more variable or hypervariable regions of an antibody of the invention immunospecifically bind to a RSV antigen. In other embodiments, peptides, polypeptides, or proteins comprising one or more variable or hypervariable regions of an antibody of the invention do not immunospecifically bind to a RSV antigen. In yet other embodiments, the variable or hypervariable regions of an antibody which comprise peptides, polypeptides, or proteins are not the variable or hypervariable regions of SYNAGIS®.

In a specific embodiment, the present invention provides peptides, polypeptides and/or proteins comprising a VH domain and/or VL domain of one of the antibodies described herein (see Table 2). In a preferred embodiment, the present invention provides peptides, polypeptides and/or proteins comprising one or more CDRs having the amino acid sequence of any of the CDRs listed in Table 2 or Table 3. In accordance with these embodiments, the peptides, polypeptides or proteins further comprise a heterologous amino acid sequence.

Peptides, polypeptides or proteins comprising one or more variable or hypervariable regions have utility, e.g., in the production of anti-idiotypic antibodies that in turn may be used to treat or ameliorate one or more symptoms associated with a RSV infection. The anti-idiotypic antibodies produced can also be utilized in immunoassays, such as, e.g., ELISAs, for the detection of antibodies which comprise a variable or hypervariable region contained in the peptide, polypeptide or protein used in the production of the anti-idiotypic antibodies.

The present invention also provides for panels of antibodies or fragments thereof that immunospecifically bind to an RSV antigen. In specific embodiments, the invention provides for panels of antibodies or fragments thereof having different affinities for an RSV antigen, different specificities for an RSV antigen, or different dissociation rates. The invention provides panels of at least 10, preferably at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, or at least 1000 antibodies or fragments thereof. Panels of antibodies can be used, for example, in 96 well plates for assays such as ELISAs.

The present invention further provides for compositions comprising one or more antibodies of the invention or fragments thereof. In a specific embodiment, a composition of the present invention comprises SYNAGIS®, AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, and/or A4B4-F52S. In another specific embodiment, a composition of the present invention comprises an antigen-binding fragment of SYNAGIS®, AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S.

In another embodiment, a composition of the present invention comprises one or more antibodies or fragments thereof comprising one or more VH domains having an amino acid sequence of any one of the VH domains listed in Table 2. In another embodiment, a composition of the present invention comprises one or more antibodies or fragments thereof comprising one or more VH CDR1s having an amino acid sequence of any one of the VH CDR1s listed in Table 2 or Table 3. In another embodiment, a composition of the present invention comprises one or more antibodies or fragments thereof comprising one or more VH CDR2s having an amino acid sequence of any one of the VH CDR2s listed in Table 2 or Table 3. In a preferred embodiment, a composition of the present invention comprises one or more antibodies or fragments thereof comprising one or more VH CDR3s having an amino acid sequence of any one of the VH CDR3s listed in Table 2 or Table 3.

In another embodiment, a composition of the present invention comprises one or more antibodies or fragments thereof comprising one or more VL domains having an amino acid sequence of any one of the VL domains listed in Table 2. In another embodiment, a composition of the present invention comprises one or more antibodies or fragments thereof comprising one or more VL CDR1s having an amino acid sequence of any one of the VH CDR1s listed in Table 2 or Table 3. In another embodiment, a composition of the present invention comprises one or more antibodies or fragments thereof comprising one or more VL CDR2s having an amino acid sequence of any one of the VL CDR2s listed in Table 2 or Table 3. In a preferred embodiment, a composition of the present invention comprises one or more antibodies or fragments thereof comprising one or more VL CDR3s having an amino acid sequence of any one of the VL CDR3s listed in Table 2 or Table 3.

In another embodiment, a composition of the present invention comprises one or more antibodies or fragments thereof comprising one or more VH domains having an amino acid sequence of any one of the VH domains listed in Table 2 and one or more VL domains having an amino acid sequence of any one of the VL domains listed in Table 2. In another embodiment, a composition of the present invention comprises one or more antibodies or fragments thereof comprising one or more VH CDR1s having an amino acid sequence of any one of the VH CDR1s listed in Table 2 or Table 3 and one or more VL CDR1s having an amino acid sequence of any one of the VL CDR1s listed in Table 2 or Table 3. In another embodiment, a composition of the present invention comprises one or more antibodies or fragments thereof comprising one or more VH CDR1s having an amino acid sequence of any one of the VH CDR1s listed in Table 2 or Table 3 and one or more VL CDR2s having an amino acid sequence of any one of the VL CDR2s listed in Table 2 or Table 3. In another embodiment, a composition of the present invention comprises one or more antibodies or fragments thereof comprising one or more VH CDR1s having an amino acid sequence of any one of the VH CDR1s listed in Table 2 or Table 3 and one or more VL CDR3s having an amino acid sequence of any one of the VL CDR3s listed in Table 2 or Table 3.

In another embodiment, a composition of the present invention comprises one or more antibodies or fragments thereof comprising one or more VH CDR2s having an amino acid sequence of any one of the VH CDR2s listed in Table 2 or Table 3 and one or more VL CDR1s having an amino acid sequence of any one of the VL CDR1s listed in Table 2 or Table 3. In another embodiment, a composition of the present invention comprises one or more antibodies or fragments thereof comprising one or more VH CDR2s having an amino acid sequence of any one of the VH CDR2s listed in Table 2 or Table 3 and one or more VL CDR2s having an amino acid sequence of any one of the VL CDR2s listed in Table 2 or Table 3. In another embodiment, a composition of the present invention comprises one or more antibodies or fragments thereof comprising one or more VH CDR2s having an amino acid sequence of any one of the VH CDR2s listed in Table 2 or Table 3 and one or more VL CDR3s having an amino acid sequence of any one of the VL CDR3s listed in Table 2 or Table 3.

In another embodiment, a composition of the present invention comprises one or more antibodies or fragments thereof comprising one or more VH CDR3s having an amino acid sequence of any one of the VH CDR3s listed in Table 2 or Table 3 and one or more VL CDR1s having an amino acid sequence of any one of the VL CDR1s listed in Table 2 or Table 3. In another embodiment, a composition of the present invention comprises one or more antibodies or fragments thereof comprising one or more VH CDR3s having an amino acid sequence of any one of the VH CDR3s listed in Table 2 or Table 3 and one or more VL CDR2s having an amino acid sequence of any one of the VL CDR2s listed in Table 2 or Table 3. In a preferred embodiment, a composition of the present invention comprises one or more antibodies or fragments thereof comprising one or more VH CDR3s having an amino acid sequence of any one of the VH CDR3s listed in Table 2 or Table 3 and one or more VL CDR3s having an amino acid sequence of any one of the VL CDR3s listed in Table 2 or Table 3.

In a specific embodiment, a composition of the invention comprises one or more antibodies or fragments thereof that compete with SYNAGIS®, AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, and/or A4B4-F52S for immunospecific binding to a RSV F glycoprotein or a fragment thereof. In another embodiment, a composition of the invention comprises one or more antibodies or fragments thereof that compete with a VH domain and/or VL domain of SYNAGIS®, AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, and/or A4B4-F52S for immunospecific binding to a RSV F glycoprotein or fragment thereof.

In a specific embodiment, a composition of the present invention comprises one or more fusion proteins of the invention. In a particular embodiment, a composition of the invention comprises one or more peptides, polypeptides, or proteins comprising a variable or hypervariable region of an antibody of the invention. In another embodiment, a composition of the invention comprises one or more peptides, polypeptides, or proteins comprising a VH domain or VL domain of an antibody of the invention. In a preferred embodiment, a composition of the invention comprises one or more peptides, polypeptides or proteins comprising one or more CDRs having the amino acid sequence of any of the CDRs listed in Table 2 or Table 3. In accordance with these embodiments, the peptides, polypeptides, and proteins further comprise a heterologous amino acid sequence.

As discussed in more detail below, a composition of the invention may be used either alone or in combination with other compositions. The antibodies or fragments thereof may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP396,387.

Antibodies of the present invention or fragments thereof may be used, for example, to purify, detect, and target RSV antigens, in both in vitro and in vivo diagnostic and therapeutic methods. For example, the antibodies or fragments have use in immunoassays for qualitatively and quantitatively measuring levels of the RSV in biological samples such as sputum. See, e.g., Harlow et al., Antibodies: A Laboratory Manual, (Cold Spring Harbor Laboratory Press, 2nd ed. 1988) (incorporated by reference herein in its entirety).

5.1.1. Antibody Conjugates

The present invention encompasses antibodies or fragments thereof recombinantly fused or chemically conjugated (including both covalently and non-covalently conjugations) to a heterologous polypeptide (or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. For example, antibodies may be used to target heterologous polypeptides to particular cell types (e.g., respiratory epithelial cells), either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., PCT publication WO 93/21232; EP439,095; Naramura et al., Immunol. Lett. 39:91-99 (1994); U.S. Pat. No. 5,474,981; Gillies et al., PNAS 89:1428-1432 (1992); and Fell et al., J. Immunol. 146:2446-2452 (1991), which are incorporated by reference in their entireties.

In one embodiment, a fusion protein of the invention comprises SYNAGIS®, AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S and a heterologous polypeptide. In another embodiment, a fusion protein of the invention comprises an antigen-binding fragment of SYNAGIS®, AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S and a heterologous polypeptide. In another embodiment, a fusion protein of the invention comprises one or more VH domains having the amino acid sequence of any one of the VH domains listed in Table 2 or one or more VL domains having the amino acid sequence of any one of the VL domains listed in Table 2 and a heterologous polypeptide. In another embodiment, a fusion protein of the present invention comprises one or more VH CDRs having the amino acid sequence of any one of the VH CDRs listed in Table 2 or Table 3 and a heterologous polypeptide. In another embodiment, a fusion protein comprises one or more VL CDRs having the amino acid sequence of any one of the VL CDRs listed in Table 2 or Table 3 and a heterologous polypeptide. In another embodiment, a fusion protein of the invention comprises at least one VH domain and at least one VL domain listed in Table 2 and a heterologous polypeptide. In yet another embodiment, a fusion protein of the invention comprises at least one VH CDR and at least one VL CDR domain listed in Table 2 or Table 3 and a heterologous polypeptide.

The present invention further includes compositions comprising heterologous polypeptides fused or conjugated to antibody fragments. For example, the heterologous polypeptides may be fused or conjugated to a Fab fragment, Fd fragment, Fv fragment, F(ab)$_2$ fragment, or portion thereof. Methods for fusing or conjugating epitope polypeptides to antibody portions are known in the art. See, e.g., U.S. Pat. Nos. 5,336, 603, 5,622,929, 5,359,046, 5,349,053, 5,447,851, and 5,112, 946; EP307,434; EP367,166; PCT publication Nos. WO 96/04388 and WO 91/06570; Ashkenazi et al., Proc. Natl. Acad. Sci. USA 88: 10535-10539 (1991); Zheng et al., J. Immunol. 154:5590-5600 (1995); and Vil et al., Proc. Natl. Acad. Sci. USA 89:11337-11341(1992) (said references incorporated by reference in their entireties).

Additional fusion proteins of the invention may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834, 252; and 5,837,458, and Patten et al., Curr. Opinion Biotechnol. 8:724-33 (1997); Harayama, Trends Biotechnol. 16(2): 76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, antibodies or fragments thereof, or the encoded antibodies or fragments thereof, may be altered by being subjected to random mutagenesis by error-prone PCR, random nucleotide insertion or other methods prior to recombination. In another embodiment, one or more portions of a polynucleotide encoding an antibody or antibody fragment, which portions immunospecifically bind to a RSV antigen may be recombined with one or more components, motifs, sections, parts, domains, fragments, etc. of one or more heterologous molecules.

Moreover, the antibodies of the present invention or fragments thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

The present invention further encompasses antibodies or fragments thereof conjugated to a diagnostic or therapeutic agent. The antibodies can be used diagnostically to, for example, monitor the development or progression of a RSV infection as part of a clinical testing procedure to, e.g., determine the efficacy of a given treatment regimen. Detection can be facilitated by coupling the antibody or fragment thereof to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, an antibody or fragment thereof may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567-1574), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Techniques for conjugating such therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

An antibody or fragment thereof, with or without a therapeutic moiety conjugated to it, administered alone or in combination with cytotoxic factor(s) and/or cytokine(s) can be used as a therapeutic.

Alternatively, an antibody can be conjugated to a second antibody to form an antibody heteroconjugate as described by Segal in U.S. Pat. No. 4,676,980, which is incorporated herein by reference in its entirety.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.2. Prophylactic and Therapeutic uses of ANTIBODIES

The present invention is directed to antibody-based therapies which involve administering antibodies of the invention or fragments thereof to a mammal, preferably a human, for preventing, treating, or ameliorating one or more symptoms associated with a RSV infection. Prophylactic and therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). Antibodies of the invention or fragments thereof may be provided in pharmaceutically acceptable compositions as known in the art or as described herein.

Antibodies of the present invention or fragments thereof that function as antagonists of a RSV infection can be administered to a mammal, preferably a human, to treat, prevent or ameliorate one or more symptoms associated with a RSV infection. For example, antibodies or fragments thereof which disrupt or prevent the interaction between a RSV antigen and its host cell receptor may be administered to a mammal, preferably a human, to treat, prevent or ameliorate one or more symptoms associated with a RSV infection.

In a specific embodiment, an antibody or fragment thereof prevents RSV from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to RSV binding to its host cell receptor in the absence of said antibodies or antibody fragments. In another embodiment, a combination of antibodies, a combination of antibody fragments, or a combination of antibodies and antibody fragments prevent RSV from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to RSV binding to its host cell receptor in the absence of said antibodies and/or antibody fragments.

Antibodies or fragments thereof which do not prevent RSV from binding its host cell receptor but inhibit or downregulate RSV replication can also be administered to a mammal to treat, prevent or ameliorate one or more symptoms associated with a RSV infection. The ability of an antibody or fragment thereof to inhibit or downregulate RSV replication may be determined by techniques described herein or otherwise known in the art. For example, the inhibition or downregulation of RSV replication can be determined by detecting the RSV titer in the lungs of a mammal, preferably a human.

In a specific embodiment, an antibody of the present invention or fragment thereof inhibits or downregulates RSV replication by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to RSV replication in absence of said antibodies or antibody fragments. In another embodiment, a combination of antibodies, a combination of antibody fragments, or a combination of antibodies and antibody fragments inhibit or downregulate RSV replication by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to RSV replication in absence of said antibodies and/or antibody fragments.

One or more antibodies of the present invention or fragments thereof that immunospecifically bind to one or more RSV antigens may be used locally or systemically in the body as a therapeutic. The antibodies of this invention or fragments thereof may also be advantageously utilized in combination with other monoclonal or chimeric antibodies, or with lymphokines or hematopoietic growth factors (such as, e.g., IL-2, IL-3 and IL-7), which, for example, serve to increase the number or activity of effector cells which interact with the antibodies. The antibodies of this invention or fragments thereof may also be advantageously utilized in combination with other monoclonal or chimeric antibodies, or with lymphokines or hematopoietic growth factors (such as, e.g., IL-2, IL-3 and IL-7), which, for example, serve to increase the immune response. The antibodies of this invention or fragments thereof may also be advantageously utilized in combination with one or more drugs used to treat RSV infection such as, for example anti-viral agents. Antibodies of the invention or fragments may be used in combination with one or more of the following drugs: NIH-351 (Gemini Technologies), recombinant RSV vaccine (Aviron), RSVf-2 (Intracel), F-50042 (Pierre Fabre), T-786 (Trimeris), VP-36676 (ViroPharma), RFI-641 (American Home Products), VP-14637 (ViroPharma), PFP-1 and PFP-2 (American Home Products), RSV vaccine (Avant Immunotherapeutics), and F-50077 (Pierre Fabre). The antibodies of the invention or fragments thereof may be used in combination with other agents as described in, e.g., International Publication Nos. WO 01/64248 and WO 01/82966, each of which is incorporated herein by reference in its entirety.

The antibodies of the invention may be administered alone or in combination with other types of treatments (e.g., hormonal therapy, immunotherapy, and anti-inflammatory agents). Generally, administration of products of a species origin or species reactivity (in the case of antibodies) that is the same species as that of the patient is preferred. Thus, in a preferred embodiment, human or humanized antibodies, fragments derivatives, analogs, or nucleic acids, are administered to a human patient for therapy or prophylaxis.

It is preferred to use high affinity and/or potent in vivo inhibiting antibodies and/or neutralizing antibodies that immunospecifically bind to a RSV antigen, for both immunoassays directed to RSV, prevention of RSV infection and therapy for RSV infection. It is also preferred to use polynucleotides encoding high affinity and/or potent in vivo inhibiting antibodies and/or neutralizing antibodies that immunospecifically bind to a RSV antigen, for both immunoassays directed to RSV and therapy for RSV infection.

Such antibodies or fragments thereof will preferably have an affinity for the RSV F glycoprotein and/or fragments of the F glycoprotein.

In one embodiment, therapeutic or pharmaceutical compositions comprising antibodies of the invention or fragments thereof are administered to a mammal, preferably a human, to treat, prevent or ameliorate one or more symptoms associated with RSV infection. In another embodiment, therapeutic or pharmaceutical compositions comprising antibodies of the invention or fragments thereof are administered to a human with cystic fibrosis, chronic lung disease (e.g., bronchopulmonary dysplasia), congenital heart disease, congenital immunodeficiency or acquired immunodeficiency, to a human who has had a stem cell transplant, or to a human who has had a bone marrow transplant to treat, prevent or ameliorate one or more symptoms associated with RSV infection. In another embodiment, therapeutic or pharmaceutical compositions comprising antibodies of the invention or fragments thereof are administered to a human infant, preferably a human infant born prematurely or a human infant at risk of hospitalization for RSV infection to treat, prevent or ameliorate one or more symptoms associated with RSV infection. In yet another embodiment, therapeutic or pharmaceutical compositions comprising antibodies of the invention or fragments thereof are administered to the elderly or people in group homes (e.g., nursing homes or rehabilitation centers).

In a specific embodiment, a mammal, preferably a human, is administered a therapeutic or pharmaceutical composition comprising one or more antibodies of the present invention or fragments thereof for the treatment, prevention or amelioration of one or more symptoms associated with a RSV infection in an amount effective for decreasing RSV titers. In accordance with this embodiment, an effective amount of antibodies or antibody fragments reduces the RSV titers in the lung as measured, for example, by the concentration of RSV in sputum samples or a lavage from the lungs from a mammal. In another embodiment, a mammal, preferably a human, is administered a therapeutic or pharmaceutical composition comprising one or more antibodies of the present invention or fragments thereof for the treatment, prevention or amelioration of symptoms associated with a RSV infection in an amount effective for inducing an immune response in the mammal.

In another embodiment, a mammal, preferably a human, is administered a first dose of a therapeutic or pharmaceutical composition comprising less than 15 mg/kg, preferably less than 10 mg/kg, less than 5 mg/kg, less than 3 mg/kg, less than 1 mg/kg or less than 0.5 mg/kg of one or more antibodies or fragments thereof that immunospecifically bind to one or more RSV antigens with higher affinity and/or higher avidity than previously known antibodies (e.g., SYNAGIS®) for the prevention, treatment or amelioration of one or more symptoms associated with a RSV infection in an amount effective to induce a serum titer of at least 1 µg/ml, preferably at least 2 µg/ml, at least 5 µg/ml, at least 10 µg/ml, at least 15 µg/ml, at least 20 µg/ml, or at least 25 µg/ml 20 days (preferably 25, 30, 35, 40 days) after the administration of the first dose and prior to the administration of a subsequent dose. Preferably, the serum titer of said antibodies or antibody fragments is less than 30 µg/ml 30 days after the administration of the first dose and prior to the administration of a subsequent dose. Preferably, said antibodies are AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, and A4B4-F52S In another embodiment, a mammal, preferably a human, is administered a first dose of a therapeutic or pharmaceutical composition comprising less than 15 mg/kg, preferably less than 5 mg/kg, less than 3 mg/kg, less than 1 mg/kg or less than 0.5 mg/kg of one or more antibodies or fragments thereof which have increased in vivo half-lives and which immunospecifically bind to one or more RSV antigens with higher affinity and/or higher avidity than previously known antibodies (e.g., SYNAGIS®) for the prevention, treatment or amelioration of one or more symptoms associated with a RSV infection in an amount effective to induce a serum titer of at least 1 µg/ml, preferably at least 2 µg/ml, at least 5 µg/ml, at least 10 µg/ml, at least 15 µg/ml, at least 20 µg/ml, or at least 25 µg/ml 25 days (preferably 30, 35, or 40 days) after the administration of the first dose and prior to the administration of a subsequent dose. Preferably, the serum titer of said antibodies or antibody fragments is less than 30 µg/ml 30 days after the administration of the first dose and prior to the administration of a subsequent dose. Preferably, the novel antibodies are AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, and A4B4-F52S.

In another embodiment, a mammal, preferably a human, is administered a first dose of a therapeutic or pharmaceutical composition comprising approximately 15 mg/kg of HL-SYNAGIS or antigen-binding fragments thereof for the prevention, treatment or amelioration of one or more symptoms associated with a RSV infection in an amount effective to induce a serum titer of at least 1 µg/ml, preferably at least 30 µg/ml, at least 35 µg/ml, at least 40 µg/ml, or at least 50 µg/ml 25 days (preferably 30, 35, or 40 days) after the administration of the first dose and prior to the administration of a subsequent dose. In another embodiment, a mammal, preferably a human, is administered a first dose of a therapeutic or pharmaceutical composition comprising less than 15 mg/kg (preferably 10 mg/kg or less, 5 mg/kg or less, 3 mg/kg or less, 1 mg/kg or less, or 0.5 mg/kg or less) of HL-SYNAGIS or antigen-binding fragments thereof for the prevention, treatment or amelioration of one or more symptoms associated with a RSV infection in an amount effective to induce a serum titer of at least 1 µg/ml, preferably at least 30 µg/ml, at least 35 µg/ml, at least 40 µg/ml, or at least 50 µg/ml 25 days (preferably 30, 35, or 40 days) after the administration of the first dose and prior to the administration of a subsequent dose.

The present invention encompasses therapeutic or pharmaceutical compositions for pulmonary delivery comprising one or more antibodies or fragments thereof which immunospecifically bind to one or more RSV antigens with a higher affinity and/or a higher avidity than previously known antibodies (e.g., SYNAGIS®). The present invention also encompasses therapeutic or pharmaceutical compositions for pulmonary delivery comprising SYNAGIS® or an antigen-binding fragment thereof.

In one embodiment, a mammal, preferably a human, is administered a first dose of a therapeutic or pharmaceutical composition for pulmonary delivery comprising less than 15 mg/kg, preferably less than 5 mg/kg, less than 3 mg/kg, less than 1 mg/kg or less than 0.5 mg/kg, or less than 0.01 mg/kg of one or more antibodies or fragments thereof which immunospecifically bind to one or more RSV antigens with higher affinity and/or higher avidity than previously known antibodies (e.g., SYNAGIS®) for the prevention, treatment or amelioration of one or more symptoms associated with a RSV infection in an amount effective to induce a titer of 20 ng per mg of lung protein (preferably at least 40 ng/mg, at least 60 ng/mg, at least 80 ng/mg, at least 50 ng/mg, at least 75 ng/mg, at least 100 ng/mg, or at least 150 ng/mg) in an intubation sample or lavage from the lungs of said mammal 20 days (preferably 25, 30, 35, or 40 days) after the administration of the first dose and prior to the administration of a subsequent dose. Preferably, the serum titer of said antibodies or antibody fragments is less than 100 ng/ml of protein 30 days after the administration of the first dose and prior to the administration of a subsequent dose. Preferably, the novel antibodies are AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L-1-7E5, L2-15B10, A13a11, A1h5, A4B4 (1), A4B4L1FR-S28R, and A4B4-F52S.

In another embodiment, a mammal, preferably a human, is administered a first dose of a therapeutic or pharmaceutical composition for pulmonary delivery comprising approximately 15 mg/kg of SYNAGIS® or fragments thereof for the prevention, treatment or amelioration of one or more symptoms associated with a RSV infection in an amount effective to induce a titer of 20 ng per mg of lung protein (preferably at least 40 ng/mg, at least 60 ng/mg, at least 80 ng/mg, at least 50 ng/mg, at least 75 ng/mg, at least 100 ng/mg, or at least 150 ng/mg) an intubation sample or lavage from the lungs of said mammal 30 days (preferably 35 or 40 days) after the administration of the first dose and prior to the administration of a subsequent dose. In another embodiment, a mammal, preferably a human, is administered a first dose of a therapeutic or pharmaceutical composition for pulmonary delivery comprising less than 15 mg/kg (preferably 10 mg/kg or less, 5 mg/kg or less, 3 mg/kg or less, 1 mg/kg or less, or 0.5 mg/kg or less) of SYNAGIS® or fragments thereof for the prevention of a RSV infection in an amount effective to induce a titer of 20 ng per mg of lung protein (preferably at least 40 ng/mg, at least 60 ng/mg, at least 80 ng/mg, at least 50 ng/mg, at least 75 ng/mg, at least 100 ng/mg, or at least 150 ng/mg) in an intubation sample or lavage from the lungs of said mammal 30 days (preferably 35 or 40 days) after the administration of the first dose and prior to the administration of a subsequent dose.

The present invention encompasses therapeutic or pharmaceutical compositions for pulmonary delivery comprising one or more antibodies or fragments thereof which have increased in vivo half-lives and which immunospecifically bind to one or more RSV antigens with a higher affinity and/or a higher avidity than previously known antibodies (e.g., SYNAGIS®). The present invention also encompasses therapeutic or pharmaceutical compositions for pulmonary delivery comprising HL-SYNAGIS or an antigen-binding fragment thereof.

The present invention encompasses sustained release compositions comprising one or more antibodies or fragments thereof which have increased in vivo half-lives and which immunospecifically bind to one or more RSV antigens with a higher affinity and/or a higher avidity than previously known antibodies (e.g., SYNAGIS®). The present invention also encompasses sustained release compositions comprising SYNAGIS® or an antigen-binding fragment thereof.

In one embodiment, a mammal, preferably a human, is administered a first dose of a sustained release formulation comprising less than 15 mg/kg, preferably less than 5 mg/kg, less than 3 mg/kg, less than 1 mg/kg or less than 0.5 mg/kg of one or more antibodies or fragments thereof which immunospecifically bind to one or more RSV antigens with higher affinity and/or higher avidity than previously known antibodies (e.g., SYNAGIS®) for the prevention, treatment or amelioration of one or more symptoms associated with a RSV infection in an amount effective to induce a serum titer of at least 1 μg/ml, preferably at least 2 μg/ml, at least 5 μg/ml, at least 10 μg/ml, at least 15 μg/ml, at least 20 μg/ml, or at least 25 μg/ml for at least 10 days (preferably at least 15, at least 20, at least 25, at least 30, at least 35, or at least 40 days) after the administration of the first dose and prior to the administration of a subsequent dose. Preferably, the serum titer of said antibodies or antibody fragments is less than 30 μg/ml 30 days after the administration of the first dose and prior to the administration of a subsequent dose. Preferably, the novel antibodies are AFFF, P12f2, P12f4, P11d4, Ale9, A12a6, A13c4, A17d4, A4B4, A8C7, IX-493L1FR, H3-3F4, M3H9, Y10H6, DG, AFFF(1), 6H8, L1-7E5, L2-15B10, A13a11, A1h5, A4B4(1), A4B4L1FR-S28R, or A4B4-F52S.

In another embodiment, a mammal, preferably a human, is administered a first dose of a sustained release formulation comprising less than 15 mg/kg, preferably less than 5 mg/kg, less than 3 mg/kg, less than 1 mg/kg or less than 0.5 mg/kg of one or more antibodies or fragments thereof which immunospecifically bind to one or more RSV antigens with higher affinity and/or higher avidity than previously known antibodies (e.g., SYNAGIS®) for the prevention, treatment, or amelioration of one or more symptoms associated with a RSV infection in an amount effective to induce a serum titer of 1 μg/ml, preferably 2 μg/ml, 5 μg/ml, 10 μg/ml, 15 μg/ml, 20 μg/ml, or 25 μg/ml that is maintained for at least 10 days (preferably at least 15, at least 20, at least 25, at least 30, at least 35, or at least 40 days) after the administration of the first dose and prior to the administration of a subsequent dose without exceeding a serum titer of 30 μg/ml.

In another embodiment, a mammal, preferably a human, is administered a first dose of a sustained release formulation comprising approximately 15 mg/kg of SYNAGIS® or fragments thereof for the prevention, treatment or amelioration of one or more symptoms associated with a RSV infection in an amount effective to induce a titer of at least 30 μg/ml, preferably at least 35 μg/ml, at least 40 μg/ml, or at least 50 μg/ml 25 days (preferably 30, 35, or 40 days) after the administration of the first dose and prior to the administration of a subsequent dose. In another embodiment, a mammal, preferably a human, is administered a first dose of a sustained release formulation comprising less than 15 mg/kg (preferably 10 mg/kg or less, 5 mg/kg or less, 3 mg/kg or less, 1 mg/kg or less, or 0.5 mg/kg or less) of SYNAGIS® or fragments thereof for the prevention of a RSV infection in an amount effective to induce at least 30 μg/ml, preferably at least 35 μg/ml, at least 40 μg/ml, or at least 50 μg/ml 25 days (preferably 30, 35, or 40 days) after the administration of the first dose and prior to the administration of a subsequent dose.

In another embodiment, a mammal, preferably a human, is administered a first dose of a sustained release formulation comprising less than 15 mg/kg, preferably less than 5 mg/kg, less than 3 mg/kg, less than 1 mg/kg or less than 0.5 mg/kg of SYNAGIS® or an antigen-binding fragment thereof for the prevention, treatment, or amelioration of one or more symptoms associated with a RSV infection in an amount effective to induce a serum titer of 1 μg/ml, preferably 2 μg/ml, 5 μ/ml, 10 μg/ml, 15 μg/ml, 20 μg/ml, or 25 μg/ml that is maintained for at least 10 days (preferably at least 15, at least 20, at least 25, at least 30, at least 35, or at least 40 days) after the administration of the first dose and prior to the administration of a subsequent dose without exceeding a serum titer of 30 μg/ml.

The present invention encompasses sustained release formulations comprising one or more antibodies or fragments thereof which have increased in vivo half-lives and which immunospecifically bind to one or more RSV antigens with a higher affinity and/or a higher avidity than previously known antibodies such as, e.g., SYNAGIS®. The present invention also encompasses sustained release formulations comprising HL-SYNAGIS or an antigen-binding fragment thereof.

The present invention encompasses sustained release formulations for pulmonary delivery comprising one or more antibodies or fragments thereof which immunospecifically bind to one or more RSV antigens with a higher affinity and/or a higher avidity than previously known antibodies (e.g., SYNAGIS®). The present invention also encompasses sustained release formulations for pulmonary delivery comprising one or more antibodies or fragments thereof which have increased in vivo half-lives and which immunospecifically bind to one or more RSV antigens with a higher affinity and/or a higher avidity than previously known antibodies (e.g., SYNAGIS®). The present invention also encompasses sustained release formulations for pulmonary delivery comprising SYNAGIS® or fragments thereof. The present invention further encompasses sustained release formulations for pulmonary delivery comprising HL-SYNAGIS or an antigen-binding fragment thereof.

In another embodiment, a mammal, preferably a human, is administered a first dose of a therapeutic or pharmaceutical composition comprising less than 10 mg/kg, less than 5 mg/kg, less than 3 mg/kg, less than 1 mg/kg or less than 0.5 mg/kg of one or more antibodies of the present invention or fragments thereof for the prevention, treatment or amelioration of one or more symptoms associated with a RSV infection in an amount effective to induce a serum titer of at least 35 μg/ml, at least 40 μg/ml, at least 50 μg/ml, at least 80 μg/ml, at least 100 μg/ml, at least 120 μg/ml, at least 150 μg/ml, at least 200 μg/ml, at least 250 μg/ml, or at least 300 μg/ml 20 days (preferably 25, 30, 35 or 40 days) after the administration of the first dose. In another embodiment, a mammal, preferably a human, is administered a first dose of a therapeutic or pharmaceutical composition comprising approximately 15 mg/kg of one or more antibodies of the present invention or fragments thereof for the prevention, treatment or amelioration of one or more symptoms associated with a RSV infection in an amount effective to induce a serum titer of at least 100 μg/ml, at least 125 μg/ml, at least 150 μg/ml, at least 200 μg/ml, at least 250 μg/ml, at least 300 μg/ml, at least 350 μg/ml, at least 400 μg/ml, or at least 450 μg/ml 20 days (preferably 25, 30, 35 or 40 days) after the administration of the first dose. The term "approximately 15 mg/kg" as used herein refers to a range of between 14 mg/kg and 16 mg/kg.

In another embodiment, a mammal, preferably a human, is administered a dose of a pharmaceutical composition comprising one or more antibodies of the present invention or fragments thereof for the prevention a RSV infection in an amount effective to induce a prophylactically effective serum titer of less than 10 μg/ml, less than 8 μg/ml, less than 5 μg/ml, less than 3 μg/ml, less than 1 μg/ml, or less than 0.5 μg/ml 30 days after the administration of the dose, wherein said prophylactically effective serum titer is the serum titer that reduces the incidence of RSV infection in the human or the serum titer in a cotton rat that results in a RSV titer 5 days after challenge with $10^5$ pfu RSV that is 99% lower than the RSV titer in the cotton rat 5 days after challenge with $10^5$ pfu of RSV in a cotton rat not administered the dose prior to challenge. Preferably, the dose of the pharmaceutical composition comprises less than 10 mg/kg, less than 5 mg/kg, less than 3 mg/kg, less than 1 mg/kg, or less than 0.5 mg/kg of one or more antibodies of the present invention or fragments thereof.

In yet another embodiment, a mammal, preferably a human, is administered a dose of a therapeutic or pharmaceutical composition comprising one or more antibodies of the present invention or fragments thereof for the treatment or amelioration of one or more symptoms associated with a RSV infection in an amount effective to induce a therapeutically effective serum titer of less than 10 μg/ml, less than 8 μg/ml, less than 5 μg/ml, less than 3 μg/ml, less than 1 μg/ml, or less than 0.5 μg/ml 30 days after the administration of the dose, wherein said therapeutically effective serum titer is the serum titer that reduces the severity or length of RSV infection or is the serum titer in a cotton rat that results in a RSV titer in the rat 5 days after challenge with $10^5$ pfu RSV that is 99% lower than the RSV titer 5 days after challenge with $10^5$ pfu of RSV in a cotton rat not administered the dose prior to challenge. Preferably, the dose of the therapeutic or pharmaceutical composition comprises less than 12 mg/kg, less than 10 mg/kg, less than 5 mg/kg, less than 3 mg/kg, less than 1 mg/kg, or less than 0.5 mg/kg of one or more antibodies of the present invention or fragments thereof.

5.3. Methods of Administration of Antibodies

The invention provides methods of treatment, prophylaxis, and amelioration of one or more symptoms associated with RSV infection by administrating to a subject of an effective amount of antibody or fragment thereof, or pharmaceutical composition comprising an antibody of the invention or fragment thereof. In a preferred aspect, an antibody or fragment thereof is substantially purified (i.e., substantially free from substances that limit its effect or produce undesired side-effects). The subject is preferably a mammal such as non-primate (e.g., cows, pigs, horses, cats, dogs, rats etc.) and a primate (e.g., monkey such as a cynomolgous monkey and a human). In a preferred embodiment, the subject is a human. In another preferred embodiment, the subject is a human infant or a human infant born prematurely. In another embodiment, the subject is a human with cystic fibrosis, chronic lung disease (e.g., bronchopulmonary dysplasia), congenital heart disease, congenital immunodeficiency or acquired immunodeficiency, a human who has had a stem cell transplant, a human who has had a bone marrow transplant, or an elderly human Various delivery systems are known and can be used to administer an antibody of the invention or a fragment thereof, or a fusion protein, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering an antibody or fragment thereof, a fusion protein, or a pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, antibodies of the present invention or fragments thereof, or pharmaceutical compositions are administered intramuscularly, intravenously, or subcutaneously. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985, 320, 5,985,309, 5,934,272, 5,874, 064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In a preferred embodiment, an antibody of the invention or fragment thereof, or composition of the invention is administered using Alkermes AIR™ pulmonary drug delivery technology (Alkermes, Inc., Cambridge, Mass.).

The invention provides for any method of administrating lower doses of known antibodies or fragments thereof which immunospecifically bind to one or more RSV antigens than previously thought to be effective for the prevention, treatment or amelioration of one or more symptoms associated with a RSV infection. Preferably, lower doses of known antibodies or fragments thereof which immunospecifically bind to one or more RSV antigens are administered by pulmonary administration. The present invention also provides for any method of administering a novel antibody of the invention or fragment thereof for the prevention, treatment or amelioration of one or more symptoms associated with a RSV infection. Preferably, novel antibodies of the invention or fragments thereof are administered by pulmonary administration.

The invention also provides that an antibody or fragment thereof is packaged in a hermetically sealed container such as an ampoule or sachette indicating the quantity of antibody or antibody fragment. In one embodiment, the antibody or antibody fragment is supplied as a dry sterilized lyophilized powder or water free concentrate in a hermetically sealed container and can be reconstituted, e.g., with water or saline to the appropriate concentration for administration to a subject. Preferably, the antibody or antibody fragment is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, at least 100 mg or at least 125 mg. The lyophilized antibody or antibody fragment should be stored at between 2 and 8° C. in its original container and the antibody or antibody fragment should be administered within 12 hours, preferably within 6 hours, within 5 hours, within 3 hours, or within 1 hour after being reconstituted. In an alternative embodiment, an antibody or fragment thereof is supplied in liquid form in a hermetically sealed container indicating the quantity and concentration of the antibody or antibody fragment. Preferably, the liquid form of the antibody or fragment thereof is supplied in a hermetically sealed container at least 1 mg/ml, more preferably at least 2.5 mg/ml, at least 5 mg/ml, at least 8 mg/ml, at least 10 mg/ml, at least 15 mg/kg, or at least 25 mg/ml.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a an antibody of the invention or fragment thereof, care must be taken to use materials to which the antibody or antibody fragment does not absorb.

In another embodiment, the composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 3 17-327; see generally ibid.).

In yet another embodiment, the composition can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the antibodies of the invention or fragments thereof (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the lungs, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more antibodies of the invention or fragments thereof. See, e.g., U.S. Pat. No. 4,526,938, PCT publication WO 91/05548, PCT publication WO 96/20698, Ning et al., 1996, "Intratumoral Radioimmunotheraphy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

In a specific embodiment where the composition of the invention is a nucleic acid encoding an antibody or antibody fragment, the nucleic acid can be administered in vivo to promote expression of its encoded antibody or antibody fragment, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox- like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

The present invention also provides pharmaceutical compositions. Such compositions comprise a prophylactically or therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a prophylactically or therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, prevention or amelioration of one or more symptoms associated with a RSV infection can be determined by standard clinical techniques. For example, the dosage of the composition which will be effective in the treatment, prevention or amelioration of one or more symptoms associated with a RSV infection can be determined by administering the composition to a cotton rat, measuring the RSV titer after challenging the cotton rat with $10^5$ pfu of RSV and comparing the RSV titer to that obtain for a cotton rat not administered the composition. Accordingly, a dosage that results in a 2 log decrease or a 99% reduction in RSV titer in the cotton rat challenged with $10^5$ pfu of RSV relative to the cotton rat challenged with $10^5$ pfu of RSV but not administered the composition is the dosage of the composition that can be administered to a human for the treatment, prevention or amelioration of symptoms associated with RSV infection. The dosage of the composition which will be effective in the treatment, prevention or amelioration of one or more symptoms associated with a RSV infection can be determined by administering the composition to an animal model (e.g., a cotton rat or monkey) and measuring the serum titer of antibodies or fragments thereof that immunospecifically bind to a RSV antigen. Accordingly, a dosage of the composition that results in a serum titer of at least 1 µg/ml, preferably 2 µg/ml, 5 µg/ml, 10 µg/ml, 20 µg/ml, 25 µg/ml, at least 35 µg/ml, at least 40 µg/ml, at least 50 µg/ml, at least 75 µg/ml, at least 100 µg/ml, at least 125 µg/ml, at least 150 µg/ml, at least 200 µg/ml, at least 250 µg/ml, at least 300 µg/ml, at least 350 µg/ml, at least 400 µg/ml, or at least 450 µg/ml can be administered to a human for the treatment, prevention or amelioration of one or more symptoms associated with RSV infection. In addition, in vitro assays may optionally be employed to help identify optimal dosage ranges.

The precise dose to be employed in the formulation will also depend on the route of administration, and the seriousness of the RSV infection, and should be decided according to the judgment of the practitioner and each patient's circumstances. Effective doses may be extrapolated from dose-response curves derived from in vitro or animal model (e.g., the cotton rat or Cynomolgous monkey) test systems.

For antibodies, peptides, polypeptides or proteins, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration (e.g., into the lung) of the antibodies by modifications such as, for example, lipidation.

In a specific embodiment, antibodies of the invention or fragments thereof, or compositions comprising antibodies of the invention or fragments thereof are administered once a month just prior to or during the RSV season. In another embodiment, antibodies of the invention or fragments thereof, or compositions comprising antibodies of the invention or fragments thereof are administered every two months just prior to or during the RSV season. In yet another embodiment, antibodies of the invention or fragments thereof, or compositions comprising antibodies of the invention or fragments thereof are administered once just prior to or during the RSV season. The term "RSV season" refers to the season when RSV infection is most likely to occur. Typically, the RSV season in the northern hemisphere commences in October/November and lasts through March, April or May.

In one embodiment, approximately 5 mg/kg or less (preferably 1.5 mg/kg or less) of an antibody or fragment thereof which immunospecifically binds to a RSV antigen with a higher avidity and/or higher affinity than previously known antibodies such as, e.g., SYNAGIS®, is administered five times, 3 times, or 1 to 2 times during a RSV season to a mammal, preferably a human. In another embodiment, approximately 1.5 mg/kg of an antibody or a fragment thereof which immunospecifically binds to a RSV antigen with a higher avidity and/or a higher affinity than known antibodies such as, e.g., SYNAGIS®, is administered monthly five times during an RSV season to a mammal, preferably a human, intramuscularly. In another embodiment, 3 mg/kg of an antibody or a fragment thereof which immunospecifically binds to a RSV antigen with a higher avidity and/or a higher affinity than known antibodies such as, e.g., SYNAGIS® is administered monthly three times during an RSV season to a mammal, preferably a human, intramuscularly. In yet another embodiment, 5 mg/kg of an antibody or a fragment thereof which immunospecifically binds to a RSV antigen with a higher avidity and/or a higher affinity than known antibodies such as, e.g., SYNAGIS® is administered monthly one to two times during an RSV season to a mammal, preferably a human, intramuscularly.

In a specific embodiment, 15 mg/kg of HL-SYNAGIS or an antigen-binding fragment thereof is administered to a mammal, preferably a human, intramuscularly five times during an RSV season. In another embodiment, approximately 5 mg/kg or less (preferably 1.5 mg/kg or less) of an antibody or fragment thereof which immunospecifically binds to a RSV antigen with a higher avidity and/or higher affinity than previously known antibodies such as, e.g., SYNAGIS®, is administered five times, 3 times, or 1 to 2 times during a RSV season to a mammal, preferably a human. In another embodiment, 3 mg/kg of antibody or a fragment thereof which immunospecifically binds to a RSV antigen with a higher avidity and/or a higher affinity known antibodies such as, e.g., SYNAGIS® and which has an increased in vivo half-life is administered monthly three times during an RSV season to a mammal, preferably a human, intramuscularly. In another embodiment, 5 mg/kg of antibody or a fragment thereof which immunospecifically binds to a RSV antigen with a higher avidity and/or a higher affinity than known antibodies such as, e.g., SYNAGIS® and which has an increased in vivo half-life is administered to a mammal, preferably a human, intramuscularly twice times during an RSV season.

In a specific embodiment, an approximately 15 mg/kg bolus of SYNAGIS® or an antigen-binding fragment thereof not in a sustained release formulation is administered to a mammal, preferably a human, and after a certain period of time less than 15 mg/kg (preferably 5 mg/kg or less, more preferably 3 mg/kg or less, and most preferably 1.5 mg/kg or less) of SYNAGIS® or an antibody fragment in a sustained release is administered to said mammal intramuscularly two, three or four times during an RSV season. In accordance with this embodiment, a certain period of time can be 1 to 5 days, a week, two weeks, or a month. In another embodiment, approximately 15 mg/kg or less (preferably at least 2 mg/kg, at least 5 mg/kg, or at least 10 mg/kg) of SYNAGIS® or an antigen-binding fragment thereof in a sustained release formulation is administered to a mammal, preferably a human, intramuscularly two, three or four times during an RSV season.

In another embodiment, approximately 15 mg/kg or less (preferably at least 2 mg/kg, at least 5 mg/kg, or at least 10 mg/kg) of one or more antibodies or fragments thereof which immunospecifically bind to one or more RSV antigens is administered to the lungs of a mammal by pulmonary delivery and then after a certain period of time (e.g., 15 minutes, 30 minutes, 45 minutes, 1 hour, 6 hours, 12 hours, 1 day, 5 days, 10 days, 20 days, 25 days, 30 days, or 40 days) approximately 15 mg/kg or less of one or more said antibodies or antibody fragments is administered intramuscularly said mammal. In another embodiment, approximately 15 mg/kg or less (preferably at least 2 mg/kg, at least 5 mg/kg, or at least 10 mg/kg) of one or more antibodies or fragments thereof which immunospecifically bind to one or more RSV antigens is administered to a mammal intramuscularly and then after a certain period of time (e.g., 15 minutes, 30 minutes, 45 minutes, 1 hour, 6 hours, 12 hours, 1 day, 5 days, 10 days, 20 days, 25 days, 30 days, or 40 days) approximately 15 mg/kg or less of one or more said antibodies or antibody fragments is administered to the lungs of said mammal.

5.3.1. Gene Therapy

In a specific embodiment, nucleic acids comprising sequences encoding antibodies or functional derivatives thereof, are administered to treat, prevent or ameliorate one or more symptoms associated with RSV infection, by way of gene therapy. Gene therapy refers to therapy performed by the administration to a subject of an expressed or expressible nucleic acid. In this embodiment of the invention, the nucleic acids produce their encoded antibody or antibody fragment that mediates a prophylactic or therapeutic effect.

Any of the methods for gene therapy available in the art can be used according to the present invention. Exemplary methods are described below.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5): 155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, N.Y. (1990).

In a preferred aspect, a composition of the invention comprises nucleic acids encoding an antibody, said nucleic acids being part of an expression vector that expresses the antibody or fragments or chimeric proteins or heavy or light chains thereof in a suitable host. In particular, such nucleic acids have promoters, preferably heterologous promoters, operably linked to the antibody coding region, said promoter being inducible or constitutive, and, optionally, tissue- specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, 1989, Proc. Natl. Acad. Sci. USA 86:8932-8935; Zijlstra et al., 1989, Nature 342:435-438). In specific embodiments, the expressed antibody molecule is a single chain antibody; alternatively, the nucleic acid sequences include sequences encoding both the heavy and light chains, or fragments thereof, of the antibody.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; W092/203 16; W093/14188, WO 93/20221). Alternatively, the nucleic acid can be introduced intracellularly and incorporated within host cell DNA for expression, by homologous recombination (Koller and Smithies, 1989, Proc. Natl. Acad. Sci. USA 86:8932-8935; and Zijlstra et al., 1989, Nature 342:435-438).

In a specific embodiment, viral vectors that contains nucleic acid sequences encoding an antibody of the invention or fragments thereof are used. For example, a retroviral vector can be used (see Miller et al., 1993, Meth. Enzymol. 217:581-599). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a subject. More detail about retroviral vectors can be found in Boesen et al., 1994, Biotherapy 6:291-302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Klein et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication W094/12649; and Wang et al., 1995, Gene Therapy 2:775-783. In a preferred embodiment, adenovirus vectors are used.

Adeno-associated virus (AAV) has also been proposed for use in gene therapy (Walsh et al., 1993, Proc. Soc. Exp. Biol. Med. 204:289-300; and U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcellmediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Clin. Pharma. Ther. 29:69-92 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, nucleic acid sequences encoding an antibody or fragment thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598; Stemple and Anderson, 1992, Cell 7 1:973-985; Rheinwald, 1980, Meth. Cell Bio. 21A: 229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

5.4. Antibody Characterization and Demonstration of Therapeutic or Prophylactic Utility Antibodies of the present invention or fragments thereof may be characterized in a variety of ways. In particular, antibodies of the invention or fragments thereof may be assayed for the ability to immunospecifically bind to a RSV antigen. Such an assay may be performed in solution (e.g., Houghten, 1992, Bio/Techniques 13:412-421), on beads (Lam, 1991, Nature 354:82-84), on chips (Fodor, 1993, Nature 364:555-556), on bacteria (U.S. Pat. No. 5,223,409), on spores (U.S. Pat. Nos. 5,571,698; 5,403,484; and 5,223, 409), on plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310l) (each of these references is incorporated herein in its entirety by reference). Antibodies or fragments thereof that have been identified to immunospecifically bind to a RSV antigen or a fragment thereof can then be assayed for their specificity and affinity for a RSV antigen.

The antibodies of the invention or fragments thereof may be assayed for immunospecific binding to a RSV antigen and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of the present invention or a fragment thereof for a RSV antigen and the binding off-rates can be determined from the data by scatchard plot analysis. Competition with a second antibody can also be determined using radioimmunoassays. In this case, a RSV antigen is incubated with an antibody of the present invention or a fragment thereof conjugated to a labeled compound (e.g., $^3$H or $^{125}$I) in the presence of increasing amounts of an unlabeled second antibody.

In a preferred embodiment, BIAcore kinetic analysis is used to determine the binding on and off rates of antibodies or fragments thereof to a RSV antigen. BIAcore kinetic analysis comprises analyzing the binding and dissociation of a RSV antigen from chips with immobilized antibodies or fragments thereof on their surface (see the Example section infra).

The antibodies of the invention or fragments thereof can also be assayed for their ability to inhibit the binding of RSV to its host cell receptor using techniques known to those of skill in the art. For example, cells expressing the receptor for RSV can be contacted with RSV in the presence or absence of an antibody or fragment thereof and the ability of the antibody or fragment thereof to inhibit RSV's binding can measured by, for example, flow cytometry or a scintillation assay. RSV (e.g., a RSV antigen such as F glycoprotein or G glycoprotein) or the antibody or antibody fragment can be labeled with a detectable compound such as a radioactive label (e.g., $^{32}$P, $^{35}$S, and $^{125}$I) or a fluorescent label (e.g., fluorescein isothiocyanate, rhodamine, phycoerythrin, phycocyanin, allophycocyanin, o-phthaldehyde and fluorescamine) to enable detection of an interaction between RSV and its host cell receptor. Alternatively, the ability of antibodies or fragments thereof to inhibit RSV from binding to its receptor can be determined in cell-free assays. For example, RSV or a RSV antigen such as G glycoprotein can be contacted with an antibody or fragment thereof and the ability of the antibody or antibody fragment to inhibit RSV or the RSV antigen from binding to its host cell receptor can be determined. Preferably, the antibody or the antibody fragment is immobilized on a solid support and RSV or a RSV antigen is labeled with a detectable compound. Alternatively, RSV or a RSV antigen is immobilized on a solid support and the antibody or fragment thereof is labeled with a detectable compound. RSV or a RSV antigen may be partially or completely purified (e.g., partially or completely free of other polypeptides) or part of a cell lysate. Further, an RSV antigen may be a fusion protein comprising the RSV antigen and a domain such as glutathionine-S-transferase. Alternatively, an RSV antigen can be biotinylated using techniques well known to those of skill in the art (e.g., biotinylation kit, Pierce Chemicals; Rockford, Ill.).

The antibodies of the invention or fragments thereof can also be assayed for their ability to inhibit or downregulate RSV replication using techniques known to those of skill in the art. For example, RSV replication can be assayed by a plaque assay such as described, e.g., by Johnson et al., 1997, Journal of Infectious Diseases 176:1215-1224. The antibodies of the invention or fragments thereof can also be assayed for their ability to inhibit or downregulate the expression of RSV polypeptides. Techniques known to those of skill in the art, including, but not limited to, Western blot analysis, Northern blot analysis, and RT-PCR can be used to measure the expression of RSV polypeptides. Further, the antibodies of the invention or fragments thereof can be assayed for their ability to prevent the formation of syncytia.

The antibodies of the invention or fragments thereof are preferably tested in vitro, and then in vivo for the desired therapeutic or prophylactic activity, prior to use in humans. For example, in vitro assays which can be used to determine whether administration of a specific antibody or composition of the present invention is indicated, include in vitro cell culture assays in which a subject tissue sample is grown in culture, and exposed to or otherwise administered an antibody or composition of the present invention, and the effect of such an antibody or composition of the present invention upon the tissue sample is observed. In various specific embodiments, in vitro assays can be carried out with representative cells of cell types involved in a RSV infection (e.g., respiratory epithelial cells), to determine if an antibody or composition of the present invention has a desired effect upon such cell types. Preferably, the antibodies or compositions of the invention are also tested in in vitro assays and animal model systems prior to administration to humans. In a specific embodiment, cotton rats are administered an antibody the invention or fragment thereof, or a composition of the invention, challenged with $10^5$ pfu of RSV, and four or more days later the rats are sacrificed and RSV titer and anti-RSV antibody serum titer is determined. Further, in accordance with this embodiment, the tissues (e.g., the lung tissues) from the sacrificed rats can be examined for histological changes.

In accordance with the invention, clinical trials with human subjects need not be performed in order to demonstrate the prophylactic and/or therapeutic efficacy of antibodies of the invention or fragments thereof. In vitro and animal model studies using the antibodies or fragments thereof can be extrapolated to humans and are sufficient for demonstrating the prophylactic and/or therapeutic utility of said antibodies or antibody fragments.

Antibodies or compositions of the present invention for use in therapy can be tested for their toxicity in suitable animal model systems, including but not limited to rats, mice, cows, monkeys, and rabbits. For in vivo testing of an antibody or composition's toxicity any animal model system known in the art may be used.

Efficacy in treating or preventing viral infection may be demonstrated by detecting the ability of an antibody or composition of the invention to inhibit the replication of the virus, to inhibit transmission or prevent the virus from establishing itself in its host, to reduce the incidence of RSV infection, or to prevent, ameliorate or alleviate one or more symptoms associated with RSV infection. The treatment is considered therapeutic if there is, for example, a reduction is viral load, amelioration of one or more symptoms, a reduction in the duration of a RSV infection, or a decrease in mortality and/or morbidity following administration of an antibody or composition of the invention. Further, the treatment is considered therapeutic if there is an increase in the immune response following the administration of one or more antibodies or fragments thereof which immunospecifically bind to one or more RSV antigens.

Antibodies or compositions of the invention can be tested in vitro and in vivo for the ability to induce the expression of cytokines such as IFN-α, IFN-β, IFN-γ, IL-2, IL-3, IL-4, IL-5, IL-6, IL-7, IL-8, IL-9, IL-10, IL-12 and IL-15. Techniques known to those of skill in the art can be used to measure the level of expression of cytokines. For example, the level of expression of cytokines can be measured by analyzing the level of RNA of cytokines by, for example, RT-PCR and Northern blot analysis, and by analyzing the level of cytokines by, for example, immunoprecipitation followed by western blot analysis and ELISA. In a preferred embodiment, an antibody or composition of the invention is tested for its ability to induce the expression of IFN-γ.

Antibodies or compositions of the invention can be tested in vitro and in vivo for their ability to modulate the biological activity of immune cells, preferably human immune cells (e.g., T-cells, B-cells, and Natural Killer cells). The ability of an antibody or composition of the invention to modulate the biological activity of immune cells can be assessed by detecting the expression of antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Antigen expression can be assayed, for example, by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs).

Antibodies or compositions of the invention can also be tested for their ability to inhibit viral replication or reduce viral load in in vitro, ex vivo and in vivo assays. Antibodies or compositions of the invention can also be tested for their ability to decrease the time course of RSV infection. Antibodies or compositions of the invention can also be tested for their ability to increase the survival period of humans suffering from RSV infection by at least 25%, preferably at least 50%, at least 60%, at least 75%, at least 85%, at least 95%, or at least 99%. Further, antibodies or compositions of the invention can be tested for their ability reduce the hospitalization period of humans suffering from RSV infection by at least 60%, preferably at least 75%, at least 85%, at least 95%, or at least 99%. Techniques known to those of skill in the art can be used to analyze the function of the antibodies or compositions of the invention in vivo.

5.5. Diagnostic Uses of Antibodies

Labeled antibodies, fragments and derivatives and analogs thereof, which immunospecifically bind to a RSV antigen can be used for diagnostic purposes to detect, diagnose, or monitor a RSV infection. The invention provides for the detection of a RSV infection, comprising: (a) assaying the expression of a RSV antigen in cells or a tissue sample of a subject using one or more antibodies or fragments thereof that immunospecifically bind to the RSV antigen; and (b) comparing the level of the RSV antigen with a control level, e.g., levels in normal tissue samples not infected with RSV, whereby an increase in the assayed level of RSV antigen compared to the control level of the RSV antigen is indicative of a RSV infection.

The invention provides a diagnostic assay for diagnosing a RSV infection, comprising: (a) assaying for the level of a RSV antigen in cells or a tissue sample of an individual using one or more antibodies or fragments thereof that immunospecifically bind to a RSV antigen; and (b) comparing the level of the RSV antigen with a control level, e.g., levels in normal tissue samples not infected with RSV, whereby an increase in the assayed RSV antigen level compared to the control level of the RSV antigen is indicative of a RSV infection. A more definitive diagnosis of RSV infection may allow health professionals to employ preventative measures or aggressive treatment earlier thereby preventing the development or further progression of RSV infection.

Antibodies of the invention or fragments thereof can be used to assay RSV antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell . Biol. 105:3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99m}$Tc); luminescent labels, such as luminol; and fluorescent labels, such as fluorescein and rhodamine, and biotin.

One aspect of the invention is the detection and diagnosis of a RSV infection in a human. In one embodiment, diagnosis comprises: a) administering (for example, parenterally, subcutaneously, or intraperitoneally) to a subject an effective amount of a labeled antibody or fragment thereof that immunospecifically binds to a RSV antigen; b) waiting for a time interval following the administering for permitting the labeled antibody or fragment thereof to preferentially concentrate at sites in the subject (e.g., the lungs) where the RSV antigen is expressed (and for unbound labeled molecule to be cleared to background level); c) determining background level; and d) detecting the labeled antibody or fragment thereof in the subject, such that detection of labeled antibody or fragment thereof above the background level indicates that the subject has a RSV infection. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a RSV infection is carried out by repeating the method for diagnosing the RSV infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

5.6. Methods Producing Antibodies

The antibodies of the invention or fragments thereof can be produced by any method known in the art for the synthesis of antibodies, in particular, by chemical synthesis or preferably, by recombinant expression techniques.

Polyclonal antibodies to a RSV antigen can be produced by various procedures well known in the art. For example, a RSV antigen can be administered to various host animals including, but not limited to, rabbits, mice, rats, etc. to induce the production of sera containing polyclonal antibodies specific for the RSV antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a RSV antigen and once an immune response is detected, e.g., antibodies specific for the RSV antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with a RSV antigen with myeloma cells and then screening the hybridomas resulting from the fusion for hybridoma clones that secrete an antibody able to bind a RSV antigen.

Antibody fragments which recognize specific RSV epitopes may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a RSV antigen of interest can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT application No. PCT/GB91/O1 134; PCT publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains comprise an EF-1α promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444, 887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules such as antibodies having a variable region derived from a human antibody and a non-human immunoglobulin constant region. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, and 4,8 16397, which are incorporated herein by reference in their entirety. Chimeric antibodies comprising one or more CDRs from human species and framework regions from a non-human immunoglobulin molecule can be produced using a variety of techniques known in the art including, for example, CDR-grafting (EP 239,400; PCT publication No. WO 91/09967; and U.S. Pat. Nos. 5,225,539, 5,530,101, and 5,585,089), veneering or resurfacing (EP 592,106; EP 519,596; Padlan, 1991, Molecular Immunology 28(4/5):489-498; Studnicka et al., 1994, Protein Engineering 7(6):805-814; and Roguska et al., 1994, PNAS 91:969-973), and chain shuffling (U.S. Pat. No. 5,565,332). In a preferred embodiment, chimeric antibodies comprise a human CDR3 having an amino acid sequence of any one of the CDR3 listed in Table 2 and non-human framework regions. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.)

Single domain antibodies, in particular, antibodies lacking light chains, can be produced by methods well known in the art. See, e.g., Riechmann et al., 1999, J. Immunol. 231:25-38; Nuttall et al., 2000, Curr. Pharm. Biotechnol. 1(3);253-263; Muylderman, 2001, J. Biotechnol. 74(4):277-302; U.S. Pat. No. 6,005,079, and International Publication Nos. WO 94/04678, WO 94/25591, and WO 01/44301, each of which are incorporated herein by reference in its entirety.

Further, the antibodies of the invention and/or peptides, polypeptides, or proteins comprising a variable or a hypervariable region (e.g., a VH domain, a VL domain or a CDR) can, in turn, be utilized to generate anti-idiotype antibodies that "mimic" RSV antigens using techniques well known to those skilled in the art. (See, e.g., Greenspan & Bona, 1989, FASEB J. 7(5):437-444; Nissinoff, 1991, J. Immunol. 147(8): 2429-2438; and U.S. Pat. No. 5,068,177, which is incorporated herein by reference in its entirety). For example, antibodies of the invention which bind to and competitively inhibit the binding of RSV (as determined by assays well known in the art and disclosed in supra) to its host cell receptor can be used to generate anti-idiotypes that "mimic" a RSV antigen binding domain and, as a consequence, bind to and neutralize RSV and/or its host cell receptor. Such neutralizing anti-idiotypes or Fab fragments of such anti-idiotypes can be used in therapeutic regimens to neutralize RSV. For example, such anti-idiotypic antibodies can be used to bind RSV and/or to bind its host cell receptors, and thereby block infection.

5.6.1. Polynucleotides Encoding an Antibody

The invention provides polynucleotides comprising a nucleotide sequence encoding an antibody of the invention or a fragment thereof. The invention also encompasses polynucleotides that hybridize under high stringency, intermediate or lower stringency hybridization conditions, e.g., as defined supra, to polynucleotides that encode an antibody of the invention.

The polynucleotides may be obtained, and the nucleotide sequence of the polynucleotides determined, by any method known in the art. Since the amino acid sequences of the antibodies are known (as described in Table 2), nucleotide sequences encoding these antibodies can be determined using methods well known in the art, i.e., nucleotide codons known to encode particular amino acids are assembled in such a way to generate a nucleic acid that encodes the antibody or fragment thereof of the invention. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, one or more of the CDRs is inserted within framework regions using routine recombinant DNA techniques. The framework regions may be naturally occurring or consensus framework regions, and preferably human framework regions (see, e.g., Chothia et al., 1998, J. Mol. Biol. 278: 457-479 for a listing of human framework regions). Preferably, the polynucleotide generated by the combination of the framework regions and CDRs encodes an antibody that specifically binds to a RSV antigen. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

5.6.2. Recombinant Expression of an Antibody

Recombinant expression of an antibody of the invention, derivative or analog thereof, (e.g., a heavy or light chain of an antibody of the invention or a portion thereof or a single chain antibody of the invention), requires construction of an expression vector containing a polynucleotide that encodes the antibody. Once a polynucleotide encoding an antibody molecule or a heavy or light chain of an antibody, or portion thereof (preferably, but not necessarily, containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody of the invention. Thus, the invention includes host cells containing a polynucleotide encoding an antibody of the invention or fragments thereof, or a heavy or light chain thereof, or portion thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding antibodies or fragments thereof which immunospecifically bind to one or more RSV antigens is regulated by a constitutive promoter, inducible promoter or tissue specific promoter.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the E. coli expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62: 191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, N.Y. (1993); Kriegler, Gene Transfer and Expression, A Laboratory Manual, Stockton Press, N.Y. (1990); and in Chapters 12 and 13, Dracopoli et al. (eds), Current Protocols in Human Genetics, John Wiley & Sons, N.Y. (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2 197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

5.7. Methods of Producing Peptides, Polypeptides, Proteins and Fusion Proteins Peptides, polypeptides, proteins and fusion proteins can be produced by standard recombinant DNA techniques or by protein synthetic techniques, e.g., by use of a peptide synthesizer. For example, a nucleic acid molecule encoding a peptide, polypeptide, protein or a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992). Moreover, a nucleic acid encoding a bioactive molecule can be cloned into an expression vector containing the Fc domain or a fragment thereof such that the bioactive molecule is linked in-frame to the Fc domain or Fc domain fragment.

Methods for fusing or conjugating polypeptides to the constant regions of antibodies are known in the art. See, e.g., U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; PCT publications WO 91/06570, WO 96/04388, WO 96/22024, WO 97/34631, and WO 99/04813; Ashkenazi et al., 1991, Proc. Natl. Acad. Sci. USA 88: 10535-10539; Traunecker et al., 1988, Nature, 331:84-86; Zheng et al., 1995, J. Immunol. 154:5590-5600; and Vil et al., 1992, Proc. Natl. Acad. Sci. USA 89:11337-11341, which are incorporated herein by reference in their entireties.

The nucleotide sequences encoding peptide, polypeptide or protein may be an be obtained from any information available to those of skill in the art (i.e., from Genbank, the literature, or by routine cloning). The nucleotide sequence coding for a peptide, polypeptide, protein a fusion protein can be inserted into an appropriate expression vector, i.e., a vector which contains the necessary elements for the transcription and translation of the inserted protein-coding sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

The expression of a peptide, polypeptide, protein or a fusion protein may be controlled by any promoter or enhancer element known in the art. Promoters which may be used to control the expression of the gene encoding fusion protein include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the μ-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Com. 253:818-823); glial fibrillary acidic protein (GFAP) promoter which is active in astrocytes (Gomes et al., 1999, Braz J Med Biol Res 32(5):619-631; Morelli et al., 1999, Gen. Virol. 80:571-83) and gonadotropic releasing hormone gene control region which is active in the hypothalamus (Mason et al., 1986, Science 234:1372-1378).

In a specific embodiment, the expression of a peptide, polypeptide, protein or a fusion protein is regulated by a constitutive promoter. In another embodiment, the expression of a peptide, polypeptide, protein or a fusion protein is regulated by an inducible promoter. In another embodiment, the expression of a polypeptide or a fusion protein is regulated by a tissue-specific promoter.

In a specific embodiment, a vector is used that comprises a promoter operably linked to a peptide-, polypeptide-, protein- or a fusion protein-encoding nucleic acid, one or more origins of replication, and, optionally, one or more selectable markers (e.g., an antibiotic resistance gene).

In mammalian host cells, a number of viral-based expression systems may be utilized. In cases where an adenovirus is used as an expression vector, the polypeptide or fusion protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 81:355-359). Specific initiation signals may also be required for efficient translation of inserted fusion protein coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51-544).

Expression vectors containing inserts of a nucleic acid sequence encoding a peptide, polypeptide, protein or a fusion protein can be identified by three general approaches: (a) nucleic acid hybridization, (b) presence or absence of "marker" gene functions, and (c) expression of inserted sequences. In the first approach, the presence of a nucleic acid sequence encoding a peptide, polypeptide, protein or a fusion protein in an expression vector can be detected by nucleic acid hybridization using probes comprising sequences that are homologous to an inserted gene encoding the peptide, polypeptide, protein or the fusion protein, respectively. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a peptide, polypeptide, protein or a fusion protein in the vector. For example, if the nucleotide sequence encoding the fusion protein is inserted within the marker gene sequence of the vector, recombinants containing the gene encoding the fusion protein insert can be identified by the absence of the marker gene function. In the third approach, recombinant expression vectors can be identified by assaying the gene product (e.g., fusion protein) expressed by the recombinant. Such assays can be based, for example, on the physical or functional properties of the peptide, polypeptide, protein or fusion protein in in vitro assay systems, e.g., binding to antibody.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, MDCK, 293, 3T3, WI38, NS0, and in particular, neuronal cell lines such as, for example, SK-N-AS, SK-N-FI, SK-N-DZ human neuroblastomas (Sugimoto et al., 1984, J. Natl. Cancer Inst. 73: 51-57), SK-N-SH human neuroblastoma (Biochim. Biophys. Acta, 1982, 704: 450-460), Daoy human cerebellar medulloblastoma (He et al., 1992, Cancer Res. 52: 1144-1148) DBTRG-05MG glioblastoma cells (Kruse et al., 1992, In Vitro Cell. Dev. Biol. 28A: 609-614), IMR-32 human neuroblastoma (Cancer Res., 1970, 30: 2110-2118), 1321N1 human astrocytoma (Proc. Natl Acad. Sci. USA ,1977, 74: 4816), MOG-G-CCM human astrocytoma (Br. J. Cancer, 1984, 49: 269), U87MG human glioblastoma-astrocytoma (Acta Pathol. Microbiol. Scand., 1968, 74: 465-486), A172 human glioblastoma (Olopade et al., 1992, Cancer Res. 52: 2523-2529), C6 rat glioma cells (Benda et al., 1968, Science 161: 370-371), Neuro-2a mouse neuroblastoma (Proc. Natl. Acad. Sci. USA, 1970, 65: 129-136), NB41A3 mouse neuroblastoma (Proc. Natl. Acad. Sci. USA, 1962, 48: 1184-1190), SCP sheep choroid plexus (Bolin et al., 1994, J. Virol. Methods 48: 211-221), G355-5, PG-4 Cat normal astrocyte (Haapala et al., 1985, J. Virol. 53: 827-833), Mpf ferret brain (Trowbridge et al., 1982, In Vitro 18:952-960), and normal cell lines such as, for example, CTX TNA2 rat normal cortex brain (Radany et al., 1992, Proc. Natl. Acad. Sci. USA 89: 6467-6471) such as, for example, CRL7030 and Hs578Bst. Furthermore, different vector/host expression systems may effect processing reactions to different extents.

For long-term, high-yield production of recombinant peptides, polypeptides, proteins or fusion proteins, stable expression is preferred. For example, cell lines which stably express a peptide, polypeptide, protein or a fusion protein may be engineered. Rather than using expression vectors which contain viral origins of replication, host cells can be transformed with DNA controlled by appropriate expression control elements (e.g., promoter, enhancer, sequences, transcription termina-tors, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express a polypeptide, protein or a fusion protein that immunospecifically binds to an RSV antigen.

Such engineered cell lines may be particularly useful in screening and evaluation of compounds that affect the activity of a polypeptide or a fusion protein that immunospecifically binds to a RSV antigen.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk-, hgprt- or aprt-cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

Once a polypeptide or a fusion protein of the invention has been produced by recombinant expression, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

5.8. Kits

The invention also provides a kit comprising one or more containers filled with one or more of the ingredients of the compositions of the invention.

The present invention provides kits that can be used in the above methods. In one embodiment, a kit comprises an antibody of the invention, preferably a purified antibody, in one or more containers. In an alterative embodiment, a kit comprises an antibody fragment that immunospecifically binds to a RSV antigen. In a specific embodiment, the kits of the present invention contain a substantially isolated RSV antigen as a control. Preferably, the kits of the present invention further comprise a control antibody which does not react with the RSV antigen. In another specific embodiment, the kits of the present invention contain a means for detecting the binding of an antibody to a RSV antigen (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized RSV antigen. The RSV antigen provided in the kit may also be attached to a solid support. In a more specific embodiment the detecting means of the above-described kit includes a solid support to which RSV antigen is attached. Such a kit may also include a non-attached reporter-labeled anti-human antibody. In this embodiment, binding of the antibody to the RSV antigen can be detected by binding of the said reporter-labeled antibody.

In an additional embodiment, the invention includes a diagnostic kit for use in screening serum containing RSV antigens. The diagnostic kit includes a substantially isolated antibody specifically immunoreactive with a RSV antigen, and means for detecting the binding of the RSV antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound RSV antigen obtained by the methods of the present invention. After the RSV antigen binds to a specific antibody, the unbound serum components are removed by washing, reporter-labeled anti-human antibody is added, unbound anti-human antibody is removed by washing, and a reagent is reacted with reporter-labeled anti-human antibody to bind reporter to the reagent in proportion to the amount of bound anti-RSV antigen antibody on the solid support. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant RSV antigen, and a reporter-labeled anti-human antibody for detecting surface-bound anti-RSV antigen antibody.

5.9. Articles of Manufacture

The present invention also encompasses a finished packaged and labeled pharmaceutical product. The present invention provides article of manufactures comprising packaging material and a pharmaceutical composition of the invention in suitable form for administration to a subject contained within said packaging material. In particular, the present invention provides article of manufactures comprising packaging material and a pharmaceutical composition of the invention in suitable form for administration to a subject contained within said packaging material wherein said pharmaceutical composition comprises one or more antibodies of the invention or fragments thereof, and a pharmaceutically acceptable carrier.

As with any pharmaceutical product, the packaging material and container of the articles of manufacture of the invention are designed to protect the stability of the product during storage and shipment. More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery. In a preferred embodiment, the unit dosage form is suitable for intravenous, intramuscular or subcutaneous delivery. Thus, the invention encompasses solutions, preferably sterile, suitable for each delivery route.

The articles of manufacture of the invention may include instructions regarding the use or administration of a pharmaceutical composition, or other informational material that advises the physician, technician or patient on how to appropriately prevent or treat a RSV infection. In other words, the article of manufacture includes instruction means indicating or suggesting a dosing regimen including, but not limited to, actual doses, monitoring procedures, and other monitoring information such as, e.g., side effects.

The following examples are presented by way of illustration and not by way of limitation of the scope

6. EXAMPLE

Kinetic Analysis of Humanized RSV Mabs by Biacore™

A typical kinetic study involved the injection of 250 µl of monoclonal antibody ("Mab") at varying concentrations (25-300 nM) in PBS buffer containing 0.05% Tween-20 (PBS/Tween). The flow rate was maintained at 75 µl/min, giving a 15 minute dissociation time. Following the injection of Mab, the flow was exchanged with PBS/Tween buffer for 30 min for determining the rate of dissociation. The sensor chip was regenerated between cycles with a 1 min pulse of 100 mM HCl. The regeneration step caused a minimal loss of binding capacity of the immobilized F-protein (4% loss per cycle). This small decrease did not change the calculated values of the rate constants for binding and dissociation (also called the $k_{on}$ and $k_{off}$, respectively).

More specifically, for measurement of $k_{asooc}$ (or $k_{on}$), F protein was directly immobilized by the EDC/NHS method (EDC=N-ethyl-N'-[3-diethylaminopropyl)-carbodiimide). Briefly, 25 mg/ml of F protein in 10 mM NaoAc, pH 5.0 was prepared and about a 5-10 µl injection gives about 30-50 RU (response units) of immobilized F protein under the above referenced conditions. The blank was subtracted for kinetic analysis. The column could be regenerated using 100 mM HCl (with 60 seconds of contact time being required for full regeneration). This treatment removed bound Fab completely without damaging the immobilized antigen and could be used for over 40 regenerations. For $k_{on}$ measurements, Fab concentrations were 0.39 nM, 0.75 nM, 1.56 nM, 3.13 nM, 12.5 nM, 25 nM, 50 nM, and 100 nM. The dissociation phase was analyzed for approximately 900 seconds. Kinetics were analyzed by 1:1 Langmuir fitting (global fitting). Measurements were done in HBS-EP buffer (10 mM HEPES, pH 7.4, 150 mM NaCl, 3 mM EDTA, 0.005% (v/v) Surfactant P20.

For measurements of combinatorial clones, as disclosed herein, the $k_{on}$ and $k_{off}$ were measured separately. The $k_{on}$ was measured at conditions that were the same as those for the single mutation clones and was analyzed similarly.

For measuring $k_{off}$, the following conditions were employed. Briefly, 4100 RU of F protein were immobilized (as above) with CM-dextran used as the blank. Here, 3000 RU of Fab was bound (with dissociated Fab high enough to offset machine fluctuation). HBS plus 5 nM F protein (about 350-2000 times higher than the $K_d$—the dissociation equilibrium constant) was used as buffer. The dissociation phase was 6-15 hours at a flow rate of 5 ml/min. Under the conditions used herein, re-binding of the dissociated Fab was minimal. For further details, see the manual with the biosensor.

The binding of the high affinity anti-RSV antibodies to the F protein, or other epitopic sites on RSV, disclosed herein was calculated from the ratio of the first order rate constant for dissociation to the second order rate constant for binding or association ($K_d = k_{off}/k_{on}$). The value for $k_{on}$ was calculated based on the following rate equation:

$$dR/dt = k_{on}[Mab]R_{max} - (k_{on}[Mab] + k_{off})R$$

where R and $R_{max}$ are the response units at time t and infinity, respectively. A plot of dr/dt as a function of R gives a slope of $(k_a[Mab] + k_d)$—since these slopes are linearly related to the [Mab], the value $k_{on}$, can be derived from a replot of the slopes versus [Mab]. The slope of the new line is equal to $k_{on}$. Although the value of $k_{off}$ can be extrapolated from the Y-intercept, a more accurate value was determined by direct measurement of $k_{off}$. Following the injection phase of the Mab, PBS/Tween buffer flows across the sensor chip. From this point, [Mab]=0. The above stated equation for dR/dt thus reduces to:

$$dr/dt = k \text{ or } dR/R = k_{off} dt$$

Integration of this equation then gives:

$$ln(R_0/R_t) = k_{off} t$$

where $R_0/R_t$ are the response units at time 0 (start of dissociation phase) and t, respectively. Lastly, plotting $ln(R_0/R_t)$ as a function of t gives a slope of $k_{off}$.

The numerical values from such antibody variants were as shown in Tables 4-7 below.

TABLE 4

Summary of Kinetic Constants for High Potency Antibodies.

| ANTIBODY | $K_{on} \times 10^5$ (M$^{-1}$s$^{-1}$) | $K_{off} \times 10^{-4}$ (s$^{-1}$) | EC$_{50}$ (nM) |
|---|---|---|---|
| **SYNAGIS ® | 2.04; 1.89; 2.18 | 7.64; 7.38; 7.02 | 3.57 |
| **AFFF | 1.08; 0.96; 1.24 | 2.74; 2.66; 2.06 | |
| *IX-493L1FR | 1.85 | 6.5 | |
| *H3-3F4 | 4.59; 4.67; 5.72; 6.25; 5.33 | 4.45; 4.02 | |
| *M3H9 | 6.05 | 3.38 | |
| *Y10H6 | 7.57 | 4.62 | |
| *DG | 2.65; 2.83; 4.16; 3.18; 2.88 | 1.67; 4.44 | |
| *AFFF | 2.12; 1.56; 1.86 | 2.45; 4.46; 2.68 | |
| *6H8 | 3.14; 4.44 | 1.78; 4.73 | |
| *L1-7E5 | 3.29; 3.57; 4.05; 3.35; 4.26 | 1.92; 3.31; 2.29 | |
| *L2-15B10 | 3.69; 2.82; 3.12; 5.33; 3.78 | 1.34; 4.16; 2.70 | |
| *P12f2 | 6.63 | 2.82 | 0.65 |
| *P12f4 | 5.27 | 2.99 | 0.70 |
| *P11d4 | 5.70; 5.72 | 7.17 | >20 |
| *A1e9 | 7.9 | 4.53 | 2.5 |
| *A12a6 | 7.43 | 2.30 | 0.62 |
| *A13a11 | 7.35 | 2.50 | 2.04 |
| *A13c4 | 7.81; 7.35 | 2.80 | 0.52 |

TABLE 5

| | Monoclonal Antibodies vs Bac-F (1:1) | | | |
|---|---|---|---|---|
| | Kon (×E + 5) | Koff (×E − 5) | KD (nM) | Chi2 |
| P12f2 | 4.07 | 12.8 | 0.31 (13) | 0.9 |
| P12f4 | 4.95 | 5.55 | 0.11 (35) | 0.6 |
| A13c4 | 3.00 | 3.96 | 0.13 (30) | 1.2 |
| A12a6 | 4.60 | 1.65 | 0.04 (98) | 1.2 |
| A1e9 | 4.33 | 14.3 | 0.33 (12) | 2.5 |
| A8c7 | 4.17 | 8.75 | 0.21 (19) | 1.8 |
| P11d4 | 4.66 | 28.9 | 0.62 (6) | 1.0 |
| A17d4 | 4.56 | 4.07 | 0.09 (43) | 0.5 |
| A4B4 | 4.34 | 1.06 | 0.02 (195) | 1.5 |
| SYNAGIS ® | 1.32 | 51.5 | 3.90 (1) | 0.6 |

TABLE 6

| | Monoclonal Antibodies vs NUF4 (1:1) | | | |
|---|---|---|---|---|
| | Kon (×E + 5) | Koff (×E − 5) | KD (nM) | Chi2 |
| P12f2 | 5.41 | 17.8 | 0.33 (26) | 1.2 |
| P12f4 | 9.43 | 22.9 | 0.24 (36) | 0.9 |
| A13c4 | 3.65 | 27.2 | 0.75 (12) | 1.8 |
| A12a6 | 4.00 | 29.1 | 0.73 (12) | 1.9 |
| A1e9 | 8.43 | 58.4 | 0.69 (13) | 0.9 |
| A8c7 | 8.25 | 53.5 | 0.65 (13) | 0.7 |
| P11d4 | 9.04 | 76.6 | 0.85 (10) | 2.5 |
| A17d4 | 4.99 | 36.2 | 0.73 (12) | 2.0 |
| A4B4 | 4.96 | 28.2 | 0.57 (15) | 1.9 |
| SYNAGIS ® | 3.04 | 265 | 8.70 (1) | 0.4 |

TABLE 7

| | Monoclonal Antibodies vs NUF4 (2:1) | | | |
|---|---|---|---|---|
| | Kon (×E + 5) | Koff (×E − 5) | KD (nM) | Chi2 |
| P12f2 | 2.82 | 23.6 | 0.84 (371) | 1.5 |
| P12f4 | 2.73 | 63.6 | 2.33 (134) | 4.9 |
| A13c4 | 3.20 | 22.5 | 0.70 (446) | 1.7 |
| A12a6 | 2.18 | 40.8 | 1.87 (167) | 1.9 |
| A1e9 | 3.29 | 139 | 4.22 (74) | 2.8 |
| A8c7 | 4.30 | 114 | 2.65 (118) | 2.0 |
| P11d4 | 3.66 | 313 | 8.55 (36) | 3.6 |
| A17d4 | 2.64 | 29.2 | 1.11 (281) | 1.7 |
| A4B4 | 2.03 | 40.06 | 2.00 (156) | 1.4 |
| SYNAGIS ® | 0.78 | 2420 | 312 (1) | 1.3 |

IX-493L1FR, H3-3F4, M3H9, Y10H6, DG, AFFF, 6H8, L1-7E5, L2-15B10, P12f2, P12f4, P11d4, Ale9, A12a6, A13a11, and A13c4 are Fab fragments having the framework sequences of FIG. 2 and the CDR sequences listed in Table 2. SYNAGIS is a monoclonal antibody with the framework sequences of FIG. 1 and constant regions as described in Johnson et al. (1997, Journal of Infectious Diseases 176: 1215-1224) and U.S. Pat. No. 5,824,307. The framework sequences of this antibody may differ slightly from those of the Fab fragments.

The amino acid sequences of the indicated CDRs in Table 1 represent the amino acid residues located at the key locations within the CDRs of the high potency antibodies produced by the methods described herein and in copending applications Ser. Nos. 60/168,426 and 60/186,252. For example, to increase the potency of an antibody by producing a higher $k_{on}$ value, the amino acids located at the key positions as taught herein by the bold and underlined residues in Table 1 for the reference antibody would be replaced by the amino acids listed under CDRs in Table 2 (and also bold and underlined). Thus, these one letter codes represent the amino acids replacing the reference amino acids at the key positions (or critical positions) of the CDRs shown in FIG. 2 (residues in bold in the sequences of Table 2) for a reference antibody whose potency is to be increased.

7. EXAMPLE

Microneutralization Assay

Neutralization of the antibodies of the present invention were determined by microneutralization assay. This microneutralization assay is a modification of the procedures described by Anderson et al. (1985, J. Clin. Microbiol. 22:1050-1052, the disclosure of which is hereby incorporated by reference in its entirety). The procedure used here is described in Johnson et al., 1999, J. Infectious Diseases 180: 35-40, the disclosure of which is hereby incorporated by reference in its entirety. Antibody dilutions were made in triplicate using a 96-well plate. Ten $TCID_{50}$ of respiratory syncytial virus (RSV—Long strain) were incubated with serial dilutions of the antibody (or Fabs) to be tested for 2 hours at 37 C in the wells of a 96-well plate. RSV susceptible HEp-2 cells ($2.5\times10^4$) were then added to each well and cultured for 5 days at 37 C in 5% $CO_2$. After 5 days, the medium was aspirated and cells were washed and fixed to the plates with 80% methanol and 20% PBS. RSV replication was then determined by F protein expression. Fixed cells were incubated with a biotin-conjugated anti-F protein monoclonal antibody (pan F protein, C-site-specific MAb 133-1H) washed and horseradish peroxidase conjugated avidin was added to the wells. The wells were washed again and turnover of substrate TMB (thionitrobenzoic acid) was measured at 450 nm. The neutralizing titer was expressed as the antibody concentration that caused at least 50% reduction in absorbency at 450 nm (the $OD_{450}$) from virus-only control cells. The results from the assay for the monoclonal antibodies and Fab fragments listed in Table 2 are shown in Table 4 supra and Table 8 infra.

TABLE 8

| End Point RSV Microneutralization Titer Of High On Rate Mutant IgG and Fab | | | | | | | |
|---|---|---|---|---|---|---|---|
| Molecule | Mean IC50 (Curve) μg/ml | STDEV Curve IC50 | Fold Difference (Curve ICX50) | Mean IC50 (Control) μg/ml | STDEV Control IC50 | Fold Difference (Control IC50) | n (assay repeat) |
| **SYNAGIS ® | 0.4527 | 0.208 | — | 0.5351 | 0.238 | — | 8 |
| **A1e9 | 0.0625 | 0.0268 | 7 | 0.0645 | 0.0223 | 8 | 3 |
| **A17d4 | 0.0342 | 0.022 | 13 | 0.0354 | 0.0187 | 15 | 4 |
| **P11d4 | 0.0217 | 0.0331 | 21 | 0.0289 | 0.0110 | 19 | 5 |

TABLE 8-continued

End Point RSV Microneutralization Titer Of High On Rate Mutant IgG and Fab

| Molecule | Mean IC50 (Curve) μg/ml | STDEV Curve IC50 | Fold Difference (Curve ICX50) | Mean IC50 (Control) μg/ml | STDEV Control IC50 | Fold Difference (Control IC50) | n (assay repeat) |
|---|---|---|---|---|---|---|---|
| **P12f2 | 0.0231 | 0.0141 | 20 | 0.0223 | 0.0083 | 24 | 6 |
| **A8c7 | 0.0337 | 0.0309 | 13 | 0.0383 | 0.0283 | 14 | 5 |
| **A12a6 | 0.0357 | 0.0316 | 13 | 0.0354 | 0.0261 | 15 | 7 |
| **P12f4 | 0.0242 | 0.0163 | 19 | 0.0235 | 0.0076 | 23 | 7 |
| **A13c4 | 0.0376 | 0.0268 | 12 | 0.0375 | 0.0213 | 14 | 6 |
| **A4B4 | 0.0171 | 0.0018 | 27 | 0.0154 | 0.00417 | 35 | 2 |
| *A1e9 | 0.157 | — | 3 | 0.125 | — | 4 | 1 |
| *A17d4 | 0.0179 | — | 25 | 0.0171 | — | 31 | 1 |
| *P11d4 | >1.00 | — | — | >1.00 | — | — | 1 |
| *P12f2 | 0.0407 | 0.0112 | 11 | 0.0326 | 0.00905 | 16 | 2 |
| *A8c7 | 0.177 | — | 3 | 0.157 | — | 34 | 1 |
| *A12a6 | 0.0287 | 0.00417 | 16 | 0.0310 | 0.00982 | 17 | 2 |
| *P12f4 | 0.0464 | 0.00791 | 10 | 0.0351 | 0.0126 | 15 | 2 |
| *A13c4 | 0.0264 | 0.00141 | 17 | 0.0258 | 0.00071 | 21 | 2 |
| *A4B4 | 0.0414 | — | 11 | 0.0411 | — | 13 | 1 |
| *A13a11 | 0.120 | 0.0222 | 4 | 0.1022 | 0.0260 | 5 | 2 |
| *A1h5 | 0.194 | 0.462 | 2 | 0.176 | 0.0625 | 3 | 2 |

**Monoclonal Antibody
*Fab Fragment

8. EXAMPLE

RSV Fusion INHIBITION Assay

The ability of the antibodies of the invention or fragments thereof to block RSV-induced fusion after viral attachment to the cells is determined in a fusion inhibition assay. This assay is identical to the microneutralization assay, except that the cells were infected with RSV (Long) for four hours prior to addition of antibody (Taylor et al, 1992, J. Gen. Virol. 73:2217-2223).

9. EXAMPLE

Isothermal Titration Calorimetry

Thermodynamics binding affinities and enthalpies were determined from isothermal titration calorimetry (ITC) measurements on the interaction of antibodies with RSV F glycoprotein (NUF4), an antigen which mimics the binding site of the RSV virus.

Methods & Materials

Antibodies & Antigen

A13c4, A17d4, A4B4, and SYNAGIS® were diluted in dialysate and the concentrations were determined by UV spectroscopic absorption measurements with a Perkin-Elmer Lambda 4B Spectrophotometer using an extinction coefficient of 217,000 $M^{-1}$ $cm^{-1}$ at the peak maximum at 280 nm. The diluted NUF4 concentrations were calculated from the ratio of the mass of the original sample to that of the diluted sample since its extinction coefficient was too low to determine an accurate concentration without employing and losing a large amount of sample.

ITC Measurements

The binding thermodynamics of the antibodies were determined from ITC measurements using a Microcal, Inc. VP Titration Calorimeter. The VP titration calorimeter consists of a matched pair of sample and reference vessels (1.409 ml) enclosed in an adiabatic enclosure and a rotating stirrer-syringe for titrating ligand solutions into the sample vessel. The ITC measurements were performed at 25° C. and 35° C. The sample vessel contained the antibody in the phosphate buffer while the reference vessel contained just the buffer solution. The phosphate buffer solution was saline 67 mM $PO_4$ at pH 7.4 from HyClone, Inc. Five or ten μl aliquots of the 0.05 to 0.1 mM NUF4 solution were titrated 3 to 4 minutes apart into the antibody sample solution until the binding was saturated as evident by the lack of a heat exchange signal. With some antibody sample solutions, additional constant amounts of heat with the addition of each aliquot were observed following binding saturation of the antibody. This was attributed to a heat of dilution of the NUF4 titrant and was subtracted from the titrant heats obtained during the titration prior to analysis of the data.

A non-linear, least square minimization software program from Microcal, Inc., Origin 5.0, was used to fit the incremental heat of the ith titration (ΔQ (i)) of the total heat, $Q_t$, to the total titrant concentration, $X_t$, according to the following equations (I), $$Q_t=nC_t\Delta H_b°V\{1+X_t/nC_t+1/nK_bC_t-[(1+X_t/nC_t+1/nK_bC_t)^2-4X_t/nC_t]^{1/2}\}/2 \quad (1a)$$

$$\Delta Q(i)=Q(i)+dVi/2V\,\{Q(i)+Q(i-1)\}-Q(i-1) \quad (1b)$$

where $C_t$ is the initial antibody concentration in the sample vessel, V is the volume of the sample vessel, and n is the stoichiometry of the binding reaction, to yield values of $K_b$, $\Delta H_b°$, and n. The optimum range of sample concentrations for the determination of $K_b$ depends on the value of $K_b$ and is defined by the following relationship.

$$C_tK_bn\leqq 500 \quad (2)$$

so that at 1 μM the maximum $K_b$ that can be determined is less than $2.5\times10^8$ $M^{-1}$. If the first titrant addition did not fit the binding isotherm, it was neglected in the final analysis since it may reflect release of an air bubble at the syringe opening-solution interface.

Results

The ITC results are summarized in Table 9. The higher than 2 stoichiometries in Table 9 indicate that either the concentration determination of the antibody or NUF4 was incorrect. Since the same NUF4 sample was used as a titrant with antibodies having the amino acid sequence of A13c4 at 35° C. and A17d4 at 35° C., which exhibit in at least one of the titrations the correct stoichiometry of 2, it is assumed that the titrant concentration was correct and that the large values of n result from incorrectly determined antibody concentrations. However, it can be shown that the binding constants are critically dependent on the titrant concentration and, thus, despite the 2-3 disparity in n, the binding constants are correct. Since the binding constants of antibodies having the amino acid sequence of A4B4 and A13c4 at 25° C. were near the upper determination limit by ITC (equation 2) and with the limited amount of available NUF4, it was decided to use 35° C. as the reference temperature for comprising the binding affinities. The results summarized in Table 9 show that the binding affinities to NUF4 are in the order A4B4>A13c4>A17d4>SYNAGIS®.

TABLE 9

Average Binding Constants and Enthalpies of NUF4 to Antibodies

| Antibody | $K_b$ | $\Delta H_b$ in kJ mol$^{-1}$ |
| --- | --- | --- |
| A4B4 | $269 \pm 74 \times 10^6$ M$^{-1}$ or ~3.7 nM* | $92.8 \pm 1.0$ |
| A13c4 | $107 \pm 28 \times 10^6$ M$^{-1}$ or 9 nM | $67 \pm 17$ |
| A17d4 | $75 \pm 14 \times 10^6$ M$^{-1}$ or 13 nM | $68 \pm 10$ |
| SYNAGIS® | $1.23 \pm 0.17 \times 10^6$ M$^{-1}$ or 810 nM | $71 \pm 5$ |

*Based only on the best titration run at 35° C.
4.0 nM is ITC lower limit of I/$K_b$ range (ITC range is limited to [antibody]$_n$ $K_b$ = 500 where n is the stoichiometry and [antibody] is the concentration of the antibody in the cell).

10. EXAMPLE

Cotton Rat Prophylaxis

To determine the ability of SYNAGIS® to prevent lower respiratory tract RSV infection in cotton rats when administered by and intravenous (IV) route and to correlate the serum concentration of SYNAGIS® with a reduction in lung RSV titer.

Materials & Methods

SYNAGIS® lot L94H048 was used for studies III-47 and III-47A. SYNAGIS® lot L95 K016 was used for study III-58. Bovine serum albumin (BSA) (fraction V, Sigma Chemicals). RSV-Long (A subtype) was propagated in Hep-2 cells.

On day 0, to groups of cotton rats (*Sigmodon hispidis*, average weight 100 g) were administered SYNAGIS®, RSV-IGIV or BSA was administered by intramuscular injection. Twenty-four hours post administration, the animals were bled and infected intranasally with 105 pfu of RSV. Twenty-four hours later, the animals were bled and infected intranasally with $10^5$ PFU or RSV (Long Strain). Four days after the infection, animals were sacrificed, and their lung tissue was harvested and pulmonary virus titers were determined by plaque titration. For studies III-47 and III-47A, the doses of monoclonal antibody ("MAb") consisted of 0.31, 0.63, 1.25, 2.5, 5.5 and 10 mg/kg (body weight). For studies III-58, the doses of MAb consisted of 0.63, 1.25, 2.5, 5.5 and 10 mg/kg (body weight). In all three studies bovine serum albumin (BSA) 10 mg/kg was used as a negative control. Human antibody concentrations in the serum at the time of challenge are determined using a sandwich ELISA.

Results

The results of the individual experiments are presented in Tables 10-12. The results of all of the experiments combined is shown in Table 13. All three studies show a significant reduction of pulmonary virus titers in animals treated with SYNAGIS®. A clear dose-response effect was observed in the animals. The combined data indicated that a dose of 2.5 mg/kg results in a greater than 99% reduction in lung RSV titer. The mean serum concentration of SYNAGIS® for this dose at the time of viral challenge was 28.6 mg/ml.

TABLE 10

EXPERIMENT III-47

| Compound | Number of Animals | Dose | Mean ± Std Error Concentration of Human IgG (mg/ml) | Lung Viral Titer Geometric Mean ± Std Error (log10 pfu/gm) |
| --- | --- | --- | --- | --- |
| BSA | 4 | 0 | | $1.4 \times 10^{5\pm}$ 1.7 |
| SYNAGIS® | 3 | 0.312 mg/kg | $3.83 \pm 1.1$ | $2.1 \times 10^{4\pm}$ 2.1 |
| SYNAGIS® | 3 | 0.625 mg/kg | $5.27 \pm 0.37$ | $7.7 \times 10^{4\pm}$ 1.6 |
| SYNAGIS® | 4 | 1.25 mg/kg | $9.15 \pm 0.16$ | $3.4 \times 10^{4\pm}$ 1.3 |
| SYNAGIS® | 3 | 2.50 mg/kg | $23.4 \pm 2.8$ | $1.4 \times 10^{3\pm}$ 1.7 |
| SYNAGIS® | 2 | 5.0 mg/kg | $42.4 \pm 13.4$ | $4.6 \times 10^{2\pm}$ 4.6 |
| SYNAGIS® | 4 | 10.0 mg/kg | $141.1 \pm 14.4$ | $1.0 \times 10^{2\pm}$ 1.0 |

TABLE 11

EXPERIMENT III-47A

| Compound | Number of Animals | Dose | Mean ± Std Error Concentration of Human IgG (mg/ml) | Lung Viral Titer Geometric Mean ± Std Error (log10 pfu/gm) |
| --- | --- | --- | --- | --- |
| BSA | 4 | | | $1.9 \times 10^{5\pm}$ 1.2 |
| SYNAGIS® | 4 | 0.312 mg/kg | $1.8 \pm 0.12$ | $8.5 \times 10^{4\pm}$ 1.2 |
| SYNAGIS® | 4 | 0.625 mg/kg | $4.0 \pm 0.19$ | $5.0 \times 10^{4\pm}$ 1.6 |
| SYNAGIS® | 4 | 1.25 mg/kg | $11.8 \pm 0.68$ | $1.9 \times 10^{3\pm}$ 1.4 |
| SYNAGIS® | 4 | 2.50 mg/kg | $18.9 \pm 2.0$ | $5.3 \times 10^{3\pm}$ 1.6 |
| SYNAGIS® | 3 | 5.0 mg/kg | $55.6 \pm 2.3$ | $1.6 \times 10^{2\pm}$ 1.3 |
| SYNAGIS® | 4 | 10.0 mg/kg | $109.7 \pm 5.22$ | $1.0 \times 10^{2\pm}$ 1.0 |

TABLE 12

EXPERIMENT III-58

| Compound | Number of Animals | Dose | Mean ± Std Error Concentration of Human IgG (mg/ml) | Lung Viral Titer Geometric Mean ± Std Error (log10 pfu/gm) |
| --- | --- | --- | --- | --- |
| BSA | 4 | | 0 | $1.1 \times 10^{5\pm}$ 1.2 |
| SYNAGIS® | 4 | 0.625 mg/kg | $5.78 \pm 0.32$ | $1.6 \times 10^{4\pm}$ 1.2 |
| SYNAGIS® | 4 | 1.25 mg/kg | $9.82 \pm 0.23$ | $1.6 \times 10^{3\pm}$ 1.3 |

TABLE 12-continued

EXPERIMENT III-58

| Compound | Number of Animals | Dose | Mean ± Std Error Concentration of Human IgG (mg/ml) | Lung Viral Titer Geometric Mean ± Std Error (log10 pfu/gm) |
|---|---|---|---|---|
| SYNAGIS ® | 4 | 2.50 mg/kg | 34.1 ± 2.11 | $4.3 \times 10^{2\pm} 1.6$ |
| SYNAGIS ® | 3 | 5.0 mg/kg | 58.3 ± 4.48 | $1.0 \times 10^{2\pm} 1.0$ |
| SYNAGIS ® | 4 | 10.0 mg/kg | 111.5 ± 5.04 | $1.0 \times 10^{2\pm} 1.0$ |

TABLE 13

III-47, III-47A and III-58 COMBINED

| Compound | Number of Animals | Dose | Mean ± Std Error Concentration of Human IgG (mg/ml) | Lung Viral Titer Geometric Mean ± Std Error (log10 pfu/gm) |
|---|---|---|---|---|
| BSA | 18 | | 0 | $1.3 \times 10^{5\pm} 1.2$ |
| SYNAGIS ® | 7 | 0.312 mg/kg | 2.67 ± 0.60 | $4.6 \times 10^{4\pm} 1.5$ |
| SYNAGIS ® | 17 | 0.625 mg/kg | 5.27 ± 0.27 | $2.7 \times 10^{4\pm} 1.3$ |
| SYNAGIS ® | 18 | 1.25 mg/kg | 10.1 ± 0.29 | $3.3 \times 10^{3\pm} 1.4$ |
| SYNAGIS ® | 17 | 2.50 mg/kg | 28.6 ± 2.15 | $9.6 \times 10^{2\pm} 1.5$ |
| SYNAGIS ® | 15 | 5.0 mg/kg | 55.6 ± 3.43 | $1.3 \times 10^{2\pm} 1.2$ |
| SYNAGIS ® | 18 | 10.0 mg/kg | 117.6 ± 5.09 | $1.0 \times 10^{2\pm} 1.0$ |

11. EXAMPLE

Intramuscular Cotton Rat Studies

This experiment demonstrates that a greater reduction in RSV titer is achieved when A4b4, A4b4-F52S or A4b4/L1FR-S28R is administered intramuscularly to a cotton rat than when the same concentration of SYNAGIS® is administered intramuscularly to a cotton rat.

Materials & Methods

Intramuscular Cotton Rat Prophylaxis

Cotton rats (*S. hispidus*, average weight 100 grams) were anesthetized with methoxyflurane and dosed with 0.1 ml of purified monoclonal antibody (MAb) or BSA control by intramuscular (i.m.) injection. Twenty-four hours later animals were again anesthetized, bled for serum MAb concentration determination, and challenged with $10^5$ PFU RSV long by intranasal (i.n.) instillation. Four days later animals were sacrificed, serum samples were obtained, and their lungs were harvested. Lungs were homogenized in 10 parts (wt/vol) of Hanks Balanced Salt solution and the resultant suspension was used to determine pulmonary viral titers by plaque assay.

Intramuscular Cotton Rat Pharmacokinetics

Cotton rats (*S. hispidus*, average weight 100 grams) were anesthetized with methoxyflurane and dosed with 0.1 ml of purified MAb or BSA control by intramuscular (i.m) injection. Twenty-four hours later all of the animals were bled for serum MAb concentration determination, and half of the animals from each group were sacrificed to perform bronchoalveolar lavage (BAL). Four days later the remaining animals were sacrificed, serum samples were obtained and BAL performed.

Results

As shown in Tables 14-16, a greater reduction in RSV titer is achieved with equivalent or lower lung levels of A4b4, A4b4-F52S, or A4b4/L1FR-S28R as with SYNAGIS®.

TABLE 14

| Intramuscular Cotton Rat Prophylaxis Data | | | | | | | | |
|---|---|---|---|---|---|---|---|---|
| | 0.5 mg/kg | | | | 0.125 mg/kg | | | |
| | Serum IgG (μg/ml) | Lung IgG (μg/ml) | Virus Titer (pfu/gm) | log Virus Titer | Serum IgG (μg/ml) | Lung IgG (μg/ml) | Virus Titer (pfu/gm) | log Virus Titer |
| Synagis | 3.4 | 0.099 | $7.3 \times 10^3$ | 3.9 | 0.893 | 0.024 | $3.1 \times 10^4$ | 4.5 |
| Ab4-F52S | 2.9 | 0.089 | $7.3 \times 10^2$ | 2.9 | 0.781 | 0.020 | $8.6 \times 10^3$ | 3.9 |
| Ab4/L1FR-S28R | 3.3 | 0.093 | $6.1 \times 10^2$ | 2.8 | 0.748 | 0.016 | $2.3 \times 10^4$ | 4.4 |
| BSA | | | $5.9 \times 10^4$ | 4.8 | | | | |

TABLE 15

| Intramuscular Cotton Rat Prophylaxis Data | | | | | | |
|---|---|---|---|---|---|---|
| | 0.5 mg/kg | | | 1 mg/kg | | |
| Molecule | Serum IgG μg/ml | Lung IgG μg/ml | log(10) Lung Virus | Serum IgG μg/ml | Lung IgG μg/ml | log(10) Lung Virus |
| A4b4 | 2.4 | 0.013 | 4.3 | 3.1 | 0.094 | 3.4 |
| Synagis | 1.9 | 0.038 | 4.4 | 4.2 | 0.212 | 3.3 |
| BSA | | | | | | 4.4 |

TABLE 16

Intramuscular Cotton Rat Pharmacokinetics Data

| Molecule | 24 Hours | | 96 hours | |
| --- | --- | --- | --- | --- |
| | Serum IgG (μg/ml) | BAL IgG (ng/ml) | Serum IgG (μg/ml) | BAL IgG (ng/ml) |
| 4b4 | 3.4 | 2.2 | 2.6 | 1.4 |
| Synagis | 4.1 | 5.3 | 2.8 | 3.5 |

12. EXAMPLE

In Vitro Isolation of SYNAGIS® Specific Monoclonal Antibody Resistant Mutants(MARM) of RSV Strain A/Long This example demonstrates that MARMs can be isolated from RSV laboratory strain A/Long upon multiple rounds of selection in the presence of SYNAGIS®.

Materials

SYNAGIS® (formulated product: ref RN1002.148), Control Pan RSV MAb Pool (Chemicon MAB858-4, a blend of three MAbs anti-F, G, and N proteins), anti-RSV Type A MAb (Chemicon MAB858-1), and anti-RSV Type B MAb (Chemicon MAB858-2) were used in this study. Secondary detecting reagents were either Alexa™488 conjugated Goat F(ab')$_2$ anti-Mouse or Human IgG (H+L). RSV A/Long strain ($5 \times 10^7$ TCID$_{50}$/ml) was propagated from Master Virus Bank 031797. HEp-2 cells were propagated in EMEM supplemented with 10% FBS and 2 mM L-Gln in a 37° C., 5% CO$_2$ environment. Total cellular RNAs were isolated from infected HEp-2 cells with the Promega RNAgents Kit. cDNAs were synthesized with the Boehringer Mannheim 1$^{st}$ Strand cDNA Synthesis Kit, using Oligo- (dT) primer. Amplification of a fragment of the F protein for DNA sequencing was performed by Polymerase Chain Reaction (PCR), using gene-specific oligonucleotides (MR-120 and MR-122) and the Boehringer Mannheim High Fidelity PCR Kit.

Methods

Selection of MARMs:

$4 \times 10^5$ HEp-2 cells were seeded per well of a 24-well plate in growth medium (EMEM, 10% FBS, 2 mM L-Gln) and incubated overnight in growth conditions (37° C., 5% CO$_2$). 40 wells were seeded for individual MARM selection. Prior to infection, a fresh vial of master virus bank RSV A/Long was thawed rapidly at 37° C. and the virus titer adjusted to $4 \times 10^6$ pfu/ml in HEp-2 growth medium. SYNAGIS® was added to the virus inoculum at a final concentration of 30 μg/ml, and the mixture was incubated at 37° C. for one hour. An aliquot of RSV was incubated with an irrelevant Human IgG1 Mab (MEDI-507) and was used as a negative control. An uninfected control well was also set up for each plate. Cells were washed once with fresh medium and were overlayed with 100 μl of RSV A/Long virus stock/MAb mixture (multiplicity of infection [m.o.i.]=4). Cells were incubated for four hours in growth conditions followed by addition of 1 ml of growth medium to each well. Cytopathic effect (CPE) was monitored on a daily basis by light microscopy. Following seven days of selection the contents of each well were supplemented with a further 30 μg/ml of SYNAGIS® or irrelevant Human IgG1 Mab, and were used to infect freshly seeded HEp-2 cells ($4 \times 10^5$ cells/well of 24-well plate). After a further seven days of selection the process was repeated one more time for a total of three rounds of selection.

Plaque Purification of MARMs:

After the third round of selection, the contents of ten independent wells were chosen at random and used for plaque purification of MARMs. The remaining supernatants were mixed 1:1 with 50% sucrose solution and immediately frozen at −80° C. Supernatants were diluted 1:10, 1:100, and 1:1000 in growth medium and incubated with 30 μg/ml of SYNAGIS® for one hour prior to infection. 1 ml of virus inoculum was overlayed on monolayers of HEp-2 cells in 60 mm round culture dishes ($1 \times 10^6$ cells/dish) and incubated for 4 hours in growth conditions. Following infection the inoculum was carefully aspirated and cells were overlayed with 3 ml growth medium supplemented with 0.8% low melting temperature agarose (Gibco BRL), and containing 30 μg/ml of SYNAGIS®. Dishes were returned to the incubator after complete solidification of agarose and monitored daily for plaque formation. Uninfected controls and wild type RSV control plates were set up for comparison. After five to six days, each plate was overlayed with an additional 2 ml of 0.8% agarose in growth medium supplemented with 50 μg/ml neutral red. Following an overnight incubation in growth conditions, plaques were scored and picked for a second round of purification.

Amplification of Clonal MARMs:

Following a second round of plaque purification two clones from each isolate were expanded for production of high titer viral stocks. Individual plaques were picked with the aid of a pipet tip and incubated in 0.1 ml of fresh medium at 4° C. overnight to elute the virus. Each aliquot was used to infect HEp-2 cells in flat bottom 96-well plates ($1 \times 10^4$ cells/well) in the presence of 30 μg/ml SYNAGIS®. After five days the entire well content was used to infect HEp-2 cells in the presence of 30 μg/ml of SYNAGIS® in 24-well plates. Each inoculum was subsequently expanded in the presence of 30 μg/ml of SYNAGIS® to a T-25 flask ($1 \times 10^6$ cells/flask) and 5 mls of high titer virus stock were produced. MARM stocks were frozen as described above.

F Protein cDNA Synthesis and DNA Sequencing:

In order to determine the nucleotide sequence of an approximately 400 nucleotide region of the F protein gene thought to contain the epitope for SYNAGIS®, First strand cDNA synthesis was performed with total cellular RNAs isolated from MARM-infected HEp-2 cells at 4 days post-infection. Amplification of a fragment of the F protein for DNA sequencing was performed as described in Materials section. Amplified MARM F-protein cDNAs were purified by phenol/chloroform extraction and ethanol precipitation, and used in a PCR sequencing reaction with gene-specific oligos and Perkin-Elmer Cetus Big-Dye Terminator reaction mix to sequence the relevant region.

Immunofluorescence Assay (IFA):

Cells infected with RSV isolates were tested for anti-RSV binding by SYNAGIS® and Control Pan RSV MAb Pool, as follows. Four to five day RSV-infected HEp-2 cultures were mixed with PBS and centrifuged at 300×g for 5 minutes at room temperature. Pellets were resuspended in a small volume of PBS for analysis. Five to ten microliters of each cell suspension were spotted per 5 mm well on acetone washed 12-well HTC super cured glass slides and allowed to air dry. Slides were fixed in cold (−20° C.) acetone for 10 minutes. Reactions were blocked by spotting 10 µl of 1% BSA in PBS into each well and incubating for 10 minutes at room temperature. Slides were washed three times in 1×PBS/0.1% Tween-20 and air-dried. Ten microliters of each primary antibody reagent diluted to 250 ng/ml in blocking buffer were spotted per well and reactions were incubated in a humidified 37° C. environment for 30 minutes. Slides were then washed for 1 minute in three changes of 1×PBS/0.1% Tween-20 and were air-dried. Ten microliters of appropriate secondary conjugated antibody reagent diluted to 250 ng/ml in blocking buffer were added to each respective well and reactions were incubated in a humidified 37° C. environment for an additional 30 minutes. Slides were then washed for 1 minute in three changes of 1×PBS/0.1% Tween-20. Five micro liters of 50% glycerol in PBS, 10 mM Tris, pH 8.0, 1 mM EDTA were spotted in each reaction well, and slides were mounted with cover slips. Each reaction well was subsequently analyzed by fluorescence microscopy at 200× power using a B-2A filter (EX 450-490 nm). Positive reactions were scored against an auto-fluorescent background obtained with unstained cells or cells stained with secondary reagent alone.

RSV positive reactions were characterized by bright fluorescence punctuated with small inclusions in the cytoplasm of infected cells.

Microneutralization Assay:

The procedure used here is described in Johnson et al., 1999, J. Infectious Diseases 180:35-40, the disclosure of which is hereby incorporated by reference in its entirety. Briefly, antibody dilutions were made in triplicate using a 96-well plate. Ten $TCID_{50}$ of RSV A MARMS were incubated with serial dilutions of the antibody to be tested for 2 hours at 37_C in the wells of a 96-well plate. The antibodies used in the assay comprised the heavy chain of SYNAGIS®, the heavy chain of SYNAGIS® with a point mutation or the heavy chain of A4B4, and the light chain of SYNAGIS®, the light chain of SYNAGIS® with point mutations, the light chain of A4B4 with point mutations, the light chain of A4B4 with point mutations, the light chain of L1FR (a.k.a. IX-493L1FR) or the light chain of L1FR with point mutations. Mab 13/19 was used in the assay as a positive control. RSV susceptible HEp-2 cells ($2.5 \times 10^4$) were then added to each well and cultured for 5 days at 37_C in 5% $CO_2$. After 5 days, the medium was aspirated and cells were washed and fixed to the plates with 80% methanol and 20% PBS. RSV replication was then determined by F protein expression. Fixed cells were incubated with a biotin-conjugated anti-F protein monoclonal antibody (pan F protein, C-site-specific MAb 133-1H) washed and horseradish peroxidase conjugated avidin was added to the wells. The wells were washed again and turnover of substrate TMB (thionitrobenzoic acid) was measured at 450 nm. The results from the assay for the monoclonal antibodies are shown in Table 19 infra.

Results and Discussion

The binding activity of SYNAGIS® was tested by IFA against a panel of 20 RSV A/Long MARMs obtained by three rounds of selection on HEp-2 cells in the presence of SYNAGIS®. A pool of monoclonal antibodies against the fusion, glycoprotein, and nuclear proteins of RSV (Control Pan RSV MAb Pool) was used as a positive control for detection of RSV. Subtyping of RSV MARMs was performed with two monoclonal antibodies that distinguish type A and type B glycoproteins. As summarized in Table 17, lack of binding activity by SYNAGIS® was demonstrated in all 20 MARMs. Contrasting with lack of binding by SYNAGIS®, binding of the Control Pan RSV MAb Pool was demonstrated for all MARMs tested. All 20 MARMs were classified as RSV type A. Wild type RSV A/Long infected HEp-2 cells bound SYNAGIS®, Pan RSV MAb Pool, and RSV Type A MAb, but failed to react with RSV Type B MAb, as expected.

DNA sequencing analysis of an approximately 400-nucleotide region of the RSV F protein cDNA encompassing the proposed SYNAGIS® epitope revealed a single mutation at the amino-acid level at position 272. Table 18 shows the amino acid change at position 272 in twelve isolates sequenced to date. Although the entire nucleotide sequence of RSV MARMs F protein has not been determined, these results suggest that amino acid 272 is a critical residue in modulating the binding of SYNAGIS® to its epitope.

The ability of various monoclonal antibodies to neutralize the replication of RSV A MARMs was determined. As shown in Table 19, the ability of the monoclonal antibodies to neutralize the replication of RSV MARMs varied depending upon the amino acid sequence of the heavy chain (HC) and light chain (LC) of the antibody.

TABLE 17

Characterization of anti-RSV Binding Activity by SYNAGIS ®, Control Pan RSV MAb Pool (anti-F, G, N proteins), anti-RSV Type A MAb, and anti-RSV Type B MAb by Immunofluorescence Assay (IFA) on RSV A/Long MARMs.

| RSV MARM sample | Reactivity w/ SYNAGIS ® | Reactivity w/ anti-RSV MAb Pool | Reactivity w/ anti-RSV type A MAb | Reactivity w/ Anti-RSV type B MAb |
|---|---|---|---|---|
| B1 | − | + | + | − |
| B2 | − | + | + | − |
| B3 | − | + | + | − |
| B4 | − | + | + | − |
| B5 | − | + | + | − |
| B6 | − | + | + | − |
| B7 | − | + | + | − |
| B8 | − | + | + | − |
| B9 | − | + | + | − |
| B10 | − | + | + | − |
| B11 | − | + | + | − |
| B12 | − | + | + | − |
| B13 | − | + | + | − |
| B14 | − | + | + | − |
| B15 | − | + | + | − |
| B16 | − | + | + | − |
| B17 | − | + | + | − |
| B18 | − | + | + | − |
| B19 | − | + | + | − |
| B20 | − | + | + | − |
| Wt RSV A/ | + | + | + | − |

TABLE 18

Amino acid sequence of a region of the wild type RSV A/Long and MARMs F Protein encompassing the proposed SYNAGIS ® epitope.

| Isolate | Amino Acid Sequence (Position number) | | | | | | | | | | | | | |
|---|---|---|---|---|---|---|---|---|---|---|---|---|---|---|
| Wild type | 266 | 267 | 268 | 269 | 270 | 271 | 272 | 273 | 274 | 275 | 276 | 277 | 278 | 279 |
| MARM B1 | I | T | N | D | Q | K | N | L | M | S | N | N | V | Q |
| MARM B2 | I | T | N | D | Q | K | M | L | M | S | N | N | V | Q |
| MARM B3 | I | T | N | D | Q | K | M | L | M | S | N | N | V | Q |
| MARM B4 | I | T | N | D | Q | K | M | L | M | S | N | N | V | Q |
| MARM B6 | I | T | N | D | Q | K | M | L | M | S | N | N | V | Q |
| MARM B7 | I | T | N | D | Q | K | T | L | M | S | N | N | V | Q |
| MARM B8 | I | T | N | D | Q | K | M | L | M | S | N | N | V | Q |
| MARM B9 | I | T | N | D | Q | K | Q | L | M | S | N | N | V | Q |
| MARM B10 | I | T | N | D | Q | K | T | L | M | S | N | N | V | Q |
| MARM B13 | I | T | N | D | Q | K | M | L | M | S | N | N | V | Q |
| MARM B14 | I | T | N | D | Q | K | Q | L | M | S | N | N | V | Q |
| MARM B15 | I | T | N | D | Q | K | M | L | M | S | N | N | V | Q |

TABLE 19

MARM analysis by Microneutralization Assay
RSV Microneutralization Assay On RSV A MARMs to Synagis with RSV Monoclonal Antibody

| | Amino Acid Change | | | | |
|---|---|---|---|---|---|
| | K272Q | K272N | K272M | K272T | |
| Antibody | MARMs to SYNAGIS ® | | | | Note |
| HC/LC | MARM B9 | MARM B1 | MARM B2 | MARM B7 | |
| SYNAGIS ®/SYNAGIS ® | − | − | − | − | Purified Ab |
| A4B4/A4B4 | + | + | + | + | Purified Ab |
| A4B4/SYNAGIS ® | + | + | + | − | Purified Ab |
| SYNAGIS ®/A4B4 | − | − | − | − | Purified Ab |
| A4B4/L1FR | + | + | + | − | Purified Ab |
| A4B4/L1FR S28R | + | + | + | + | Purified Ab |
| A4R4/L1FR S28R, S52F | + | + | + | + | Purified Ab |
| A4B4/L1FR-28R, 52F, F93 | − | − | − | − | Purified Ab |
| A4B4/A4b428S | + | + | + | + | Purified Ab |
| A4B4/A4b452S | + | + | + | + | Purified Ab |
| Mab 13/19 | + | + | + | + | Purified Ab |
| SYNAGIS ®/K53F | − | − | − | − | 293H sup |
| SYNAGIS ®/S28R | − | − | − | − | 293H sup |
| SYNAGIS ®/Q26S | − | − | − | − | 293H sup |
| SYNAGIS ®/A55D | − | − | − | − | 293H sup |
| SYNAGIS ®/K24S | − | − | − | − | 293H sup |
| SYNAGIS ®/C25A | − | − | − | − | 293H sup |
| SYNAGIS ®/L27S | − | − | − | − | 293H sup |
| SYNAGIS ®/S52F | − | − | − | − | 293H sup |
| SYNAGIS ®/L105V | − | − | − | − | 293H sup |
| T98F/SYNAGIS ® | − | − | − | − | Purified ab |
| S32A/SYNAGIS ® | − | − | − | − | 293H sup |
| S95D/SYNAGIS ® | − | − | − | − | 293H sup |
| D58H/SYNAGIS ® | − | − | − | − | 293H sup |
| A105Q/SYNAGIS ® | − | − | − | − | 293H sup |
| S65D/SYNAGIS ® | − | − | − | − | 293H sup |
| W100F/SYNAGIS ® | − | − | − | − | 293H sup |

+ = neutralization detected;
− = no neutralization detected

13. EXAMPLE

In vitro Isolation of A4B4 Specific Monoclonal Antibody Resistant Mutants (MARM) of RSV Strain A/Long This example demonstrates that MARMs can be isolated from RSV laboratory strain A/Long upon multiple rounds of selection in the presence of A4B4

Materials

A4B4 (Lot # 524-9, 3.57 mg/ml), Control Pan RSV MAb Pool (Chemicon MAB858-4, a blend of three MAbs anti-F, G, and N proteins), anti-RSV Type A MAb (Chemicon MAB858-1), and anti-RSV Type B MAb (Chemicon MAB858-2) were used in this study. Secondary detecting reagents were either Alexa™488 conjugated Goat F (ab')$_2$ anti-Mouse or Human IgG (H+L). Virus bank of RSV A/Long strain NWVB020500 (2.38×10$^7$ TCID$_{50}$/ml) propagated from Master Virus Bank 031797. HEp-2 cells were propagated in EMEM supplemented with 10% FBS and 2 mM L-Gln in a 37° C., 5% CO$_2$ environment. Messenger RNA was purified from the infected cells using the mRNA Capture Kit (Roche). The mRNA samples were used to make cDNA using the reagents from the cDNA First Strand Reaction Kit (Roche), followed by amplification of the RSV F protein gene by the Polymerase Chain Reaction (PCR) using gene specific primers.

Methods

Selection of MARMs:

4×10$^5$ HEp-2 cells were seeded per well of a 24-well plate in growth medium (EMEM, 10% FBS, 2 mM L-Gln) and incubated overnight in growth conditions (37° C., 5% CO$_2$). 44 wells were seeded for individual MARM selection. Prior to infection, a fresh vial of virus bank RSV A/Long was thawed rapidly at 37° C. and the virus titer adjusted to 4×10$^6$ pfu/ml in HEp-2 growth medium. A4B4 was added to the virus inoculum at a final concentration of 2 µg/ml, and the mixture was incubated at 37° C. for one hour. An aliquot of RSV was incubated with an irrelevant Human IgGl Mab (MEDI-507) and was used as a negative control. An uninfected control well was also set up for each plate. Cells were washed once with fresh medium and were overlayed with 100 µl of RSV A/Long virus stock/MAb mixture. Cells were incubated for four hours in growth conditions followed by addition of 1 ml of growth medium to each well. Cytopathic effect (CPE) was monitored on a daily basis by light microscopy. Following seven days of selection the contents of each well were supplemented with a further 4 µg/ml of A4B4 or irrelevant Human IgGl Mab, and were used to infect freshly seeded HEp-2 cells (4×10$^5$ cells/well of 24-well plate). After a further seven days of selection the process was repeated one more time for a total of three rounds of selection. The contents of wells showing clear CPE were mixed 1:1 with 50% sucrose solution and immediately frozen at −80° C.

Plaque Purification of MARMs:

After the third round of selection, the contents of two independent wells were chosen at random and used for plaque purification of MARMs. A fresh vial of MARM stock (was frozen after third round of selection) was thawed at room temperature and was diluted 1:10, 1:100, and 1:1000 in growth medium and incubated with 4 µg/ml of A4B4 for one hour prior to infection. 0.5 ml of virus inoculum was overlayed on monolayers of HEp-2 cells in 6 well plates (5×10$^5$ cells/well) and incubated for 4 hours in growth conditions. Following infection the inoculum was carefully aspirated and cells were overlayed with 2 ml growth medium supplemented with 0.8% low melting temperature agarose (Gibco BRL), and containing 4 µg/ml of A4B4. Dishes were returned to the incubator after complete solidification of agarose and monitored daily for plaque formation. Uninfected controls and wild type RSV control plates were set up for comparison. After five to six days, each plate was overlayed with an additional 2 ml of 0.8% agarose in growth medium supplemented with 50 µg/ml neutral red. Following an overnight incubation in growth conditions, plaques were scored and picked for a second round of purification.

Amplification of Clonal MARMs:

Following a second round of plaque purification three clones from each isolate were expanded for production of high titer viral stocks. Individual plaques were picked with the aid of a pipet tip and incubated in 0.2 ml of fresh medium at 4° C. overnight to elute the virus. Each aliquot was used to infect HEp-2 cells in flat bottom 24-well plates (2.5×10$^5$ cells/well-seeded day before) in the presence of 4 µg/ml A4B4. After five days the entire well content was used to infect HEp-2 cells in the presence of 4 µg/ml of A4b4 in 24-well plates. Each inoculum was subsequently expanded in the presence of 4 µg/ml of A4b4 to a T-25 flask (6.5×10$^5$ cells/flask—seeded day before) and 5 mls of high titer virus stock were produced. MARM stocks were frozen as described above.

F Protein cDNA Synthesis and DNA Sequencing:

In order to determine the nucleotide sequence of an approximately 800 nucleotide region of the F protein gene thought to contain the epitope for SYNAGIS®, First strand cDNA synthesis was performed with mRNAs isolated from MARM-infected HEp-2 cells at 4 days post-infection. RSV infected Hep2 cells were lysed in 150 µl of lysis buffer provided with the mRNA capture kit. Biotinylated oligo dT was diluted 1:10 with nuclease free H$_2$O and 4 µl was added to each lysate. Samples were incubated 10 minutes at 42° C. to allow the oligo dT to anneal to the mRNA. A 50 µl aliquot of the lysate was transferred to a streptavidin coated PCR tube and incubated for three minutes at 37° C. The lysates were removed from the PCR tubes and discarded. The RNA captured in the tubes was washed three times with 200 µl of wash buffer.

RT reactions were performed using reagents from the First Strand cDNA kit (Roche Molecular Biochemicals). A master mix was prepared so that each reaction contained 5 µl 10× buffer, 5 µl dNTPs, 10 µl MgCl$_2$, 1 µl gelatin, 2 µl RNase Inhibitor, 2 µl AMV-RT, in a final volume of 50 µl. Fifty microliter aliquots of the master mix were transferred to the PCR tubes containing the captured mRNA. Samples were placed in a thermalcycler and incubated for two hours at 42° C. The cDNA reaction mix was then removed from the PCR tubes and discarded. The cDNA captured in the PCR tubes was washed with 200 µl of wash buffer To obtain enough of the RSV F protein gene for sequence analysis, the cDNA was subjected to PCR using gene specific primers. Each reactions contained 10 mM Tris-HCl, pH 8.3, 50 mM KCl, 2.5 mM MgCl$_2$, 200 µM dNTPs, 125 ng of each forward (5'AGT-GTCTTAACCAGCAAAGTGTTAGA 3'; SEQ ID NO:258) and reverse (5' TCATTGACTTGAGATATTGATGCATC 3'; SEQ ID NO:259) primer, and 2.5 units of Taq polymerase (PE Biosystems) in a final volume of 50 µl. The temperature profile for all reactions was 95° C. for 2 min, followed by 40 cycles of 95° C. for 30 sec., 55° C. for 45 sec, 72° C. for 45 sec, with a final extension at 72° C. for 10 minutes.

All PCR products were separated by electrophoresis on a 2% agarose gel in 1×TBE and visualized by ethidium bromide fluorescence.

PCR products were purified using Qiaquick spin columns (Qiagen and sequenced using the Big Dye-terminator PRISM kit (Applied Biosystems (ABI)). The reactions contained 70 ng of PCR product as template, 3 pmols of primer, and 8.0 µl of the PRISM dye-terminator reaction mix in a final volume of 20 µl. The reactions were subjected to thermal cycling according to ABI's dye-terminator sequencing instructions. Unincorporated dyes were removed from the extension products using Centri-Sep spin columns (Princeton Separations). Extension products were dried in a Savant SpeedVac and then dissolved in 10 µl HiDi Formamide (ABI) loading buffer. Samples were applied by electrophoresis in an ABI 3100 automated sequencer. Sequence data collected by the sequencer was analyzed using Lasargene (DNA Star).

Immunofluorescence Assay (IFA):

Cells infected with RSV isolates were tested for anti-RSV binding by A4B4, SYNAGIS® and Control Pan RSV MAb Pool, as follows. Four to five day RSV-infected HEp-2 cultures were mixed with PBS and centrifuged at 300×g for 5 minutes at room temperature. Pellets were resuspended in a small volume of PBS for analysis. Five to ten micro liters of each cell suspension were spotted per 5 mm well on acetone washed 12-well HTC supercured glass slides and allowed to air dry. Slides were fixed in cold (−20° C.) acetone for 10 minutes. Reactions were blocked by spotting 10 µl of 1% BSA in PBS into each well and incubating for 10 minutes at room temperature. Slides were washed three times in 1×PBS/ 0.1% Tween-20 and air-dried. Ten micro liters of each primary antibody reagent diluted to 250 ng/ml in blocking buffer were spotted per well and reactions were incubated in a humidified 37° C. environment for 30 minutes. Slides were then washed for 1 minute in three changes of 1×PBS/0.1% Tween-20 and were air-dried. Ten micro liters of appropriate secondary conjugated antibody reagent diluted to 250 ng/ml in blocking buffer were added to each respective well and reactions were incubated in a humidified 37° C. environment for an additional 30 minutes. Slides were then washed for 1 minute in three changes of 1×PBS/0.1% Tween-20. Five micro liters of 50% glycerol in PBS, 10 mM Tris, pH 8.0, 1 mM EDTA were spotted in each reaction well, and slides were mounted with cover slips. Each reaction well was subsequently analyzed by fluorescence microscopy at 200× power using a B-2A filter (EX 450-490 nm). Positive reactions were scored against an auto fluorescent background obtained with unstained cells or cells stained with secondary reagent alone.

RSV positive reactions were characterized by bright fluorescence punctuated with small inclusions in the cytoplasm of infected cells.

Microneutralization Assay:

The procedure used here is described in Johnson et al., 1999, J. Infectious Diseases 180:35-40, the disclosure of which is hereby incorporated by reference in its entirety. Briefly, antibody dilutions were made in triplicate using a 96-well plate. Ten $TCID_{50}$ of RSV A MARMS were incubated with serial dilutions of the antibody to be tested for 2 hours at 37 C in the wells of a 96-well plate. The antibodies used in the assay comprised the heavy and light chain of SYNAGIS®, the heavy and light chain of A4b4, the combination of the heavy and light chain of SYNAGIS® and A4b4, the SYNAGIS® heavy chain or light chain with a point mutation in light chain or heavy chain, or A4b4 heavy chain with point mutations in light chain. Mab 13/19 was used as a positive control in the assay. RSV susceptible HEp-2 cells ($2.5 \times 10^4$) were then added to each well and cultured for 5 days at 37 C in 5% $CO_2$. After 5 days, the medium was aspirated and cells were washed and fixed to the plates with 80% methanol and 20% PBS. RSV replication was then determined by F protein expression. Fixed cells were incubated with a biotin-conjugated anti-F protein monoclonal antibody (pan F protein, C-site-specific MAb 133-1H) washed and horseradish peroxidase conjugated avidin was added to the wells. The wells were washed again and turnover of substrate TMB (thionitrobenzoic acid) was measured at 450 nm. The results from the assay for the monoclonal antibodies are shown in Table 22 infra.

Results and Discussion

The binding activity of A4B4 was tested by IFA against a panel of RSV A/Long MARMs obtained by three rounds of selection on HEp-2 cells in the presence of SYNAGIS®. A pool of monoclonal antibodies against the fusion, glycoprotein, and nuclear proteins of RSV (Control Pan RSV MAb Pool) was used as a positive control for detection of RSV. Subtyping of RSV MARMs was performed with two monoclonal antibodies that distinguish type A and type B glycoproteins. As summarized in Table 20, lack of binding activity by A4B4 and SYNAGIS® was demonstrated in MARMs. Contrasting with lack of binding by A4B4 and SYNAGIS®, binding of the Control Pan RSV MAb Pool was demonstrated for all MARMs tested. Both MARMs were classified as RSV type A. Wild type RSV A/Long infected HEp-2 cells bound to A4B4 and SYNAGIS®, Pan RSV MAb Pool, and RSV Type A MAb, but failed to react with RSV Type B MAb, as expected.

DNA sequencing analysis of an approximately 800-nucleotide region of the RSV F protein cDNA encompassing the proposed A4B4 epitope revealed mutation at the amino-acid level at position 272 and 276. Table 21 shows the amino acid change in isolates sequenced to date. Although the entire nucleotide sequence of RSV MARMs F protein has not been determined, these results suggest that amino acid 272 and 276 is a critical residue in modulating the binding of A4B4 to its epitope.

The ability of various monoclonal antibodies to neutralize the replication of a RSV A MARM was determined. As shown in Table 22, the ability of the monoclonal antibodies to neutralize the replication of a RSV MARM varied depending upon the amino acid sequence of the heavy chain (HC) and light chain (LC) of the antibody.

TABLE 20

Characterization of anti-RSV Binding Activity by A4B4, Synagis ®, Control Pan RSV MAb Pool (anti-F, G, N proteins), anti-RSV Type A MAb, and anti-RSV Type B MAb by Immunofluorescence Assay (IFA) on RSV A/Long MARMs.

| RSV MARM sample | Reactivity w/ Synagis ® | Reactivity w/ Anti-RSV MAb Pool | Reactivity w/ Anti-RSV type A MAb | Reactivity w/ Anti-RSV type B MAb | Reactivity w/ A4B4 |
|---|---|---|---|---|---|
| MARM #6 | − | + | + | − | − |
| MARM #9 | − | + | + | − | − |
| MARM #10 | − | + | + | − | − |
| MARM #11 | − | + | + | − | − |
| Wt | + | + | + | − | + |

TABLE 21

Amino acid sequence of a region of the wild type RSV A/Long and MARMs F Protein.

| Isolate | Amino Acid Sequence (Position number) | | | | | | | | | | | | | |
|---|---|---|---|---|---|---|---|---|---|---|---|---|---|---|
| | 266 | 267 | 268 | 269 | 270 | 271 | 272 | 273 | 274 | 275 | 276 | 277 | 278 | 279 |
| Wild type RSV | I | T | N | D | Q | K | K | L | M | S | N | N | V | Q |
| MARM #10 | I | T | N | D | Q | K | E | L | M | S | Y | N | V | Q |
| MARM #6 | I | T | N | D | Q | K | E | L | M | S | N | N | V | Q |
| MARM #9 | I | T | N | D | Q | K | E | L | M | S | N | N | V | Q |
| MARM #11 | I | T | N | D | Q | K | E | L | M | S | N | N | V | Q |
| MARM #14 | I | T | N | D | Q | K | E | L | M | S | N | N | V | Q |

TABLE 22

MARM analysis by Microneutralization Assay RSV Microneutralization Assay On RSV A MARMs to A4B4 with RSV Monoclonal Antibody

| Antibody HC/LC | K272E, N276Y MARM to MARM 10 | Note |
|---|---|---|
| SYNAGIS ®/SYNAGIS ® | − | Purified Ab |
| A4B4/A4B4 | − | Purified Ab |
| A4b4/SYNAGIS ® | − | Purified Ab |
| SYNAGIS ®/A4B4 | − | Purified Ab |
| A4B4/L1FR | − | Purified Ab |
| A4B4/L1FR S28R | − | Purified Ab |
| A4B4/L1FR S28R, S52F | − | Purified Ab |
| A4B4/L1FR-28R, 52F, 93F | − | Purified Ab |
| A4B4/A4B428S | − | Purified Ab |
| A4B4/A4B452S | − | Purified Ab |
| Mab 13/19 | + | Purified Ab |

+ = neutralization detected;
− = no neutralization detected

14. EXAMPLE

In vitro Isolation of A4B4 Specific Monoclonal Antibody Resistant Mutants (MARM) of MARM B9 (MARM of RSV Strain A/Long to Synagis)

This example demonstrates that MARMs can be isolated from MARM of RSVA long to Synagis (MARM B9) upon multiple rounds of selection in the presence of A4B4

Materials

A4B4 (Lot # 524-9, 3.57 mg/ml), Control Pan RSV MAb Pool (Chemicon MAB858-4, a blend of three MAbs anti-F, G, and N proteins), anti-RSV Type A MAb (Chemicon MAB858-1), and anti-RSV Type B MAb (Chemicon MAB858-2) were used in this study. Secondary detecting reagents were either Alexa™488 conjugated Goat F (ab')$_2$ anti-Mouse or Human IgG (H+L). MARM B9 ($1.78 \times 10^6$ TCID$_{50}$/ml) was used here. HEp-2 cells were propagated in EMEM supplemented with 10% FBS and 2 mM L-Gln in a 37° C., 5% CO$_2$ environment. Messenger RNA was purified from the infected cells using the mRNA Capture Kit (Roche). The mRNA samples were used to make cDNA using the reagents from the cDNA First Strand Reaction Kit (Roche), followed by amplification of the RSV F protein gene by the Polymerase Chain Reaction (PCR) using gene specific primers.

Methods

Selection of MARMs:

$4 \times 10^5$ HEp-2 cells were seeded per well of a 24-well plate in growth medium (EMEM, 10% FBS, 2 mM L-Gln) and incubated overnight in growth conditions (37° C., 5% CO$_2$). 44 wells were seeded for individual MARM selection. Prior to infection, a fresh vial of virus bank MARM B9 was thawed rapidly at 37° C. and the virus titer adjusted to $6 \times 10^5$ pfu/ml in HEp-2 growth medium. A4B4 was added to the virus inoculum at a final concentration of 2 μg/ml, and the mixture was incubated at 37° C. for one hour. An aliquot of RSV was incubated with an irrelevant Human IgG1 Mab (MEDI-507) and was used as a negative control. An uninfected control well was also set up for each plate. Cells were washed once with fresh medium and were overlayed with 100 µl of RSV A/Long virus stock/MAb mixture. Cells were incubated for four hours in growth conditions followed by addition of 1 ml of growth medium to each well. Cytopathic effect (CPE) was monitored on a daily basis by light microscopy. Following seven days of selection the contents of each well were supplemented with a further 4 µg/ml of A4B4 or irrelevant Human IgG1 Mab, and were used to infect freshly seeded HEp-2 cells ($4 \times 10^5$ cells/well of 24-well plate). After a further seven days of selection the process was repeated one more time for a total of three rounds of selection. The contents of wells showing clear CPE were mixed 1:1 with 50% sucrose solution and immediately frozen at ×80° C.

Plaque Purification of MARMs:

After the third round of selection, the contents of independent wells were used for plaque purification of MARMs. A fresh vial of MARM stock (was frozen after third round of selection) was thawed at room temperature and was diluted 1:10, 1:100, and 1:1000 in growth medium and incubated with 4 μg/ml of A4B4 for one hour prior to infection. 0.5 ml of virus inoculum was overlayed on monolayers of HEp-2 cells in 6 well plates ($5\times10^5$ cells/well) and incubated for 4 hours in growth conditions. Following infection the inoculum was carefully aspirated and cells were overlayed with 2 ml growth medium supplemented with 0.8% low melting temperature agarose (Gibco BRL), and containing 4 μg/ml of A4B4. Dishes were returned to the incubator after complete solidification of agarose and monitored daily for plaque formation. Uninfected controls and MARM B9 RSV control plates were set up for comparison. After five to six days, each plate was overlayed with an additional 2 ml of 0.8% agarose in growth medium supplemented with 50 μg/ml neutral red. Following an overnight incubation in growth conditions, plaques were scored and picked for a second round of purification.

Amplification of Clonal MARMs:

Following a second round of plaque purification three clones from isolate were expanded for production of high titer viral stocks. Individual plaques were picked with the aid of a pipet tip and incubated in 0.2 ml of fresh medium at 4° C. overnight to elute the virus. Each aliquot was used to infect HEp-2 cells in flat bottom 24-well plates ($2.5\times10^5$ cells/well—seeded day before) in the presence of 4 μg/ml A4B4. After five days the entire well content was used to infect HEp-2 cells in the presence of 4 μg/ml of A4B4 in 24-well plates. Each inoculum was subsequently expanded in the presence of 4 μg/ml of A4B4 to a T-25 flask ($6.5\times10^5$ cells/flask—seeded day before) and 5 mls of high titer virus stock were produced. MARM stocks were frozen as described above.

F Protein cDNA Synthesis and DNA Sequencing:

In order to determine the nucleotide sequence of an approximately 800 nucleotide region of the F protein gene thought to contain the epitope for SYNAGIS®, First strand cDNA synthesis was performed with mRNAs isolated from MARM-infected HEp-2 cells at 4 days post-infection. RSV infected Hep2 cells were lysed in 150 μl of lysis buffer provided with the mRNA capture kit. Biotinylated oligo dT was diluted 1:10 with nuclease free $H_2O$ and 4 μl was added to each lysate. Samples were incubated 10 minutes at 42° C. to allow the oligo dT to anneal to the mRNA. A 50 μl aliquot of the lysate was transferred to a streptavidin coated PCR tube and incubated for three minutes at 37° C. The lysates were removed from the PCR tubes and discarded. The RNA captured in the tubes was washed three times with 200 μl of wash buffer.

RT reactions were performed using reagents from the First Strand cDNA kit (Roche Molecular Biochemicals). A master mix was prepared so that each reaction contained 5 μl 10× buffer, 5 μl dNTPs, 10 μl $MgCl_2$, 1 μl gelatin, 2 μl RNase Inhibitor, 2 μl AMV-RT, in a final volume of 50 μl. Fifty microliter aliquots of the master mix were transferred to the PCR tubes containing the captured mRNA. Samples were placed in a thermalcycler and incubated for two hours at 42° C. The cDNA reaction mix was then removed from the PCR tubes and discarded. The cDNA captured in the PCR tubes was washed with 200 μl of wash buffer To obtain enough of the RSV F protein gene for sequence analysis, the cDNA was subjected to PCR using gene specific primers. Each reactions contained 10 mM Tris-HCl, pH 8.3, 50 mM KCl, 2.5 mM $MgCl_2$, 200 μM dNTPs, 125 ng of each forward (5'AGTGTCTTAACCAGCAAAGTGTTAGA 3'; SEQ ID NO:258) and reverse (5'TCATTGACTTGAGATATTGATGCATC 3'; SEQ ID NO:259) primer, and 2.5 units of Taq polymerase (PE Biosystems) in a final volume of 50 μl. The temperature profile for all reactions was 95° C. for 2 min, followed by 40 cycles of 95° C. for 30 sec., 55° C. for 45 sec, 72° C. for 45 sec, with a final extension at 72° C. for 10 minutes.

All PCR products were separated by electrophoresis on a 2% agarose gel in 1×TBE and visualized by ethidium bromide fluorescence.

PCR products were purified using Qiaquick spin columns (Qiagen and sequenced using the Big Dye-terminator PRISM kit (Applied Biosystems (ABI)). The reactions contained 70 ng of PCR product as template, 3 pmols of primer, and 8.0 μl of the PRISM dye-terminator reaction mix in a final volume of 20 μl. The reactions were subjected to thermal cycling according to ABI's dye-terminator sequencing instructions. Unincorporated dyes were removed from the extension products using Centri-Sep spin columns (Princeton Separations). Extension products were dried in a Savant Speed Vac and then dissolved in 10 μl HiDi Formamide (ABI) loading buffer. Samples were applied by electrophoresis in an ABI 3100 automated sequencer. Sequence data collected by the sequencer was analyzed using Lasargene (DNA Star).

Immunofluorescence Assay (IFA):

Cells infected with RSV isolates were tested for anti-RSV binding by A4B4, SYNAGIS®, and Control Pan RSV MAb Pool, as follows. Four to five day RSV-infected HEp-2 cultures were mixed with PBS and centrifuged at 300×g for 5 minutes at room temperature. Pellets were resuspended in a small volume of PBS for analysis. Five to ten micro liters of each cell suspension were spotted per 5 mm well on acetone washed 12-well HTC super cured glass slides and allowed to air dry. Slides were fixed in cold (−20° C.) acetone for 10 minutes. Reactions were blocked by spotting 10 μl of 1% BSA in PBS into each well and incubating for 10 minutes at room temperature. Slides were washed three times in 1×PBS/0.1% Tween-20 and air-dried. Ten micro liters of each primary antibody reagent diluted to 250 ng/ml in blocking buffer were spotted per well and reactions were incubated in a humidified 37° C. environment for 30 minutes. Slides were then washed for 1 minute in three changes of 1×PBS/0.1% Tween-20 and were air-dried. Ten micro liters of appropriate secondary conjugated antibody reagent diluted to 250 ng/ml in blocking buffer were added to each respective well and reactions were incubated in a humidified 37° C. environment for an additional 30 minutes. Slides were then washed for 1 minute in three changes of 1×PBS/0.1% Tween-20. Five micro liters of 50% glycerol in PBS, 10 mM Tris, pH 8.0, 1 mM EDTA were spotted in each reaction well, and slides were mounted with cover slips. Each reaction well was subsequently analyzed by fluorescence microscopy at 200× power using a B-2A filter (EX 450-490 nm). Positive reactions were scored against an auto fluorescent background obtained with unstained cells or cells stained with secondary reagent alone.

RSV positive reactions were characterized by bright fluorescence punctuated with small inclusions in the cytoplasm of infected cells.

Microneutralization Assay:

The procedure used here is described in Johnson et al., 1999, J. Infectious Diseases 180:35-40, the disclosure of which is hereby incorporated by reference in its entirety. Briefly, antibody dilutions were made in triplicate using a 96-well plate. Ten $TCID_{50}$ of RSV A MARMS were incubated with serial dilutions of the antibody to be tested for 2 hours at 37° C. in the wells of a 96-well plate. The antibodies used in the assay comprised the heavy chain of SYNAGIS® or the heavy chain of A4B4, and the light chain of SYNAGIS®, the light chain of A4B4, the light chain of A4B4 with a point mutation, the light chain of L1FR or the light chain of L1FR with point mutations. Mab 13/19 was used as a positive control in the assays. RSV susceptible HEp-2 cells ($2.5×10^4$) were then added to each well and cultured for 5 days at 37° C. in 5% $CO_2$. After 5 days, the medium was aspirated and cells were washed and fixed to the plates with 80% methanol and 20% PBS. RSV replication was then determined by F protein expression. Fixed cells were incubated with a biotin-conjugated anti-F protein monoclonal antibody (pan F protein, C-site-specific MAb 133-1H) washed and horseradish peroxidase conjugated avidin was added to the wells. The wells were washed again and turnover of substrate TMB (thionitrobenzoic acid) was measured at 450 nm. The results from the assay for the monoclonal antibodies are shown in Table 25 infra.

Results and Discussion

The binding activity of A4B4 was tested by IFA against a MARM obtained by three rounds of selection on HEp-2 cells in the presence of A4B4. A pool of monoclonal antibodies against the fusion, glycoprotein, and nuclear proteins of RSV (Control Pan RSV MAb Pool) was used as a positive control for detection of RSV. Subtyping of RSV MARMs was performed with two monoclonal antibodies that distinguish type A and type B glycoproteins. As summarized in Table 23, lack of binding activity by A4B4 and SYNAGIS® was demonstrated in both MARMs. Contrasting with lack of binding by A4B4 and SYNAGIS®, binding of the Control Pan RSV MAb Pool was demonstrated for all MARMs tested. Both MARMs were classified as RSV type A. Wild type RSV A/Long infected HEp-2 cells bound to A4B4 and SYNAGIS®, Pan RSV MAb Pool, and RSV Type A MAb, but failed to react with RSV Type B MAb, as expected.

DNA sequencing analysis of an approximately 800 nucleotide region of the RSV F protein cDNA encompassing the proposed A4B4 epitope revealed mutation at the amino-acid level at position 272 and 262. Table 24 shows the amino acid change in isolates sequenced to date. Although the entire nucleotide sequence of RSV MARMs F protein has not been determined, these results suggest that amino acid 272 and 262 is a critical residue in modulating the binding of A4B4 to its epitope.

The ability of various monoclonal antibodies to neutralize the replication of RSV A MARMs was determined. As shown in Table 25, the ability of the monoclonal antibodies to neutralize the replication of RSV MARMs varied depending upon the amino acid sequence of the heavy chain (HC) and light chain (LC) of the antibody.

TABLE 23

Characterization of anti-RSV Binding Activity by A4B4, SYNAGIS ®, Control Pan RSV MAb Pool (anti-F, G, N proteins), anti-RSV Type A MAb, and anti-RSV Type B MAb by Immunofluorescence Assay (IFA) on RSV A/Long MARMs.

| RSV MARM sample | Reactivity w/ Synagis ® | Reactivity w/ Anti-RSV MAb Pool | Reactivity w/ Anti-RSV type A MAb | Reactivity w/ Anti-RSV type B MAb | Reactivity w/ A4B4 |
|---|---|---|---|---|---|
| MARM #13 | − | + | + | − | − |
| B9 | − | + | + | − | + |
| Wt | + | + | + | − | − |

TABLE 24

Amino acid sequence of a region of the wild type RSV A/Long and MARMs F Protein.

| Isolate | Amino Acid Sequence (Position number) | | | | | | | | | | | | |
|---|---|---|---|---|---|---|---|---|---|---|---|---|---|
| Wild type RSV Long A | 262 N | 266 I | 267 T | 268 N | 269 D | 270 Q | 271 K | 272 K | 273 L | 274 M | 275 S | 276 N | 277 N | 278 V | 279 Q |
| MARM #13 | 262 K | 266 I | 267 T | 268 N | 269 D | 270 Q | 271 K | 272 Q | 273 L | 274 M | 275 S | 276 N | 277 N | 278 V | 279 Q |

TABLE 25

| MARM analysis by Microneutralization Assay RSV Microneutralization Assay On RSV A MARMs to A4B4 with RSV Monoclonal Antibody | | |
|---|---|---|
| Antibody HC/LC | K272Q, N262K MARM to SYNAGIS ® & A4B4 MARM 13 | Note |
| SYNAGIS ®/SYNAGIS ® | – | Purified Ab |
| A4B4/A4B4 | – | Purified Ab |
| A4B4/SYNAGIS ® | – | Purified Ab |
| SYNAGIS ®/A4B4 | – | Purified Ab |
| A4B4/L1FR | – | Purified Ab |
| A4B4/L1FR S28R | – | Purified Ab |
| A4B4/L1FR S28R, S52F | – | Purified Ab |
| A4B4/L1FR-28R, 52F, 93F | – | Purified Ab |
| A4B4/A4B428S | – | Purified Ab |
| A4B4/A4B452S | – | Purified Ab |
| Mab 13/19 | + | Purified Ab |

+ = neutralization detected;
– = no neutralization detected

15. EXAMPLE

Clinical Trials

Antibodies of the invention or fragments thereof tested in in vitro assays and animal models may be further evaluated for safety, tolerance and pharmacokinetics in groups of normal healthy adult volunteers. The volunteers are administered intramuscularly, intravenously or by a pulmonary delivery system a single dose of 0.5 mg/kg, 3 mg/kg, 5 mg/kg, 10 mg/kg or 15 mg/kg of an antibody or fragment thereof which immunospecifically binds to a RSV antigen. Each volunteer is monitored at least 24 hours prior to receiving the single dose of the antibody or fragment thereof and each volunteer will be monitored for at least 48 hours after receiving the dose at a clinical site. Then volunteers are monitored as outpatients on days 3, 7, 14, 21, 28, 35, 42, 49, and 56 postdose.

Blood samples are collected via an indwelling catheter or direct venipuncture using 10 ml red-top Vacutainer tubes at the following intervals: (1) prior to administering the dose of the antibody or antibody fragment; (2) during the administration of the dose of the antibody or antibody fragment; (3) 5 minutes, 10 minutes, 15 minutes, 20 minutes, 30 minutes, 1 hour, 2 hours, 4 hours, 8 hours, 12 hours, 24 hours, and 48 hours after administering the dose of the antibody or antibody fragment; and (4) 3 days, 7 days 14 days, 21 days, 28 days, 35 days, 42 days, 49 days, and 56 days after administering the dose of the antibody or antibody fragment. Samples are allowed to clot at room temperature and serum will be collected after centrifugation.

The antibody or antibody fragment is partially purified from the serum samples and the amount of antibody or antibody fragment in the samples will be quantitated by ELISA. Briefly, the ELISA consists of coating microtiter plates overnight at 4° C. with an antibody that recognizes the antibody or antibody fragment administered to the volunteer. The plates are then blocked for approximately 30 minutes at room temperate with PBS-Tween-0.5% BSA. Standard curves are constructed using purified antibody or antibody fragment, not administered to a volunteer. Samples are diluted in PBS-Tween-BSA. The samples and standards are incubated for approximately 1 hour at room temperature. Next, the bound antibody is treated with a labeled antibody (e.g., horseradish peroxidase conjugated goat-anti-human IgG) for approximately 1 hour at room temperature. Binding of the labeled antibody is detected, e.g., by a spectrophotometer.

The concentration of antibody or antibody fragment levels in the serum of volunteers are corrected by subtracting the predose serum level (background level) from the serum levels at each collection interval after administration of the dose. For each volunteer the pharmacokinetic parameters are computed according to the model-independent approach (Gibaldi et al., eds., 1982, *Pharmacokinetics,* 2nd edition, Marcel Dekker, New York) from the corrected serum antibody or antibody fragment concentrations.

Equivalents

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

16. SEQUENCE LISTING

This application includes a submitted Sequence Listing, recorded on two compact discs, including one duplicate, containing Filename “seqlisting 10271-198-999.txt” of file size 212,381 bytes, created Dec. 19, 2006. The Sequence Listing on the compact disc(s) is incorporated by reference herein in its entirety.

What is claimed is:

1. An antibody that immunospecifically binds to a respiratory syncytial virus (RSV) F antigen, wherein the antibody comprises:
   (a) a variable light (VL) chain having the amino acid sequence of SEQ ID NO:257;
   (b) a VL domain having the amino acid sequence of SEQ ID NO:76;
   (c) a variable heavy (VH) chain having the amino acid sequence of SEQ ID NO:256, and
      a VL chain having the amino acid sequence of SEQ ID NO:257;
   (d) a VH domain having the amino acid sequence of SEQ ID NO:48, and
      a VL domain having the amino acid sequence of SEQ ID NO:76;
   (e) a VH chain having the amino acid sequence of SEQ ID NO:256, and
      a VL domain having the amino acid sequence of SEQ ID NO:76;
   (f) a VH domain having the amino acid sequence of SEQ ID NO:48, and
      a VL chain having the amino acid sequence of SEQ ID NO:257;
   (g) a VH chain or VH domain comprising a VH complementary determining region (CDR) 1 having the amino acid sequence of SEQ ID NO:10, a VH CDR2 having the amino acid sequence of SEQ ID NO:19, a VH CDR3 having the amino acid sequence of SEQ ID NO:20, and
      a VL chain or VL domain comprising a VL CDR1 having the amino acid sequence of SEQ ID NO:39, a VL CDR2 having the amino acid sequence of SEQ ID NO:77, and a VL CDR3 having the amino acid sequence of SEQ ID NO:6;
   (h) a VH chain having the amino acid sequence of SEQ ID NO:256, and
      a VL chain or VL domain comprising a VL CDR1 having the amino acid sequence of SEQ ID NO:39, a VL CDR2 having the amino acid sequence of SEQ ID NO:77, and a VL CDR3 having the amino acid sequence of SEQ ID NO:6;
   (i) a VH domain having the amino acid sequence of SEQ ID NO:48, and
      a VL chain or VL domain comprising a VL CDR1 having the amino acid sequence of SEQ ID NO:39, a VL CDR2 having the amino acid sequence of SEQ ID NO:77, and a VL CDR3 having the amino acid sequence of SEQ ID NO:6;
   (j) a VH chain or VH domain comprising a VH CDR1 having the amino acid sequence of SEQ ID NO:10, a VH CDR2 having the amino acid sequence of SEQ ID NO:19, a VH CDR3 having the amino acid sequence of SEQ ID NO:20, and
      a VL domain having the amino acid sequence of SEQ ID NO:76; or
   (k) a VH chain or VH domain comprising a VH CDR1 having the amino acid sequence of SEQ ID NO:10, a VH CDR2 having the amino acid sequence of SEQ ID NO:19, a VH CDR3 having the amino acid sequence of SEQ ID NO:20, and
      a VL chain having the amino acid sequence of SEQ ID NO:257.

2. The antibody of claim 1, comprising:
   a VH domain having the amino acid sequence of SEQ ID NO:48, and
   a VL domain having the amino acid sequence of SEQ ID NO:76.

3. The antibody of claim 1, comprising:
   a VH chain having the amino acid sequence of SEQ ID NO:256, and
   a VL chain having the amino acid sequence of SEQ ID NO:257.

4. The antibody of claim 1, comprising:
   a VH chain or VH domain comprising a VH CDR1 having the amino acid sequence of SEQ ID NO: 10, a VH CDR2 having the amino acid sequence of SEQ ID NO: 19, a VH CDR3 having the amino acid sequence of SEQ ID NO:20; and
   a VL chain or VL domain comprising a VL CDR1 having the amino acid sequence of SEQ ID NO:39, a VL CDR2 having the amino acid sequence of SEQ ID NO:77, and a VL CDR3 having the amino acid sequence of SEQ ID NO:6.

5. An antibody that immunospecifically binds to a RSV F antigen, wherein the antibody comprises:
   a VL chain or VL domain having a VL complementary determining region (CDR) 1 having the amino acid sequence of SEQ ID NO:39, a VL CDR2 having the amino acid sequence of SEQ ID NO:77, and a VL CDR3 having the amino acid sequence of SEQ ID NO:6; and
   the framework regions in FIG. 1A (SEQ ID NO:260) or FIG. 2A (SEQ ID NO:262).

6. The antibody of claim 1, 2, 3, 4 or 5, wherein the antibody is a monoclonal antibody.

7. The antibody of claim 1, 4 or 5, wherein the antibody is a Fab or F(ab')$_2$ fragment.

8. The antibody of claim 1, 2, 4 or 5, wherein said antibody is a humanized antibody.

9. The antibody of claim 1 or 4, wherein the antibody comprises the framework regions in FIG. 2A (SEQ ID NO:262) or FIG. 2B (SEQ ID NO:263).

10. A composition comprising the antibody of claim 1, 2, 3, 4 or 5 and a pharmaceutically acceptable carrier.

11. A kit comprising the antibody of claim 1, 2, 3, 4 or 5 in a container, and instructions for use.

12. An antibody conjugate comprising a non-IgG polypeptide conjugated to the antibody of claim 1, 2, 3, 4 or 5.

13. The antibody conjugate of claim 12, wherein the non-IgG polypeptide is a diagnostic or therapeutic agent.

14. A composition comprising the antibody conjugate of claim 12 and a pharmaceutically acceptable carrier.

15. A kit comprising the antibody conjugate of claim 12, in a container, and instructions for use.

16. A sustained release formulation comprising the antibody of claim 1, 2, 3, 4 or 5.

17. A composition comprising the antibody of claim 1, 2, 3, 4 or 5 formulated for pulmonary delivery.

18. A composition comprising the antibody of claim 1, 2, 3, 4 or 5 formulated for intradermal, intramuscular, intraperitoneal, intravenous, subcutaneous, or intranasal delivery.

* * * * *

SEQUENCE LISTING

```
<160> NUMBER OF SEQ ID NOS: 263

<210> SEQ ID NO 1
<211> LENGTH: 7
<212> TYPE: PRT
<213> ORGANISM: Homo sapiens

<400> SEQUENCE: 1

Thr Ser Gly Met Ser Val Gly
1               5
```

<210> SEQ ID NO 2
<211> LENGTH: 16
<212> TYPE: PRT
<213> ORGANISM: Homo sapiens

<400> SEQUENCE: 2

Asp Ile Trp Trp Asp Asp Lys Lys Asp Tyr Asn Pro Ser Leu Lys Ser
1               5                   10                  15

<210> SEQ ID NO 3
<211> LENGTH: 10
<212> TYPE: PRT
<213> ORGANISM: Homo sapiens

<400> SEQUENCE: 3

Ser Met Ile Thr Asn Trp Tyr Phe Asp Val
1               5                   10

<210> SEQ ID NO 4
<211> LENGTH: 10
<212> TYPE: PRT
<213> ORGANISM: Homo sapiens

<400> SEQUENCE: 4

Lys Cys Gln Leu Ser Val Gly Tyr Met His
1               5                   10

<210> SEQ ID NO 5
<211> LENGTH: 7
<212> TYPE: PRT
<213> ORGANISM: Homo sapiens

<400> SEQUENCE: 5

Asp Thr Ser Lys Leu Ala Ser
1               5

<210> SEQ ID NO 6
<211> LENGTH: 9
<212> TYPE: PRT
<213> ORGANISM: Homo sapiens

<400> SEQUENCE: 6

Phe Gln Gly Ser Gly Tyr Pro Phe Thr
1               5

<210> SEQ ID NO 7
<211> LENGTH: 120
<212> TYPE: PRT
<213> ORGANISM: Homo sapiens

<400> SEQUENCE: 7

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
        50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

```
Cys Ala Arg Ser Met Ile Thr Asn Trp Tyr Phe Asp Val Trp Gly Ala
            100                 105                 110

Gly Thr Thr Val Thr Val Ser Ser
        115                 120

<210> SEQ ID NO 8
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 9
<211> LENGTH: 120
<212> TYPE: PRT
<213> ORGANISM: Homo sapiens
<220> FEATURE:
<221> NAME/KEY: misc_feature
<223> OTHER INFORMATION: VH Domain

<400> SEQUENCE: 9

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Phe Tyr Phe Asp Val Trp Gly Ala
            100                 105                 110

Gly Thr Thr Val Thr Val Ser Ser
        115                 120

<210> SEQ ID NO 10
<211> LENGTH: 7
<212> TYPE: PRT
<213> ORGANISM: Homo sapiens
```

```
<400> SEQUENCE: 10

Thr Ala Gly Met Ser Val Gly
1               5

<210> SEQ ID NO 11
<211> LENGTH: 106
<212> TYPE: PRT
<213> ORGANISM: Homo sapiens

<400> SEQUENCE: 11

Asp Ile Gln Met Thr Gln Ser Pro Ser Thr Leu Ser Ala Ser Val Gly
1               5                  10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 12
<211> LENGTH: 10
<212> TYPE: PRT
<213> ORGANISM: Homo sapiens

<400> SEQUENCE: 12

Ser Met Ile Thr Asn Phe Tyr Phe Asp Val
1               5                   10

<210> SEQ ID NO 13
<211> LENGTH: 106
<212> TYPE: PRT
<213> ORGANISM: Homo sapiens

<400> SEQUENCE: 13

Asp Ile Gln Met Thr Gln Ser Pro Ser Thr Leu Ser Ala Ser Val Gly
1               5                  10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Phe Ser Gly Tyr Pro Phe Thr
                85                  90                  95

Phe Gly Gly Gly Thr Lys Leu Glu Ile Lys
            100                 105

<210> SEQ ID NO 14
<211> LENGTH: 10
<212> TYPE: PRT
```

<213> ORGANISM: Homo sapiens

<400> SEQUENCE: 14

Ser Ala Ser Ser Ser Val Gly Tyr Met His
1               5                   10

<210> SEQ ID NO 15
<211> LENGTH: 7
<212> TYPE: PRT
<213> ORGANISM: Homo sapiens

<400> SEQUENCE: 15

Asp Thr Phe Lys Leu Ala Ser
1               5

<210> SEQ ID NO 16
<211> LENGTH: 9
<212> TYPE: PRT
<213> ORGANISM: Homo sapiens

<400> SEQUENCE: 16

Phe Gln Phe Ser Gly Tyr Pro Phe Thr
1               5

<210> SEQ ID NO 17
<211> LENGTH: 120
<212> TYPE: PRT
<213> ORGANISM: Homo sapiens

<400> SEQUENCE: 17

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Ala
            100                 105                 110

Gly Thr Thr Val Thr Val Ser Ser
        115                 120

<210> SEQ ID NO 18
<211> LENGTH: 7
<212> TYPE: PRT
<213> ORGANISM: Homo sapiens

<400> SEQUENCE: 18

Thr Pro Gly Met Ser Val Gly
1               5

<210> SEQ ID NO 19
<211> LENGTH: 16
<212> TYPE: PRT
<213> ORGANISM: Homo sapiens

<400> SEQUENCE: 19

Asp Ile Trp Trp Asp Asp Lys Lys His Tyr Asn Pro Ser Leu Lys Asp
1               5                   10                  15

<210> SEQ ID NO 20
<211> LENGTH: 10
<212> TYPE: PRT
<213> ORGANISM: Homo sapiens

<400> SEQUENCE: 20

Asp Met Ile Phe Asn Phe Tyr Phe Asp Val
1               5                   10

<210> SEQ ID NO 21
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 21

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
                20                  25                  30

His Trp Tyr Gln Gln Lys Pro Gly Lys Ala Pro Lys Leu Leu Ile Tyr
            35                  40                  45

Asp Thr Phe Tyr Leu Ser Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 22
<211> LENGTH: 10
<212> TYPE: PRT
<213> ORGANISM: Homo sapiens

<400> SEQUENCE: 22

Ser Leu Ser Ser Arg Val Gly Tyr Met His
1               5                   10

<210> SEQ ID NO 23
<211> LENGTH: 7
<212> TYPE: PRT
<213> ORGANISM: Homo sapiens

<400> SEQUENCE: 23

Asp Thr Phe Tyr Leu Ser Ser
1               5

<210> SEQ ID NO 24
<211> LENGTH: 120
<212> TYPE: PRT
<213> ORGANISM: Homo sapiens
<220> FEATURE:
<221> NAME/KEY: misc_feature
<223> OTHER INFORMATION: VH Domain

<400> SEQUENCE: 24

```
Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys His Tyr Asn Pro Ser
50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
            115                 120

<210> SEQ ID NO 25
<211> LENGTH: 16
<212> TYPE: PRT
<213> ORGANISM: Homo sapiens

<400> SEQUENCE: 25

Asp Ile Trp Trp Asp Gly Lys Lys His Tyr Asn Pro Ser Leu Lys Asp
 1               5                  10                  15

<210> SEQ ID NO 26
<211> LENGTH: 106
<212> TYPE: PRT
<213> ORGANISM: Homo sapiens

<400> SEQUENCE: 26

Asp Ile Gln Met Thr Gln Ser Pro Ser Thr Leu Ser Ala Ser Val Gly
 1               5                  10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Arg Gly Leu Pro Ser Gly Val Pro Ser Arg Phe Ser Gly Ser
50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 27
<211> LENGTH: 7
<212> TYPE: PRT
<213> ORGANISM: Homo sapiens

<400> SEQUENCE: 27

Asp Thr Arg Gly Leu Pro Ser
 1               5

<210> SEQ ID NO 28
<211> LENGTH: 120
```

```
<212> TYPE: PRT
<213> ORGANISM: Homo sapiens

<400> SEQUENCE: 28

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser
        115                 120

<210> SEQ ID NO 29
<211> LENGTH: 10
<212> TYPE: PRT
<213> ORGANISM: Homo sapiens

<400> SEQUENCE: 29

Asp Met Ile Phe Asn Trp Tyr Phe Asp Val
1               5                   10

<210> SEQ ID NO 30
<211> LENGTH: 106
<212> TYPE: PRT
<213> ORGANISM: Homo sapiens

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys Ser Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Arg Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 31
<211> LENGTH: 10
<212> TYPE: PRT
<213> ORGANISM: Homo sapiens

<400> SEQUENCE: 31

Ser Pro Ser Ser Arg Val Gly Tyr Met His
1               5                   10
```

<210> SEQ ID NO 32
<211> LENGTH: 7
<212> TYPE: PRT
<213> ORGANISM: Homo sapiens

<400> SEQUENCE: 32

Asp Thr Met Arg Leu Ala Ser
1               5

<210> SEQ ID NO 33
<211> LENGTH: 120
<212> TYPE: PRT
<213> ORGANISM: Homo sapiens

<400> SEQUENCE: 33

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser
        115                 120

<210> SEQ ID NO 34
<211> LENGTH: 106
<212> TYPE: PRT
<213> ORGANISM: Homo sapiens

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 35
<211> LENGTH: 7
<212> TYPE: PRT
<213> ORGANISM: Homo sapiens

```
<400> SEQUENCE: 35

Asp Thr Phe Lys Leu Ser Ser
1               5

<210> SEQ ID NO 36
<211> LENGTH: 120
<212> TYPE: PRT
<213> ORGANISM: Homo sapiens

<400> SEQUENCE: 36

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys Asp Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Asp Val Trp Gly Gln
            100                 105                 110

Gly Thr Thr Val Thr Val Ser Ser
        115                 120

<210> SEQ ID NO 37
<211> LENGTH: 16
<212> TYPE: PRT
<213> ORGANISM: Homo sapiens

<400> SEQUENCE: 37

Asp Ile Trp Trp Asp Gly Lys Lys Asp Tyr Asn Pro Ser Leu Lys Asp
1               5                   10                  15

<210> SEQ ID NO 38
<211> LENGTH: 106
<212> TYPE: PRT
<213> ORGANISM: Homo sapiens

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 39
```

```
<211> LENGTH: 10
<212> TYPE: PRT
<213> ORGANISM: Homo sapiens

<400> SEQUENCE: 39

Ser Ala Ser Ser Arg Val Gly Tyr Met His
1               5                   10

<210> SEQ ID NO 40
<211> LENGTH: 120
<212> TYPE: PRT
<213> ORGANISM: Homo sapiens

<400> SEQUENCE: 40

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys Ser Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
        115                 120

<210> SEQ ID NO 41
<211> LENGTH: 16
<212> TYPE: PRT
<213> ORGANISM: Homo sapiens

<400> SEQUENCE: 41

Asp Ile Trp Trp Asp Gly Lys Lys Ser Tyr Asn Pro Ser Leu Lys Asp
1               5                   10                  15

<210> SEQ ID NO 42
<211> LENGTH: 106
<212> TYPE: PRT
<213> ORGANISM: Homo sapiens

<400> SEQUENCE: 42

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Tyr Gln Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
```

100        105

<210> SEQ ID NO 43
<211> LENGTH: 7
<212> TYPE: PRT
<213> ORGANISM: Homo sapiens

<400> SEQUENCE: 43

Asp Thr Met Tyr Gln Ser Ser
1               5

<210> SEQ ID NO 44
<211> LENGTH: 120
<212> TYPE: PRT
<213> ORGANISM: Homo sapiens

<400> SEQUENCE: 44

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys Ser Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
        115                 120

<210> SEQ ID NO 45
<211> LENGTH: 16
<212> TYPE: PRT
<213> ORGANISM: Homo sapiens

<400> SEQUENCE: 45

Asp Ile Trp Trp Asp Asp Lys Lys Ser Tyr Asn Pro Ser Leu Lys Asp
1               5                   10                  15

<210> SEQ ID NO 46
<211> LENGTH: 106
<212> TYPE: PRT
<213> ORGANISM: Homo sapiens

<400> SEQUENCE: 46

Asp Ile Gln Met Thr Gln Ser Pro Ser Thr Leu Ser Ala Ser Val Gly
1               5                   10                  15

Asp Arg Val Thr Ile Thr Cys Leu Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Tyr Gln Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

```
Asp Phe Ala Thr Tyr Tyr Cys Phe Gln Phe Ser Gly Tyr Pro Phe Thr
                85                  90                  95

Phe Gly Gly Gly Thr Lys Leu Glu Ile Lys
            100                 105

<210> SEQ ID NO 47
<211> LENGTH: 10
<212> TYPE: PRT
<213> ORGANISM: Homo sapiens

<400> SEQUENCE: 47

Leu Pro Ser Ser Arg Val Gly Tyr Met His
1               5                   10

<210> SEQ ID NO 48
<211> LENGTH: 120
<212> TYPE: PRT
<213> ORGANISM: Homo sapiens

<400> SEQUENCE: 48

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
        115                 120

<210> SEQ ID NO 49
<211> LENGTH: 106
<212> TYPE: PRT
<213> ORGANISM: Homo sapiens

<400> SEQUENCE: 49

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Phe Leu Asp Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105
```

```
<210> SEQ ID NO 50
<211> LENGTH: 7
<212> TYPE: PRT
<213> ORGANISM: Homo sapiens

<400> SEQUENCE: 50

Asp Thr Phe Phe Leu Asp Ser
1               5

<210> SEQ ID NO 51
<211> LENGTH: 120
<212> TYPE: PRT
<213> ORGANISM: Homo sapiens

<400> SEQUENCE: 51

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Ser Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser
        115                 120

<210> SEQ ID NO 52
<211> LENGTH: 106
<212> TYPE: PRT
<213> ORGANISM: Homo sapiens

<400> SEQUENCE: 52

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Arg Tyr Gln Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 53
<211> LENGTH: 7
<212> TYPE: PRT
<213> ORGANISM: Homo sapiens

<400> SEQUENCE: 53
```

```
Asp Thr Arg Tyr Gln Ser Ser
1               5
```

```
<210> SEQ ID NO 54
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 54
```

```
Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105
```

```
<210> SEQ ID NO 55
<211> LENGTH: 120
<212> TYPE: PRT
<213> ORGANISM: Homo sapiens

<400> SEQUENCE: 55
```

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
        50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Ala
            100                 105                 110

Gly Thr Thr Val Thr Val Ser Ser
            115                 120
```

```
<210> SEQ ID NO 56
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 56
```

```
Asp Ile Gln Met Thr Gln Ser Pro Ser Thr Leu Ser Ala Ser Val Gly
```

```
                 1               5                  10                 15
Asp Arg Val Thr Ile Thr Cys Ser Ala Ser Ser Val Gly Tyr Met
                20                  25                  30

His Trp Tyr Gln Gln Lys Pro Gly Lys Ala Pro Lys Leu Leu Ile Tyr
                35                  40                  45

Asp Thr Phe Lys Leu Ala Ser Gly Val Pro Ser Arg Phe Ser Gly Ser
           50                  55                  60

Gly Ser Gly Thr Glu Phe Thr Leu Thr Ile Ser Ser Leu Gln Pro Asp
 65                 70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
                100                 105

<210> SEQ ID NO 57
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 57

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Val Gly Tyr Met
                20                  25                  30

His Trp Tyr Gln Gln Lys Pro Gly Lys Ala Pro Lys Leu Leu Ile Tyr
                35                  40                  45

Asp Thr Tyr Lys Gln Thr Ser Gly Val Pro Ser Arg Phe Ser Gly Ser
           50                  55                  60

Gly Ser Gly Thr Glu Phe Thr Leu Thr Ile Ser Ser Leu Gln Pro Asp
 65                 70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
                100                 105

<210> SEQ ID NO 58
<211> LENGTH: 7
<212> TYPE: PRT
<213> ORGANISM: Homo sapiens

<400> SEQUENCE: 58

Asp Thr Tyr Lys Gln Thr Ser
 1               5

<210> SEQ ID NO 59
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 59

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Val Gly Tyr Met
                20                  25                  30
```

His Trp Tyr Gln Gln Lys Pro Gly Lys Ala Pro Lys Leu Leu Ile Tyr
            35                  40                  45

Asp Thr Arg Tyr Leu Ser Ser Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 60
<211> LENGTH: 106
<212> TYPE: PRT
<213> ORGANISM: Homo sapiens

<400> SEQUENCE: 60

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Phe Tyr Pro Phe Thr
                85                  90                  95

Phe Gly Gly Gly Thr Lys Leu Glu Ile Lys
            100                 105

<210> SEQ ID NO 61
<211> LENGTH: 9
<212> TYPE: PRT
<213> ORGANISM: Homo sapiens

<400> SEQUENCE: 61

Phe Gln Gly Ser Phe Tyr Pro Phe Thr
1               5

<210> SEQ ID NO 62
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 62

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Phe Lys Leu Thr Ser Gly Val Pro Ser Arg Phe Ser Gly Ser
    50                  55                  60

```
Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
            100                 105

<210> SEQ ID NO 63
<211> LENGTH: 7
<212> TYPE: PRT
<213> ORGANISM: Homo sapiens

<400> SEQUENCE: 63

Asp Thr Phe Lys Leu Thr Ser
 1               5

<210> SEQ ID NO 64
<211> LENGTH: 106
<212> TYPE: PRT
<213> ORGANISM: Homo sapiens
<220> FEATURE:
<221> NAME/KEY: misc_feature
<223> OTHER INFORMATION: VL Domain

<400> SEQUENCE: 64

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Ser Val Gly Tyr Met
                 20                  25                  30

His Trp Tyr Gln Gln Lys Pro Gly Lys Ala Pro Lys Leu Leu Ile Tyr
             35                  40                  45

Asp Thr Phe Arg Leu Ala Ser Gly Val Pro Ser Arg Phe Ser Gly Ser
         50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
            100                 105

<210> SEQ ID NO 65
<211> LENGTH: 106
<212> TYPE: PRT
<213> ORGANISM: Homo sapiens

<400> SEQUENCE: 65

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Ser Val Gly Tyr Met
                 20                  25                  30

His Trp Tyr Gln Gln Lys Pro Gly Lys Ala Pro Lys Leu Leu Ile Tyr
             35                  40                  45

Asp Thr Phe Arg Leu Ala Ser Gly Val Pro Ser Arg Phe Ser Gly Ser
         50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
```

```
                100             105

<210> SEQ ID NO 66
<211> LENGTH: 7
<212> TYPE: PRT
<213> ORGANISM: Homo sapiens

<400> SEQUENCE: 66

Asp Thr Phe Arg Leu Ala Ser
1               5

<210> SEQ ID NO 67
<211> LENGTH: 120
<212> TYPE: PRT
<213> ORGANISM: Homo sapiens

<400> SEQUENCE: 67

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Ala
            100                 105                 110

Gly Thr Thr Val Thr Val Ser Ser
        115                 120

<210> SEQ ID NO 68
<211> LENGTH: 106
<212> TYPE: PRT
<213> ORGANISM: Homo sapiens

<400> SEQUENCE: 68

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met Met
            20                  25                  30

His Trp Tyr Gln Gln Lys Pro Gly Lys Ala Pro Lys Leu Leu Ile Tyr
        35                  40                  45

Asp Thr Tyr Arg His Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 69
<211> LENGTH: 7
<212> TYPE: PRT
<213> ORGANISM: Homo sapiens
```

```
<400> SEQUENCE: 69

Asp Thr Tyr Arg His Ser Ser
1               5

<210> SEQ ID NO 70
<211> LENGTH: 106
<212> TYPE: PRT
<213> ORGANISM: Homo sapiens

<400> SEQUENCE: 70

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Tyr Lys Gln Thr Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 71
<211> LENGTH: 106
<212> TYPE: PRT
<213> ORGANISM: Homo sapiens

<400> SEQUENCE: 71

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Phe His Arg Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 72
<211> LENGTH: 10
<212> TYPE: PRT
<213> ORGANISM: Homo sapiens

<400> SEQUENCE: 72

Ser Leu Ser Ser Ser Val Gly Tyr Met His
1               5                   10

<210> SEQ ID NO 73
<211> LENGTH: 7
<212> TYPE: PRT
```

<213> ORGANISM: Homo sapiens

<400> SEQUENCE: 73

Asp Thr Phe Phe His Arg Ser
1               5

<210> SEQ ID NO 74
<211> LENGTH: 106
<212> TYPE: PRT
<213> ORGANISM: Homo sapiens

<400> SEQUENCE: 74

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Leu Leu Leu Asp Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 75
<211> LENGTH: 7
<212> TYPE: PRT
<213> ORGANISM: Homo sapiens

<400> SEQUENCE: 75

Asp Thr Leu Leu Leu Asp Ser
1               5

<210> SEQ ID NO 76
<211> LENGTH: 106
<212> TYPE: PRT
<213> ORGANISM: Homo sapiens

<400> SEQUENCE: 76

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Phe Leu Asp Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 77
<211> LENGTH: 7

```
<212> TYPE: PRT
<213> ORGANISM: Homo sapiens

<400> SEQUENCE: 77

Asp Thr Ser Phe Leu Asp Ser
1               5

<210> SEQ ID NO 78
<211> LENGTH: 120
<212> TYPE: PRT
<213> ORGANISM: Homo sapiens

<400> SEQUENCE: 78

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Thr Asn Phe Tyr Phe Asp Val Trp Gly Ala
            100                 105                 110

Gly Thr Thr Val Thr Val Ser Ser
        115                 120

<210> SEQ ID NO 79
<211> LENGTH: 10
<212> TYPE: PRT
<213> ORGANISM: Homo sapiens

<400> SEQUENCE: 79

Asp Met Ile Thr Asn Phe Tyr Phe Asp Val
1               5                   10

<210> SEQ ID NO 80
<211> LENGTH: 10
<212> TYPE: PRT
<213> ORGANISM: Homo sapiens

<400> SEQUENCE: 80

Lys Cys Gln Ser Ser Val Gly Tyr Met His
1               5                   10

<210> SEQ ID NO 81
<211> LENGTH: 7
<212> TYPE: PRT
<213> ORGANISM: Homo sapiens

<400> SEQUENCE: 81

Asp Thr Ser Tyr Leu Ala Ser
1               5

<210> SEQ ID NO 82
<211> LENGTH: 16
<212> TYPE: PRT
<213> ORGANISM: Homo sapiens
```

```
<400> SEQUENCE: 82

Asp Ile Trp Trp Asp Asp Lys Lys His Tyr Asn Pro Ser Leu Lys Ser
1               5                   10                  15

<210> SEQ ID NO 83
<211> LENGTH: 10
<212> TYPE: PRT
<213> ORGANISM: Homo sapiens

<400> SEQUENCE: 83

Asp Met Ile Thr Asn Trp Tyr Phe Asp Val
1               5                   10

<210> SEQ ID NO 84
<211> LENGTH: 10
<212> TYPE: PRT
<213> ORGANISM: Homo sapiens

<400> SEQUENCE: 84

Lys Cys Gln Ser Arg Val Gly Tyr Met His
1               5                   10

<210> SEQ ID NO 85
<211> LENGTH: 7
<212> TYPE: PRT
<213> ORGANISM: Homo sapiens

<400> SEQUENCE: 85

Asp Thr Ser Tyr Leu Ser Ser
1               5

<210> SEQ ID NO 86
<211> LENGTH: 16
<212> TYPE: PRT
<213> ORGANISM: Homo sapiens

<400> SEQUENCE: 86

Asp Ile Trp Trp Asp Asp Lys Lys Asp Tyr Asn Pro Ser Leu Lys Asp
1               5                   10                  15

<210> SEQ ID NO 87
<211> LENGTH: 10
<212> TYPE: PRT
<213> ORGANISM: Homo sapiens

<400> SEQUENCE: 87

Lys Cys Gln Leu Arg Val Gly Tyr Met His
1               5                   10

<210> SEQ ID NO 88
<211> LENGTH: 7
<212> TYPE: PRT
<213> ORGANISM: Homo sapiens

<400> SEQUENCE: 88

Asp Thr Lys Lys Leu Ser Ser
1               5

<210> SEQ ID NO 89
<211> LENGTH: 10
<212> TYPE: PRT
<213> ORGANISM: Homo sapiens

<400> SEQUENCE: 89
```

Lys Leu Gln Leu Ser Val Gly Tyr Met His
1               5                   10

<210> SEQ ID NO 90
<211> LENGTH: 7
<212> TYPE: PRT
<213> ORGANISM: Homo sapiens

<400> SEQUENCE: 90

Asp Thr Phe Tyr Leu Ser Ser
1               5

<210> SEQ ID NO 91
<211> LENGTH: 16
<212> TYPE: PRT
<213> ORGANISM: Homo sapiens

<400> SEQUENCE: 91

Asp Ile Trp Trp Asp Asp Lys Lys His Tyr Asn Pro Ser Leu Lys Ser
1               5                   10                  15

<210> SEQ ID NO 92
<211> LENGTH: 10
<212> TYPE: PRT
<213> ORGANISM: Homo sapiens

<400> SEQUENCE: 92

Lys Leu Gln Ser Ser Val Gly Tyr Met His
1               5                   10

<210> SEQ ID NO 93
<211> LENGTH: 16
<212> TYPE: PRT
<213> ORGANISM: Homo sapiens

<400> SEQUENCE: 93

Asp Ile Trp Trp Asp Asp Lys Lys His Tyr Asn Pro Ser Leu Lys Ser
1               5                   10                  15

<210> SEQ ID NO 94
<211> LENGTH: 10
<212> TYPE: PRT
<213> ORGANISM: Homo sapiens

<400> SEQUENCE: 94

Ser Met Ile Phe Asn Trp Tyr Phe Asp Val
1               5                   10

<210> SEQ ID NO 95
<211> LENGTH: 10
<212> TYPE: PRT
<213> ORGANISM: Homo sapiens

<400> SEQUENCE: 95

Lys Leu Gln Ser Arg Val Gly Tyr Met His
1               5                   10

<210> SEQ ID NO 96
<211> LENGTH: 7
<212> TYPE: PRT
<213> ORGANISM: Homo sapiens

<400> SEQUENCE: 96

Asp Thr Phe Lys Leu Ser Ser
1               5

```
<210> SEQ ID NO 97
<211> LENGTH: 10
<212> TYPE: PRT
<213> ORGANISM: Homo sapiens

<400> SEQUENCE: 97

Ser Met Ile Phe Asn Phe Tyr Phe Asp Val
1               5                   10

<210> SEQ ID NO 98
<211> LENGTH: 10
<212> TYPE: PRT
<213> ORGANISM: Homo sapiens

<400> SEQUENCE: 98

Lys Leu Gln Leu Arg Val Gly Tyr Met His
1               5                   10

<210> SEQ ID NO 99
<211> LENGTH: 7
<212> TYPE: PRT
<213> ORGANISM: Homo sapiens

<400> SEQUENCE: 99

Asp Thr Phe Tyr Leu Ala Ser
1               5

<210> SEQ ID NO 100
<211> LENGTH: 16
<212> TYPE: PRT
<213> ORGANISM: Homo sapiens

<400> SEQUENCE: 100

Asp Ile Trp Trp Asp Gly Lys Lys Asp Tyr Asn Pro Ser Leu Lys Ser
1               5                   10                  15

<210> SEQ ID NO 101
<211> LENGTH: 10
<212> TYPE: PRT
<213> ORGANISM: Homo sapiens

<400> SEQUENCE: 101

Lys Leu Ser Leu Ser Val Gly Tyr Met His
1               5                   10

<210> SEQ ID NO 102
<211> LENGTH: 7
<212> TYPE: PRT
<213> ORGANISM: Homo sapiens

<400> SEQUENCE: 102

Asp Thr Ser Lys Leu Pro Ser
1               5

<210> SEQ ID NO 103
<211> LENGTH: 16
<212> TYPE: PRT
<213> ORGANISM: Homo sapiens

<400> SEQUENCE: 103

Asp Ile Trp Trp Asp Gly Lys Lys Asp Tyr Asn Pro Ser Leu Lys Asp
1               5                   10                  15
```

```
<210> SEQ ID NO 104
<211> LENGTH: 10
<212> TYPE: PRT
<213> ORGANISM: Homo sapiens

<400> SEQUENCE: 104

Lys Leu Ser Ser Ser Val Gly Tyr Met His
1               5                   10

<210> SEQ ID NO 105
<211> LENGTH: 7
<212> TYPE: PRT
<213> ORGANISM: Homo sapiens

<400> SEQUENCE: 105

Asp Thr Ser Gly Leu Ala Ser
1               5

<210> SEQ ID NO 106
<211> LENGTH: 16
<212> TYPE: PRT
<213> ORGANISM: Homo sapiens

<400> SEQUENCE: 106

Asp Ile Trp Trp Asp Gly Lys Lys His Tyr Asn Pro Ser Leu Lys Ser
1               5                   10                  15

<210> SEQ ID NO 107
<211> LENGTH: 10
<212> TYPE: PRT
<213> ORGANISM: Homo sapiens

<400> SEQUENCE: 107

Lys Leu Ser Ser Arg Val Gly Tyr Met His
1               5                   10

<210> SEQ ID NO 108
<211> LENGTH: 7
<212> TYPE: PRT
<213> ORGANISM: Homo sapiens

<400> SEQUENCE: 108

Asp Thr Ser Gly Leu Pro Ser
1               5

<210> SEQ ID NO 109
<211> LENGTH: 16
<212> TYPE: PRT
<213> ORGANISM: Homo sapiens

<400> SEQUENCE: 109

Asp Ile Trp Trp Asp Asp Lys Lys Ser Tyr Asn Pro Ser Leu Lys Ser
1               5                   10                  15

<210> SEQ ID NO 110
<211> LENGTH: 10
<212> TYPE: PRT
<213> ORGANISM: Homo sapiens

<400> SEQUENCE: 110

Lys Leu Ser Leu Arg Val Gly Tyr Met His
1               5                   10

<210> SEQ ID NO 111
<211> LENGTH: 16
```

```
<212> TYPE: PRT
<213> ORGANISM: Homo sapiens

<400> SEQUENCE: 111

Asp Ile Trp Trp Asp Lys Lys Ser Tyr Asn Pro Ser Leu Lys Ser
1               5                   10                  15

<210> SEQ ID NO 112
<211> LENGTH: 10
<212> TYPE: PRT
<213> ORGANISM: Homo sapiens

<400> SEQUENCE: 112

Lys Cys Ser Leu Ser Val Gly Tyr Met His
1               5                   10

<210> SEQ ID NO 113
<211> LENGTH: 7
<212> TYPE: PRT
<213> ORGANISM: Homo sapiens

<400> SEQUENCE: 113

Asp Thr Arg Lys Leu Ala Ser
1               5

<210> SEQ ID NO 114
<211> LENGTH: 16
<212> TYPE: PRT
<213> ORGANISM: Homo sapiens

<400> SEQUENCE: 114

Asp Ile Trp Trp Asp Gly Lys Lys Ser Tyr Asn Pro Ser Leu Lys Ser
1               5                   10                  15

<210> SEQ ID NO 115
<211> LENGTH: 10
<212> TYPE: PRT
<213> ORGANISM: Homo sapiens

<400> SEQUENCE: 115

Lys Cys Ser Ser Ser Val Gly Tyr Met His
1               5                   10

<210> SEQ ID NO 116
<211> LENGTH: 7
<212> TYPE: PRT
<213> ORGANISM: Homo sapiens

<400> SEQUENCE: 116

Asp Thr Arg Gly Leu Ala Ser
1               5

<210> SEQ ID NO 117
<211> LENGTH: 10
<212> TYPE: PRT
<213> ORGANISM: Homo sapiens

<400> SEQUENCE: 117

Lys Cys Ser Leu Arg Val Gly Tyr Met His
1               5                   10

<210> SEQ ID NO 118
<211> LENGTH: 7
<212> TYPE: PRT
<213> ORGANISM: Homo sapiens
```

```
<400> SEQUENCE: 118

Asp Thr Arg Lys Leu Pro Ser
1               5

<210> SEQ ID NO 119
<211> LENGTH: 10
<212> TYPE: PRT
<213> ORGANISM: Homo sapiens

<400> SEQUENCE: 119

Lys Cys Ser Leu Arg Val Gly Tyr Met His
1               5                   10

<210> SEQ ID NO 120
<211> LENGTH: 10
<212> TYPE: PRT
<213> ORGANISM: Homo sapiens

<400> SEQUENCE: 120

Ser Leu Ser Leu Ser Val Gly Tyr Met His
1               5                   10

<210> SEQ ID NO 121
<211> LENGTH: 7
<212> TYPE: PRT
<213> ORGANISM: Homo sapiens

<400> SEQUENCE: 121

Asp Thr Met Lys Leu Ala Ser
1               5

<210> SEQ ID NO 122
<211> LENGTH: 10
<212> TYPE: PRT
<213> ORGANISM: Homo sapiens

<400> SEQUENCE: 122

Ser Leu Ser Ser Ser Val Gly Tyr Met His
1               5                   10

<210> SEQ ID NO 123
<211> LENGTH: 7
<212> TYPE: PRT
<213> ORGANISM: Homo sapiens

<400> SEQUENCE: 123

Asp Thr Ser Arg Leu Ala Ser
1               5

<210> SEQ ID NO 124
<211> LENGTH: 7
<212> TYPE: PRT
<213> ORGANISM: Homo sapiens

<400> SEQUENCE: 124

Asp Thr Ser Leu Leu Ala Ser
1               5

<210> SEQ ID NO 125
<211> LENGTH: 10
<212> TYPE: PRT
<213> ORGANISM: Homo sapiens

<400> SEQUENCE: 125
```

```
Ser Leu Ser Leu Arg Val Gly Tyr Met His
1               5                   10

<210> SEQ ID NO 126
<211> LENGTH: 7
<212> TYPE: PRT
<213> ORGANISM: Homo sapiens

<400> SEQUENCE: 126

Asp Thr Ser Leu Leu Asp Ser
1               5

<210> SEQ ID NO 127
<211> LENGTH: 10
<212> TYPE: PRT
<213> ORGANISM: Homo sapiens

<400> SEQUENCE: 127

Ser Cys Gln Leu Ser Val Gly Tyr Met His
1               5                   10

<210> SEQ ID NO 128
<211> LENGTH: 7
<212> TYPE: PRT
<213> ORGANISM: Homo sapiens

<400> SEQUENCE: 128

Asp Thr Ser Lys Leu Asp Ser
1               5

<210> SEQ ID NO 129
<211> LENGTH: 10
<212> TYPE: PRT
<213> ORGANISM: Homo sapiens

<400> SEQUENCE: 129

Ser Cys Gln Ser Ser Val Gly Tyr Met His
1               5                   10

<210> SEQ ID NO 130
<211> LENGTH: 10
<212> TYPE: PRT
<213> ORGANISM: Homo sapiens

<400> SEQUENCE: 130

Ser Cys Gln Ser Arg Val Gly Tyr Met His
1               5                   10

<210> SEQ ID NO 131
<211> LENGTH: 7
<212> TYPE: PRT
<213> ORGANISM: Homo sapiens

<400> SEQUENCE: 131

Asp Thr Leu Lys Leu Asp Ser
1               5

<210> SEQ ID NO 132
<211> LENGTH: 10
<212> TYPE: PRT
<213> ORGANISM: Homo sapiens

<400> SEQUENCE: 132

Ser Cys Gln Leu Arg Val Gly Tyr Met His
```

```
                 1               5                   10
```

<210> SEQ ID NO 133
<211> LENGTH: 7
<212> TYPE: PRT
<213> ORGANISM: Homo sapiens

<400> SEQUENCE: 133

```
Asp Thr Leu Leu Leu Ala Ser
1               5
```

<210> SEQ ID NO 134
<211> LENGTH: 10
<212> TYPE: PRT
<213> ORGANISM: Homo sapiens

<400> SEQUENCE: 134

```
Ser Leu Gln Leu Ser Val Gly Tyr Met His
1               5                   10
```

<210> SEQ ID NO 135
<211> LENGTH: 7
<212> TYPE: PRT
<213> ORGANISM: Homo sapiens

<400> SEQUENCE: 135

```
Asp Thr Leu Lys Leu Ala Ser
1               5
```

<210> SEQ ID NO 136
<211> LENGTH: 10
<212> TYPE: PRT
<213> ORGANISM: Homo sapiens

<400> SEQUENCE: 136

```
Ser Leu Gln Ser Ser Val Gly Tyr Met His
1               5                   10
```

<210> SEQ ID NO 137
<211> LENGTH: 7
<212> TYPE: PRT
<213> ORGANISM: Homo sapiens

<400> SEQUENCE: 137

```
Asp Thr Ser Lys Leu Ser Ser
1               5
```

<210> SEQ ID NO 138
<211> LENGTH: 10
<212> TYPE: PRT
<213> ORGANISM: Homo sapiens

<400> SEQUENCE: 138

```
Ser Leu Gln Ser Arg Val Gly Tyr Met His
1               5                   10
```

<210> SEQ ID NO 139
<211> LENGTH: 7
<212> TYPE: PRT
<213> ORGANISM: Homo sapiens

<400> SEQUENCE: 139

```
Asp Thr Ser Lys Gln Ala Ser
1               5
```

<210> SEQ ID NO 140
<211> LENGTH: 10
<212> TYPE: PRT
<213> ORGANISM: Homo sapiens

<400> SEQUENCE: 140

Ser Leu Gln Leu Arg Val Gly Tyr Met His
1               5                   10

<210> SEQ ID NO 141
<211> LENGTH: 7
<212> TYPE: PRT
<213> ORGANISM: Homo sapiens

<400> SEQUENCE: 141

Asp Thr Ser Lys Gln Ser Ser
1               5

<210> SEQ ID NO 142
<211> LENGTH: 10
<212> TYPE: PRT
<213> ORGANISM: Homo sapiens

<400> SEQUENCE: 142

Ser Cys Ser Leu Ser Val Gly Tyr Met His
1               5                   10

<210> SEQ ID NO 143
<211> LENGTH: 7
<212> TYPE: PRT
<213> ORGANISM: Homo sapiens

<400> SEQUENCE: 143

Asp Thr Ser Tyr Leu Ala Ser
1               5

<210> SEQ ID NO 144
<211> LENGTH: 10
<212> TYPE: PRT
<213> ORGANISM: Homo sapiens

<400> SEQUENCE: 144

Ser Cys Ser Ser Ser Val Gly Tyr Met His
1               5                   10

<210> SEQ ID NO 145
<211> LENGTH: 7
<212> TYPE: PRT
<213> ORGANISM: Homo sapiens

<400> SEQUENCE: 145

Asp Thr Ser Tyr Leu Ser Ser
1               5

<210> SEQ ID NO 146
<211> LENGTH: 10
<212> TYPE: PRT
<213> ORGANISM: Homo sapiens

<400> SEQUENCE: 146

Ser Cys Ser Ser Arg Val Gly Tyr Met His
1               5                   10

<210> SEQ ID NO 147

```
<211> LENGTH: 7
<212> TYPE: PRT
<213> ORGANISM: Homo sapiens

<400> SEQUENCE: 147

Asp Thr Ser Tyr Gln Ala Ser
1               5

<210> SEQ ID NO 148
<211> LENGTH: 10
<212> TYPE: PRT
<213> ORGANISM: Homo sapiens

<400> SEQUENCE: 148

Ser Cys Ser Leu Arg Val Gly Tyr Met His
1               5                   10

<210> SEQ ID NO 149
<211> LENGTH: 7
<212> TYPE: PRT
<213> ORGANISM: Homo sapiens

<400> SEQUENCE: 149

Asp Thr Ser Tyr Gln Ser Ser
1               5

<210> SEQ ID NO 150
<211> LENGTH: 10
<212> TYPE: PRT
<213> ORGANISM: Homo sapiens

<400> SEQUENCE: 150

Lys Pro Ser Ser Arg Val Gly Tyr Met His
1               5                   10

<210> SEQ ID NO 151
<211> LENGTH: 7
<212> TYPE: PRT
<213> ORGANISM: Homo sapiens

<400> SEQUENCE: 151

Asp Thr Met Tyr Gln Ala Ser
1               5

<210> SEQ ID NO 152
<211> LENGTH: 10
<212> TYPE: PRT
<213> ORGANISM: Homo sapiens

<400> SEQUENCE: 152

Lys Pro Ser Leu Arg Val Gly Tyr Met His
1               5                   10

<210> SEQ ID NO 153
<211> LENGTH: 10
<212> TYPE: PRT
<213> ORGANISM: Homo sapiens

<400> SEQUENCE: 153

Lys Pro Ser Ser Ser Val Gly Tyr Met His
1               5                   10

<210> SEQ ID NO 154
<211> LENGTH: 7
<212> TYPE: PRT
```

<213> ORGANISM: Homo sapiens

<400> SEQUENCE: 154

Asp Thr Met Lys Gln Ala Ser
1               5

<210> SEQ ID NO 155
<211> LENGTH: 10
<212> TYPE: PRT
<213> ORGANISM: Homo sapiens

<400> SEQUENCE: 155

Lys Pro Ser Leu Ser Val Gly Tyr Met His
1               5                   10

<210> SEQ ID NO 156
<211> LENGTH: 7
<212> TYPE: PRT
<213> ORGANISM: Homo sapiens

<400> SEQUENCE: 156

Asp Thr Met Lys Gln Ser Ser
1               5

<210> SEQ ID NO 157
<211> LENGTH: 10
<212> TYPE: PRT
<213> ORGANISM: Homo sapiens

<400> SEQUENCE: 157

Lys Pro Gln Ser Arg Val Gly Tyr Met His
1               5                   10

<210> SEQ ID NO 158
<211> LENGTH: 7
<212> TYPE: PRT
<213> ORGANISM: Homo sapiens

<400> SEQUENCE: 158

Asp Thr Met Tyr Leu Ala Ser
1               5

<210> SEQ ID NO 159
<211> LENGTH: 10
<212> TYPE: PRT
<213> ORGANISM: Homo sapiens

<400> SEQUENCE: 159

Lys Pro Gln Leu Arg Val Gly Tyr Met His
1               5                   10

<210> SEQ ID NO 160
<211> LENGTH: 7
<212> TYPE: PRT
<213> ORGANISM: Homo sapiens

<400> SEQUENCE: 160

Asp Thr Met Tyr Leu Ser Ser
1               5

<210> SEQ ID NO 161
<211> LENGTH: 10
<212> TYPE: PRT
<213> ORGANISM: Homo sapiens

```
<400> SEQUENCE: 161

Lys Pro Gln Ser Ser Val Gly Tyr Met His
1               5                   10

<210> SEQ ID NO 162
<211> LENGTH: 7
<212> TYPE: PRT
<213> ORGANISM: Homo sapiens

<400> SEQUENCE: 162

Asp Thr Met Lys Leu Ala Ser
1               5

<210> SEQ ID NO 163
<211> LENGTH: 10
<212> TYPE: PRT
<213> ORGANISM: Homo sapiens

<400> SEQUENCE: 163

Lys Pro Gln Leu Ser Val Gly Tyr Met His
1               5                   10

<210> SEQ ID NO 164
<211> LENGTH: 7
<212> TYPE: PRT
<213> ORGANISM: Homo sapiens

<400> SEQUENCE: 164

Asp Thr Met Lys Leu Ser Ser
1               5

<210> SEQ ID NO 165
<211> LENGTH: 7
<212> TYPE: PRT
<213> ORGANISM: Homo sapiens

<400> SEQUENCE: 165

Asp Thr Ser Lys Leu Ser Ser
1               5

<210> SEQ ID NO 166
<211> LENGTH: 10
<212> TYPE: PRT
<213> ORGANISM: Homo sapiens

<400> SEQUENCE: 166

Ser Pro Ser Leu Arg Val Gly Tyr Met His
1               5                   10

<210> SEQ ID NO 167
<211> LENGTH: 7
<212> TYPE: PRT
<213> ORGANISM: Homo sapiens

<400> SEQUENCE: 167

Asp Thr Ser Lys Leu Ser Ser
1               5

<210> SEQ ID NO 168
<211> LENGTH: 10
<212> TYPE: PRT
<213> ORGANISM: Homo sapiens

<400> SEQUENCE: 168
```

-continued

Ser Pro Ser Ser Ser Val Gly Tyr Met His
1               5                   10

<210> SEQ ID NO 169
<211> LENGTH: 10
<212> TYPE: PRT
<213> ORGANISM: Homo sapiens

<400> SEQUENCE: 169

Ser Pro Ser Leu Ser Val Gly Tyr Met His
1               5                   10

<210> SEQ ID NO 170
<211> LENGTH: 7
<212> TYPE: PRT
<213> ORGANISM: Homo sapiens

<400> SEQUENCE: 170

Asp Thr Arg Tyr Gln Ala Ser
1               5

<210> SEQ ID NO 171
<211> LENGTH: 10
<212> TYPE: PRT
<213> ORGANISM: Homo sapiens

<400> SEQUENCE: 171

Ser Pro Gln Ser Arg Val Gly Tyr Met His
1               5                   10

<210> SEQ ID NO 172
<211> LENGTH: 7
<212> TYPE: PRT
<213> ORGANISM: Homo sapiens

<400> SEQUENCE: 172

Asp Thr Arg Lys Gln Ser Ser
1               5

<210> SEQ ID NO 173
<211> LENGTH: 10
<212> TYPE: PRT
<213> ORGANISM: Homo sapiens

<400> SEQUENCE: 173

Ser Pro Gln Leu Arg Val Gly Tyr Met His
1               5                   10

<210> SEQ ID NO 174
<211> LENGTH: 7
<212> TYPE: PRT
<213> ORGANISM: Homo sapiens

<400> SEQUENCE: 174

Asp Thr Arg Lys Leu Ala Ser
1               5

<210> SEQ ID NO 175
<211> LENGTH: 7
<212> TYPE: PRT
<213> ORGANISM: Homo sapiens

<400> SEQUENCE: 175

Asp Thr Arg Lys Leu Ser Ser
1               5

```
<210> SEQ ID NO 176
<211> LENGTH: 10
<212> TYPE: PRT
<213> ORGANISM: Homo sapiens

<400> SEQUENCE: 176

Ser Pro Gln Ser Ser Val Gly Tyr Met His
1               5                   10

<210> SEQ ID NO 177
<211> LENGTH: 10
<212> TYPE: PRT
<213> ORGANISM: Homo sapiens

<400> SEQUENCE: 177

Ser Pro Gln Leu Ser Val Gly Tyr Met His
1               5                   10

<210> SEQ ID NO 178
<211> LENGTH: 7
<212> TYPE: PRT
<213> ORGANISM: Homo sapiens

<400> SEQUENCE: 178

Asp Thr Arg Tyr Leu Ala Ser
1               5

<210> SEQ ID NO 179
<211> LENGTH: 10
<212> TYPE: PRT
<213> ORGANISM: Homo sapiens

<400> SEQUENCE: 179

Lys Ala Gln Ser Arg Val Gly Tyr Met His
1               5                   10

<210> SEQ ID NO 180
<211> LENGTH: 10
<212> TYPE: PRT
<213> ORGANISM: Homo sapiens

<400> SEQUENCE: 180

Lys Ala Gln Leu Arg Val Gly Tyr Met His
1               5                   10

<210> SEQ ID NO 181
<211> LENGTH: 10
<212> TYPE: PRT
<213> ORGANISM: Homo sapiens

<400> SEQUENCE: 181

Lys Ala Gln Ser Ser Val Gly Tyr Met His
1               5                   10

<210> SEQ ID NO 182
<211> LENGTH: 10
<212> TYPE: PRT
<213> ORGANISM: Homo sapiens

<400> SEQUENCE: 182

Lys Ala Gln Leu Ser Val Gly Tyr Met His
1               5                   10
```

```
<210> SEQ ID NO 183
<211> LENGTH: 10
<212> TYPE: PRT
<213> ORGANISM: Homo sapiens

<400> SEQUENCE: 183

Lys Ala Ser Ser Arg Val Gly Tyr Met His
1               5                   10

<210> SEQ ID NO 184
<211> LENGTH: 10
<212> TYPE: PRT
<213> ORGANISM: Homo sapiens

<400> SEQUENCE: 184

Lys Ala Ser Leu Arg Val Gly Tyr Met His
1               5                   10

<210> SEQ ID NO 185
<211> LENGTH: 10
<212> TYPE: PRT
<213> ORGANISM: Homo sapiens

<400> SEQUENCE: 185

Lys Ala Ser Ser Ser Val Gly Tyr Met His
1               5                   10

<210> SEQ ID NO 186
<211> LENGTH: 10
<212> TYPE: PRT
<213> ORGANISM: Homo sapiens

<400> SEQUENCE: 186

Lys Ala Ser Leu Ser Val Gly Tyr Met His
1               5                   10

<210> SEQ ID NO 187
<211> LENGTH: 10
<212> TYPE: PRT
<213> ORGANISM: Homo sapiens

<400> SEQUENCE: 187

Ser Ala Ser Leu Arg Val Gly Tyr Met His
1               5                   10

<210> SEQ ID NO 188
<211> LENGTH: 10
<212> TYPE: PRT
<213> ORGANISM: Homo sapiens

<400> SEQUENCE: 188

Ser Ala Ser Leu Ser Val Gly Tyr Met His
1               5                   10

<210> SEQ ID NO 189
<211> LENGTH: 10
<212> TYPE: PRT
<213> ORGANISM: Homo sapiens

<400> SEQUENCE: 189

Ser Ala Gln Ser Arg Val Gly Tyr Met His
1               5                   10

<210> SEQ ID NO 190
<211> LENGTH: 10
```

```
<212> TYPE: PRT
<213> ORGANISM: Homo sapiens

<400> SEQUENCE: 190

Ser Ala Gln Leu Arg Val Gly Tyr Met His
1               5                   10

<210> SEQ ID NO 191
<211> LENGTH: 10
<212> TYPE: PRT
<213> ORGANISM: Homo sapiens

<400> SEQUENCE: 191

Ser Ala Gln Ser Ser Val Gly Tyr Met His
1               5                   10

<210> SEQ ID NO 192
<211> LENGTH: 10
<212> TYPE: PRT
<213> ORGANISM: Homo sapiens

<400> SEQUENCE: 192

Leu Pro Ser Leu Ser Val Gly Tyr Met His
1               5                   10

<210> SEQ ID NO 193
<211> LENGTH: 10
<212> TYPE: PRT
<213> ORGANISM: Homo sapiens

<400> SEQUENCE: 193

Leu Pro Ser Ser Ser Val Gly Tyr Met His
1               5                   10

<210> SEQ ID NO 194
<211> LENGTH: 10
<212> TYPE: PRT
<213> ORGANISM: Homo sapiens

<400> SEQUENCE: 194

Leu Pro Ser Leu Arg Val Gly Tyr Met His
1               5                   10

<210> SEQ ID NO 195
<211> LENGTH: 10
<212> TYPE: PRT
<213> ORGANISM: Homo sapiens

<400> SEQUENCE: 195

Leu Cys Ser Ser Arg Val Gly Tyr Met His
1               5                   10

<210> SEQ ID NO 196
<211> LENGTH: 10
<212> TYPE: PRT
<213> ORGANISM: Homo sapiens

<400> SEQUENCE: 196

Leu Cys Ser Leu Ser Val Gly Tyr Met His
1               5                   10

<210> SEQ ID NO 197
<211> LENGTH: 10
<212> TYPE: PRT
<213> ORGANISM: Homo sapiens
```

```
<400> SEQUENCE: 197

Leu Cys Ser Ser Ser Val Gly Tyr Met His
1               5                   10

<210> SEQ ID NO 198
<211> LENGTH: 10
<212> TYPE: PRT
<213> ORGANISM: Homo sapiens

<400> SEQUENCE: 198

Leu Cys Ser Leu Arg Val Gly Tyr Met His
1               5                   10

<210> SEQ ID NO 199
<211> LENGTH: 10
<212> TYPE: PRT
<213> ORGANISM: Homo sapiens

<400> SEQUENCE: 199

Leu Pro Gln Ser Arg Val Gly Tyr Met His
1               5                   10

<210> SEQ ID NO 200
<211> LENGTH: 10
<212> TYPE: PRT
<213> ORGANISM: Homo sapiens

<400> SEQUENCE: 200

Leu Pro Gln Leu Ser Val Gly Tyr Met His
1               5                   10

<210> SEQ ID NO 201
<211> LENGTH: 10
<212> TYPE: PRT
<213> ORGANISM: Homo sapiens

<400> SEQUENCE: 201

Leu Pro Gln Ser Ser Val Gly Tyr Met His
1               5                   10

<210> SEQ ID NO 202
<211> LENGTH: 10
<212> TYPE: PRT
<213> ORGANISM: Homo sapiens

<400> SEQUENCE: 202

Leu Pro Gln Leu Arg Val Gly Tyr Met His
1               5                   10

<210> SEQ ID NO 203
<211> LENGTH: 10
<212> TYPE: PRT
<213> ORGANISM: Homo sapiens

<400> SEQUENCE: 203

Leu Cys Gln Ser Arg Val Gly Tyr Met His
1               5                   10

<210> SEQ ID NO 204
<211> LENGTH: 10
<212> TYPE: PRT
<213> ORGANISM: Homo sapiens

<400> SEQUENCE: 204
```

Leu Cys Gln Leu Ser Val Gly Tyr Met His
1               5                   10

<210> SEQ ID NO 205
<211> LENGTH: 10
<212> TYPE: PRT
<213> ORGANISM: Homo sapiens

<400> SEQUENCE: 205

Leu Cys Gln Ser Ser Val Gly Tyr Met His
1               5                   10

<210> SEQ ID NO 206
<211> LENGTH: 10
<212> TYPE: PRT
<213> ORGANISM: Homo sapiens

<400> SEQUENCE: 206

Leu Cys Gln Leu Arg Val Gly Tyr Met His
1               5                   10

<210> SEQ ID NO 207
<211> LENGTH: 10
<212> TYPE: PRT
<213> ORGANISM: Homo sapiens

<400> SEQUENCE: 207

Ser Ala Gln Leu Ser Val Gly Tyr Met His
1               5                   10

<210> SEQ ID NO 208
<211> LENGTH: 450
<212> TYPE: PRT
<213> ORGANISM: Homo sapiens

<400> SEQUENCE: 208

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro

-continued

```
                180                 185                 190
Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 209
<211> LENGTH: 213
<212> TYPE: PRT
<213> ORGANISM: Homo sapiens

<400> SEQUENCE: 209

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95
```

```
Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 210
<211> LENGTH: 450
<212> TYPE: PRT
<213> ORGANISM: Homo sapiens

<400> SEQUENCE: 210

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 211
<211> LENGTH: 213
<212> TYPE: PRT
<213> ORGANISM: Homo sapiens

<400> SEQUENCE: 211

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Phe Ser Gly Tyr Pro Phe Thr
            85                  90                  95

Phe Gly Gly Gly Thr Lys Val Glu Ile Lys Arg Thr Val Ala Ala Pro
        100                 105                 110

Ser Val Phe Ile Phe Pro Pro Ser Asp Glu Gln Leu Lys Ser Gly Thr
    115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser

```
                    165                 170                 175
Thr Leu Thr Leu Ser Lys Ala Asp Tyr Glu Lys His Lys Val Tyr Ala
                180                 185                 190
Cys Glu Val Thr His Gln Gly Leu Ser Ser Pro Val Thr Lys Ser Phe
                195                 200                 205
Asn Arg Gly Glu Cys
    210

<210> SEQ ID NO 212
<211> LENGTH: 450
<212> TYPE: PRT
<213> ORGANISM: Homo sapiens

<400> SEQUENCE: 212

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 213
<211> LENGTH: 213
<212> TYPE: PRT
<213> ORGANISM: Homo sapiens

<400> SEQUENCE: 213

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Tyr Leu Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 214
```

<211> LENGTH: 450
<212> TYPE: PRT
<213> ORGANISM: Homo sapiens

<400> SEQUENCE: 214

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
```

```
                385                 390                 395                 400
Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
                    420                 425                 430

Glu Ala Leu His Asn His Tyr Thr Gln Lys Ser Leu Ser Leu Ser Pro
                    435                 440                 445

Gly Lys
    450

<210> SEQ ID NO 215
<211> LENGTH: 213
<212> TYPE: PRT
<213> ORGANISM: Homo sapiens

<400> SEQUENCE: 215

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
                20                  25                  30

His Trp Tyr Gln Gln Lys Pro Gly Lys Ala Pro Lys Leu Leu Ile Tyr
            35                  40                  45

Asp Thr Arg Gly Leu Pro Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 216
<211> LENGTH: 450
<212> TYPE: PRT
<213> ORGANISM: Homo sapiens

<400> SEQUENCE: 216

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
                20                  25                  30

Gly Met Ser Val Gly Trp Ile Arg Gln Pro Pro Gly Lys Ala Leu Glu
```

-continued

```
                35                  40                  45
Trp Leu Ala Asp Ile Trp Trp Asp Gly Lys Lys His Tyr Asn Pro Ser
     50                  55                  60
Leu Lys Asp Arg Leu Thr Ile Ser Lys Asp Thr Ser Lys Asn Gln Val
 65                  70                  75                  80
Val Leu Lys Val Thr Asn Met Asp Pro Ala Asp Thr Ala Thr Tyr Tyr
                 85                  90                  95
Cys Ala Arg Asp Met Ile Phe Asn Trp Tyr Phe Asp Val Trp Gly Gln
                100                 105                 110
Gly Thr Thr Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450
```

<210> SEQ ID NO 217
<211> LENGTH: 213
<212> TYPE: PRT
<213> ORGANISM: Homo sapiens

<400> SEQUENCE: 217

```
Asp Ile Gln Met Thr Gln Ser Pro Ser Thr Leu Ser Ala Ser Val Gly
1               5                   10                  15

Asp Arg Val Thr Ile Thr Cys Ser Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Arg Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 218
<211> LENGTH: 450
<212> TYPE: PRT
<213> ORGANISM: Homo sapiens

<400> SEQUENCE: 218

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110
```

```
Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 219
<211> LENGTH: 213
<212> TYPE: PRT
<213> ORGANISM: Homo sapiens

<400> SEQUENCE: 219

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
```

-continued

```
                 20                  25                  30
His Trp Tyr Gln Gln Lys Pro Gly Lys Ala Pro Lys Leu Leu Ile Tyr
            35                  40                  45

Asp Thr Phe Lys Leu Ser Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 220
<211> LENGTH: 450
<212> TYPE: PRT
<213> ORGANISM: Homo sapiens

<400> SEQUENCE: 220

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys Asp Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 221
<211> LENGTH: 213
<212> TYPE: PRT
<213> ORGANISM: Homo sapiens

<400> SEQUENCE: 221

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95
```

```
Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
    195                 200                 205

Asn Arg Gly Glu Cys
    210

<210> SEQ ID NO 222
<211> LENGTH: 450
<212> TYPE: PRT
<213> ORGANISM: Homo sapiens

<400> SEQUENCE: 222

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys Ser Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                    245                 250                 255
Ser Arg Thr Pro Glu Val Thr Cys Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 223
<211> LENGTH: 213
<212> TYPE: PRT
<213> ORGANISM: Homo sapiens

<400> SEQUENCE: 223

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Tyr Gln Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 224
<211> LENGTH: 450
<212> TYPE: PRT
<213> ORGANISM: Homo sapiens

<400> SEQUENCE: 224

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys Ser Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 225
<211> LENGTH: 213
<212> TYPE: PRT
<213> ORGANISM: Homo sapiens

<400> SEQUENCE: 225

Asp Ile Gln Met Thr Gln Ser Pro Ser Thr Leu Ser Ala Ser Val Gly
1               5                   10                  15

Asp Arg Val Thr Ile Thr Cys Leu Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Tyr Gln Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 226
<211> LENGTH: 450
<212> TYPE: PRT
<213> ORGANISM: Homo sapiens

<400> SEQUENCE: 226

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 227
<211> LENGTH: 213
<212> TYPE: PRT
<213> ORGANISM: Homo sapiens

<400> SEQUENCE: 227

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
            35                  40                  45

Asp Thr Phe Phe Leu Asp Ser Gly Val Pro Ser Arg Phe Ser Gly Ser
    50                  55                  60

Gly Ser Gly Thr Glu Phe Thr Leu Thr Ile Ser Ser Leu Gln Pro Asp
65              70                  75                  80

Asp Phe Ala Thr Tyr Tyr Cys Phe Gln Gly Ser Gly Tyr Pro Phe Thr
            85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 228
<211> LENGTH: 450
<212> TYPE: PRT
<213> ORGANISM: Homo sapiens

<400> SEQUENCE: 228

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30
```

-continued

```
Gly Met Ser Val Gly Trp Ile Arg Gln Pro Gly Lys Ala Leu Glu
         35                  40                  45

Trp Leu Ala Asp Ile Trp Trp Asp Asp Lys Lys Ser Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Trp Tyr Phe Asp Val Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
```

450

<210> SEQ ID NO 229
<211> LENGTH: 213
<212> TYPE: PRT
<213> ORGANISM: Homo sapiens

<400> SEQUENCE: 229

```
Asp Ile Gln Met Thr Gln Ser Pro Ser Thr Leu Ser Ala Ser Val Gly
1               5                   10                  15

Asp Arg Val Thr Ile Thr Cys Ser Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Arg Tyr Gln Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 230
<211> LENGTH: 451
<212> TYPE: PRT
<213> ORGANISM: Homo sapiens

<400> SEQUENCE: 230

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Tyr Trp Ile Arg Gln Pro Pro Gly Lys Ala Leu
        35                  40                  45

Glu Trp Leu Ala Asp Ile Trp Trp Asp Asp Lys Lys Asp Tyr Asn Pro
    50                  55                  60

Ser Leu Lys Ser Arg Leu Thr Ile Ser Lys Asp Thr Ser Lys Asn Gln
65                  70                  75                  80

Val Val Leu Lys Val Thr Asn Met Asp Pro Ala Asp Thr Ala Thr Tyr
                85                  90                  95

Tyr Cys Ala Arg Ser Met Ile Thr Asn Trp Tyr Phe Asp Val Trp Gly
```

```
                100              105              110
Gln Gly Thr Thr Val Thr Val Ser Ser Ala Ser Thr Lys Gly Pro Ser
            115              120              125
Val Phe Pro Leu Ala Pro Ser Ser Lys Ser Thr Ser Gly Gly Thr Ala
            130              135              140
Ala Leu Gly Cys Leu Val Lys Asp Tyr Phe Pro Glu Pro Val Thr Val
145              150              155              160
Ser Trp Asn Ser Gly Ala Leu Thr Ser Gly Val His Thr Phe Pro Ala
            165              170              175
Val Leu Gln Ser Ser Gly Leu Tyr Ser Leu Ser Ser Val Val Thr Val
            180              185              190
Pro Ser Ser Ser Leu Gly Thr Gln Thr Tyr Ile Cys Asn Val Asn His
            195              200              205
Lys Pro Ser Asn Thr Lys Val Asp Lys Arg Val Glu Pro Lys Ser Cys
            210              215              220
Asp Lys Thr His Thr Cys Pro Pro Cys Pro Ala Pro Glu Leu Leu Gly
225              230              235              240
Gly Pro Ser Val Phe Leu Phe Pro Pro Lys Pro Lys Asp Thr Leu Met
            245              250              255
Ile Ser Arg Thr Pro Glu Val Thr Cys Val Val Val Asp Val Ser His
            260              265              270
Glu Asp Pro Glu Val Lys Phe Asn Trp Tyr Val Asp Gly Val Glu Val
            275              280              285
His Asn Ala Lys Thr Lys Pro Arg Glu Glu Gln Tyr Asn Ser Thr Tyr
            290              295              300
Arg Val Val Ser Val Leu Thr Val Leu His Gln Asp Trp Leu Asn Gly
305              310              315              320
Lys Glu Tyr Lys Cys Lys Val Ser Asn Lys Ala Leu Pro Ala Pro Ile
            325              330              335
Glu Lys Thr Ile Ser Lys Ala Lys Gly Gln Pro Arg Glu Pro Gln Val
            340              345              350
Tyr Thr Leu Pro Pro Ser Arg Glu Glu Met Thr Lys Asn Gln Val Ser
            355              360              365
Leu Thr Cys Leu Val Lys Gly Phe Tyr Pro Ser Asp Ile Ala Val Glu
            370              375              380
Trp Glu Ser Asn Gly Gln Pro Glu Asn Asn Tyr Lys Thr Thr Pro Pro
385              390              395              400
Val Leu Asp Ser Asp Gly Ser Phe Phe Leu Tyr Ser Lys Leu Thr Val
            405              410              415
Asp Lys Ser Arg Trp Gln Gln Gly Asn Val Phe Ser Cys Ser Val Met
            420              425              430
His Glu Ala Leu His Asn His Tyr Thr Gln Lys Ser Leu Ser Leu Ser
            435              440              445
Pro Gly Lys
    450

<210> SEQ ID NO 231
<211> LENGTH: 213
<212> TYPE: PRT
<213> ORGANISM: Homo sapiens

<400> SEQUENCE: 231

Asp Ile Gln Met Thr Gln Ser Pro Ser Thr Leu Ser Ala Ser Val Gly
1               5                   10                  15
```

```
Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 232
<211> LENGTH: 450
<212> TYPE: PRT
<213> ORGANISM: Homo sapiens

<400> SEQUENCE: 232

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

-continued

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 233
<211> LENGTH: 213
<212> TYPE: PRT
<213> ORGANISM: Homo sapiens

<400> SEQUENCE: 233

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr

```
                    85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 234
<211> LENGTH: 450
<212> TYPE: PRT
<213> ORGANISM: Homo sapiens

<400> SEQUENCE: 234

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 235
<211> LENGTH: 213
<212> TYPE: PRT
<213> ORGANISM: Homo sapiens

<400> SEQUENCE: 235

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Tyr Lys Gln Thr Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160
```

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 236
<211> LENGTH: 450
<212> TYPE: PRT
<213> ORGANISM: Homo sapiens

<400> SEQUENCE: 236

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65              70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys

```
                305                 310                 315                 320
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 237
<211> LENGTH: 213
<212> TYPE: PRT
<213> ORGANISM: Homo sapiens

<400> SEQUENCE: 237

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
                20                  25                  30

His Trp Tyr Gln Gln Lys Pro Gly Lys Ala Pro Lys Leu Leu Ile Tyr
            35                  40                  45

Asp Thr Arg Tyr Leu Ser Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 238
<211> LENGTH: 450
<212> TYPE: PRT
<213> ORGANISM: Homo sapiens

<400> SEQUENCE: 238

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Thr Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 239
<211> LENGTH: 213
<212> TYPE: PRT
<213> ORGANISM: Homo sapiens

<400> SEQUENCE: 239

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 240
<211> LENGTH: 450
<212> TYPE: PRT
<213> ORGANISM: Homo sapiens

<400> SEQUENCE: 240

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30
```

```
Gly Met Ser Val Gly Trp Ile Arg Gln Pro Pro Gly Lys Ala Leu Glu
         35                  40                  45

Trp Leu Ala Asp Ile Trp Trp Asp Asp Lys Lys Asp Tyr Asn Pro Ser
 50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Ser Met Ile Thr Asn Phe Tyr Phe Asp Val Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

```
Gly Lys
    450

<210> SEQ ID NO 241
<211> LENGTH: 213
<212> TYPE: PRT
<213> ORGANISM: Homo sapiens

<400> SEQUENCE: 241

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Phe Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 242
<211> LENGTH: 450
<212> TYPE: PRT
<213> ORGANISM: Homo sapiens

<400> SEQUENCE: 242

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95
```

```
Cys Ala Arg Asp Met Ile Thr Asn Phe Tyr Phe Asp Val Trp Gly Gln
            100                 105                 110
Gly Thr Thr Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 243
<211> LENGTH: 213
<212> TYPE: PRT
<213> ORGANISM: Homo sapiens

<400> SEQUENCE: 243

Asp Ile Gln Met Thr Gln Ser Pro Ser Thr Leu Ser Ala Ser Val Gly
1               5                   10                  15
```

```
Asp Arg Val Thr Ile Thr Cys Ser Ala Ser Ser Val Gly Tyr Met
                20                  25                  30

His Trp Tyr Gln Gln Lys Pro Gly Lys Ala Pro Lys Leu Leu Ile Tyr
         35                  40                  45

Asp Thr Phe Lys Leu Thr Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 244
<211> LENGTH: 450
<212> TYPE: PRT
<213> ORGANISM: Homo sapiens

<400> SEQUENCE: 244

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
             35                  40                  45

Trp Leu Ala Asp Ile Trp Trp Asp Asp Lys Lys Asp Tyr Asn Pro Ser
     50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Thr Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

-continued

```
                165                 170                 175
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 245
<211> LENGTH: 213
<212> TYPE: PRT
<213> ORGANISM: Homo sapiens

<400> SEQUENCE: 245

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80
```

-continued

```
Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 246
<211> LENGTH: 450
<212> TYPE: PRT
<213> ORGANISM: Homo sapiens

<400> SEQUENCE: 246

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Thr Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Lys Pro Lys Asp Thr Leu Met Ile
                245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 247
<211> LENGTH: 213
<212> TYPE: PRT
<213> ORGANISM: Homo sapiens

<400> SEQUENCE: 247

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Arg Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
```

```
                145                 150                 155                 160
Ser Val Thr Glu Gln Asp Ser Lys Asp Ser Thr Tyr Ser Leu Ser Ser
                    165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
            210

<210> SEQ ID NO 248
<211> LENGTH: 450
<212> TYPE: PRT
<213> ORGANISM: Homo sapiens

<400> SEQUENCE: 248

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 249
<211> LENGTH: 214
<212> TYPE: PRT
<213> ORGANISM: Homo sapiens

<400> SEQUENCE: 249

Asp Ile Gln Met Thr Gln Ser Pro Ser Thr Leu Ser Ala Ser Val Gly
1               5                   10                  15

Asp Arg Val Thr Ile Thr Cys Ser Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Tyr Arg His Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Phe Gln Gly Ser Gly Tyr Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 250
<211> LENGTH: 450
<212> TYPE: PRT
<213> ORGANISM: Homo sapiens

<400> SEQUENCE: 250

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
```

```
                370             375             380
Glu Ser Asn Gly Gln Pro Glu Asn Asn Tyr Lys Thr Thr Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 251
<211> LENGTH: 213
<212> TYPE: PRT
<213> ORGANISM: Homo sapiens

<400> SEQUENCE: 251

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Phe His Arg Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 252
<211> LENGTH: 450
<212> TYPE: PRT
<213> ORGANISM: Homo sapiens

<400> SEQUENCE: 252

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
```

-continued

```
                    20                  25                  30
Gly Met Ser Val Gly Trp Ile Arg Gln Pro Gly Lys Ala Leu Glu
                35                  40                  45

Trp Leu Ala Asp Ile Trp Trp Asp Asp Lys Lys His Tyr Asn Pro Ser
50                      55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

<210> SEQ ID NO 253
<211> LENGTH: 213
<212> TYPE: PRT
<213> ORGANISM: Homo sapiens

<400> SEQUENCE: 253

```
Asp Ile Gln Met Thr Gln Ser Pro Ser Thr Leu Ser Ala Ser Val Gly
1               5                   10                  15
Asp Arg Val Thr Ile Thr Cys Ser Ala Ser Ser Arg Val Gly Tyr Met
            20                  25                  30
His Trp Tyr Gln Gln Lys Pro Gly Lys Ala Pro Lys Leu Leu Ile Tyr
        35                  40                  45
Asp Thr Leu Leu Asp Ser Gly Val Pro Ser Arg Phe Ser Gly Ser
    50                  55                  60
Gly Ser Gly Thr Glu Phe Thr Leu Thr Ile Ser Ser Leu Gln Pro Asp
65                  70                  75                  80
Asp Phe Ala Thr Tyr Tyr Cys Phe Gln Gly Ser Gly Tyr Pro Phe Thr
                85                  90                  95
Phe Gly Gly Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 254
<211> LENGTH: 450
<212> TYPE: PRT
<213> ORGANISM: Homo sapiens

<400> SEQUENCE: 254

```
Gln Val Thr Leu Arg Glu Ser Gly Pro Ala Leu Val Lys Pro Thr Gln
1               5                   10                  15
Thr Leu Thr Leu Thr Cys Thr Phe Ser Gly Phe Ser Leu Ser Thr Ala
            20                  25                  30
Gly Met Ser Val Gly Trp Ile Arg Gln Pro Pro Gly Lys Ala Leu Glu
        35                  40                  45
Trp Leu Ala Asp Ile Trp Trp Asp Asp Lys Lys His Tyr Asn Pro Ser
    50                  55                  60
Leu Lys Asp Arg Leu Thr Ile Ser Lys Asp Thr Ser Lys Asn Gln Val
65                  70                  75                  80
Val Leu Lys Val Thr Asn Met Asp Pro Ala Asp Thr Ala Thr Tyr Tyr
                85                  90                  95
```

```
Cys Ala Arg Asp Met Ile Phe Asn Phe Tyr Phe Asp Val Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 255
<211> LENGTH: 213
<212> TYPE: PRT
<213> ORGANISM: Homo sapiens

<400> SEQUENCE: 255

Asp Ile Gln Met Thr Gln Ser Pro Ser Thr Leu Ser Ala Ser Val Gly
```

```
                1               5                   10                  15
Asp Arg Val Thr Ile Thr Cys Ser Ala Ser Ser Arg Val Gly Tyr Met
                    20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                    85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 256
<211> LENGTH: 450
<212> TYPE: PRT
<213> ORGANISM: Homo sapiens

<400> SEQUENCE: 256

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
                    20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys His Tyr Asn Pro Ser
        50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                    85                  90                  95

Cys Ala Arg Asp Met Ile Phe Asn Phe Tyr Phe Asp Val Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 257
<211> LENGTH: 213
<212> TYPE: PRT
<213> ORGANISM: Homo sapiens

<400> SEQUENCE: 257

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Phe Leu Asp Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80
```

```
Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 258
<211> LENGTH: 26
<212> TYPE: DNA
<213> ORGANISM: Artificial Sequences
<220> FEATURE:
<223> OTHER INFORMATION: Description of Artificial Sequence: Primer

<400> SEQUENCE: 258
agtgtcttaa ccagcaaagt gttaga                                        26

<210> SEQ ID NO 259
<211> LENGTH: 26
<212> TYPE: DNA
<213> ORGANISM: Artificial Sequences
<220> FEATURE:
<223> OTHER INFORMATION: Description of Artificial Sequence: Primer

<400> SEQUENCE: 259
tcattgactt gagatattga tgcatc                                        26

<210> SEQ ID NO 260
<211> LENGTH: 106
<212> TYPE: PRT
<213> ORGANISM: Homo sapiens
<220> FEATURE:
<223> OTHER INFORMATION: VL domain of SYNAGIS

<400> SEQUENCE: 260

```
Asp Ile Gln Met Thr Gln Ser Pro Ser Thr Leu Ser Ala Ser Val Gly
 1               5                  10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95
```

Phe Gly Gly Gly Thr Lys Leu Glu Ile Lys
            100                 105

<210> SEQ ID NO 261
<211> LENGTH: 120
<212> TYPE: PRT
<213> ORGANISM: Homo sapiens
<220> FEATURE:
<223> OTHER INFORMATION: VH domain of SYNAGIS

<400> SEQUENCE: 261

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120

<210> SEQ ID NO 262
<211> LENGTH: 106
<212> TYPE: PRT
<213> ORGANISM: Homo sapiens

<400> SEQUENCE: 262

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 263
<211> LENGTH: 120
<212> TYPE: PRT
<213> ORGANISM: Homo sapiens

<400> SEQUENCE: 263

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser

-continued

```
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                      70                  75                  80

Val Leu Lys Val Thr Asn Met Asp Pro Ala Asp Ala Thr Tyr Tyr
                85                  90                  95

Cys Ala Arg Ser Met Ile Thr Asn Trp Tyr Phe Asp Val Trp Gly Gln
            100                 105                 110

Gly Thr Thr Val Thr Val Ser Ser
        115                 120
```